(12) United States Patent
Monia et al.

(10) Patent No.: US 7,981,868 B2
(45) Date of Patent: Jul. 19, 2011

(54) ANTISENSE MODULATION OF P38 MITOGEN ACTIVATED PROTEIN KINASE EXPRESSION

(75) Inventors: Brett P. Monia, Carlsbad, CA (US); Kenneth W. Dobie, Del Mar, CA (US); Susan M. Freier, San Diego, CA (US); Ian Popoff, Encinitas, CA (US); James G. Karras, San Marcos, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 31 days.

(21) Appl. No.: 10/568,488

(22) PCT Filed: Aug. 12, 2004

(86) PCT No.: PCT/US2004/026344
§ 371 (c)(1),
(2), (4) Date: Mar. 25, 2008

(87) PCT Pub. No.: WO2005/016947
PCT Pub. Date: Feb. 24, 2005

(65) Prior Publication Data
US 2008/0194503 A1 Aug. 14, 2008

Related U.S. Application Data

(60) Provisional application No. 10/641,455, filed on Aug. 15, 2003.

(51) Int. Cl.
*C07H 21/00* (2006.01)
*C07H 21/02* (2006.01)
*C12N 15/11* (2006.01)
*A61K 48/00* (2006.01)

(52) U.S. Cl. ..... 514/44; 536/23.1; 536/24.3; 536/24.33; 536/24.5

(58) Field of Classification Search ............. 536/23.1, 536/24.3, 24.33, 24.5
See application file for complete search history.

(56) References Cited

U.S. PATENT DOCUMENTS

| | | | |
|---|---|---|---|
| 5,652,355 A | 7/1997 | Metelev et al. | |
| 5,801,154 A | 9/1998 | Baracchini et al. | |
| 5,856,462 A | 1/1999 | Agrawal | |
| 5,872,242 A | 2/1999 | Monia et al. | |
| 5,877,309 A | 3/1999 | Dean et al. | |
| 5,994,076 A * | 11/1999 | Chenchik et al. | 435/6 |

(Continued)

FOREIGN PATENT DOCUMENTS

WO   WO 91/14002 A   9/1991

(Continued)

OTHER PUBLICATIONS

Skerra, A. (Nucleic Acids Research, 1992 vol. 20:3551-3554).*

(Continued)

*Primary Examiner* — Sean McGarry
*Assistant Examiner* — Terra Cotta Gibbs
(74) *Attorney, Agent, or Firm* — Knobbe, Martens, Olson & Bear LLP

(57) ABSTRACT

Compositions and methods for the treatment and diagnosis of diseases or conditions amenable to treatment through modulation of expression of a gene encoding a p38 mitogen-activated protein kinase (p38 MAPK) are provided. Methods for decreasing airway hyperresponsiveness or airway inflammation in an animal are also provided.

13 Claims, 6 Drawing Sheets

U.S. PATENT DOCUMENTS

| | | | |
|---|---|---|---|
| 6,140,124 | A | 10/2000 | Monia et al. |
| 6,448,079 | B1 * | 9/2002 | Monia et al. .................. 435/375 |
| 6,582,908 | B2 | 6/2003 | Fodor et al. |
| 6,906,186 | B1 * | 6/2005 | Wyatt et al. .................. 536/24.5 |
| 2001/0053519 | A1 | 12/2001 | Fodor et al. |
| 2003/0176383 | A1 | 9/2003 | Monia et al. |
| 2003/0228597 | A1 | 12/2003 | Cowsert et al. |
| 2004/0171566 | A1 | 9/2004 | Monia et al. |

FOREIGN PATENT DOCUMENTS

| | | |
|---|---|---|
| WO | WO 97/04104 A | 2/1997 |
| WO | 9835978 A1 | 8/1998 |
| WO | 9960166 A1 | 11/1999 |
| WO | WO 00/59919 | 10/2000 |

OTHER PUBLICATIONS

Branch, AD. A good antisense molecule is hard to find. TIBS, 1998 vol. 23:45-50.*

Escott, K.G., etal., "Effect of the p38 kinase inhibitor, SB 203580, on allergic airway inflammation in the rat," British Journal of Pharmacology (2000) 131:173-176.

Taube, et al., Inhibition of Early Airway Neutrophilia Does Not Affect Development of Airway Hyperresponsiveness, 2004, American Journal of Respiratory Cell and Molecular Biology, vol. 30 pp. 837-843.

Underwood, et al., SB 239063, a Potent p38 MAP Kinase Inhibitor, Reduces Inflammatory Cytokine Production, Airways Eosinophil Infiltration, and Persistance, 2000, The Journal of Pharmacology and Experimental Therapeutics, vol. 293, No. 1, pp. 281-288.

Agrawal, S. et al., "Antisense therapeutics: is it as simple as complementary base recognition?" Molecular Medicine Today (2000) 6:72-81.

Aoshiba, K. et al., "Role of p38-Mitogen-Activated Protein Kinase in Spontaneous Apoptosis of Human Neutrophils," J. Immunol. (1999) 162:1692-1700.

Arima, H. et al., "Specific Inhibition of Nitric Oxide Production in Macrophages by Phosphorothioate Antisense Oligonucleotides," J. Pharm. Sci. (1997) 86(10):1079-1084.

Branch, A. D., "A good antisense molecule is hard to find," TIBS (1998) 23:45-50.

Chialda, L. et al., "Inhibitors of mitogen-activated protein kinases differentially regulate costimulated T cell cytokine production and mouse airway eosinophilia," Respiratory Research (2005) 6:36.

Cohen, P. S. et al., "The Critical Role of p38 MAP Kinase in T Cell HIV-1 Replication," Molecular Medicine (1997) 3(5):339-346.

Crooke, S. T., "Basic Principles of Antisense Therapeutics," Antisense Research and Application (1998) Springer-Verlag, New York, pp. 1-50.

Database EMBL:HS1206359 "zv26e08.s1 Soares_NhHMPu_S1 *Homo sapiens* cDNA clone IMAG:754790 3' similar to TR:G1304132 G1304132 TPRD.;, mRNA sequence," May 4, 1997 XP002302626 retrieved from EBI accession No. EM_EST:1206359 Database accession No. HS1206359.

Duan, W. et al., "Inhaled p38 Mitogen-Activated Protein Kinase Antisense Oligonucleotides Attenuates Asthma in Mice," Am. J. Respir. Crit. Care Med. (2005) 171:571-578.

Green, D. W. et al., "Antisense Oligonucleotides: An Evolving Technology for the Modulation of Gene Expression in Human Disease," J. Am. Coll. Surg. (2000) 191:93-105.

Han, J. et al., "A MAP Kinase Targeted by Endotoxin and Hyperosmolarity in Mammalian Cells," Science (1994) 265:808-811.

Jen, K.-Y. et al., "Suppression of Gene Expression by Targeted Disruption of Messenger RNA: Available Options and Current Strategies," Stem Cells (2000) 18:307-319.

Kumar, R. K. et al., "Murine Model of Chronic Human Asthma," Immunology and Cell Biology (2001) 79:141-144.

Nagata, Y. et al., "Activation of p38 MAP Kinase and JNK But Not ERK Is Required for Erythropoietin-Induced Erythroid Differentiation," Blood (1998) 92(6):1859-1869.

Nick, J. A. et al., "Role of p38 Mitogen-Activated Protein Kinase in a Murine Model of Pulmonary Inflammation," J. Immunol. (2000) 164:2151-2159.

Nyce, J. W., "Respirable antisense oligonucleotides as novel therapeutic agents for asthma and other pulmonary diseases," Expert. Opin. Investig. Drugs (1997) 6(9):1149-1156.

Nyce, J. W. et al., "DNA antisense therapy for asthma in an animal model," Nature (1997) 385(6618):721-725.

Richards, I. M., "Mouse models of allergic disease; how do they relate to asthma in man?" Clinical and Experimental Allergy (1996) 26:618-620.

Sale, E. M. et al., "Use of an antisense strategy to dissect the role of MAP kinases in cellular signaling," Biochemical Society Transactions (1998) 26(3):S254.

Temelkovski, J. et al., "An improved murine model of asthma selective airway inflammation, epithelial lesions and increased methacholine responsiveness following chronic exposure to aerosolised allergen," Thorax (1998) 53:849-856.

Wong, W. S. F., "Inhibitors of the tyrosine kinase signaling cascade for asthma," Current Opinion in Pharmacology (2005) 5:264-271.

Chin, Andrew "On the Preparation and Utilization of Isolated and Purified Oligonucleotides." Document purportedly located on a CD-ROM and contributed to the public collection of the Katherine R. Everett Law Library of the University of North Carolina on Mar. 14, 2002.

Gura, Trisha. Antisense Has Growing Pains, Science, pp. 575-577, Oct. 1995.

New England BioLabs, Inc. Catalogue (1998): 121, 284.

Reynolds et al., Rational siRNA design for RNA interference, Mar. 2004, Nature Biotechnology, vol. 22, pp. 326-330.

Sanghvi et al., "Heterocyclic Base Modifications in Nucleic Acids and Their Applications in Antisense Oligonucleotides" Antisense Research and Applications (1993) pp. 273-288.

GenBank Accession No. L35253.

International Search Report from PCT/US2004/026344, dated Nov. 21, 2005.

Supplementary European Search Report from EP 04 78 1089, dated Jan. 9, 2007.

Supplementary European Search Report from EP 04 78 1089, dated Oct. 20, 2006.

Han et al., "Molecular cloning of human p38 MAP kinase" Biochimica et Biophysica Acta (1995) 1265:224-227.

Supplementary Partial European Search Report for Application No. EP 00920053.6 dated Aug. 30, 2004.

Supplementary Partial European Search Report for Application No. EP 00920053.6 dated Nov. 23, 2004.

International Search Report for Application No. PCT/US00/08794 dated Aug. 7, 2000.

* cited by examiner

SEQUENCE LISTING

```
<160> NUMBER OF SEQ ID NOS: 412

<210> SEQ ID NO 1
<211> LENGTH: 1539
<212> TYPE: DNA
<213> ORGANISM: Homo sapiens
<220> FEATURE:
<221> NAME/KEY: CDS
<222> LOCATION: (295)..(1377)
<300> PUBLICATION INFORMATION:
<303> JOURNAL: Science
<304> VOLUME: 265
<305> ISSUE: 5173
<306> PAGES: 808-811
<307> DATE: 1994-08-05
<308> DATABASE ACCESSION NUMBER: L35253
<309> DATABASE ENTRY DATE: 1995-08-14

<400> SEQUENCE: 1
ggaattccgg gcccggtctt tcctcccgcc gccgccggcc tggtcccggg gactggcctc      60
cacgtccgac tcgtccgagc tgaagcccag cagcactttg ctgccagccg cggggcggc     120 ggaggcgccc ccgggccctc ccaggaggct ctctgggcca gaggccgaga ttcggcacag     180
gcccccagga gtccgtaagt aggagaggtc gcccgagacc ggccggaccc ccatcccgc     240
```

-continued

| | |
|---|---|
| ggccgccgcc gccgctggtc ccgcggctgc gaccgtggcg gctgccgctg gaaa atg<br>                                                                                                                                  Met<br>                                                                                                                                  1 | 297 |
| tct cag gag agg ccc acg ttc tac cgg cag gag ctg aac aag aca atc<br>Ser Gln Glu Arg Pro Thr Phe Tyr Arg Gln Glu Leu Asn Lys Thr Ile<br>              5                         10                    15 | 345 |
| tgg gag gtg ccc gag cgt tac cag aac ctg tct cca gtg ggc tct ggc<br>Trp Glu Val Pro Glu Arg Tyr Gln Asn Leu Ser Pro Val Gly Ser Gly<br>        20                     25                   30 | 393 |
| gcc tat ggc tct gtg tgt gct gct ttt gac aca aaa acg ggg tta cgt<br>Ala Tyr Gly Ser Val Cys Ala Ala Phe Asp Thr Lys Thr Gly Leu Arg<br>      35                    40                     45 | 441 |
| gtg gca gtg aag aag ctc tcc aga cca ttt cag tcc atc att cat gcg<br>Val Ala Val Lys Lys Leu Ser Arg Pro Phe Gln Ser Ile Ile His Ala<br>50                      55                     60                   65 | 489 |
| aaa aga acc tac aga gaa ctg cgg tta ctt aaa cat atg aaa cat gaa<br>Lys Arg Thr Tyr Arg Glu Leu Arg Leu Leu Lys His Met Lys His Glu<br>                    70                     75                       80 | 537 |
| aat gtg att ggt ctg ttg gac gtt ttt aca cct gca agg tct ctg gag<br>Asn Val Ile Gly Leu Leu Asp Val Phe Thr Pro Ala Arg Ser Leu Glu<br>                85                     90                    95 | 585 |
| gaa ttc aat gat gtg tat ctg gtg acc cat ctc atg ggg gca gat ctg<br>Glu Phe Asn Asp Val Tyr Leu Val Thr His Leu Met Gly Ala Asp Leu<br>            100                    105                 110 | 633 |
| aac aac att gtg aaa tgt cag aag ctt aca gat gac cat gtt cag ttc<br>Asn Asn Ile Val Lys Cys Gln Lys Leu Thr Asp Asp His Val Gln Phe<br>      115                   120                   125 | 681 |
| ctt atc tac caa att ctc cga ggt cta aag tat ata cat tca gct gac<br>Leu Ile Tyr Gln Ile Leu Arg Gly Leu Lys Tyr Ile His Ser Ala Asp<br>130                  135                 140               145 | 729 |
| ata att cac agg gac cta aaa cct agt aat cta gct gtg aat gaa gac<br>Ile Ile His Arg Asp Leu Lys Pro Ser Asn Leu Ala Val Asn Glu Asp<br>                150                   155                 160 | 777 |
| tgt gag ctg aag att ctg gat ttt gga ctg gct cgg cac aca gat gat<br>Cys Glu Leu Lys Ile Leu Asp Phe Gly Leu Ala Arg His Thr Asp Asp<br>           165                    170                 175 | 825 |
| gaa atg aca ggc tac gtg gcc act agg tgg tac agg gct cct gag atc<br>Glu Met Thr Gly Tyr Val Ala Thr Arg Trp Tyr Arg Ala Pro Glu Ile<br>                180                   185                 190 | 873 |
| atg ctg aac tgg atg cat tac aac cag aca gtt gat att tgg tca gtg<br>Met Leu Asn Trp Met His Tyr Asn Gln Thr Val Asp Ile Trp Ser Val<br>      195                 200                   205 | 921 |
| gga tgc ata atg gcc gag ctg ttg act gga aga aca ttg ttt cct ggt<br>Gly Cys Ile Met Ala Glu Leu Leu Thr Gly Arg Thr Leu Phe Pro Gly<br>210                  215                 220               225 | 969 |
| aca gac cat att gat cag ttg aag ctc att tta aga ctc gtt gga acc<br>Thr Asp His Ile Asp Gln Leu Lys Leu Ile Leu Arg Leu Val Gly Thr<br>                230                   235                 240 | 1017 |
| cca ggg gct gag ctt ttg aag aaa atc tcc tca gag tct gca aga aac<br>Pro Gly Ala Glu Leu Leu Lys Lys Ile Ser Ser Glu Ser Ala Arg Asn<br>           245                    250                 255 | 1065 |
| tat att cag tct ttg act cag atg ccg aag atg aac ttt gcg aat gta<br>Tyr Ile Gln Ser Leu Thr Gln Met Pro Lys Met Asn Phe Ala Asn Val<br>                260                   265                 270 | 1113 |
| ttt att ggt gcc aat ccc ctg gct gtc gac ttg ctg gag aag atg ctt<br>Phe Ile Gly Ala Asn Pro Leu Ala Val Asp Leu Leu Glu Lys Met Leu<br>      275               280                   285 | 1161 |
| gta ttg gac tca gat aag aga att aca gcg gcc caa gcc ctt gca cat<br>Val Leu Asp Ser Asp Lys Arg Ile Thr Ala Ala Gln Ala Leu Ala His<br>290                  295                 300               305 | 1209 |

```
gcc tac ttt gct cag tac cac gat cct gat gat gaa cca gtg gcc gat    1257
Ala Tyr Phe Ala Gln Tyr His Asp Pro Asp Asp Glu Pro Val Ala Asp
        310                 315                 320 cct tat gat cag tcc ttt gaa agc agg gac ctc ctt ata gat gag tgg    1305
Pro Tyr Asp Gln Ser Phe Glu Ser Arg Asp Leu Leu Ile Asp Glu Trp
        325                 330                 335 aaa agc ctg acc tat gat gaa gtc atc agc ttt gtg cca cca ccc ctt    1353
Lys Ser Leu Thr Tyr Asp Glu Val Ile Ser Phe Val Pro Pro Pro Leu
        340                 345                 350 gac caa gaa gag atg gag tcc tga gcacctggtt tctgttctgt tgatcccact   1407
Asp Gln Glu Glu Met Glu Ser
        355             360 tcactgtgag gggaaggcct ttcacgggaa actctccaaa tattattcaa gtgcctcttg   1467
ttgcagagat ttcctccatg gtggaagggg gtgtgcgtgc gtgtgcgtgc gtgttagtgt   1527
gtgtgcatgt gt                                                      1539

<210> SEQ ID NO 2

<400> SEQUENCE: 2

000

<210> SEQ ID NO 3
<211> LENGTH: 20
<212> TYPE: DNA
<213> ORGANISM: Artificial Sequence
<220> FEATURE:
<223> OTHER INFORMATION: antisense sequence

<400> SEQUENCE: 3
aagaccgggc ccggaattcc                                                 20

<210> SEQ ID NO 4
<211> LENGTH: 30
<212> TYPE: DNA
<213> ORGANISM: Artificial Sequence
<220> FEATURE:
<223> OTHER INFORMATION: antisense sequence

<400> SEQUENCE: 4
gtggaggcca gtccccggga ccggaattcc                                      30

<210> SEQ ID NO 5
<211> LENGTH: 20
<212> TYPE: DNA
<213> ORGANISM: Artificial Sequence
<220> FEATURE:
<223> OTHER INFORMATION: antisense sequence

<400> SEQUENCE: 5
tggcagcaaa gtgctgctgg                                                 20

<210> SEQ ID NO 6
<211> LENGTH: 20
<212> TYPE: DNA
<213> ORGANISM: Artificial Sequence
<220> FEATURE:
<223> OTHER INFORMATION: antisense sequence

<400> SEQUENCE: 6
cagagagcct cctgggaggg                                                 20

<210> SEQ ID NO 7
<211> LENGTH: 20
```

```
<212> TYPE: DNA
<213> ORGANISM: Artificial Sequence
<220> FEATURE:
<223> OTHER INFORMATION: antisense sequence

<400> SEQUENCE: 7
tgtgccgaat ctcggcctct                                            20

<210> SEQ ID NO 8
<211> LENGTH: 20
<212> TYPE: DNA
<213> ORGANISM: Artificial Sequence
<220> FEATURE:
<223> OTHER INFORMATION: antisense sequence

<400> SEQUENCE: 8
ggtctcgggc gacctctcct                                            20

<210> SEQ ID NO 9
<211> LENGTH: 20
<212> TYPE: DNA
<213> ORGANISM: Artificial Sequence
<220> FEATURE:
<223> OTHER INFORMATION: antisense sequence

<400> SEQUENCE: 9
cagccgcggg accagcggcg                                            20

<210> SEQ ID NO 10
<211> LENGTH: 20
<212> TYPE: DNA
<213> ORGANISM: Artificial Sequence
<220> FEATURE:
<223> OTHER INFORMATION: antisense sequence

<400> SEQUENCE: 10
cattttccag cggcagccgc                                            20

<210> SEQ ID NO 11
<211> LENGTH: 20
<212> TYPE: DNA
<213> ORGANISM: Artificial Sequence
<220> FEATURE:
<223> OTHER INFORMATION: antisense sequence

<400> SEQUENCE: 11
tcctgagaca ttttccagcg                                            20

<210> SEQ ID NO 12
<211> LENGTH: 20
<212> TYPE: DNA
<213> ORGANISM: Artificial Sequence
<220> FEATURE:
<223> OTHER INFORMATION: antisense sequence

<400> SEQUENCE: 12
ctgccggtag aacgtgggcc                                            20

<210> SEQ ID NO 13
<211> LENGTH: 20
<212> TYPE: DNA
<213> ORGANISM: Artificial Sequence
<220> FEATURE:
<223> OTHER INFORMATION: antisense sequence

<400> SEQUENCE: 13
gtaagcttct gacatttcac                                            20
```

```
<210> SEQ ID NO 14
<211> LENGTH: 20
<212> TYPE: DNA
<213> ORGANISM: Artificial Sequence
<220> FEATURE:
<223> OTHER INFORMATION: antisense sequence

<400> SEQUENCE: 14
tttaggtccc tgtgaattat                                               20

<210> SEQ ID NO 15
<211> LENGTH: 20
<212> TYPE: DNA
<213> ORGANISM: Artificial Sequence
<220> FEATURE:
<223> OTHER INFORMATION: antisense sequence

<400> SEQUENCE: 15
atgttcttcc agtcaacagc                                               20

<210> SEQ ID NO 16
<211> LENGTH: 20
<212> TYPE: DNA
<213> ORGANISM: Artificial Sequence
<220> FEATURE:
<223> OTHER INFORMATION: antisense sequence

<400> SEQUENCE: 16
taaggaggtc cctgctttca                                               20

<210> SEQ ID NO 17
<211> LENGTH: 20
<212> TYPE: DNA
<213> ORGANISM: Artificial Sequence
<220> FEATURE:
<223> OTHER INFORMATION: antisense sequence

<400> SEQUENCE: 17
aaccaggtgc tcaggactcc                                               20

<210> SEQ ID NO 18
<211> LENGTH: 20
<212> TYPE: DNA
<213> ORGANISM: Artificial Sequence
<220> FEATURE:
<223> OTHER INFORMATION: antisense sequence

<400> SEQUENCE: 18
gaagtgggat caacagaaca                                               20

<210> SEQ ID NO 19
<211> LENGTH: 20
<212> TYPE: DNA
<213> ORGANISM: Artificial Sequence
<220> FEATURE:
<223> OTHER INFORMATION: antisense sequence

<400> SEQUENCE: 19
tgaaaaggcc ttcccctcac                                               20

<210> SEQ ID NO 20
<211> LENGTH: 20
<212> TYPE: DNA
<213> ORGANISM: Artificial Sequence
<220> FEATURE:
<223> OTHER INFORMATION: antisense sequence
```

-continued

```
<400> SEQUENCE: 20
aggcacttga ataatatttg                                                    20

<210> SEQ ID NO 21
<211> LENGTH: 20
<212> TYPE: DNA
<213> ORGANISM: Artificial Sequence
<220> FEATURE:
<223> OTHER INFORMATION: antisense sequence

<400> SEQUENCE: 21
cttccaccat ggaggaaatc                                                    20

<210> SEQ ID NO 22
<211> LENGTH: 20
<212> TYPE: DNA
<213> ORGANISM: Artificial Sequence
<220> FEATURE:
<223> OTHER INFORMATION: antisense sequence

<400> SEQUENCE: 22
acacatgcac acacactaac                                                    20

<210> SEQ ID NO 23
<211> LENGTH: 2180
<212> TYPE: DNA
<213> ORGANISM: Homo sapiens
<220> FEATURE:
<221> NAME/KEY: CDS
<222> LOCATION: (20)..(1138)
<300> PUBLICATION INFORMATION:
<308> DATABASE ACCESSION NUMBER: U53442
<309> DATABASE ENTRY DATE: 1996-07-30

<400> SEQUENCE: 23
gtgaaattct gctccggac atg tcg ggc cct cgc gcc ggc ttc tac cgg cag        52
                    Met Ser Gly Pro Arg Ala Gly Phe Tyr Arg Gln
                      1               5                  10 gag ctg aac aag acc gtg tgg gag gtg ccg cag cgg ctg cag ggg ctg        100
Glu Leu Asn Lys Thr Val Trp Glu Val Pro Gln Arg Leu Gln Gly Leu
             15                  20                  25 cgc ccg gtg ggc tcc ggc gcc tac ggc tcc gtc tgt tcg gcc tac gac        148
Arg Pro Val Gly Ser Gly Ala Tyr Gly Ser Val Cys Ser Ala Tyr Asp
         30                  35                  40 gcc cgg ctg cgc cag aag gtg gcg gtg aag aag ctg tcg cgc ccc ttc        196
Ala Arg Leu Arg Gln Lys Val Ala Val Lys Lys Leu Ser Arg Pro Phe
     45                  50                  55 cag tcg ctg atc cac gcg cgc aga acg tac cgg gag ctg cgg ctg ctc        244
Gln Ser Leu Ile His Ala Arg Arg Thr Tyr Arg Glu Leu Arg Leu Leu
 60                  65                  70                  75 aag cac ctg aag cac gag aac gtc atc ggg ctt ctg gac gtc ttc acg        292
Lys His Leu Lys His Glu Asn Val Ile Gly Leu Leu Asp Val Phe Thr
                 80                  85                  90 ccg gcc acg tcc atc gag gac ttc agc gaa gtg tac ttg gtg acc acc        340
Pro Ala Thr Ser Ile Glu Asp Phe Ser Glu Val Tyr Leu Val Thr Thr
             95                 100                 105 ctg atg ggc gcc gac ctg aac aac atc gtc aag tgc cag gcg ggc gcc        388
Leu Met Gly Ala Asp Leu Asn Asn Ile Val Lys Cys Gln Ala Gly Ala
         110                 115                 120 cat cag ggt gcc cgc ctg gca ctt gac gag cac gtt caa ttc ctg gtt        436
His Gln Gly Ala Arg Leu Ala Leu Asp Glu His Val Gln Phe Leu Val
     125                 130                 135 tac cag ctg ctg cgc ggg ctg aag tac atc cac tcg gcc ggg atc atc        484
```

```
Tyr Gln Leu Leu Arg Gly Leu Lys Tyr Ile His Ser Ala Gly Ile Ile
140                 145                 150                 155 cac cgg gac ctg aag ccc agc aac gtg gct gtg aac gag gac tgt gag        532
His Arg Asp Leu Lys Pro Ser Asn Val Ala Val Asn Glu Asp Cys Glu
                160                 165                 170 ctc agg atc ctg gat ttc ggg ctg gcg cgc cag gcg gac gag gag atg        580
Leu Arg Ile Leu Asp Phe Gly Leu Ala Arg Gln Ala Asp Glu Glu Met
            175                 180                 185 acc ggc tat gtg gcc acg cgc tgg tac cgg gca cct gag atc atg ctc        628
Thr Gly Tyr Val Ala Thr Arg Trp Tyr Arg Ala Pro Glu Ile Met Leu
        190                 195                 200 aac tgg atg cat tac aac caa aca gtg gat atc tgg tcc gtg ggc tgc        676
Asn Trp Met His Tyr Asn Gln Thr Val Asp Ile Trp Ser Val Gly Cys
    205                 210                 215 atc atg gct gag ctg ctc cag ggc aag gcc ctc ttc ccg gga agc gac        724
Ile Met Ala Glu Leu Leu Gln Gly Lys Ala Leu Phe Pro Gly Ser Asp
220                 225                 230                 235 tac att gac cag ctg aag cgc atc atg gaa gtg gtg ggc aca ccc agc        772
Tyr Ile Asp Gln Leu Lys Arg Ile Met Glu Val Val Gly Thr Pro Ser
                240                 245                 250 cct gag gtt ctg gca aaa atc tcc tcg gaa cac gcc cgg aca tat atc        820
Pro Glu Val Leu Ala Lys Ile Ser Ser Glu His Ala Arg Thr Tyr Ile
            255                 260                 265 cag tcc ctg ccc ccc atg ccc cag aag gac ctg agc agc atc ttc cgt        868
Gln Ser Leu Pro Pro Met Pro Gln Lys Asp Leu Ser Ser Ile Phe Arg
        270                 275                 280 gga gcc aac ccc ctg gcc ata gac ctc ctt gga agg atg ctg gtg ctg        916
Gly Ala Asn Pro Leu Ala Ile Asp Leu Leu Gly Arg Met Leu Val Leu
    285                 290                 295 gac agt gac cag agg gtc agt gca gct gag gca ctg gcc cac gcc tac        964
Asp Ser Asp Gln Arg Val Ser Ala Ala Glu Ala Leu Ala His Ala Tyr
300                 305                 310                 315 ttc agc cag tac cac gac ccc gag gat gag cca gag gcc gag cca tat       1012
Phe Ser Gln Tyr His Asp Pro Glu Asp Glu Pro Glu Ala Glu Pro Tyr
                320                 325                 330 gat gag agc gtt gag gcc aag gag cgc acg ctg gag gag tgg aag gag       1060
Asp Glu Ser Val Glu Ala Lys Glu Arg Thr Leu Glu Glu Trp Lys Glu
            335                 340                 345 ctc act tac cag gaa gtc ctt agc ttc aag ccc cca gag cca ccg aag       1108
Leu Thr Tyr Gln Glu Val Leu Ser Phe Lys Pro Pro Glu Pro Pro Lys
        350                 355                 360 cca cct ggc agc ctg gag att gag cag tga ggtgctgccc agcagcccct        1158
Pro Pro Gly Ser Leu Glu Ile Glu Gln
    365                 370 gagagcctgt ggaggggctt gggcctgcac ccttccacag ctggcctggt ttcctcgaga    1218
ggcacctccc acactcctat ggtcacagac ttctggccta ggaccccctcg ccttcaggag   1278 aatctacacg catgtatgca tgcacaaaca tgtgtgtaca tgtgcttgcc atgtgtagga    1338
gtctgggcac aagtgtccct gggcctacct tggtcctcct gtcctcttct ggctactgca    1398
ctctccactg gaacctgact gtggggtcct agatgccaaa ggggttcccc tgcggagttc    1458
ccctgtctgt cccaggccga cccaaggag tgtcagcctt gggctctctt ctgtcccagg     1518
gctttctgga gggcgcgctg gggccgggac cccgggagac tcaaaggag aggtctcagt     1578 ggttagagct gctcagcctg gaggtagggc gctgtcttgg tcactgctga cccacagg      1638 tctaagagga gaggcagagc cagtgtgcca ccaggctggg cagggacaac caccaggtgt    1698
caaatgagaa aagctgcctg gagtcttgtg ttcacccgtg ggtgtgtgtg ggcacgtgtg    1758
gatgagcgtg cactccccgt gttcatatgt cagggcacat gtgatgtggt gcgtgtgaat    1818
```

-continued

```
ctgtgggcgc ccaaggccag cagccatatc tggcaagaag ctggagccgg ggtgggtgtg    1878
ctgttgcctt ccctctcctc ggttcctgat gccttgaggg gtgtttcaga ctggcggcac    1938
cgttgtggcc ctgcagccgg agatctgagg tgctctggtc tgtgggtcag tcctctttcc    1998
ttgtcccagg atggagctga tccagtaacc tcggagacgg gaccctgccc agagctgagt    2058
tgggggtgtg gctctgccct ggaaaggggg tgacctcttg cctcgagggg cccaggggaag   2118 cctgggtgtc aagtgcctgc accaggggtg cacaataaag ggggttctct ctcagaaaaa    2178
aa                                                                   2180
```

<210> SEQ ID NO 24
<211> LENGTH: 372
<212> TYPE: PRT
<213> ORGANISM: Homo sapiens

<400> SEQUENCE: 24

```
Met Ser Gly Pro Arg Ala Gly Phe Tyr Arg Gln Glu Leu Asn Lys Thr
  1               5                  10                  15

Val Trp Glu Val Pro Gln Arg Leu Gln Gly Leu Arg Pro Val Gly Ser
             20                  25                  30

Gly Ala Tyr Gly Ser Val Cys Ser Ala Tyr Asp Ala Arg Leu Arg Gln
         35                  40                  45

Lys Val Ala Val Lys Lys Leu Ser Arg Pro Phe Gln Ser Leu Ile His
     50                  55                  60

Ala Arg Arg Thr Tyr Arg Glu Leu Arg Leu Leu Lys His Leu Lys His
 65                  70                  75                  80

Glu Asn Val Ile Gly Leu Leu Asp Val Phe Thr Pro Ala Thr Ser Ile
             85                  90                  95

Glu Asp Phe Ser Glu Val Tyr Leu Val Thr Thr Leu Met Gly Ala Asp
            100                 105                 110

Leu Asn Asn Ile Val Lys Cys Gln Ala Gly Ala His Gln Gly Ala Arg
        115                 120                 125

Leu Ala Leu Asp Glu His Val Gln Phe Leu Val Tyr Gln Leu Leu Arg
    130                 135                 140

Gly Leu Lys Tyr Ile His Ser Ala Gly Ile Ile His Arg Asp Leu Lys
145                 150                 155                 160

Pro Ser Asn Val Ala Val Asn Glu Asp Cys Glu Leu Arg Ile Leu Asp
                165                 170                 175

Phe Gly Leu Ala Arg Gln Ala Asp Glu Glu Met Thr Gly Tyr Val Ala
            180                 185                 190

Thr Arg Trp Tyr Arg Ala Pro Glu Ile Met Leu Asn Trp Met His Tyr
        195                 200                 205

Asn Gln Thr Val Asp Ile Trp Ser Val Gly Cys Ile Met Ala Glu Leu
    210                 215                 220

Leu Gln Gly Lys Ala Leu Phe Pro Gly Ser Asp Tyr Ile Asp Gln Leu
225                 230                 235                 240

Lys Arg Ile Met Glu Val Val Gly Thr Pro Ser Pro Glu Val Leu Ala
                245                 250                 255

Lys Ile Ser Ser Glu His Ala Arg Thr Tyr Ile Gln Ser Leu Pro Pro
            260                 265                 270

Met Pro Gln Lys Asp Leu Ser Ser Ile Phe Arg Gly Ala Asn Pro Leu
        275                 280                 285

Ala Ile Asp Leu Leu Gly Arg Met Leu Val Leu Asp Ser Asp Gln Arg
    290                 295                 300
```

```
Val Ser Ala Ala Glu Ala Leu Ala His Ala Tyr Phe Ser Gln Tyr His
305                 310                 315                 320

Asp Pro Glu Asp Glu Pro Ala Glu Pro Tyr Asp Glu Ser Val Glu
            325                 330                 335

Ala Lys Glu Arg Thr Leu Glu Glu Trp Lys Glu Leu Thr Tyr Gln Glu
            340                 345                 350

Val Leu Ser Phe Lys Pro Pro Glu Pro Pro Lys Pro Pro Gly Ser Leu
        355                 360                 365

Glu Ile Glu Gln
    370

<210> SEQ ID NO 25
<211> LENGTH: 20
<212> TYPE: DNA
<213> ORGANISM: Artificial Sequence
<220> FEATURE:
<223> OTHER INFORMATION: antisense sequence

<400> SEQUENCE: 25
cgacatgtcc ggagcagaat                                           20

<210> SEQ ID NO 26
<211> LENGTH: 20
<212> TYPE: DNA
<213> ORGANISM: Artificial Sequence
<220> FEATURE:
<223> OTHER INFORMATION: antisense sequence

<400> SEQUENCE: 26
ttcagctcct gccggtagaa                                           20

<210> SEQ ID NO 27
<211> LENGTH: 20
<212> TYPE: DNA
<213> ORGANISM: Artificial Sequence
<220> FEATURE:
<223> OTHER INFORMATION: antisense sequence

<400> SEQUENCE: 27
tgcggcacct cccacacggt                                           20

<210> SEQ ID NO 28
<211> LENGTH: 20
<212> TYPE: DNA
<213> ORGANISM: Artificial Sequence
<220> FEATURE:
<223> OTHER INFORMATION: antisense sequence

<400> SEQUENCE: 28
ccgaacagac ggagccgtat                                           20

<210> SEQ ID NO 29
<211> LENGTH: 20
<212> TYPE: DNA
<213> ORGANISM: Artificial Sequence
<220> FEATURE:
<223> OTHER INFORMATION: antisense sequence

<400> SEQUENCE: 29
gtgcttcagg tgcttgagca                                           20

<210> SEQ ID NO 30
<211> LENGTH: 20
<212> TYPE: DNA
<213> ORGANISM: Artificial Sequence
```

```
<220> FEATURE:
<223> OTHER INFORMATION: antisense sequence

<400> SEQUENCE: 30
gcgtgaagac gtccagaagc                                                    20

<210> SEQ ID NO 31
<211> LENGTH: 20
<212> TYPE: DNA
<213> ORGANISM: Artificial Sequence
<220> FEATURE:
<223> OTHER INFORMATION: antisense sequence

<400> SEQUENCE: 31
acttgacgat gttgttcagg                                                    20

<210> SEQ ID NO 32
<211> LENGTH: 20
<212> TYPE: DNA
<213> ORGANISM: Artificial Sequence
<220> FEATURE:
<223> OTHER INFORMATION: antisense sequence

<400> SEQUENCE: 32
aacgtgctcg tcaagtgcca                                                    20

<210> SEQ ID NO 33
<211> LENGTH: 20
<212> TYPE: DNA
<213> ORGANISM: Artificial Sequence
<220> FEATURE:
<223> OTHER INFORMATION: antisense sequence

<400> SEQUENCE: 33
atcctgagct cacagtcctc                                                    20

<210> SEQ ID NO 34
<211> LENGTH: 20
<212> TYPE: DNA
<213> ORGANISM: Artificial Sequence
<220> FEATURE:
<223> OTHER INFORMATION: antisense sequence

<400> SEQUENCE: 34
actgtttggt tgtaatgcat                                                    20

<210> SEQ ID NO 35
<211> LENGTH: 20
<212> TYPE: DNA
<213> ORGANISM: Artificial Sequence
<220> FEATURE:
<223> OTHER INFORMATION: antisense sequence

<400> SEQUENCE: 35
atgatgcgct tcagctggtc                                                    20

<210> SEQ ID NO 36
<211> LENGTH: 20
<212> TYPE: DNA
<213> ORGANISM: Artificial Sequence
<220> FEATURE:
<223> OTHER INFORMATION: antisense sequence

<400> SEQUENCE: 36
gccagtgcct cagctgcact                                                    20
```

```
<210> SEQ ID NO 37
<211> LENGTH: 20
<212> TYPE: DNA
<213> ORGANISM: Artificial Sequence
<220> FEATURE:
<223> OTHER INFORMATION: antisense sequence

<400> SEQUENCE: 37
aacgctctca tcatatggct                                               20

<210> SEQ ID NO 38
<211> LENGTH: 20
<212> TYPE: DNA
<213> ORGANISM: Artificial Sequence
<220> FEATURE:
<223> OTHER INFORMATION: antisense sequence

<400> SEQUENCE: 38
cagcacctca ctgctcaatc                                               20

<210> SEQ ID NO 39
<211> LENGTH: 20
<212> TYPE: DNA
<213> ORGANISM: Artificial Sequence
<220> FEATURE:
<223> OTHER INFORMATION: antisense sequence

<400> SEQUENCE: 39
tctgtgacca taggagtgtg                                               20

<210> SEQ ID NO 40
<211> LENGTH: 20
<212> TYPE: DNA
<213> ORGANISM: Artificial Sequence
<220> FEATURE:
<223> OTHER INFORMATION: antisense sequence

<400> SEQUENCE: 40
acacatgttt gtgcatgcat                                               20

<210> SEQ ID NO 41
<211> LENGTH: 20
<212> TYPE: DNA
<213> ORGANISM: Artificial Sequence
<220> FEATURE:
<223> OTHER INFORMATION: antisense sequence

<400> SEQUENCE: 41
cctacacatg gcaagcacat                                               20

<210> SEQ ID NO 42
<211> LENGTH: 20
<212> TYPE: DNA
<213> ORGANISM: Artificial Sequence
<220> FEATURE:
<223> OTHER INFORMATION: antisense sequence

<400> SEQUENCE: 42
tccaggctga gcagctctaa                                               20

<210> SEQ ID NO 43
<211> LENGTH: 20
<212> TYPE: DNA
<213> ORGANISM: Artificial Sequence
<220> FEATURE:
<223> OTHER INFORMATION: antisense sequence

<400> SEQUENCE: 43
```
agtgcacgct catccacacg                                               20

<210> SEQ ID NO 44
<211> LENGTH: 20
<212> TYPE: DNA
<213> ORGANISM: Artificial Sequence
<220> FEATURE:
<223> OTHER INFORMATION: antisense sequence

<400> SEQUENCE: 44
cttgccagat atggctgctg                                               20

<210> SEQ ID NO 45
<211> LENGTH: 3132
<212> TYPE: DNA
<213> ORGANISM: Rattus norvegicus
<220> FEATURE:
<221> NAME/KEY: CDS
<222> LOCATION: (12)..(1094)
<300> PUBLICATION INFORMATION:
<308> DATABASE ACCESSION NUMBER: U73142
<309> DATABASE ENTRY DATE: 1996-10-22

<400> SEQUENCE: 45

```
gccgctggaa a atg tcg cag gaa agg ccc acg ttc tac cgg cag gag ctg      50
             Met Ser Gln Glu Arg Pro Thr Phe Tyr Arg Gln Glu Leu
              1               5                  10 aac aag acc gtc tgg gag gtg ccc gag cga tac cag aac ctg tcc ccg      98
Asn Lys Thr Val Trp Glu Val Pro Glu Arg Tyr Gln Asn Leu Ser Pro
 15                  20                  25 gtg ggc tcg gga gcc tac ggc tcg gtg tgt gct gct ttt gat aca aag     146
Val Gly Ser Gly Ala Tyr Gly Ser Val Cys Ala Ala Phe Asp Thr Lys
 30                  35                  40                  45 acg gga cat cgt gtg gca gtg aag aag ctg tcg aga ccg ttt cag tcc     194
Thr Gly His Arg Val Ala Val Lys Lys Leu Ser Arg Pro Phe Gln Ser
                 50                  55                  60 atc att cac gcc aaa agg acc tac agg gag ctg cgg ctg ctg aag cac     242
Ile Ile His Ala Lys Arg Thr Tyr Arg Glu Leu Arg Leu Leu Lys His
             65                  70                  75 atg aag cac gag aat gtg att ggt ctg ttg gat gtg ttt aca cct gca     290
Met Lys His Glu Asn Val Ile Gly Leu Leu Asp Val Phe Thr Pro Ala
         80                  85                  90 agg tcc ctg gaa gaa ttc aac gat gtg tac ctg gtg acc cat ctc atg     338
Arg Ser Leu Glu Glu Phe Asn Asp Val Tyr Leu Val Thr His Leu Met
     95                 100                 105 ggg gca gac ctg aac aac atc gtg aag tgt cag aag ctt acc gat gac     386
Gly Ala Asp Leu Asn Asn Ile Val Lys Cys Gln Lys Leu Thr Asp Asp
110                 115                 120                 125 cac gtt cag ttt ctt atc tac cag atc ctg cga ggg ctg aag tat ata     434
His Val Gln Phe Leu Ile Tyr Gln Ile Leu Arg Gly Leu Lys Tyr Ile
                130                 135                 140 cac tcg gct gac ata atc cac agg gac cta aag ccc agc aac ctc gct     482
His Ser Ala Asp Ile Ile His Arg Asp Leu Lys Pro Ser Asn Leu Ala
            145                 150                 155 gtg aat gaa gac tgt gag ctg aag att ctg gat ttt ggg ctg gct cgg     530
Val Asn Glu Asp Cys Glu Leu Lys Ile Leu Asp Phe Gly Leu Ala Arg
        160                 165                 170 cac act gat gac gaa atg acc ggc tac gtg gct acc cgg tgg tac aga     578
His Thr Asp Asp Glu Met Thr Gly Tyr Val Ala Thr Arg Trp Tyr Arg
    175                 180                 185 gcc ccc gag att atg ctg aat tgg atg cac tac aac cag aca gtg gat     626
Ala Pro Glu Ile Met Leu Asn Trp Met His Tyr Asn Gln Thr Val Asp
190                 195                 200                 205
```

```
att tgg tcc gtg ggc tgc atc atg gct gag ctg ttg acc gga aga acg      674
Ile Trp Ser Val Gly Cys Ile Met Ala Glu Leu Leu Thr Gly Arg Thr
            210                 215                 220 ttg ttt cct ggt aca gac cat att gat cag ttg aag ctc att tta aga      722
Leu Phe Pro Gly Thr Asp His Ile Asp Gln Leu Lys Leu Ile Leu Arg
225                 230                 235 ctc gtt gga acc cca ggg gct gag ctt ctg aag aaa atc tcc tca gag      770
Leu Val Gly Thr Pro Gly Ala Glu Leu Leu Lys Lys Ile Ser Ser Glu
        240                 245                 250 tct gca aga aac tac att cag tct ctg gcc cag atg ccg aag atg aac      818
Ser Ala Arg Asn Tyr Ile Gln Ser Leu Ala Gln Met Pro Lys Met Asn
    255                 260                 265 ttc gca aat gta ttt att ggt gcc aat ccc ctg gct gtc gac ctg ctg      866
Phe Ala Asn Val Phe Ile Gly Ala Asn Pro Leu Ala Val Asp Leu Leu
270                 275                 280                 285 gaa aag atg ctg gtt ttg gac tcg gat aag agg atc aca gca gcc caa      914
Glu Lys Met Leu Val Leu Asp Ser Asp Lys Arg Ile Thr Ala Ala Gln
                290                 295                 300 gct ctt gcg cat gcc tac ttt gct cag tac cac gac cct gat gat gag      962
Ala Leu Ala His Ala Tyr Phe Ala Gln Tyr His Asp Pro Asp Asp Glu
            305                 310                 315 cca gtg gct gaa cct tat gac cag tcc ttt gaa agc agg gac ttc ctt     1010
Pro Val Ala Glu Pro Tyr Asp Gln Ser Phe Glu Ser Arg Asp Phe Leu
        320                 325                 330 ata gac gaa tgg aag agc ctg acc tac gat gaa gtc att agc ttt gtg     1058
Ile Asp Glu Trp Lys Ser Leu Thr Tyr Asp Glu Val Ile Ser Phe Val
    335                 340                 345 cca ccg ccc ctt gac caa gaa gaa atg gag tcc tga gcaccttgct          1104
Pro Pro Pro Leu Asp Gln Glu Glu Met Glu Ser
350                 355                 360 tctgttctgt ccatcccact tcactgtgag gggaaggcct gttcatggga actctccaaa   1164
taccattcaa gtgcctcttg ttgaaagatt ccttcatggt ggaaggggt gcatgtatgt    1224 gcgtagtgtt tgtgtgtgtc tgtctgtctg tccgtttgtc catgtatctt tgtggaagtc   1284
attgtgatgg cagtgacttc atgagtggta gatgctcctt ggcagtctgc ctgctctctc   1344
agagtccggg caggccgatg ggaactgccg tctccttagg gatgtgtgtg tgtatgttaa   1404
gtgcaaagta agaatattaa aatatccctg ttcctagtta ccttgccact tcggcttctc   1464
ctgtggccct gcctttacca tatcacagtg acagagagag gctgcttcag gtctgaggct   1524
atccctcagc catgcataaa gcccaagaga accaactggc tcctgggctc tagcctgtga   1584
tcggcttgct catgtcctca gaacctgtca gtctgtttgt gccttaaaag gagagaaggg   1644
cgcgttgtgg tagttacaga atctcagttg ctggcgttct gagccaggca aggcacaggg   1704
ctgttggatg gccagtgggg agctggacaa aacaaggcag ccttcaagga ggccatgggt   1764
gcatgtttgc atgagtgtat gtgcaaccgc cctccctcac ctccaggagc aagctgtttt   1824
ctatgcttac ctaagttcac ctcagtgcag aggtctccag tgccaggcac aggctcctgc   1884
catcagtagc ttcctatgtc atcttcacgt catgcgggtg tttgcatgct gtgctctgga   1944
gcttgtcctg tcttctggaa gccctgggcc gggcgtgtga agacttccca gcagtcctat   2004
ccacgcacct cagctgaggc cacgggcaca ctgctgcttc ctcactccag ctacgttgtg   2064
ttgaacacaa ctgatcctcc aggtgcttgt ggtgcaggaa acgggacgaa cagagcacct   2124
gaacccttgc catctgacat caccgacaca ggagaacagt cctctcctct cctctcctct   2184
cctctcctag gacagtcccc ggctctggaa tcatgttctt ctcactcatg gtagccagct   2244
aagaaagctg caaaccgaac aaagggagaa ccgagctcct gaagccagga gctccttta   2304
```

-continued

```
ctgtccttct caaaataggg tcattagaca cagccaagtc gtcaaaggcc cctttccttg    2364
tacgggcccc cccgcccccc ggcagcttga cactgatttc agtgtctatt tggggagaaa    2424
gcaattttgt cttggaattt tgtatgttgt aggaatcctt agagagtgtg gttccttctg    2484
atggggagaa agggcaaatt attttaatat tttgtatttc acctttataa acatgaatcc    2544
tcaggggtga agaacagttt gcataatttt ctgaatttca ggcactttgt gctatatgag    2604
gacccatata tttaagcttt ttgtgcagta agaaagtgta aagccaattc cagtgttgga    2664
cgaaacaggt ctcgtattta ggtcaaggtg tctccattct ctatcagtgc agggacatgc    2724
agtttctgtg gggcagggta ggaccctgca tcatttggag cccagaagga ggccgactgg    2784
ccaggcctca ccgcctcagt atgcagtcca gctccacgtc atcccctcac aatggttagt    2844
agcaacgtct gggtttgaac gccaggcgtg gttatattat tgaggatgcc tttgcacatg    2904
tggccatgct gtgttaggac tgtgcccag ggcccggact tgaagctaga gctggcagaa    2964
gagctcctgg catccatggt gcgatgctgc cgccacccag tttctccatt ggaagacaag    3024
ggaatgagaa gactgctgtg tatgtgtatt tgtgaacttg gttgtgatct ggtatgccat    3084
aggatgtcag acaatatcac tggttaaagt aaagcctatt tttcagat                3132
```

<210> SEQ ID NO 46

<400> SEQUENCE: 46

000

<210> SEQ ID NO 47
<211> LENGTH: 20
<212> TYPE: DNA
<213> ORGANISM: Artificial Sequence
<220> FEATURE:
<223> OTHER INFORMATION: antisense sequence

<400> SEQUENCE: 47
ctgcgacatt ttccagcggc                    20

<210> SEQ ID NO 48
<211> LENGTH: 20
<212> TYPE: DNA
<213> ORGANISM: Artificial Sequence
<220> FEATURE:
<223> OTHER INFORMATION: antisense sequence

<400> SEQUENCE: 48
ggtaagcttc tgacacttca                    20

<210> SEQ ID NO 49
<211> LENGTH: 20
<212> TYPE: DNA
<213> ORGANISM: Artificial Sequence
<220> FEATURE:
<223> OTHER INFORMATION: antisense sequence

<400> SEQUENCE: 49
ggccagagac tgaatgtagt                    20

<210> SEQ ID NO 50
<211> LENGTH: 20
<212> TYPE: DNA
<213> ORGANISM: Artificial Sequence
<220> FEATURE:
<223> OTHER INFORMATION: antisense sequence

```
<400> SEQUENCE: 50
catcatcagg gtcgtggtac                                               20

<210> SEQ ID NO 51
<211> LENGTH: 20
<212> TYPE: DNA
<213> ORGANISM: Artificial Sequence
<220> FEATURE:
<223> OTHER INFORMATION: antisense sequence

<400> SEQUENCE: 51
ggcacaaagc taatgacttc                                               20

<210> SEQ ID NO 52
<211> LENGTH: 20
<212> TYPE: DNA
<213> ORGANISM: Artificial Sequence
<220> FEATURE:
<223> OTHER INFORMATION: antisense sequence

<400> SEQUENCE: 52
aggtgctcag gactccattt                                               20

<210> SEQ ID NO 53
<211> LENGTH: 20
<212> TYPE: DNA
<213> ORGANISM: Artificial Sequence
<220> FEATURE:
<223> OTHER INFORMATION: antisense sequence

<400> SEQUENCE: 53
ggatggacag aacagaagca                                               20

<210> SEQ ID NO 54
<211> LENGTH: 20
<212> TYPE: DNA
<213> ORGANISM: Artificial Sequence
<220> FEATURE:
<223> OTHER INFORMATION: antisense sequence

<400> SEQUENCE: 54
gagcaggcag actgccaagg                                               20

<210> SEQ ID NO 55
<211> LENGTH: 20
<212> TYPE: DNA
<213> ORGANISM: Artificial Sequence
<220> FEATURE:
<223> OTHER INFORMATION: antisense sequence

<400> SEQUENCE: 55
aggctagagc ccaggagcca                                               20

<210> SEQ ID NO 56
<211> LENGTH: 20
<212> TYPE: DNA
<213> ORGANISM: Artificial Sequence
<220> FEATURE:
<223> OTHER INFORMATION: antisense sequence

<400> SEQUENCE: 56
gagcctgtgc ctggcactgg                                               20

<210> SEQ ID NO 57
<211> LENGTH: 20
<212> TYPE: DNA
```

```
<213> ORGANISM: Artificial Sequence
<220> FEATURE:
<223> OTHER INFORMATION: antisense sequence

<400> SEQUENCE: 57
tgcaccacaa gcacctggag                                                   20

<210> SEQ ID NO 58
<211> LENGTH: 20
<212> TYPE: DNA
<213> ORGANISM: Artificial Sequence
<220> FEATURE:
<223> OTHER INFORMATION: antisense sequence

<400> SEQUENCE: 58
ggctaccatg agtgagaaga                                                   20

<210> SEQ ID NO 59
<211> LENGTH: 20
<212> TYPE: DNA
<213> ORGANISM: Artificial Sequence
<220> FEATURE:
<223> OTHER INFORMATION: antisense sequence

<400> SEQUENCE: 59
gtccctgcac tgatagagaa                                                   20

<210> SEQ ID NO 60
<211> LENGTH: 20
<212> TYPE: DNA
<213> ORGANISM: Artificial Sequence
<220> FEATURE:
<223> OTHER INFORMATION: antisense sequence

<400> SEQUENCE: 60
tcttccaatg gagaaactgg                                                   20

<210> SEQ ID NO 61
<211> LENGTH: 749
<212> TYPE: DNA
<213> ORGANISM: Mus musculus

<400> SEQUENCE: 61
tgctgggcgt ggggcgcggg ccgggtgctg cgcgcgggga tccggggcgc tcgctccagc        60
tgcttctgtg gatatgtcgg gtccgcgcgc gggattctac cggcaagagc tgaacaaaac       120
agtatgggag gtgccgcagc ggctgcaggg cctacgcccg gtgggctccg gcgcctacgg       180
ctcagtctgc tcggcctacg acgcgcggct gcgccagaag gtggctgtaa agaagctgtc       240
tcgccctttc caatcgctga tccacgcgag gaggacatac cgtgagctgc gcctactcaa       300
gcacctgaag cacgagaacg tcataggact tttggacgtc ttcacgccgg ccacatccat       360
cgaggatttc agcgaagtgt acctcgtgac gaccctgatg ggcgccgacc tgaataacat       420
cgtcaagtgt caggccctga gcgatgagca tgttcaattc cttgtctacc agctgctgcg       480
tgggctgaag tatatccact cggcgggcat cattcaccgg gacctgaagc ccagcaatgt       540
agcggtgaac gaggactgcg agctgaggat cctggacttt gggctagcac gccaggctga      600
tgaggagatg accggatatg tggccacacg gtggtaccgg gcgccagaga tcatgctaaa       660
ctggatgcac tacaaccaga cagtggacat ctggtctgtg gcctgcttca tggcttgaac       720
tgctggaagg gaagggcctt ctttcctgg                                          749

<210> SEQ ID NO 62
```

<400> SEQUENCE: 62

000

<210> SEQ ID NO 63
<211> LENGTH: 20
<212> TYPE: DNA
<213> ORGANISM: Artificial Sequence
<220> FEATURE:
<223> OTHER INFORMATION: antisense sequence

<400> SEQUENCE: 63
cacagaagca gctggagcga                                              20

<210> SEQ ID NO 64
<211> LENGTH: 20
<212> TYPE: DNA
<213> ORGANISM: Artificial Sequence
<220> FEATURE:
<223> OTHER INFORMATION: antisense sequence

<400> SEQUENCE: 64
tgcggcacct cccatactgt                                              20

<210> SEQ ID NO 65
<211> LENGTH: 20
<212> TYPE: DNA
<213> ORGANISM: Artificial Sequence
<220> FEATURE:
<223> OTHER INFORMATION: antisense sequence

<400> SEQUENCE: 65
ccctgcagcc gctgcggcac                                              20

<210> SEQ ID NO 66
<211> LENGTH: 20
<212> TYPE: DNA
<213> ORGANISM: Artificial Sequence
<220> FEATURE:
<223> OTHER INFORMATION: antisense sequence

<400> SEQUENCE: 66
gcagactgag ccgtaggcgc                                              20

<210> SEQ ID NO 67
<211> LENGTH: 20
<212> TYPE: DNA
<213> ORGANISM: Artificial Sequence
<220> FEATURE:
<223> OTHER INFORMATION: antisense sequence

<400> SEQUENCE: 67
ttacagccac cttctggcgc                                              20

<210> SEQ ID NO 68
<211> LENGTH: 20
<212> TYPE: DNA
<213> ORGANISM: Artificial Sequence
<220> FEATURE:
<223> OTHER INFORMATION: antisense sequence

<400> SEQUENCE: 68
gtatgtcctc ctcgcgtgga                                              20

<210> SEQ ID NO 69
<211> LENGTH: 20

```
<212> TYPE: DNA
<213> ORGANISM: Artificial Sequence
<220> FEATURE:
<223> OTHER INFORMATION: antisense sequence

<400> SEQUENCE: 69
atggatgtgg ccggcgtgaa                                           20

<210> SEQ ID NO 70
<211> LENGTH: 20
<212> TYPE: DNA
<213> ORGANISM: Artificial Sequence
<220> FEATURE:
<223> OTHER INFORMATION: antisense sequence

<400> SEQUENCE: 70
gaattgaaca tgctcatcgc                                           20

<210> SEQ ID NO 71
<211> LENGTH: 20
<212> TYPE: DNA
<213> ORGANISM: Artificial Sequence
<220> FEATURE:
<223> OTHER INFORMATION: antisense sequence

<400> SEQUENCE: 71
acattgctgg gcttcaggtc                                           20

<210> SEQ ID NO 72
<211> LENGTH: 20
<212> TYPE: DNA
<213> ORGANISM: Artificial Sequence
<220> FEATURE:
<223> OTHER INFORMATION: antisense sequence

<400> SEQUENCE: 72
atcctcagct cgcagtcctc                                           20

<210> SEQ ID NO 73
<211> LENGTH: 20
<212> TYPE: DNA
<213> ORGANISM: Artificial Sequence
<220> FEATURE:
<223> OTHER INFORMATION: antisense sequence

<400> SEQUENCE: 73
taccaccgtg tggccacata                                           20

<210> SEQ ID NO 74
<211> LENGTH: 20
<212> TYPE: DNA
<213> ORGANISM: Artificial Sequence
<220> FEATURE:
<223> OTHER INFORMATION: antisense sequence

<400> SEQUENCE: 74
cagtttagca tgatctctgg                                           20

<210> SEQ ID NO 75
<211> LENGTH: 20
<212> TYPE: DNA
<213> ORGANISM: Artificial Sequence
<220> FEATURE:
<223> OTHER INFORMATION: antisense sequence

<400> SEQUENCE: 75
caggccacag accagatgtc                                           20
```

```
<210> SEQ ID NO 76
<211> LENGTH: 20
<212> TYPE: DNA
<213> ORGANISM: Artificial Sequence
<220> FEATURE:
<223> OTHER INFORMATION: antisense sequence

<400> SEQUENCE: 76
ccttccagca gttcaagcca                                               20

<210> SEQ ID NO 77
<211> LENGTH: 20
<212> TYPE: DNA
<213> ORGANISM: Artificial Sequence
<220> FEATURE:
<223> OTHER INFORMATION: control sequence

<400> SEQUENCE: 77
cagcaccatg gacgcggaac                                               20

<210> SEQ ID NO 78
<211> LENGTH: 20
<212> TYPE: DNA
<213> ORGANISM: Artificial Sequence
<220> FEATURE:
<223> OTHER INFORMATION: antisense sequence

<400> SEQUENCE: 78
ctgagacatt ttccagcggc                                               20

<210> SEQ ID NO 79
<211> LENGTH: 20
<212> TYPE: DNA
<213> ORGANISM: Artificial Sequence
<220> FEATURE:
<223> OTHER INFORMATION: antisense sequence

<400> SEQUENCE: 79
acgctcgggc acctcccaga                                               20

<210> SEQ ID NO 80
<211> LENGTH: 20
<212> TYPE: DNA
<213> ORGANISM: Artificial Sequence
<220> FEATURE:
<223> OTHER INFORMATION: antisense sequence

<400> SEQUENCE: 80
agcttcttca ctgccacacg                                               20

<210> SEQ ID NO 81
<211> LENGTH: 20
<212> TYPE: DNA
<213> ORGANISM: Artificial Sequence
<220> FEATURE:
<223> OTHER INFORMATION: antisense sequence

<400> SEQUENCE: 81
aatgatggac tgaaatggtc                                               20

<210> SEQ ID NO 82
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 82
tccaacagac caatcacatt                                              20

<210> SEQ ID NO 83
<211> LENGTH: 20
<212> TYPE: DNA
<213> ORGANISM: Artificial Sequence
<220> FEATURE:
<223> OTHER INFORMATION: antisense sequence

<400> SEQUENCE: 83
tgtaagcttc tgacatttca                                              20

<210> SEQ ID NO 84
<211> LENGTH: 20
<212> TYPE: DNA
<213> ORGANISM: Artificial Sequence
<220> FEATURE:
<223> OTHER INFORMATION: antisense sequence

<400> SEQUENCE: 84
tgaatgtata tactttagac                                              20

<210> SEQ ID NO 85
<211> LENGTH: 20
<212> TYPE: DNA
<213> ORGANISM: Artificial Sequence
<220> FEATURE:
<223> OTHER INFORMATION: antisense sequence

<400> SEQUENCE: 85
ctcacagtct tcattcacag                                              20

<210> SEQ ID NO 86
<211> LENGTH: 20
<212> TYPE: DNA
<213> ORGANISM: Artificial Sequence
<220> FEATURE:
<223> OTHER INFORMATION: antisense sequence

<400> SEQUENCE: 86
cacgtagcct gtcatttcat                                              20

<210> SEQ ID NO 87
<211> LENGTH: 20
<212> TYPE: DNA
<213> ORGANISM: Artificial Sequence
<220> FEATURE:
<223> OTHER INFORMATION: antisense sequence

<400> SEQUENCE: 87
catcccactg accaaatatc                                              20

<210> SEQ ID NO 88
<211> LENGTH: 20
<212> TYPE: DNA
<213> ORGANISM: Artificial Sequence
<220> FEATURE:
<223> OTHER INFORMATION: antisense sequence

<400> SEQUENCE: 88
tatggtctgt accaggaaac                                              20

<210> SEQ ID NO 89
<211> LENGTH: 20
```

```
<212> TYPE: DNA
<213> ORGANISM: Artificial Sequence
<220> FEATURE:
<223> OTHER INFORMATION: antisense sequence

<400> SEQUENCE: 89
agtcaaagac tgaatatagt                                               20

<210> SEQ ID NO 90
<211> LENGTH: 20
<212> TYPE: DNA
<213> ORGANISM: Artificial Sequence
<220> FEATURE:
<223> OTHER INFORMATION: antisense sequence

<400> SEQUENCE: 90
ttctcttatc tgagtccaat                                               20

<210> SEQ ID NO 91
<211> LENGTH: 20
<212> TYPE: DNA
<213> ORGANISM: Artificial Sequence
<220> FEATURE:
<223> OTHER INFORMATION: antisense sequence

<400> SEQUENCE: 91
catcatcagg atcgtggtac                                               20

<210> SEQ ID NO 92
<211> LENGTH: 20
<212> TYPE: DNA
<213> ORGANISM: Artificial Sequence
<220> FEATURE:
<223> OTHER INFORMATION: antisense sequence

<400> SEQUENCE: 92
tcaaaggact gatcataagg                                               20

<210> SEQ ID NO 93
<211> LENGTH: 20
<212> TYPE: DNA
<213> ORGANISM: Artificial Sequence
<220> FEATURE:
<223> OTHER INFORMATION: antisense sequence

<400> SEQUENCE: 93
ggcacaaagc tgatgacttc                                               20

<210> SEQ ID NO 94
<211> LENGTH: 20
<212> TYPE: DNA
<213> ORGANISM: Artificial Sequence
<220> FEATURE:
<223> OTHER INFORMATION: antisense sequence

<400> SEQUENCE: 94
aggtgctcag gactccatct                                               20

<210> SEQ ID NO 95
<211> LENGTH: 20
<212> TYPE: DNA
<213> ORGANISM: Artificial Sequence
<220> FEATURE:
<223> OTHER INFORMATION: antisense sequence

<400> SEQUENCE: 95
gcaacaagag gcacttgaat                                               20
```

```
<210> SEQ ID NO 96
<211> LENGTH: 20
<212> TYPE: DNA
<213> ORGANISM: Artificial Sequence
<220> FEATURE:
<223> OTHER INFORMATION: antisense sequence

<400> SEQUENCE: 96
ttatcctagc ttagacctat                                               20

<210> SEQ ID NO 97
<211> LENGTH: 20
<212> TYPE: DNA
<213> ORGANISM: Artificial Sequence
<220> FEATURE:
<223> OTHER INFORMATION: antisense sequence

<400> SEQUENCE: 97
acagacggag ccgtaggcgc                                               20

<210> SEQ ID NO 98
<211> LENGTH: 20
<212> TYPE: DNA
<213> ORGANISM: Artificial Sequence
<220> FEATURE:
<223> OTHER INFORMATION: antisense sequence

<400> SEQUENCE: 98
caccgccacc ttctggcgca                                               20

<210> SEQ ID NO 99
<211> LENGTH: 20
<212> TYPE: DNA
<213> ORGANISM: Artificial Sequence
<220> FEATURE:
<223> OTHER INFORMATION: antisense sequence

<400> SEQUENCE: 99
gtacgttctg cgcgcgtgga                                               20

<210> SEQ ID NO 100
<211> LENGTH: 20
<212> TYPE: DNA
<213> ORGANISM: Artificial Sequence
<220> FEATURE:
<223> OTHER INFORMATION: antisense sequence

<400> SEQUENCE: 100
atggacgtgg ccggcgtgaa                                               20

<210> SEQ ID NO 101
<211> LENGTH: 20
<212> TYPE: DNA
<213> ORGANISM: Artificial Sequence
<220> FEATURE:
<223> OTHER INFORMATION: antisense sequence

<400> SEQUENCE: 101
caggaattga acgtgctcgt                                               20

<210> SEQ ID NO 102
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 102
acgttgctgg gcttcaggtc                                          20

<210> SEQ ID NO 103
<211> LENGTH: 20
<212> TYPE: DNA
<213> ORGANISM: Artificial Sequence
<220> FEATURE:
<223> OTHER INFORMATION: antisense sequence

<400> SEQUENCE: 103
taccagcgcg tggccacata                                          20

<210> SEQ ID NO 104
<211> LENGTH: 20
<212> TYPE: DNA
<213> ORGANISM: Artificial Sequence
<220> FEATURE:
<223> OTHER INFORMATION: antisense sequence

<400> SEQUENCE: 104
cagttgagca tgatctcagg                                          20

<210> SEQ ID NO 105
<211> LENGTH: 20
<212> TYPE: DNA
<213> ORGANISM: Artificial Sequence
<220> FEATURE:
<223> OTHER INFORMATION: antisense sequence

<400> SEQUENCE: 105
cggaccagat atccactgtt                                          20

<210> SEQ ID NO 106
<211> LENGTH: 20
<212> TYPE: DNA
<213> ORGANISM: Artificial Sequence
<220> FEATURE:
<223> OTHER INFORMATION: antisense sequence

<400> SEQUENCE: 106
tgccctggag cagctcagcc                                          20

<210> SEQ ID NO 107
<211> LENGTH: 20
<212> TYPE: DNA
<213> ORGANISM: Artificial Sequence
<220> FEATURE:
<223> OTHER INFORMATION: antisense sequence

<400> SEQUENCE: 107
gttcgatcgg ctcgtgtcga                                          20

<210> SEQ ID NO 108
<211> LENGTH: 20
<212> TYPE: DNA
<213> ORGANISM: Artificial Sequence
<220> FEATURE:
<223> OTHER INFORMATION: PCR Primer

<400> SEQUENCE: 108
gatgagtgga aaagcctgac                                          20

<210> SEQ ID NO 109
<211> LENGTH: 20
```

```
<212> TYPE: DNA
<213> ORGANISM: Artificial Sequence
<220> FEATURE:
<223> OTHER INFORMATION: PCR Primer

<400> SEQUENCE: 109
ctgcaacaag aggcacttga                                              20

<210> SEQ ID NO 110
<211> LENGTH: 50
<212> TYPE: DNA
<213> ORGANISM: Artificial Sequence
<220> FEATURE:
<223> OTHER INFORMATION: PCR Probe

<400> SEQUENCE: 110
gatgaagtca tcagctttgt gccaccaccc cttgaccaag aagagatgga             50

<210> SEQ ID NO 111
<211> LENGTH: 19
<212> TYPE: DNA
<213> ORGANISM: Artificial Sequence
<220> FEATURE:
<223> OTHER INFORMATION: PCR Primer

<400> SEQUENCE: 111
gaaggtgaag gtcggagtc                                               19

<210> SEQ ID NO 112
<211> LENGTH: 20
<212> TYPE: DNA
<213> ORGANISM: Artificial Sequence
<220> FEATURE:
<223> OTHER INFORMATION: PCR Primer

<400> SEQUENCE: 112
gaagatggtg atgggatttc                                              20

<210> SEQ ID NO 113
<211> LENGTH: 20
<212> TYPE: DNA
<213> ORGANISM: Artificial Sequence
<220> FEATURE:
<223> OTHER INFORMATION: PCR Probe

<400> SEQUENCE: 113
caagcttccc gttctcagcc                                              20

<210> SEQ ID NO 114
<211> LENGTH: 3450
<212> TYPE: DNA
<213> ORGANISM: M. musculus
<220> FEATURE:
<221> NAME/KEY: CDS
<222> LOCATION: (297)...(1379)

<400> SEQUENCE: 114
cgggcgctga agcgcgagcg ggtgtcttgc ggcgtcggcg tgcgctccct ccccggggag   60
cggctgcagg aggaccgcgg cgggagcagc ctcgagccgt gcagccggct ccggcacctt  120
gccgacgctc gtaggagccg ccgcggctga caggggcggc gggtcgcagc ctccacacct  180
gcgcgggtgg cgggcgcggg gtccggtctg ccgcgggcgg gcgcagagga gagcgtgcgg  240
ctgcaggcag gagccccgc  tcggccacct cctcgccccg ctgctgccgc tggaag atg   299
                                                                Met
                                                                  1
```

```
tcg cag gag agg ccc acg ttc tac cgg cag gag ctg aac aag acc atc      347
Ser Gln Glu Arg Pro Thr Phe Tyr Arg Gln Glu Leu Asn Lys Thr Ile
             5                  10                  15 tgg gag gtg ccc gaa cga tac cag aac ctg tcc ccg gtg ggc tcg ggc      395
Trp Glu Val Pro Glu Arg Tyr Gln Asn Leu Ser Pro Val Gly Ser Gly
         20                  25                  30 gcc tat ggc tcg gtg tgt gct gct ttt gat aca aag acg ggg cat cgt      443
Ala Tyr Gly Ser Val Cys Ala Ala Phe Asp Thr Lys Thr Gly His Arg
     35                  40                  45 gtg gca gtt aag aag ctg tcg aga ccg ttt cag tcc atc att cac gcc      491
Val Ala Val Lys Lys Leu Ser Arg Pro Phe Gln Ser Ile Ile His Ala
 50                  55                  60                  65 aaa agg acc tac cga gag ttg cgt ctg ctg aag cac atg aaa cac gaa      539
Lys Arg Thr Tyr Arg Glu Leu Arg Leu Leu Lys His Met Lys His Glu
                 70                  75                  80 aat gtg att ggt ctg ttg gat gtg ttc aca ccc gca agg tca ctg gag      587
Asn Val Ile Gly Leu Leu Asp Val Phe Thr Pro Ala Arg Ser Leu Glu
             85                  90                  95 gaa ttc aat gac gtg tac ctg gtg acc cat ctc atg ggg gcg gac ctg      635
Glu Phe Asn Asp Val Tyr Leu Val Thr His Leu Met Gly Ala Asp Leu
         100                 105                 110 aac aac atc gtg aag tgc cag aag ctg acc gac gac cac gtt cag ttt      683
Asn Asn Ile Val Lys Cys Gln Lys Leu Thr Asp Asp His Val Gln Phe
     115                 120                 125 ctc atc tac cag atc ctc cga ggg ctg aag tat ata cat tcg gct gac      731
Leu Ile Tyr Gln Ile Leu Arg Gly Leu Lys Tyr Ile His Ser Ala Asp
130                 135                 140                 145 ata att cac agg gac cta aag ccc agc aac cta gct gtg aac gaa gac      779
Ile Ile His Arg Asp Leu Lys Pro Ser Asn Leu Ala Val Asn Glu Asp
                 150                 155                 160 tgt gag ctc aag att ctg gat ttt ggg ctg gct cgg cac act gat gat      827
Cys Glu Leu Lys Ile Leu Asp Phe Gly Leu Ala Arg His Thr Asp Asp
             165                 170                 175 gag atg aca ggc tac gtg gct acc agg tgg tac cga gcc cca gag atc      875
Glu Met Thr Gly Tyr Val Ala Thr Arg Trp Tyr Arg Ala Pro Glu Ile
         180                 185                 190 atg ctg aat tgg atg cac tat aac cag aca gtg gat att tgg tcc gtg      923
Met Leu Asn Trp Met His Tyr Asn Gln Thr Val Asp Ile Trp Ser Val
195                 200                 205 ggc tgc atc atg gct gag ctg ttg acc gga aga acg ttg ttt cct ggt      971
Gly Cys Ile Met Ala Glu Leu Leu Thr Gly Arg Thr Leu Phe Pro Gly
210                 215                 220                 225 aca gac cat att gat cag ttg aag ctc att tta aga ctc gtt gga acc     1019
Thr Asp His Ile Asp Gln Leu Lys Leu Ile Leu Arg Leu Val Gly Thr
                 230                 235                 240 cca ggg gct gag ctt ctg aag aaa atc tcc tca gag tct gca aga aac     1067
Pro Gly Ala Glu Leu Leu Lys Lys Ile Ser Ser Glu Ser Ala Arg Asn
             245                 250                 255 tac att cag tct ctg gcc cag atg ccg aag atg aac ttc gca aat gta     1115
Tyr Ile Gln Ser Leu Ala Gln Met Pro Lys Met Asn Phe Ala Asn Val
         260                 265                 270 ttt att ggt gcc aat ccc ctg gct gtc gac cta ctg gag aag atg ctc     1163
Phe Ile Gly Ala Asn Pro Leu Ala Val Asp Leu Leu Glu Lys Met Leu
     275                 280                 285 gtt ttg gac tca gat aag agg atc aca gca gcc caa gct ctt gcg cat     1211
Val Leu Asp Ser Asp Lys Arg Ile Thr Ala Ala Gln Ala Leu Ala His
290                 295                 300                 305 gcc tac ttt gct cag tac cac gac cct gat gat gag cct gtt gct gac     1259
Ala Tyr Phe Ala Gln Tyr His Asp Pro Asp Asp Glu Pro Val Ala Asp
             310                 315                 320
```

|  |  |  |  |  |  |  |  |  |  |  |  |  |  |  |
|---|---|---|---|---|---|---|---|---|---|---|---|---|---|---|
| cct | tat | gac | cag | tcc | ttt | gaa | agc | agg | gac | ctt | ctc | ata | gat | gag | tgg | 1307 |
| Pro | Tyr | Asp | Gln | Ser | Phe | Glu | Ser | Arg | Asp | Leu | Leu | Ile | Asp | Glu | Trp |  |
|  |  |  | 325 |  |  |  | 330 |  |  |  |  | 335 |  |  |

|  |  |  |  |  |  |  |  |  |  |  |  |  |  |  |  |  |
|---|---|---|---|---|---|---|---|---|---|---|---|---|---|---|---|---|
| aag | agc | ctg | acc | tat | gat | gaa | gtc | atc | agc | ttt | gtg | cca | cca | ccc | ctt | 1355 |
| Lys | Ser | Leu | Thr | Tyr | Asp | Glu | Val | Ile | Ser | Phe | Val | Pro | Pro | Pro | Leu |  |
|  | 340 |  |  |  |  | 345 |  |  |  |  | 350 |  |  |  |  |

|  |  |  |  |  |  |  |  |  |  |
|---|---|---|---|---|---|---|---|---|---|
| gac | caa | gaa | gaa | atg | gag | tcc | tga | gcacctggtt tctgttctgt ctatctcact | 1409 |
| Asp | Gln | Glu | Glu | Met | Glu | Ser |  |  |  |
|  | 355 |  |  |  | 360 |  |  |  |  |

| | |
|---|---|
| tcactgtgag gggaagacct tctcatggga actctccaaa taccattcaa gtgcctcttg | 1469 |
| ttgaaagatt ccttcatggt ggaagggggt gcatgtatgt gttagtgttt gtgtgtgtgt | 1529 |
| gtgtgtctgt ctgttcgtct gtccacctat ctttgtggaa gtcactgtga tggtagtgac | 1589 |
| tttatgagtt gtgaatggtc cttggcagtc tgcctgcttt ctcagagtct gggcaggccg | 1649 |
| atgggaactg tcatctcctt agggatgtgt gtgttcagtg caaagtaaga aatatgaaaa | 1709 |
| tatccctgtt cttagttacc ttgccacttt ggcttctcct gtggccctgc ctttaccata | 1769 |
| tcagtgacag agagaggctg cttcaggtct gaggctatcc ctcagccatg cataaagtcc | 1829 |
| aagagaacca actggctcct ggtctctagc ctgtgaccgg cttgcttaat gtcctcagaa | 1889 |
| cctgacaggt atgttcaaaa ctgtcagtct gtttgtgcct taaaagggtg agaagggcgc | 1949 |
| gtagatagtt acagagtctc agctgctgac gttctgagcc aggcaagtgc acggggctgt | 2009 |
| tggatggcca gtggggagct ggaaaaaaca aggcagcctt taggaaggcc atggtgcatg | 2069 |
| tgtgtgcatg cgtgtatgtg cagccgccct ccctcacttc aggagcaagc tgtttgctgt | 2129 |
| gcttaccctt cacctcagtg cagaggtctc cagtgccgag cacaggcacc tgccatcagt | 2189 |
| agttcctgtg tcatcttcac atctagcaga gcacggatgt gtttgcatgc tgtgctcttg | 2249 |
| gagcttgtcc tgtcttctgg aagccctgga caaggcgtgt gaaggcttcc cagaagttcc | 2309 |
| tgtccacatt gcctccgccc accgacgcca tgggcacact gctccctcct cctcctccag | 2369 |
| ctactttgtg ttgaacacaa ttgattctcc aggtgctcat ggtgcaggaa acaggacag | 2429 |
| acagagagca ctgaaccctt gccatctgat gtcaccaatt caggaaaacg agtcctctcc | 2489 |
| taggactatc cccggttctg gaaatcatgt tctcctcact catggtgaca agctaagaaa | 2549 |
| gctgaacaaa gggagagacg agagcgcctg aagccaggag ctcctttact atctttctca | 2609 |
| aaagggttgt tagacacaaa ccaagtcatc aaggccccgc tcctctcctc ggaagggtcc | 2669 |
| cccaccccc ggcagcttga cactgaatcc agtgtcaatt tggggagaaa gcagttttgt | 2729 |
| cttggaattt tgtatgttgt aggaatcctt agagagtgtg gttccttctg atggggagaa | 2789 |
| agggcaaatt attttaatat tttgtatttt cacctttata aacatgaatc ctcaggggtg | 2849 |
| aagaactgtt tgcataattt tctgaatttt gagcactttg tgctatataa ggacccatat | 2909 |
| ttaagctttg tgtgcagtaa gaaagtgtaa agccaattcc agtgttggac gtgacaggtc | 2969 |
| ttgtgtttag gtcaaggtgt ctcctctcag tgcaggaca tgcctgctct gtggggcagg | 3029 |
| cgaggaccct gaatcatttg gagcccagaa ggaggcagac tggccaggtc tcaccacctc | 3089 |
| agtgtgcagt tcaactccat gccatcccat caagatgggt tagtagcagt gtctgttttt | 3149 |
| gaatgccaag tgtgatttcc aacaattctg ctctggttat ttcattgaag acatctttgc | 3209 |
| acatgtgacc atgctgtgtt aggggctgtg ttccagggac tggactcgaa gctagaactg | 3269 |
| gcagaagagt tctggcatcc acagcgcaat gctgccacca cccagtttct tcatcagaag | 3329 |
| acaagggaac gagaaaactg ctgttcgttt gtatttgtga acttggctgt aatctggtat | 3389 |
| gccataggat gtcagataat accactggtt aaaataaagc ctagttttca aattcaaccg | 3449 |

| | 3450 |
|---|---|
| g | |

<210> SEQ ID NO 115
<211> LENGTH: 23
<212> TYPE: DNA
<213> ORGANISM: Artificial Sequence
<220> FEATURE:
<223> OTHER INFORMATION: PCR Primer
<400> SEQUENCE: 115

| aagggaacga gaaaactgct gtt | 23 |
|---|---|

<210> SEQ ID NO 116
<211> LENGTH: 31
<212> TYPE: DNA
<213> ORGANISM: Artificial Sequence
<220> FEATURE:
<223> OTHER INFORMATION: PCR Primer
<400> SEQUENCE: 116

| tattttaacc agtggtatta tctgacatcc t | 31 |
|---|---|

<210> SEQ ID NO 117
<211> LENGTH: 35
<212> TYPE: DNA
<213> ORGANISM: Artificial Sequence
<220> FEATURE:
<223> OTHER INFORMATION: PCR Probe
<400> SEQUENCE: 117

| ttgtatttgt gaacttggct gtaatctggt atgcc | 35 |
|---|---|

<210> SEQ ID NO 118
<211> LENGTH: 20
<212> TYPE: DNA
<213> ORGANISM: Artificial Sequence
<220> FEATURE:
<223> OTHER INFORMATION: PCR Primer
<400> SEQUENCE: 118

| ggcaaattca acggcacagt | 20 |
|---|---|

<210> SEQ ID NO 119
<211> LENGTH: 20
<212> TYPE: DNA
<213> ORGANISM: Artificial Sequence
<220> FEATURE:
<223> OTHER INFORMATION: PCR Primer
<400> SEQUENCE: 119

| gggtctcgct cctggaagat | 20 |
|---|---|

<210> SEQ ID NO 120
<211> LENGTH: 27
<212> TYPE: DNA
<213> ORGANISM: Artificial Sequence
<220> FEATURE:
<223> OTHER INFORMATION: PCR Probe
<400> SEQUENCE: 120

| aaggccgaga atgggaagct tgtcatc | 27 |
|---|---|

<210> SEQ ID NO 121
<211> LENGTH: 21
<212> TYPE: DNA
<213> ORGANISM: Artificial Sequence
<220> FEATURE:

```
<223> OTHER INFORMATION: PCR Primer

<400> SEQUENCE: 121
atcatttgga gcccagaagg a                                        21

<210> SEQ ID NO 122
<211> LENGTH: 21
<212> TYPE: DNA
<213> ORGANISM: Artificial Sequence
<220> FEATURE:
<223> OTHER INFORMATION: PCR Primer

<400> SEQUENCE: 122
tggagctgga ctgcatactg a                                        21

<210> SEQ ID NO 123
<211> LENGTH: 18
<212> TYPE: DNA
<213> ORGANISM: Artificial Sequence
<220> FEATURE:
<223> OTHER INFORMATION: PCR Probe

<400> SEQUENCE: 123
ctggccaggc ctcaccgc                                            18

<210> SEQ ID NO 124
<211> LENGTH: 23
<212> TYPE: DNA
<213> ORGANISM: Artificial Sequence
<220> FEATURE:
<223> OTHER INFORMATION: PCR Primer

<400> SEQUENCE: 124
tgttctagag acagccgcat ctt                                      23

<210> SEQ ID NO 125
<211> LENGTH: 21
<212> TYPE: DNA
<213> ORGANISM: Artificial Sequence
<220> FEATURE:
<223> OTHER INFORMATION: PCR Primer

<400> SEQUENCE: 125
caccgacctt caccatcttg t                                        21

<210> SEQ ID NO 126
<211> LENGTH: 24
<212> TYPE: DNA
<213> ORGANISM: Artificial Sequence
<220> FEATURE:
<223> OTHER INFORMATION: PCR Probe

<400> SEQUENCE: 126
ttgtgcagtg ccagcctcgt ctca                                     24

<210> SEQ ID NO 127
<211> LENGTH: 3757
<212> TYPE: DNA
<213> ORGANISM: H. sapiens
<220> FEATURE:
<221> NAME/KEY: CDS
<222> LOCATION: (363)...(1445)

<400> SEQUENCE: 127
ggaaccgcga ccactggagc cttagcgggc gcagcagctg gaacgggagt actgcgacgc    60
agcccggagt cggccttgta ggggcgaagg tgcagggaga tcgcggcggg cgcagtcttg   120
```

-continued

```
agcgccggag cgcgtccctg cccttagcgg ggcttgcccc agtcgcaggg gcacatccag        180
ccgctgcggc tgacagcagc cgcgcgcgcg ggagtctgcg gggtcgcggc agccgcacct        240
gcgcgggcga ccagcgcaag gtccccgccc ggctgggcgg gcagcaaggg ccggggagag        300
ggtgcgggtg caggcggggg ccccacaggg ccaccttctt gcccggcggc tgccgctgga        360 aa atg tct cag gag agg ccc acg ttc tac cgg cag gag ctg aac aag          407
   Met Ser Gln Glu Arg Pro Thr Phe Tyr Arg Gln Glu Leu Asn Lys
   1               5                   10                  15 aca atc tgg gag gtg ccc gag cgt tac cag aac ctg tct cca gtg ggc         455
Thr Ile Trp Glu Val Pro Glu Arg Tyr Gln Asn Leu Ser Pro Val Gly
                20                  25                  30 tct ggc gcc tat ggc tct gtg tgt gct gct ttt gac aca aaa acg ggg         503
Ser Gly Ala Tyr Gly Ser Val Cys Ala Ala Phe Asp Thr Lys Thr Gly
             35                  40                  45 tta cgt gtg gca gtg aag aag ctc tcc aga cca ttt cag tcc atc att         551
Leu Arg Val Ala Val Lys Lys Leu Ser Arg Pro Phe Gln Ser Ile Ile
         50                  55                  60 cat gcg aaa aga acc tac aga gaa ctg cgg tta ctt aaa cat atg aaa         599
His Ala Lys Arg Thr Tyr Arg Glu Leu Arg Leu Leu Lys His Met Lys
 65                  70                  75 cat gaa aat gtg att ggt ctg ttg gac gtt ttt aca cct gca agg tct         647
His Glu Asn Val Ile Gly Leu Leu Asp Val Phe Thr Pro Ala Arg Ser
 80              85                  90                  95 ctg gag gaa ttc aat gat gtg tat ctg gtg acc cat ctc atg ggg gca         695
Leu Glu Glu Phe Asn Asp Val Tyr Leu Val Thr His Leu Met Gly Ala
             100                 105                 110 gat ctg aac aac att gtg aaa tgt cag aag ctt aca gat gac cat gtt         743
Asp Leu Asn Asn Ile Val Lys Cys Gln Lys Leu Thr Asp Asp His Val
         115                 120                 125 cag ttc ctt atc tac caa att ctc cga ggt cta aag tat ata cat tca         791
Gln Phe Leu Ile Tyr Gln Ile Leu Arg Gly Leu Lys Tyr Ile His Ser
     130                 135                 140 gct gac ata att cac agg gac cta aaa cct agt aat cta gct gtg aat         839
Ala Asp Ile Ile His Arg Asp Leu Lys Pro Ser Asn Leu Ala Val Asn
 145                 150                 155 gaa gac tgt gag ctg aag att ctg gat ttt gga ctg gct cgg cac aca         887
Glu Asp Cys Glu Leu Lys Ile Leu Asp Phe Gly Leu Ala Arg His Thr
160                 165                 170                 175 gat gat gaa atg aca ggc tac gtg gcc act agg tgg tac agg gct cct         935
Asp Asp Glu Met Thr Gly Tyr Val Ala Thr Arg Trp Tyr Arg Ala Pro
             180                 185                 190 gag atc atg ctg aac tgg atg cat tac aac cag aca gtt gat att tgg         983
Glu Ile Met Leu Asn Trp Met His Tyr Asn Gln Thr Val Asp Ile Trp
         195                 200                 205 tca gtg gga tgc ata atg gcc gag ctg ttg act gga aga aca ttg ttt        1031
Ser Val Gly Cys Ile Met Ala Glu Leu Leu Thr Gly Arg Thr Leu Phe
     210                 215                 220 cct ggt aca gac cat att aac cag ctt cag cag att atg cgt ctg aca        1079
Pro Gly Thr Asp His Ile Asn Gln Leu Gln Gln Ile Met Arg Leu Thr
 225                 230                 235 gga aca ccc ccc gct tat ctc att aac agg atg cca agc cat gag gca        1127
Gly Thr Pro Pro Ala Tyr Leu Ile Asn Arg Met Pro Ser His Glu Ala
240                 245                 250                 255 aga aac tat att cag tct ttg act cag atg ccg aag atg aac ttt gcg        1175
Arg Asn Tyr Ile Gln Ser Leu Thr Gln Met Pro Lys Met Asn Phe Ala
             260                 265                 270 aat gta ttt att ggt gcc aat ccc ctg gct gtc gac ttg ctg gag aag        1223
Asn Val Phe Ile Gly Ala Asn Pro Leu Ala Val Asp Leu Leu Glu Lys
         275                 280                 285
```

```
atg ctt gta ttg gac tca gat aag aga att aca gcg gcc caa gcc ctt         1271
Met Leu Val Leu Asp Ser Asp Lys Arg Ile Thr Ala Ala Gln Ala Leu
        290                 295                 300 gca cat gcc tac ttt gct cag tac cac gat cct gat gat gaa cca gtg         1319
Ala His Ala Tyr Phe Ala Gln Tyr His Asp Pro Asp Asp Glu Pro Val
305                 310                 315 gcc gat cct tat gat cag tcc ttt gaa agc agg gac ctc ctt ata gat         1367
Ala Asp Pro Tyr Asp Gln Ser Phe Glu Ser Arg Asp Leu Leu Ile Asp
320                 325                 330                 335 gag tgg aaa agc ctg acc tat gat gaa gtc atc agc ttt gtg cca cca         1415
Glu Trp Lys Ser Leu Thr Tyr Asp Glu Val Ile Ser Phe Val Pro Pro
                340                 345                 350 ccc ctt gac caa gaa gag atg gag tcc tga gcacctggtt tctgttctgt           1465
Pro Leu Asp Gln Glu Glu Met Glu Ser
                355                 360 tgatcccact tcactgtgag gggaaggcct tttcacggga actctccaaa tattattcaa       1525
gtgcctcttg ttgcagagat ttcctccatg gtggaagggg gtgtgcgtgc gtgtgcgtgc       1585
gtgttagtgt gtgtgcatgt gtgtgtctgt ctttgtggga gggtaagaca atatgaacaa       1645
actatgatca cagtgacttt acaggaggtt gtggatgctc cagggcagcc tccaccttgc       1705
tcttctttct gagagttggc tcaggcagac aagagctgct gtccttttag gaatatgttc       1765
aatgcaaagt aaaaaaatat gaattgtccc caatcccggt catgcttttg ccactttggc       1825
ttctcctgtg accccacctt gacggtgggg cgtagacttg acaacatccc acagtggcac       1885
ggagagaagg cccatacctt ctggttgctt cagacctgac accgtccctc agtgatacgt       1945
acagccaaaa aggaccaact ggcttctgtg cactagcctg tgattaactt gcttagtatg       2005
gttctcagat cttgacagta tatttgaaac tgtaaatatg tttgtgcctt aaaaggagag       2065
aagaaagtgt agatagttaa aagactgcag ctgctgaagt tctgagccgg gcaagtcgag       2125
agggctgttg gacagctgct tgtgggcccg gagtaatcag gcagccttca taggcggtca       2185
tgtgtgcatg tgagcacatg cgtatatgtg cgtctctctt tctccctcac ccccaggtgt       2245
tgccatttct ctgcttaccc ttcacctttg gtgcagaggt tcttgaata tctgccccag        2305
tagtcagaag caggttcttg atgtcatgta cttcctgtgt actctttatt tctagcagag       2365
tgaggatgtg ttttgcacgt cttgctattt gagcatgcac agctgcttgt cctgctctct       2425
tcaggaggcc ctggtgtcag gcaggtttgc cagtgaagac ttcttgggta gtttagatcc       2485
catgtcacct cagctgatat tatggcaagt gatatcacct ctcttcagcc cctagtgcta       2545
ttctgtgttg aacacaattg atacttcagg tgcttttgat gtgaaaatca tgaaaagagg       2605
aacaggtgga tgtatagcat ttttattcat gccatctgtt ttcaaccaac tattttgag        2665
gaattatcat gggaaaagac cagggctttt cccaggaata tcccaaactt cggaaacaag       2725
ttattctctt cactcccaat aactaatgct aagaaatgct gaaaatcaaa gtaaaaaatt       2785
aaagcccata aggccagaaa ctccttttgc tgtctttctc taaatatgat tactttaaaa       2845
taaaaagta acaaggtgtc ttttccactc ctatggaaaa gggtcttctt ggcagcttaa        2905
cattgacttc ttggtttggg gagaaataaa ttttgtttca gaattttgta tattgtagga      2965
atccctttga gaatgtgatt cctttgatg gggagaaagg gcaaattatt ttaatatttt       3025
gtattttcaa ctttataaag ataaaatatc ctcaggggtg gagaagtgtc gttttcataa       3085
cttgctgaat tcaggcatt ttgttctaca tgaggactca tatatttaag ccttttgtgt       3145
aataagaaaa tataaagtca cttccagtgt tggctgtgtg acagaatctt gtatttgggc      3205
caaggtgttt ccatttctca atcagtgcag tgatacatgt actccagagg gacagggtgg      3265
```

-continued

```
accccctgag tcaactggag caagaaggaa ggaggcagac tgatggcgat tccctctcac      3325
ccgggactct cccccttcca aggaaagtga acctttaaag taaaggcctc atctccttta      3385
ttgcagttca aatcctcacc atccacagca agatgaattt tatcagccat gtttggttgt      3445
aaatgctcgt gtgatttcct acagaaatac tgctctgaat attttgtaat aaaggtcttt      3505
gcacatgtga ccacatacgt gttaggaggc tgcatgctct ggaagcctgg actctaagct      3565
ggagctcttg gaagagctct tcggtttctg agcataatgc tcccatctcc tgatttctct      3625
gaacagaaaa caaagagag aatgagggaa attgctattt tatttgtatt catgaacttg       3685
gctgtaatca gttatgccgt ataggatgtc agacaatacc actggttaaa ataaagccta      3745
tttttcaaat tt                                                          3757
```

<210> SEQ ID NO 128
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 128
gagcaaagta ggcatgtgca                                                  20

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
gtttccgaag tttgggatat                                                  20

<210> SEQ ID NO 130
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 130
gcattagtta ttgggagtga                                                  20

<210> SEQ ID NO 131
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 131
ccctggagca tccacaacct                                                  20

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
tgtaccagga aacaatgttc                                                  20

```
<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
cgggcaagaa ggtggccctg                                        20

<210> SEQ ID NO 134
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 134
atcgccatca gtctgcctcc                                        20

<210> SEQ ID NO 135
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 135
tgacatcaag aacctgcttc                                        20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ggcccacaag cagctgtcca                                        20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 137
tgaaaacgac acttctccac                                        20

<210> SEQ ID NO 138
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 138
ggtgagaggg aatcgccatc                                        20

<210> SEQ ID NO 139
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 139
```
atactgtcaa gatctgagaa                                          20

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
tttccgaagt ttgggatatt                                          20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
agagagacgc acatatacgc                                          20

<210> SEQ ID NO 142
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 142
caagaggcac ttgaataata                                          20

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
attcctccag agaccttgca                                          20

<210> SEQ ID NO 144
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 144
aagacaccct gttactttt                                           20

<210> SEQ ID NO 145
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 145
tgcccttctc ccccatcaaa                                          20

<210> SEQ ID NO 146
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 146
tggcatcctg ttaatgagat                                               20

<210> SEQ ID NO 147
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 147
aaggccttcc cctcacagtg                                               20

<210> SEQ ID NO 148
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 148
aataggcttt attttaacca                                               20

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
acccaagaag tcttcactgg                                               20

<210> SEQ ID NO 150
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 150
tttcttatta cacaaaaggc                                               20

<210> SEQ ID NO 151
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 151
ggaaatcaca cgagcattta                                               20

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
ggtccctgtg aattatgtca                                               20
```

```
<210> SEQ ID NO 153
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 153
aatatatgag tcctcatgta                                              20

<210> SEQ ID NO 154
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 154
ctaacacgta tgtggtcaca                                              20

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
tttctcccca tcaaaaggaa                                              20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
ctgaacatgg tcatctgtaa                                              20

<210> SEQ ID NO 157
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 157
ataactgatt acagccaagt                                              20

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
ttctcaaagg gattcctaca                                              20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
``` tctgcccca tgagatgggt                                           20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
ttcgcatgaa tgatggactg                                          20

<210> SEQ ID NO 161
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 161
tactgagcaa agtaggcatg                                          20

<210> SEQ ID NO 162
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 162
gtccctgctt tcaaaggact                                          20

<210> SEQ ID NO 163
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 163
catatgttta agtaaccgca                                          20

<210> SEQ ID NO 164
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 164
cacattctca aagggattcc                                          20

<210> SEQ ID NO 165
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 165
ggactccatc tcttcttggt caa                                      23

<210> SEQ ID NO 166
<211> LENGTH: 24
<212> TYPE: DNA
<213> ORGANISM: Artificial Sequence -continued

```
<220> FEATURE:
<223> OTHER INFORMATION: Antisense Oligonucleotide

<400> SEQUENCE: 166
gaagtgggat caacagaaca gaaa                                              24

<210> SEQ ID NO 167
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 167
agcccactgg agacaggttc t                                                 21

<210> SEQ ID NO 168
<211> LENGTH: 3352
<212> TYPE: DNA
<213> ORGANISM: M. musculus
<220> FEATURE:
<221> NAME/KEY: CDS
<222> LOCATION: (230)...(1312)

<400> SEQUENCE: 168
aggaggaccg cggcgggagc agcctcgagc cgtgcagccg gctccggcac cttgccgacg        60
ctcgtaggag ccgccgcggc tgacaggggc ggcgggtcgc agcctccaca cctgcgcggg       120
tggcgggcgc ggggtccggt ctgccgcggg cgggcgcaga ggagagcgtg cggctgcagg       180
caggagcccc cgctcggcca cctcctcgcc ccgctgctgc cgctggaag atg tcg cag      238
                                                     Met Ser Gln
                                                       1 gag agg ccc acg ttc tac cgg cag gag ctg aac aag acc atc tgg gag        286
Glu Arg Pro Thr Phe Tyr Arg Gln Glu Leu Asn Lys Thr Ile Trp Glu
  5                  10                  15 gtg ccc gaa cga tac cag aac ctg tcc ccg gtg ggc tcg ggc gcc tat        334
Val Pro Glu Arg Tyr Gln Asn Leu Ser Pro Val Gly Ser Gly Ala Tyr
 20                  25                  30                  35 ggc tcg gtg tgt gct gct ttt gat aca aag acg ggg cat cgt gtg gca        382
Gly Ser Val Cys Ala Ala Phe Asp Thr Lys Thr Gly His Arg Val Ala
                 40                  45                  50 gtt aag aag ctg tcg aga ccg ttt cag tcc atc att cac gcc aaa agg        430
Val Lys Lys Leu Ser Arg Pro Phe Gln Ser Ile Ile His Ala Lys Arg
             55                  60                  65 acc tac cga gag ttg cgt ctg ctg aag cac atg aaa cac gaa aat gtg        478
Thr Tyr Arg Glu Leu Arg Leu Leu Lys His Met Lys His Glu Asn Val
         70                  75                  80 att ggt ctg ttg gat gtg ttc aca ccc gca agg tca ctg gag gaa ttc        526
Ile Gly Leu Leu Asp Val Phe Thr Pro Ala Arg Ser Leu Glu Glu Phe
     85                  90                  95 aat gac gtg tac ctg gtg acc cat ctc atg ggg gcg gac ctg aac aac        574
Asn Asp Val Tyr Leu Val Thr His Leu Met Gly Ala Asp Leu Asn Asn
100                 105                 110                 115 atc gtg aag tgc cag aag ctg acc gac gac cac gtt cag ttt ctc atc        622
Ile Val Lys Cys Gln Lys Leu Thr Asp Asp His Val Gln Phe Leu Ile
                120                 125                 130 tac cag atc ctc cga ggg ctg aag tat ata cat tcg gct gac ata att        670
Tyr Gln Ile Leu Arg Gly Leu Lys Tyr Ile His Ser Ala Asp Ile Ile
            135                 140                 145 cac agg gac cta aag ccc agc aac cta gct gtg aac gaa gac tgt gag        718
His Arg Asp Leu Lys Pro Ser Asn Leu Ala Val Asn Glu Asp Cys Glu
        150                 155                 160
```

```
ctc aag att ctg gat ttt ggg ctg gct cgg cac act gat gat gag atg      766
Leu Lys Ile Leu Asp Phe Gly Leu Ala Arg His Thr Asp Asp Glu Met
    165                 170                 175 aca ggc tac gtg gct acc agg tgg tac cga gcc cca gag atc atg ctg      814
Thr Gly Tyr Val Ala Thr Arg Trp Tyr Arg Ala Pro Glu Ile Met Leu
180                 185                 190                 195 aat tgg atg cac tat aac cag aca gtg gat att tgg tcc gtg ggc tgc      862
Asn Trp Met His Tyr Asn Gln Thr Val Asp Ile Trp Ser Val Gly Cys
                200                 205                 210 atc atg gct gag ctg ttg acc gga aga acg ttg ttt cct ggt aca gac      910
Ile Met Ala Glu Leu Leu Thr Gly Arg Thr Leu Phe Pro Gly Thr Asp
            215                 220                 225 cat att aac cag ctt cag cag ata atg cgt atg acg ggg aca ccc cct      958
His Ile Asn Gln Leu Gln Gln Ile Met Arg Met Thr Gly Thr Pro Pro
        230                 235                 240 gct tat ctc att aac agg atg cca agc cat gag gca aga aac tac att     1006
Ala Tyr Leu Ile Asn Arg Met Pro Ser His Glu Ala Arg Asn Tyr Ile
    245                 250                 255 cag tct ctg gcc cag atg ccg aag atg aac ttc gca aat gta ttt att     1054
Gln Ser Leu Ala Gln Met Pro Lys Met Asn Phe Ala Asn Val Phe Ile
260                 265                 270                 275 ggt gcc aat ccc ctg gct gtc gac cta ctg gag aag atg ctc gtt ttg     1102
Gly Ala Asn Pro Leu Ala Val Asp Leu Leu Glu Lys Met Leu Val Leu
                280                 285                 290 gac tca gat aag agg atc aca gca gcc caa gct ctt gcg cat gcc tac     1150
Asp Ser Asp Lys Arg Ile Thr Ala Ala Gln Ala Leu Ala His Ala Tyr
            295                 300                 305 ttt gct cag tac cac gac cct gat gat gag cct gtt gct gac cct tat     1198
Phe Ala Gln Tyr His Asp Pro Asp Asp Glu Pro Val Ala Asp Pro Tyr
        310                 315                 320 gac cag tcc ttt gaa agc agg gac ctt ctc ata gat gag tgg aag agc     1246
Asp Gln Ser Phe Glu Ser Arg Asp Leu Leu Ile Asp Glu Trp Lys Ser
    325                 330                 335 ctg acc tat gat gaa gtc atc agc ttt gtg cca cca ccc ctt gac caa     1294
Leu Thr Tyr Asp Glu Val Ile Ser Phe Val Pro Pro Pro Leu Asp Gln
340                 345                 350                 355 gaa gaa atg gag tcc tga gcacctggtt tctgttctgt ctatctcact            1342
Glu Glu Met Glu Ser
            360 tcactgtgag gggaagacct tctcatggga actctccaaa taccattcaa gtgcctcttg   1402 ttgaaagatt ccttcatggt ggaagggggt gcatgtatgt gttagtgttt gtgtgtgtgt   1462 gtgtgtctgt ctgttcgtct gtccacctat ctttgtggaa gtcactgtga tggtagtgac   1522 tttatgagtt gtgaatggtc cttggcagtc tgcctgcttt ctcagagtct gggcaggccg   1582 atgggaactg tcatctcctt agggatgtgt gtgttcagtg caaagtaaga aatatgaaaa   1642 tatccctgtt cttagttacc ttgccacttt ggcttctcct gtggccctgc ctttaccata   1702 tcagtgacag agagaggctg cttcaggtct gaggctatcc ctcagccatg cataaagtcc   1762 aagagaacca actggctcct ggtctctagc ctgtgaccgg cttgcttaat gtcctcagaa   1822 cctgacaggt atgttcaaaa ctgtcagtct gtttgtgcct taaagggtg agaagggcgc    1882 gtagatagtt acagagtctc agctgctgac gttctgagcc aggcaagtgc acgggctgt    1942 tggatggcca gtggggagct ggaaaaaaca aggcagcctt taggaaggcc atggtgcatg   2002 tgtgtgcatg cgtgtatgtg cagccgccct ccctcacttc aggagcaagc tgtttgctgt   2062 gcttaccctt cacctcagtg cagaggtctc cagtgccgag cacaggcacc tgccatcagt   2122 agttcctgtg tcatcttcac atctagcaga gcacggatgt gtttgcatgc tgtgctcttg   2182
```

```
gagcttgtcc tgtcttctgg aagccctgga caaggcgtgt gaaggcttcc cagaagttcc    2242
tgtccacatt gcctccgccc accgacgcca tgggcacact gctccctcct cctcctccag    2302
ctactttgtg ttgaacacaa ttgattctcc aggtgctcat ggtgcaggaa acaggacag     2362 acagagagca ctgaacccctt gccatctgat gtcaccaatt caggaaaacg agtcctctcc   2422
taggactatc cccggttctg gaaatcatgt tctcctcact catggtgaca agctaagaaa    2482
gctgaacaaa gggagagacg agagcgcctg aagccaggag ctcctttact atctttctca    2542
aaagggttgt tagacacaaa ccaagtcatc aaggccccgc tcctctcctc ggaagggtcc    2602 cccaccccc ggcagcttga cactgaatcc agtgtcaatt ggggagaaa gcagttttgt      2662 cttggaattt tgtatgttgt aggaatcctt agagagtgtg gttccttctg atggggagaa    2722
agggcaaatt attttaatat tttgtatttt cacctttata aacatgaatc ctcaggggtg    2782
aagaactgtt tgcataattt tctgaatttt gagcactttg tgctatataa ggacccatat    2842
ttaagctttg tgtgcagtaa gaaagtgtaa agccaattcc agtgttggac gtgacaggtc    2902
ttgtgtttag gtcaaggtgt ctcctctcag tgcagggaca tgcctgctct gtggggcagg    2962 cgaggacccct gaatcatttg gagcccagaa ggaggcagac tggccaggtc tcaccacctc   3022
agtgtgcagt tcaactccat gccatcccat caagatgggt tagtagcagt gtctgttttt    3082
gaatgccaag tgtgatttcc aacaattctg ctctggttat ttcattgaag acatctttgc    3142
acatgtgacc atgctgtgtt aggggctgtg ttccagggac tggactcgaa gctagaactg    3202
gcagaagagt tctggcatcc acagcgcaat gctgccacca cccagttttct tcatcagaag   3262 acaagggaac gagaaaactg ctgttcgttt gtatttgtga acttggctgt aatctggtat    3322
gccataggat gtcagataat accactggtt                                     3352

<210> SEQ ID NO 169
<211> LENGTH: 503
<212> TYPE: DNA
<213> ORGANISM: M. musculus

<400> SEQUENCE: 169
cgcaagaata aagtcagtgg tcacaaatag aggggggtcag tggctagaag aagagtaagc    60
ctgaattgag catcccagac agtggtccat acgggccgtc agctagctca ttccctgaga   120
tcactaacac tactgaacat agtcattctg aaagtctgtg tttttacagg caagaaacta   180
cattcagtct ctggcccag atg ccg aag atg aac ttc gca aat gta ttt att   232 ggt gcc aat ccc ctg gct gtc gac cta ctg gag aag atg ctc gtt ttg    280 gac tca gat aag agg atc aca gca gcc caa gct ctt gcg cat gct act    328 ttg ctc agt acc acg acc ctg atg atg agc ctg ttg ctg acc ctt atg    376 acc agt cct ttg aaa gca ggg acc ttc tca tag atgagtggaa gagcctgacc   429
tatgatgaag tcatcagctt tgtgccacca ccccttgacc aagaagagat ggagtcctga   489
gcacctggtt tctg                                                     503

<210> SEQ ID NO 170
<211> LENGTH: 1500
<212> TYPE: DNA
<213> ORGANISM: M. musculus
<220> FEATURE:
<221> NAME/KEY: CDS
<222> LOCATION: (297)...(1073)

<400> SEQUENCE: 170
cgggcgctga agcgcgagcg ggtgtcttgc ggcgtcggcg tgcgctccct ccccggggag     60
```

```
cggctgcagg aggaccgcgg cgggagcagc ctcgagccgt gcagccggct ccggcacctt      120
gccgacgctc gtaggagccg ccgcggctga caggggcggc gggtcgcagc ctccacacct      180
gcgcgggtgg cgggcgcggg gtccggtctg ccgcggcgg gcgcagagga gagcgtgcgg       240
ctgcaggcag gagccccgc tcggccacct cctcgccccg ctgctgccgc tggaag atg       299
                                                              Met
                                                                1 tcg cag gag agg ccc acg ttc tac cgg cag gag ctg aac aag acc atc        347
Ser Gln Glu Arg Pro Thr Phe Tyr Arg Gln Glu Leu Asn Lys Thr Ile
            5                  10                  15 tgg gag gtg ccc gaa cga tac cag aac ctg tcc ccg gtg ggc tcg ggc        395
Trp Glu Val Pro Glu Arg Tyr Gln Asn Leu Ser Pro Val Gly Ser Gly
        20                  25                  30 gcc tat ggc tcg gtg tgt gct gct ttt gat aca aag acg ggg cat cgt        443
Ala Tyr Gly Ser Val Cys Ala Ala Phe Asp Thr Lys Thr Gly His Arg
    35                  40                  45 gtg gca gtt aag aag ctg tcg aga ccg ttt cag tcc atc att cac gcc        491
Val Ala Val Lys Lys Leu Ser Arg Pro Phe Gln Ser Ile Ile His Ala
50                  55                  60                  65 aaa agg acc tac cga gag ttg cgt ctg ctg aag cac atg aaa cac gaa        539
Lys Arg Thr Tyr Arg Glu Leu Arg Leu Leu Lys His Met Lys His Glu
                70                  75                  80 aat gtg att ggt ctg ttg gat gtg ttc aca ccc gca agg tca ctg gag        587
Asn Val Ile Gly Leu Leu Asp Val Phe Thr Pro Ala Arg Ser Leu Glu
            85                  90                  95 gaa ttc aat gac gtg tac ctg gtg acc cat ctc atg ggg gcg gac ctg        635
Glu Phe Asn Asp Val Tyr Leu Val Thr His Leu Met Gly Ala Asp Leu
        100                 105                 110 aac aac atc gtg aag tgc cag aag ctg acc gac gac cac gtt cag ttt        683
Asn Asn Ile Val Lys Cys Gln Lys Leu Thr Asp Asp His Val Gln Phe
    115                 120                 125 ctc atc tac cag atc ctc cga ggg ctg aag tat ata cat tcg gct gac        731
Leu Ile Tyr Gln Ile Leu Arg Gly Leu Lys Tyr Ile His Ser Ala Asp
130                 135                 140                 145 ata att cac agg gac cta aag ccc agc aac cta gct gtg aac gaa gac        779
Ile Ile His Arg Asp Leu Lys Pro Ser Asn Leu Ala Val Asn Glu Asp
                150                 155                 160 tgt gag ctc aag att ctg gat ttt ggg ctg gct cgg cac act gat gat        827
Cys Glu Leu Lys Ile Leu Asp Phe Gly Leu Ala Arg His Thr Asp Asp
            165                 170                 175 gag atg aca ggc tac gtg gct acc agg tgg tac cga gcc cca gag atc        875
Glu Met Thr Gly Tyr Val Ala Thr Arg Trp Tyr Arg Ala Pro Glu Ile
        180                 185                 190 atg ctg aat tgg atg cac tat aac cag aca gtg gat att tgg tcc gtg        923
Met Leu Asn Trp Met His Tyr Asn Gln Thr Val Asp Ile Trp Ser Val
    195                 200                 205 ggc tgc atc atg gct gag ctg ttg acc gga aga acg ttg ttt cct ggt        971
Gly Cys Ile Met Ala Glu Leu Leu Thr Gly Arg Thr Leu Phe Pro Gly
210                 215                 220                 225 aca gac cat att gat cag ttg aag ctc att tta aga ctc gtt gga acc       1019
Thr Asp His Ile Asp Gln Leu Lys Leu Ile Leu Arg Leu Val Gly Thr
                230                 235                 240 cca ggg gct gag ctt ctg aag aaa atc tcc tca gag tct gat gcc aag       1067
Pro Gly Ala Glu Leu Leu Lys Lys Ile Ser Ser Glu Ser Asp Ala Lys
            245                 250                 255 cca tga ggtgagaaca aacagcatgc acagggaagt ctacctcgga ggccaccttc        1123
Pro
tcgtggtagt gtctgtgtat agccagcagt ttctaatgtc accgaatgct tgcatgtgcc     1183
ccaagaaccg ttaaagcagt actggctgtg tgctagcgga gtgttggcat ttaggatgca     1243
```

```
gtctcctgag cctgcgaggc agcgatgcag tgtagggcag tgttccctag tgtttggctt    1303
tctgatcttg tgcttgaggt aacaagtgtc gttgcagttg tatgtagtta gggtgtgcta    1363
cagccgtgtc atgggtgcat ggaacagagt tcattagtgt gctttgctct ccacccattt    1423
tacaaccaag agaagactgc atgcaagcac gcactataaa attccttgtg ctaataaaaa    1483
aaaaaaaaaa aaaaaaa                                                    1500
```

<210> SEQ ID NO 171
<211> LENGTH: 384
<212> TYPE: DNA
<213> ORGANISM: M. musculus

<400> SEQUENCE: 171

```
ttgcaaggac gctccagctc gccgcttagt cacataccac tgctcatttc agtattgttt      60
gacaaaacag ttttccatac cgagcagagg ggcgcccctc aagatcaaga agtgctgctt     120
ttgatacaaa gacggggcat cgtgtggcag ttaagaagct gtcgagaccg tttcagtcca     180
tcattcacgc caaaaggacc taccgagagt tgcgtctgct gaagcacatg aaacacgaaa     240
atgtgattgg tctgttggat gtgttcacac ccgcaaggtc actggaggaa ttcaatgacg     300
tgtacctggt gacccatctc atgggggcgg acctgaacaa catcgtgaag tgccagaagc     360
tgaccgacga ccacgttcag tttc                                            384
```

<210> SEQ ID NO 172
<211> LENGTH: 463
<212> TYPE: DNA
<213> ORGANISM: M. musculus
<220> FEATURE:
<221> NAME/KEY: misc_feature
<222> LOCATION: 429
<223> OTHER INFORMATION: n = A, T, C, or G

<400> SEQUENCE: 172

```
atattgggta agatctggat tcagagcggg gcctccttgg agctgttctc gcgagagttc      60
cgcgagaggc tcccggccgc tgcctgtggg atcgccgcca ctggagccca agcggggcgc     120
tgaagcgcga gcgggtgtct tgcggcgtcg gcgtgcgctc cctccccggg gagcggctgc     180
aggaggaccg cggcgggagc agcctcgagc cgtgcagccg gctccggcac cttgccgacg     240
ctcgtaggag ccgccgcggc tgacaggggc ggcgggtcgc accctccaca cctgcgcggg     300 tggcggggcgc ggggtccggt ctgccgcggg cgggcgcaga ggagagcgtg cggctgcagg     360
caggagcccc cgctcggcca cctcctcgcc ccgctgctgc cgctggaaga tgtcgcagga     420
gaggcccang ttctaccggc aggagctgaa caagaccatc tgg                       463
```

<210> SEQ ID NO 173
<211> LENGTH: 1083
<212> TYPE: DNA
<213> ORGANISM: R. norvegicus
<220> FEATURE:
<221> NAME/KEY: CDS
<222> LOCATION: (1)...(1083)

<400> SEQUENCE: 173

```
atg tct cag gag agg ccc acg ttc tac cgg cag gag ctg aac aag acc       48
Met Ser Gln Glu Arg Pro Thr Phe Tyr Arg Gln Glu Leu Asn Lys Thr
 1               5                  10                  15 gtc tgg gag gtg ccc gag cga tac cag aac ctg tcc ccg gtg ggc tcg       96
Val Trp Glu Val Pro Glu Arg Tyr Gln Asn Leu Ser Pro Val Gly Ser
             20                  25                  30
```

```
gga gcc tac ggc tcg gtg tgt gct gct ttt gat aca aag acg gga cat         144
Gly Ala Tyr Gly Ser Val Cys Ala Ala Phe Asp Thr Lys Thr Gly His
         35                  40                  45 cgt gtg gca gtg aag aag ctg tcg aga ccg gtt cag ccc atc att cac         192
Arg Val Ala Val Lys Lys Leu Ser Arg Pro Val Gln Pro Ile Ile His
 50                  55                  60 gcc aaa agg tcc tac agg gag ctg cgg ctg ctg aag cac atg aag cac         240
Ala Lys Arg Ser Tyr Arg Glu Leu Arg Leu Leu Lys His Met Lys His
 65                  70                  75                  80 gag aat gtg att ggt ctg ttg gat gtg ttt aca cct gca agg tcc ctg         288
Glu Asn Val Ile Gly Leu Leu Asp Val Phe Thr Pro Ala Arg Ser Leu
                 85                  90                  95 gag gaa ttc aac gat gtg tac ctg gtg acc cat ctc atg ggg gca gac         336
Glu Glu Phe Asn Asp Val Tyr Leu Val Thr His Leu Met Gly Ala Asp
            100                 105                 110 ctg aac aac atc gtg aag tgt cag aag ctt acc gat gac cac gtt cag         384
Leu Asn Asn Ile Val Lys Cys Gln Lys Leu Thr Asp Asp His Val Gln
        115                 120                 125 ttt ctt atc tac cag atc ctg cga ggg ctg aag tat ata cac tcg gct         432
Phe Leu Ile Tyr Gln Ile Leu Arg Gly Leu Lys Tyr Ile His Ser Ala
    130                 135                 140 gac ata atc cac agg gac cta aag ccc agc aac ctc gct gtg aat gaa         480
Asp Ile Ile His Arg Asp Leu Lys Pro Ser Asn Leu Ala Val Asn Glu
145                 150                 155                 160 gac tgt gag ctg aag att ctg gat ttt ggg ctg gct cgg cac act gat         528
Asp Cys Glu Leu Lys Ile Leu Asp Phe Gly Leu Ala Arg His Thr Asp
                165                 170                 175 gac gaa atg acc ggc tac gtg gct acc cgg tgg tac aga gcc ccc gag         576
Asp Glu Met Thr Gly Tyr Val Ala Thr Arg Trp Tyr Arg Ala Pro Glu
            180                 185                 190 att atg ctg aat tgg atg cac tac aac cag aca gtg gat att tgg tcc         624
Ile Met Leu Asn Trp Met His Tyr Asn Gln Thr Val Asp Ile Trp Ser
        195                 200                 205 gtg ggc tgc atc atg gct gag ctg ttg acc gga aga acg ttg ttt cct         672
Val Gly Cys Ile Met Ala Glu Leu Leu Thr Gly Arg Thr Leu Phe Pro
210                 215                 220 ggt aca gac cat att gat cag ttg aag ctc att tta aga ctc gtt gga         720
Gly Thr Asp His Ile Asp Gln Leu Lys Leu Ile Leu Arg Leu Val Gly
225                 230                 235                 240 acc cca ggg gct gag ctt ctg aag aaa atc tcc tca gag tct gca aga         768
Thr Pro Gly Ala Glu Leu Leu Lys Lys Ile Ser Ser Glu Ser Ala Arg
                245                 250                 255 aac tac att cag tct ctg gcc cag atg ccg aag atg aac ttc gca aat         816
Asn Tyr Ile Gln Ser Leu Ala Gln Met Pro Lys Met Asn Phe Ala Asn
            260                 265                 270 gta ttt att ggt gcc aat ccc ctg gct gtc gac ctg ctg gaa aag atg         864
Val Phe Ile Gly Ala Asn Pro Leu Ala Val Asp Leu Leu Glu Lys Met
        275                 280                 285 ctg gtt ttg gac tca gat aag agg atc aca gca gcc caa gct ctt gcg         912
Leu Val Leu Asp Ser Asp Lys Arg Ile Thr Ala Ala Gln Ala Leu Ala
    290                 295                 300 cat gcc tac ttt gct cag tac cac gac cct gat gat gag cca gtg gct         960
His Ala Tyr Phe Ala Gln Tyr His Asp Pro Asp Asp Glu Pro Val Ala
305                 310                 315                 320 gac cct tat gac cag tcc ttt gaa agc agg gac ctc ctt ata gac gaa        1008
Asp Pro Tyr Asp Gln Ser Phe Glu Ser Arg Asp Leu Leu Ile Asp Glu
                325                 330                 335 tgg aag agc ctg acc tac gat gaa gtc att agc ttt gtg cca ccg ccc        1056
Trp Lys Ser Leu Thr Tyr Asp Glu Val Ile Ser Phe Val Pro Pro Pro
            340                 345                 350
```

```
ctt gac caa gaa gaa atg gac tcc tga                              1083
Leu Asp Gln Glu Glu Met Asp Ser
        355                 360
```

<210> SEQ ID NO 174
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 174
gtgcgcgcga gcccgaaatc                                              20

<210> SEQ ID NO 175
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 175
ctgcgacatt ttccagcggc                                              20

<210> SEQ ID NO 176
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 176
catcatcagg gtcgtggtac                                              20

<210> SEQ ID NO 177
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 177
aggtgctcag gactccattt                                              20

<210> SEQ ID NO 178
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 178
gtccctgctt tcaaaggact                                              20

<210> SEQ ID NO 179
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 179
ggccagagac tgaatgtagt                                              20

<210> SEQ ID NO 180
<211> LENGTH: 20
<212> TYPE: DNA

<213> ORGANISM: Artificial Sequence
<220> FEATURE:
<223> OTHER INFORMATION: Antisense Oligonucleotide

<400> SEQUENCE: 180
agctcctgcc ggtagaacgt         20

<210> SEQ ID NO 181
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 181
tcaaaagcag cacacaccga         20

<210> SEQ ID NO 182
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 182
cccgtctttg tatcaaaagc         20

<210> SEQ ID NO 183
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 183
aacggtctcg acagcttctt         20

<210> SEQ ID NO 184
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 184
taggtccttt tggcgtgaat         20

<210> SEQ ID NO 185
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 185
agatgggtca ccaggtacac         20

<210> SEQ ID NO 186
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 186
gcccccatga gatgggtcac         20

```
<210> SEQ ID NO 187
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 187
tcatcagtgt gccgagccag                                          20

<210> SEQ ID NO 188
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 188
gtcaacagct cagccatgat                                          20

<210> SEQ ID NO 189
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 189
cgttcttccg gtcaacagct                                          20

<210> SEQ ID NO 190
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 190
atcaatatgg tctgtaccag                                          20

<210> SEQ ID NO 191
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 191
cttaaaatga gcttcaactg                                          20

<210> SEQ ID NO 192
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 192
gggttccaac gagtcttaaa                                          20

<210> SEQ ID NO 193
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 193
tcagaagctc agcccctggg                                           20

<210> SEQ ID NO 194
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 194
ggagattttc ttcagaagct                                           20

<210> SEQ ID NO 195
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 195
cagactctga ggagattttc                                           20

<210> SEQ ID NO 196
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 196
tagtttcttg cagactctga                                           20

<210> SEQ ID NO 197
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 197
agactgaatg tagtttcttg                                           20

<210> SEQ ID NO 198
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 198
ttcatcttcg gcatctgggc                                           20

<210> SEQ ID NO 199
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 199
atttgcgaag ttcatcttcg                                           20

<210> SEQ ID NO 200
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 200
caataaatac atttgcgaag                                              20

<210> SEQ ID NO 201
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 201
ggattggcac caataaatac                                              20

<210> SEQ ID NO 202
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 202
gctgctgtga tcctcttatc                                              20

<210> SEQ ID NO 203
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 203
aggcatgcgc aagagcttgg                                              20

<210> SEQ ID NO 204
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 204
tgagcaaagt aggcatgcgc                                              20

<210> SEQ ID NO 205
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 205
tcaaaggact ggtcataagg                                              20

<210> SEQ ID NO 206
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 206
catttcttct tggtcaaggg                                              20
```

```
<210> SEQ ID NO 207
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 207
aggactccat ttcttcttgg                                               20

<210> SEQ ID NO 208
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 208
cttcccctca cagtgaagtg                                               20

<210> SEQ ID NO 209
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 209
tatttggaga gttcccatga                                               20

<210> SEQ ID NO 210
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 210
acttgaatgg tatttggaga                                               20

<210> SEQ ID NO 211
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 211
aacaagaggc acttgaatgg                                               20

<210> SEQ ID NO 212
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 212
acccccttcc accatgaagg                                               20

<210> SEQ ID NO 213
<211> LENGTH: 20
<212> TYPE: DNA
<213> ORGANISM: Artificial Sequence
<220> FEATURE:
<223> OTHER INFORMATION: Antisense Oligonucleotide
```

-continued

```
<400> SEQUENCE: 213
agcaggcaga ctgccaagga                                              20

<210> SEQ ID NO 214
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 214
cacacacatc cctaaggaga                                              20

<210> SEQ ID NO 215
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 215
taaaggcagg gccacaggag                                              20

<210> SEQ ID NO 216
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 216
gcagcctctc tctgtcactg                                              20

<210> SEQ ID NO 217
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 217
gggatagcct cagacctgaa                                              20

<210> SEQ ID NO 218
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 218
gcatggctga gggatagcct                                              20

<210> SEQ ID NO 219
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 219
gagccagttg gttctcttgg                                              20

<210> SEQ ID NO 220
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 220
aggcacaaac agactgacag                                               20

<210> SEQ ID NO 221
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 221
ccttttaagg cacaaacaga                                               20

<210> SEQ ID NO 222
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 222
gacctctgca ctgaggtgaa                                               20

<210> SEQ ID NO 223
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 223
ggcactggag acctctgcac                                               20

<210> SEQ ID NO 224
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 224
agagcacagc atgcaaacac                                               20

<210> SEQ ID NO 225
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 225
ccagggcttc cagaagacag                                               20

<210> SEQ ID NO 226
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 226
aaggagctcc tggcttcagg                                               20
```

```
<210> SEQ ID NO 227
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 227
ggattcctac aacatacaaa                                              20

<210> SEQ ID NO 228
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 228
gaaggaacca cactctctaa                                              20

<210> SEQ ID NO 229
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 229
tttgcccttt ctccccatca                                              20

<210> SEQ ID NO 230
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 230
aatattaaaa taatttgccc                                              20

<210> SEQ ID NO 231
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 231
tcatgtttat aaaggtgaaa                                              20

<210> SEQ ID NO 232
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 232
ccctgaggat tcatgtttat                                              20

<210> SEQ ID NO 233
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 233
ggaattggct ttacactttc                                              20

<210> SEQ ID NO 234
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 234
cgtccaacac tggaattggc                                              20

<210> SEQ ID NO 235
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 235
ccttctgggc tccaaatgat                                              20

<210> SEQ ID NO 236
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 236
tctgacatcc tatggcatac                                              20

<210> SEQ ID NO 237
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 237
gttaatatgg tctgtaccag                                              20

<210> SEQ ID NO 238
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 238
gctgaagctg gttaatatgg                                              20

<210> SEQ ID NO 239
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 239
cgcattatct gctgaagctg                                              20

<210> SEQ ID NO 240
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 240
tgttaatgag ataagcaggg                                               20

<210> SEQ ID NO 241
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 241
cttggcatcc tgttaatgag                                               20

<210> SEQ ID NO 242
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 242
tgcctcatgg cttggcatcc                                               20

<210> SEQ ID NO 243
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 243
actgaatgta gtttcttgcc                                               20

<210> SEQ ID NO 244
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 244
cttgcctgta aaaacacaga                                               20

<210> SEQ ID NO 245
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 245
tcacctcatg gcttggcatc                                               20

<210> SEQ ID NO 246
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 246
tttgttctca cctcatggct                                               20
```

```
<210> SEQ ID NO 247
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 247
tgctggctat acacagacac                                               20

<210> SEQ ID NO 248
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 248
tggaaaactg ttttgtcaaa                                               20

<210> SEQ ID NO 249
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 249
actctcgcga gaacagctcc                                               20

<210> SEQ ID NO 250
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 250
tcccacaggc agcggccggg                                               20

<210> SEQ ID NO 251
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 251
cccgcttggg ctccagtggc                                               20

<210> SEQ ID NO 252
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 252
gcagttttct cgttcccttg                                               20

<210> SEQ ID NO 253
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 253
ctgagcaaag taggcatgcg                                            20

<210> SEQ ID NO 254
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 254
ggaggcaatg tggacaggaa                                            20

<210> SEQ ID NO 255
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 255
cattttcgtg tttcatgtgc ttc                                        23

<210> SEQ ID NO 256
<211> LENGTH: 31
<212> TYPE: DNA
<213> ORGANISM: Artificial Sequence
<220> FEATURE:
<223> OTHER INFORMATION: Antisense Oligonucleotide

<400> SEQUENCE: 256
tattttaacc agtggtatta tctgacatcc t                               31

<210> SEQ ID NO 257
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 257
ctgcgacatc ttccagcggc                                            20

<210> SEQ ID NO 258
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 258
ggtcagcttc tggcacttca                                            20

<210> SEQ ID NO 259
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 259
aagcaggcag actgccaagg                                            20

<210> SEQ ID NO 260
<211> LENGTH: 18
<212> TYPE: DNA

```
<213> ORGANISM: Artificial Sequence
<220> FEATURE:
<223> OTHER INFORMATION: Antisense Oligonucleotide

<400> SEQUENCE: 260
aggcatgcgc aagagctt                                                 18

<210> SEQ ID NO 261
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 261
gggacaggtt ctggtatcgc                                               20

<210> SEQ ID NO 262
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 262
tctcgtgctt catgtgcttc a                                             21

<210> SEQ ID NO 263
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 263
tggagctgga ctgcatactg a                                             21

<210> SEQ ID NO 264
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 264
catcagggtc gtggtac                                                  17

<210> SEQ ID NO 265
<211> LENGTH: 15
<212> TYPE: DNA
<213> ORGANISM: Artificial Sequence
<220> FEATURE:
<223> OTHER INFORMATION: Antisense Oligonucleotide

<400> SEQUENCE: 265
catcatcagg gtcgt                                                    15

<210> SEQ ID NO 266
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 266
agctgatctg gcctacagtt                                               20
```

-continued

```
<210> SEQ ID NO 267
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 267
cgagaggcgg acgggaccgt t                                              21

<210> SEQ ID NO 268
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 268
ttgctctccg cctgccctgg c                                              21

<210> SEQ ID NO 269
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 269
cgagaggcgg acgggaccg                                                 19

<210> SEQ ID NO 270
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 270
gctctccgcc tgccctggc                                                 19

<210> SEQ ID NO 271
<211> LENGTH: 3757
<212> TYPE: DNA
<213> ORGANISM: Homo sapiens
<220> FEATURE:

<400> SEQUENCE: 271
ggaaccgcga ccactggagc cttagcgggc gcagcagctg aacgggagt actgcgacgc     60 agcccggagt cggccttgta ggggcgaagg tgcagggaga tcgcggcggg cgcagtcttg    120
agcgccggag cgcgtccctg cccttagcgg ggcttgcccc agtcgcaggg gcacatccag    180
ccgctgcggc tgacagcagc cgcgcgcgcg ggagtctgcg gggtcgcggc agccgcacct    240
gcgcgggcga ccagcgcaag gtccccgccc ggctgggcgg gcagcaaggg ccggggagag    300
ggtgcgggtg caggcggggg ccccacaggg ccaccttctt gcccggcggc tgccgctgga    360
aaatgtctca ggagaggccc acgttctacc ggcaggagct gaacaagaca atctgggagg    420
tgcccgagcg ttaccagaac ctgtctccag tgggctctgg cgcctatggc tctgtgtgtg    480
ctgcttttga cacaaaaacg gggttacgtg tggcagtgaa gaagctctcc agaccatttc    540
agtccatcat tcatgcgaaa agaacctaca gagaactgcg gttacttaaa catatgaaac    600
atgaaaatgt gattggtctg ttggacgttt ttacacctgc aaggtctctg gaggaattca    660
atgatgtgta tctggtgacc catctcatgg gggcagatct gaacaacatt gtgaaatgtc    720
```

| | | | | |
|---|---|---|---|---|
| agaagcttac | agatgaccat | gttcagttcc | ttatctacca | aattctccga ggtctaaagt | 780 |
| atatacattc | agctgacata | attcacaggg | acctaaaacc | tagtaatcta gctgtgaatg | 840 |
| aagactgtga | gctgaagatt | ctggattttg | gactggctcg | gcacacagat gatgaaatga | 900 |
| caggctacgt | ggccactagg | tggtacaggg | ctcctgagat | catgctgaac tggatgcatt | 960 |
| acaaccagac | agttgatatt | tggtcagtgg | gatgcataat | ggccgagctg ttgactggaa | 1020 |
| gaacattgtt | tcctggtaca | gaccatattg | atcagttgaa | gctcatttta agactcgttg | 1080 |
| gaacccagg | ggctgagctt | tgaagaaaa | tctcctcaga | gtctgcaaga aactatattc | 1140 |
| agtctttgac | tcagatgccg | aagatgaact | ttgcgaatgt | atttattggt gccaatcccc | 1200 |
| tggctgtcga | cttgctggag | aagatgcttg | tattggactc | agataagaga attacagcgg | 1260 |
| cccaagccct | tgcacatgcc | tactttgctc | agtaccacga | tcctgatgat gaaccagtgg | 1320 |
| ccgatcctta | tgatcagtcc | tttgaaagca | gggacctcct | tatagatgag tggaaaagcc | 1380 |
| tgacctatga | tgaagtcatc | agctttgtgc | caccacccct | tgaccaagaa gagatggagt | 1440 |
| cctgagcacc | tggtttctgt | tctgttgatc | ccacttcact | gtgaggggaa ggccttttca | 1500 |
| cgggaactct | ccaaatatta | ttcaagtgcc | tcttgttgca | gagatttcct ccatggtgga | 1560 |
| agggggtgtg | cgtgcgtgtg | cgtgcgtgtt | agtgtgtgtg | catgtgtgtg tctgtctttg | 1620 |
| tgggagggta | agacaatatg | aacaaactat | gatcacagtg | actttacagg aggttgtgga | 1680 |
| tgctccaggg | cagcctccac | cttgctcttc | tttctgagag | ttggctcagg cagacaagag | 1740 |
| ctgctgtcct | tttaggaata | tgttcaatgc | aaagtaaaaa | aatatgaatt gtccccaatc | 1800 |
| ccggtcatgc | ttttgccact | ttggcttctc | ctgtgacccc | accttgacgg tggggcgtag | 1860 |
| acttgacaac | atcccacagt | ggcacggaga | gaaggcccat | accttctggt tgcttcagac | 1920 |
| ctgacaccgt | ccctcagtga | tacgtacagc | caaaaggac | caactggctt ctgtgcacta | 1980 |
| gcctgtgatt | aacttgctta | gtatggttct | cagatcttga | cagtatattt gaaactgtaa | 2040 |
| atatgtttgt | gccttaaaag | gagagaagaa | agtgtagata | gttaaaagac tgcagctgct | 2100 |
| gaagttctga | gccgggcaag | tcgagagggc | tgttggacag | ctgcttgtgg gcccggagta | 2160 |
| atcaggcagc | cttcataggc | ggtcatgtgt | gcatgtgagc | acatgcgtat atgtgcgtct | 2220 |
| ctctttctcc | ctcacccca | ggtgttgcca | tttctctgct | tacccttcac ctttggtgca | 2280 |
| gaggtttctt | gaatatctgc | cccagtagtc | agaagcaggt | tcttgatgtc atgtacttcc | 2340 |
| tgtgtactct | ttatttctag | cagagtgagg | atgtgttttg | cacgtcttgc tatttgagca | 2400 |
| tgcacagctg | cttgtcctgc | tctcttcagg | aggccctggt | gtcaggcagg tttgccagtg | 2460 |
| aagacttctt | gggtagttta | gatcccatgt | cacctcagct | gatattatgg caagtgtatat | 2520 |
| cacctctctt | cagcccctag | tgctattctg | tgttgaacac | aattgatact tcaggtgctt | 2580 |
| ttgatgtgaa | aatcatgaaa | agaggaacag | gtggatgtat | agcattttta ttcatgccat | 2640 |
| ctgttttcaa | ccaactattt | tgaggaatt | atcatgggaa | aagaccaggg cttttcccag | 2700 |
| gaatatccca | aacttcggaa | acaagttatt | ctcttcactc | ccaataacta atgctaagaa | 2760 |
| atgctgaaaa | tcaaagtaaa | aaattaaagc | ccataaggcc | agaaactcct tttgctgtct | 2820 |
| ttctctaaat | atgattactt | taaaataaaa | aagtaacaag | gtgtctttc cactcctatg | 2880 |
| gaaaagggtc | ttcttggcag | cttaacattg | acttcttggt | ttggggagaa ataaattttg | 2940 |
| tttcagaatt | ttgtatattg | taggaatccc | tttgagaatg | tgattccttt tgatggggag | 3000 |
| aaagggcaaa | ttattttaat | atttttgtatt | ttcaacttta | taaagataaa atatcctcag | 3060 |
| gggtggagaa | gtgtcgtttt | cataacttgc | tgaatttcag | gcattttgtt ctacatgagg | 3120 |

| | |
|---|---|
| actcatatat ttaagccttt tgtgtaataa gaaagtataa agtcacttcc agtgttggct | 3180 |
| gtgtgacaga atcttgtatt tgggccaagg tgtttccatt tctcaatcag tgcagtgata | 3240 |
| catgtactcc agagggacag ggtggacccc ctgagtcaac tggagcaaga aggaaggagg | 3300 |
| cagactgatg gcgattccct ctcacccggg actctccccc tttcaaggaa agtgaacctt | 3360 |
| taaagtaaag gcctcatctc ctttattgca gttcaaatcc tcaccatcca cagcaagatg | 3420 |
| aattttatca gccatgtttg gttgtaaatg ctcgtgtgat ttcctacaga aatactgctc | 3480 |
| tgaatatttt gtaataaagg tcttttgcaca tgtgaccaca tacgtgttag gaggctgcat | 3540 |
| gctctggaag cctggactct aagctggagc tcttggaaga gctcttcggt ttctgagcat | 3600 |
| aatgctccca tctcctgatt tctctgaaca gaaaacaaaa gagagaatga gggaaattgc | 3660 |
| tattttatt gtattcatga acttggctgt aatcagttat gccgtatagg atgtcagaca | 3720 |
| ataccactgg ttaaaataaa gcctattttt caaattt | 3757 |

<210> SEQ ID NO 272
<211> LENGTH: 1312
<212> TYPE: DNA
<213> ORGANISM: Homo sapiens
<220> FEATURE:

<400> SEQUENCE: 272

| | |
|---|---|
| ggaaccgcga ccactggagc cttagcgggc gcagcagctg gaacgggagt actgcgacgc | 60 |
| agcccggagt cggccttgta gggggcgaagg tgcaggaga tcgcggcggg cgcagtcttg | 120 |
| agcgccggag cgcgtccctg cccttagcgg ggcttgcccc agtcgcaggg gcacatccag | 180 |
| ccgctgcggc tgacagcagc cgcgcgcgcg ggagtctgcg gggtcgcggc agccgcacct | 240 |
| gcgcgggcga ccagcgcaag gtccccgccc ggctgggcgg gcagcaaggg ccggggagag | 300 |
| ggtgcgggtg caggcggggg ccccacaggg ccaccttctt gcccggcggc tgccgctgga | 360 |
| aaatgtctca ggagaggccc acgttctacc ggcaggagc gaacaagaca atctgggagg | 420 |
| tgcccgagcg ttaccagaac ctgtctccag tgggctctgg cgcctatggc tctgtgtgtg | 480 |
| ctgcttttga cacaaaaacg gggttacgtg tggcagtgaa gaagctctcc agaccatttc | 540 |
| agtccatcat tcatgcgaaa agaacctaca gagaactgcg gttacttaaa catatgaaac | 600 |
| atgaaaatgt gattggtctg ttggacgttt ttacacctgc aaggtctctg gaggaattca | 660 |
| atgatgtgta tctggtgacc catctcatgg gggcagatct gaacaacatt gtgaaatgtc | 720 |
| agaagcttac agatgaccat gttcagttcc ttatctacca aattctccga ggtctaaagt | 780 |
| atatacattc agctgacata attcacaggg acctaaaacc tagtaatcta gctgtgaatg | 840 |
| aagactgtga gctgaagatt ctggattttg gactggctcg gcacacagat gatgaaatga | 900 |
| caggctacgt ggccactagg tggtacaggg ctcctgagat catgctgaac tggatgcatt | 960 |
| acaaccagac agttgatatt tggtcagtgg gatgcataat ggccgagctg ttgactggaa | 1020 |
| gaacattgtt tcctggtaca gaccatattg atcagttgaa gctcattta agactcgttg | 1080 |
| gaaccccagg ggctgagctt ttgaagaaaa tctcctcaga gtctgcaaga aactatattc | 1140 |
| agtctttgac tcagatgccg aagatgaact ttgcgaatgt atttattggt gccaatcccc | 1200 |
| tgggtaagtt gaccatatat cctcaccctca tggatattga attggttatg atataaattg | 1260 |
| gggatttgaa gaagagtttc tccttttgac caaataaagt accattagtt ga | 1312 |

<210> SEQ ID NO 273
<211> LENGTH: 3679
<212> TYPE: DNA

<213> ORGANISM: Homo sapiens
<220> FEATURE:

<400> SEQUENCE: 273

```
ggaaccgcga ccactggagc cttagcgggc gcagcagctg gaacgggagt actgcgacgc      60
agcccggagt cggccttgta ggggcgaagg tgcagggaga tcgcggcggg cgcagtcttg     120
agcgccggag cgcgtccctg cccttagcgg ggcttgcccc agtcgcaggg gcacatccag     180
ccgctgcggc tgacagcagc cgcgcgcgcg ggagtctgcg gggtcgcggc agccgcacct     240
gcgcgggcga ccagcgcaag gtccccgccc ggctgggcgg gcagcaaggg ccggggagag     300
ggtgcgggtg caggcggggg ccccacaggg ccaccttctt gcccggcggc tgccgctgga     360
aaatgtctca ggagaggccc acgttctacc ggcaggagct gaacaagaca atctgggagg     420
tgcccgagcg ttaccagaac ctgtctccag tgggctctgg cgcctatggc tctgtgtgtg     480
ctgcttttga cacaaaaacg gggttacgtg tggcagtgaa gaagctctcc agaccatttc     540
agtccatcat tcatgcgaaa agaacctaca gagaactgcg gttacttaaa catatgaaac     600
atgaaaatgt gattggtctg ttggacgttt ttacacctgc aaggtctctg gaggaattca     660
atgatgtgta tctggtgacc catctcatgg gggcagatct gaacaacatt gtgaaatgtc     720
agaagcttac agatgaccat gttcagttcc ttatctacca aattctccga ggtctaaagt     780
atatacattc agctgacata attcacaggg acctaaaacc tagtaatcta gctgtgaatg     840
aagactgtga gctgaagatt ctggattttg gactggctcg gcacacagat gatgaaatga     900
caggctacgt ggccactagg tggtacaggg ctcctgagat catgctgaac tggatgcatt     960
acaaccagac agttgatatt tggtcagtgg gatgcataat ggccgagctg ttgactggaa    1020
gaacattgtt tcctggtaca gaccatattg atcagttgaa gctcatttta agactcgttg    1080
gaaccccagg ggctgagctt ttgaagaaaa tctcctcaga gtctctgtcg acttgctgga    1140
gaagatgctt gtattggact cagataagag aattacagcg gcccaagccc ttgcacatgc    1200
ctactttgct cagtaccacg atcctgatga tgaaccagtg gccgatcctt atgatcagtc    1260
ctttgaaagc agggacctcc ttatagatga gtggaaaagc ctgacctatg atgaagtcat    1320
cagctttgtg ccaccacccc ttgaccaaga agagatggag tcctgagcac ctggtttctg    1380
ttctgttgat cccacttcac tgtgagggga aggccttttc acgggaacct ctccaaatat    1440
tattcaagtg cctcttgttg cagagatttc ctccatggtg gaagggggtg tgcgtgcgtg    1500
tgcgtgcgtg ttagtgtgtg tgcatgtgtg tgtctgtctt tgtgggaggg taagacaata    1560
tgaacaaact atgatcacag tgactttaca ggaggttgtg gatgctccag ggcagcctcc    1620
accttgctct tctttctgag agttggctca ggcagacaag agctgctgtc cttttaggaa    1680
tatgttcaat gcaaagtaaa aaaatatgaa ttgtccccaa tcccggtcat gcttttgcca    1740
ctttggcttc tcctgtgacc ccaccttgac ggtggggcgt agacttgaca acatcccaca    1800
gtggcacgga gagaaggccc ataccttctg gttgcttcag acctgacacc gtccctcagt    1860
gatacgtaca gccaaaaagg accaactggc ttctgtgcac tagcctgtga ttaacttgct    1920
tagtatggtt ctcagatctt gacagtatat ttgaaactgt aaatatgttt gtgccttaaa    1980
aggagagaag aaagtgtaga tagttaaaag actgcagctg ctgaagttct gagccgggca    2040
agtcgagagg gctgttggac agctgcttgt gggcccggga taatcaggca gccttcatag    2100
gcggtcatgt gtgcatgtga gcacatgcgt atatgtgcgt ctctctttct ccctcacccc    2160
caggtgttgc catttctctg cttacccttc acctttggtg cagagagtttc ttgaatatct    2220
gccccagtag tcagaagcag gttcttgatg tcatgtactt cctgtgtact ctttatttct    2280
```

```
agcagagtga ggatgtgttt tgcacgtctt gctatttgag catgcacagc tgcttgtcct    2340
gctctcttca ggaggccctg gtgtcaggca ggtttgccag tgaagacttc ttgggtagtt    2400
tagatcccat gtcacctcag ctgatattat ggcaagtgat atcacctctc ttcagcccct    2460
agtgctattc tgtgttgaac acaattgata cttcaggtgc ttttgatgtg aaaatcatga    2520
aaagaggaac aggtggatgt atagcatttt tattcatgcc atctgttttc aaccaactat    2580
ttttgaggaa ttatcatggg aaaagaccag ggcttttccc aggaatatcc caaacttcgg    2640
aaacaagtta ttctcttcac tcccaataac taatgctaag aaatgctgaa atcaaagta    2700 aaaaattaaa gcccataagg ccagaaactc cttttgctgt ctttctctaa atatgattac    2760
tttaaaataa aaaagtaaca aggtgtcttt tccactccta tggaaaaggg tcttcttggc    2820
agcttaacat tgacttcttg gtttggggag aaataaattt tgtttcagaa ttttgtatat    2880
tgtaggaatc cctttgagaa tgtgattcct tttgatgggg agaaagggca aattatttta    2940
atattttgta ttttcaactt tataaagata aaatatcctc aggggtggag aagtgtcgtt    3000
ttcataactt gctgaatttc aggcattttg ttctacatga ggactcatat atttaagcct    3060
tttgtgtaat aagaaagtat aaagtcactt ccagtgttgg ctgtgtgaca gaatcttgta    3120
tttgggccaa ggtgtttcca tttctcaatc agtgcagtga tacatgtact ccagagggac    3180
agggtggacc ccctgagtca actggagcaa gaaggaagga ggcagactga tggcgattcc    3240
ctctcacccg ggactctccc cctttcaagg aaagtgaacc tttaaagtaa aggcctcatc    3300
tcctttattg cagttcaaat cctcaccatc cacagcaaga tgaatttat cagccatgtt    3360 tggttgtaaa tgctcgtgtg atttcctaca gaaatactgc tctgaatatt ttgtaataaa    3420
ggtctttgca catgtgacca catacgtgtt aggaggctgc atgctctgga agcctggact    3480
ctaagctgga gctcttggaa gagctcttcg gtttctgagc ataatgctcc catctcctga    3540
tttctctgaa cagaaaacaa aagagagaat gagggaaatt gctattttat ttgtattcat    3600
gaacttggct gtaatcagtt atgccgtata ggatgtcaga caataccact ggttaaaata    3660
aagcctattt ttcaaatttt                                                 3679
```

<210> SEQ ID NO 274
<211> LENGTH: 83763
<212> TYPE: DNA
<213> ORGANISM: Homo sapiens
<220> FEATURE:

<400> SEQUENCE: 274

```
tttggggtt caggtgagca ggtgctctgc tgctggtaac tactcgcagt taaagatctt     60
ttgactcttt ccccgacacg ctatttgtca gtgtcgtttt ccaccacaga gccaggtatt    120
tgccccgccg gccacggtga ggcgcgcgag gcgtgtgctg ccagcttctc tcttccttcc    180
ccggtccgcc ttcgcgccct taaggagaca gtccctggga gtttctgcct ttggtctcca    240
gttattgttc tcttctcgcg agaactgctc ctcccatcct cttctctcac gaagccccgc    300
ccgcggagag gttccatatt gggtaaaatc tcggctctcg gagagtcccg ggagctgttc    360
tcgcgagagt actgcgggag gctcccgttt gctggctctt ggaaccgcga ccactggagc    420
cttagcgggc gcagcagctg gaacgggagt actgcgacgc agcccggagt cggccttgta    480
ggggcgaagg tgcagggaga tcgcggcggg cgcagtcttg agcgccggag cgcgtccctg    540
cccttagcgg ggcttgcccc agtcgcaggg gcacatccag ccgctgcggc tgacagcagc    600
cgcgcgcgcg ggagtctgcg gggtcgcggc agccgcacct gcgcgggcga ccagcgcaag    660
```

```
gtccccgccc ggctgggcgg gcagcaaggg ccggggagag ggtgcgggtg caggcggggg      720
ccccacaggg ccaccttctt gcccggcggc tgccgctgga aaatgtctca ggagaggccc      780
acgttctacc ggcaggagct gaacaagaca atctgggagg tgcccgagcg ttaccagaac      840
ctgtctccag tgggctctgg cgcctatggc tctgtgtggt gagtgtcgct gggcctgggg      900
ccgctgtggg cagggtggcc cctcgcgccc gagggccagg cctgctccac tgctcagcgt      960
tgcgtcaagt ggcaggaatt tccctcgggg gagggcattg ctgcccttc gagctctgcc      1020 cgttctgcac ctccagcacc cctcgccctg cactcacgca ggtatgcggt ccaccgtgtg      1080
cagcactcag gtccgctgcg agaggtaggt ggtggtgctg gagctcggtt ctggctagca      1140
ccctgcgcct tccctctcg gagggttgct gctcggcaac aggcaccggg ggaagggccg      1200
cttccttggg ggtctccctg cctacctgga gcagaaggac cctctcccgt gatgcgccca      1260
cgctggggct ccggaccctg ggtcctctga gcagacaagc tcggggaact gccgggagaa      1320
gcagaagggc acagcccaac ccgaagactg cggtcatctg aacaaaactg accaggaagg      1380
gagctctctc cgggcctttt tttttttttt ttttttcaa aactctgtcg aaatcccatc      1440
ttgaaaagcg ttctttttga attcgcactt gaattaacag cgatccatag agcttaaaat      1500
accgacttta tctcggtgag cactgtgcca gcttgagtgg tgtgtttccg attcggttga      1560
aagcgtattt cctttccgtg gaggggcggc ggtggtagtg cctgcaagaa cactgcagct      1620
tgagaaactg gcaggctcac tgattagtca cataccactg ctcatttaag tattgttcga      1680 caaacaatt ttctcatttg gagcaagaaa gattcagatc tgtaaggcgc cctcaagatc      1740
aaaaagttat taacagtgct gggaggtatt gtaaatattt tttgagataa ttcctgcgaa      1800
tactgtgttt taaaagtccc ttagagagct tgcaggagt tatctagtta tctgcattta      1860
tggcctgagg tacacgatgg ttttcgtaag gatatggaac cacatagaaa aggaaggaa      1920 gagatacttt ttagctttaa tttacaccgt gagtgtgttt taaattaagt cgatagcata      1980
taatttccag acctgaaata tttcactaac tgctctctta acttccaagg ttttataccc      2040
tgtattttag attttctata atttgaaagc tacggatctt aaactaagta tcagatttaa      2100
ctgttagctt tttctgtgtt ttagtaattc gtattgtatg cgtcatttga aaacgggcct      2160 gtaaatcgt tttttgttt tggaacaaat tccaggcttt tggatgtgtt aatctttaaa      2220
tatgatttct gtgtttccca aagtcacatc atgaatttcc tgtttggtag aatcttctgg      2280
gtaattgaga ttgtgcaatt gtgtccagca acagatcata ttgcattttc tagttcaagt      2340
tgcttaagtt atgttgcaga tagcaccgtg cttgacatct ttctcccatt tttacagcat      2400
ggcagtttac attttaaagg aatttgcagc attttacatt cagagagtgt gtgtgtgtag      2460
ttggtttgca gcattttaca ttcagtatat acatattata taggtatata cattcagtat      2520
atacatatta tataggtata tacattcagt atatacatat tatatatatc tagttgattt      2580
gctaattttc aaagacgtat ttggatcatt gctcttttaa tattttatag ctcattaata      2640
tacttccatt ttttcattct tgaattgaca tacatttctg tagtatcacg ttttcgtttt      2700
caatgctatt taaattttaa tggagtgata cagcagaata actcaactat agagggtttg      2760
ggtgaactcc aattgaattg cttgcaaggg ttcgctacta ttggtgacta gctctgcact      2820
ggaacaggag attcagattt acagtgaagt accattaaaa ttaactccac agttcttag      2880 tggtatactt ttctgtggta tagaagccag cagtatctga cacttaaaag tacttttatt      2940
ttattgaaca gatttttaa aatacattga cattgtataa aatttgaaag ttttacaaag      3000
gtactcagtg ggccgggtgc agtggctcac gcctgtaatc ccagcacttt gggaggccga      3060
```

```
ggcgggtgga tcacagcgtc aggagatcga gaccatcctg gctaacacgg tgaaaccccg   3120
tctctactaa aaatacaaaa aattagccgc ccgtggtggc gggcgcctgt actcccagct   3180
actcaggagg ctgaggcagg aggatgattt gaacccggga ggcggaggtt gcaatgagct   3240
gagatcgctc cactgcactc cagcctgggc gaaagtgcga gacgccgtct caaaaaaaaa   3300
aaaaaaaaag atattcagtg aaaagtctcc tttccttttt gttctccagc cactctactc   3360
tctcaaagac aggcactgtt aagtgtcttg tgtctttcca gagaggcagt ttttttatt    3420
tgcttgtttg tttagtagtc tttctactaa agggatttaa gatgtaacct acagcatatt   3480
ggtgaaagaa aatacaactg aaactgaaat tgtatgacaa ttgacaataa acaaattata   3540
actaatgttg gaatgaaaat accagaattt agatttacaa ttaagtgtta tcttattcag   3600
agattcagcg tagttatttg aagttttttct tttctttgag acgaagtctc actctgtcgc  3660
ccaggcttga gtgcagtggt gccatcttgg ctcactgcaa cttccacctc ctgggttcaa   3720
gcgattctcc tgcctcagcc tcccctagtag ctgggactac aggtgcccgc caccataccc  3780
agctaatttt tgtatttta gtagagacgg ggtttctccat gttggccagg ctggtctcag   3840
actcctgacc tcaagtgatc tgctctcctt ggcctcccaa agtgctggga ttataggcct   3900
cagccacggt gcccagcctg aagttgttct ttcaatgagt acctttttag gtgtggcaga   3960
aaacattttt tggaacttct tttagaatcc actttggagc ctgtgatatt cttcttcttt   4020
tttattttga acagagtctc cattctgttg tccaagttgg agtgcagtgg caccatctct   4080
gctcactata acctccacct catgggttca agcgattctc ctgccttagg ctcccaagta   4140
gctgggatac aagtgcgcaa caccatgccc ggatgatttt tgtatttta atacagacag   4200
ggtttcacca tgttggccag gctgatctct aactcctgac ctcaggtgat ccacttgcct   4260
tggcctccca aagtgctgag attacagggg tgagccaccg tctctggcca tccatcttca   4320
tttttttgag agcagatttg attttaggga ataacagttc atttgaatcc aaataattta   4380
gggaatttgg actcaagtct gataagaaag ataaggcaat caggttggtg atactactgt   4440
tttaggtcag ataggagtta taactataaa gtaacaacac ataatttttt gtgtgacttc   4500
ttgaactgga cctgaagtct acttccaaaa aaatctccga atttttatttt atttatttat  4560
ttattttgta gagataggg cttactgtgt tgcccaggtt ggtctcaaac tcctggcctc    4620
aagcagttcc cccaccttgg cctcccgaag tgctgggatt ataggatga gccaccacac    4680
ccagcccctg aattttattt tcaagaatga aaataaatga atagaatatt tcaatgaata   4740
aaattcattc attgaaatat ttgtcagttt ccgaattta ttgctctaaa gtgtggtata    4800
ctttgtaaca tttacaaatt attttaagcc tatattattt taatttatac taagtatagt   4860
aaaaaaacaa gtgaagcct gtgtgataac caactatgaa tcaaatagataa gttttacaaa  4920
tatgcctttc cgttaaaggg taagggaac tagactaggt cttgcagttt taaggaactt    4980
tatgcattgt ctgtgagggg aaatgaagca aaattgttta agaatacatt gttgcaaagc   5040
attgattttg gggttttggg acagaagggg agaatctttg tggtgagttt aaggaaatac   5100
aaacaggaac ttaagtgcct ttcctctggg gtagggttct tccaggccct tgctgttgat   5160
tagaggaggt gggacactgg taaccatgaa ataggaggtg acagttgaga attactctta   5220
gatcttattc aactgtttat tcaacagtgt ttattgaata cctaccatgg gccagatagc   5280
taggttctgg aaatagagtg ctaaacaaga cagaaacaag acaatccatt ctctcctgga   5340
acttacagcc tagtgggttt aataactaca ttttgtggat tgcttgctat gttctagcat   5400
tgtgctgtgc actttatcat cagcataaaa agtatataac aaaacctttg gtaaaaggat   5460
```

```
agcaaaactt gctaagaaat caaatacaac ttcctaagtg ctttgtggaa caagattatt    5520
ctagtataaa agaaataagt gaagctaact ttttttaact attaatggcc attcaccatt    5580
ttaaatctat ttttttttt ttttagaatg agccagggca caaagaaata aaagtgcatg    5640
attattaagt atacaagggt gactttcttg actcctgacc agtgagaagg gtgtgccctt    5700
tacttttcta gtagtgatag taggtccatg ctgagctttc cattcttttc tttgtaacca    5760
aaagtaaggt agttgcctgt atgttaccag tgccagtcaa taagaagtct ttaaacataa    5820
ttaacggcaa gcatttgtat tattgatgta taaagattgt tttaagaaag agttcattcg    5880
aagctggcta taaagtcatt ttattatcaa atcccatttt tccactttt ttttttttg     5940 agacggagtc ttgctgtgtt gcccaggctg ggcgcagtg gtgcaatctc ggctcacggc     6000
agcctctgcc tcccgagttc aagcaattct cctgcctcag cctcctgaat agctgagatt    6060
acaagtgcgt gccaccatgc ctggctgatt tttgtatttt tagtagagac ggggttttac    6120
catgttggtc aggccagtct cgaactcctg accttgtgat ctgcccacct tggcctccca    6180
aagtgctggg attacaggaa tgagccacca cacccagcct ccactggttc ttctttaaaa    6240
taagcttatc ctggatctcc aggttttcag ttctgccagt ttgatttctt gatactgagg    6300
agtactctgc ttttgatttc tttctagccc agtctcagag atgatgtgtt gactttgcct    6360
ttcatgggca agagtgcaga tattgctgag cccctgggc ctagaattca aagatggaag     6420
aattcactgg ggtagatcac cctcactta gaattaactg acatttttag ggattttgc     6480 agtttataaa gtgttttcat tcaaagcatt atcaatcagt tctcactagc tccatggagg    6540
ctcatattta ttaactccat tttatagatg gggagctgga ctcattcatt aaaggaatgg    6600
catacttgtc aatgctactt ttagtagtct cctttctgat agatgtgggc tgctgaggtt    6660
gcgcggtggc accttctctt atgcagttaa cctcctcttg tgaaaaggg gttgctgagt     6720 cactcggaat agagcttgag tgtaggaaag cagttccacc agtgtcattg cccagtttat    6780 gtgagggta atgacttaac ccatttaacc cattagagtc atgtctcttc ctcagaactg     6840
ataaatcaaa aatgcactca ttgcccagat taaaattttt tctgaaggaa ttattaggca    6900
gtgcaaatag ttaattcctg aatttatgaa tcctattgga ttgaaattct tcagtgtaca    6960
tttatgtaaa gttgggactg tctgtacatg tttgtgttac ataagtatag gatataaata    7020
gaaataactg cctctccagc cctttgaaaa tacattagat ttttgctttt tgcagtaaaa    7080
tttggggtaa aactgatttg ttcttatcta agaggtataa ttactgcagt gctcagaaaa    7140
gcctcattat aaagtgggct cccctgactt ggaacttagg gatgtcttct catggctgct    7200
atggaagtca tgcagctgtt tcgtcaggaa aataaccaaa aacttcttta aacttggaaa    7260 tgttttgta aaagaaactt tcagtattca gagtagtttg tctttcacag tgcttccata     7320
aattaagcac aggcacaact cgttttatta tgcttcacag ataattgctt ttttttgca    7380 aattgaaggt tagtgacaac cctgtggtaa gcgagtcttt tggcaccatt tttccaaaag    7440
catgtgctca cttcatgtct ctgtgtcaca ttttggtaat tctcgcaata tttctttctt    7500 tcttttttt tttttttt tgagacggag ttctgctctg tcgcccagac tggagtgcca    7560
tggtgcgatc tcggctcact gcaacctccg ccttccggtt tcaagtgatt ctcctgcctc    7620
agcctcccaa gtagctggga ctacaggcat gtgccaccac acctggctaa ttttttgtatt   7680 tttagtagag atggggtttc accatgttgg tcaggctggt ctcgaactcc tgaccttgtg    7740
atctgcctgc cttggcctcc caaagtgctg ggattacagg tgtgagccac catgcccggc    7800
agttctgctg ggattacagg tgtgagccac tgtgcccggc agttctcgca atatttcaaa    7860
```

```
ctttctcatt attattaaat attatgggga tctgagatca ctgatctttg atgttgctgt   7920
tgtaattgtt ttgaggtgtc tggaaccatg cccataggca gacttaattg ataaacattg   7980
tgtgtgttct gactgctctg ccaaccagct gttccctctc tccatctcct aaggcgtcct   8040
tattccctga gacacaataa tactgaaatt aggccaatta ataacactac agtggtttct   8100
gaatgttcaa gtgaaaggaa tgtttgcatg tctcttactt taaatcaaaa gctagaaatg   8160
attaagcata gtgaggaagg catgtcgaaa actgagataa gctgaaagct aggcttcttg   8220
taccaaacag ccaatttgtg aatgcaaatg aaaagttttt gaaggaaatt aaaaattata   8280
ttccagtaaa caaatgaatg attagaaagc aacacagcct tgttgctgag ctggagaaag   8340
ttttagtggt ctggataaaa gatcagacca accacaacat gcccttaagt caaagcctaa   8400
tctagagcaa agccctaact ctctttaatt gtatgaagtt tgagacaggt gagaaagctg   8460
caaaagataa gtttgaagct agcagagggt ggttcatagg tttaaggaaa gaacctgtct   8520
ccatagcata acttatagtg caaggtggct ggggcggtg gctaacacct gtaatttcag    8580
cactttggga ggctgaggca ggcagatcat ctgaggtcag gagtttgaga ccagcctggc   8640
caacatggcg aaactctgcc tctagaaaaa atacaaaaat tgtttttta tattttttgg    8700
tgttgtggtg tacacctata gtcccagctg cttgggaggc tgaggcagga gaattgcttg   8760
aacctgggaa gtggaggttg cagtgagcca ctgcaaccaa gtggcaaccg agatcgtgcc   8820
actgcactcc agcctgggcg atagagcaag agtacatctc aaaaaaaaaa aaaaaaaatc   8880
aatagatgag aaattgcttc tcaggaatga ataaataaag tagtttcttg aggtggaatc   8940
tgctgttggg gaagatgctt atgaacattg ttgaaatgac aacaagggt ttagaatatt    9000
acataaactt agttgataaa gcagcagcaa ggtttgagag gattgactcc cattttgaaa   9060
gtagttctac tgtgggtaaa atgctatcaa acaccattgc aggctacaga gaaatctatc   9120
acgaaaggaa gaataaatca atgcagcaat tcaccgttgt cttattttta gaaattgcca   9180
tagtcattcc agtcttcagc agttatcacc ctgagtagtc agcagccatc accctgagta   9240
ggcagcagcc atcaacactg agacaagacc ctccaccagc aagaagataa taacttgctg   9300
aaggctcagg tgacccttag cattttttag caaaaaaata tttatttatt tatttatttt   9360
ttctagatgg agtctcgctc tgttgcccag cctggagtgc agtggcacga tcttggctca   9420
ctgcaccctc cacctcccag gttcaagcaa ttctcccacc ttagcctccc gagtagctgg   9480
gattacaggt gtgcaccacc atgcccagcc aattttgta tttttaatag atgggggtt     9540
tcaccatgtt ggctagcctg gtctcaaact cttgacctca gcgatcctc ctgcctcggc    9600
ctcccaaagt gctgagagta ataggtatga gccactgtgc ccggctaata aaatattttt   9660
aaattaaggt atgtgcatat atatattttt ttgacatact gctagtgcat acttaataga   9720
ctacagtatc atgtaaatat aacttttata tgcactggga aaccaaaaaa tttatgtcac   9780
tcattttttt gtgatattca ctgtgttgtg gttgtctgga actgaactca tgatatcttt   9840
gaggtacacc tgtatgtatg tgttaaggat ttacaaaatt aaccagcttt cccgtgcagt   9900
gttcaagtct tttaataatt tattataggg aagaagaagt ggtggtttgt aaattctgta   9960
cttgacaaat ggatactggg ttttgggcat gcttggctcc aaggctgaat gttggggaa   10020
agaagtatag gagagtgagg agtctaggat ttctaagttt tggccttggg caaatggata  10080
tattttagtg ccattttctg aactttgtgt tacaaagtta caaagagtg ttacagggta   10140
caagattgta gagagaaagg ggaaggagca taggttcatg gtaatctcct tgaggacagg  10200
actcattata ccttgagtgc ctaccatgta tggtttgccg taagtgctgg agatgaaatg  10260
```

```
tgaacaaaag agacaaaaat ttctgcctta agaagctata ttctggccag gtgcagtgag   10320
tggctcacac ctgtaattcc tgcactttgg gaggccaagg taggtttcct tgagcccagt   10380
agttagaaac cagcatcctg ggaaaaatgg ggaggctcct ctactaaaaa ataaaaataa   10440
aaaattaggg atgcttggtg gcacactcct gtagttccaa ctacttggga ggctgaggtg   10500
gagggattgc ttgagcctaa gaggattgct tgagcctggg aagttgaggc tgtagtgagc   10560
tgtgatcctg ccactgtact ccagcttggg tgacagagtg ataccctgtc tccaaaagaa   10620
aaaaaaaag gaagctatat tctaatgggg atggcagtgg aagtagataa taaacaaaat   10680
atatagtgtg tcagataagt gctgtggaga aaatgcaaga agggaaggag agtgagtgct   10740
aggatggctg ttgcactttt aagaaaggtg aatacggtaa gcatcattga taaagtaaca   10800
attgagcaaa aacctgaaga aggtgatata ggacactggt tggacatggg tgaggatgtg   10860
ataacattct aggctgagga ttagcaagtg tgcaaaagcc ctgaggtaag ggccctgtgc   10920
tccaggaaat agctaagaga ccagtacagc tagagctaaa tgaaccaggg gccaaatata   10980
gggagaaaag tggggtgagg agagggttgc agatatgcag ggatcatgta gggtcttatt   11040
tgcctttgta cagactgtga ctttttccttt aagtgagagg ggaagccttg gagggttatg   11100
accagaggaa ggacatgacc taaatcttgt tttaacagat tactgtgctc tagggtccca   11160
agttttttcgt ttcggttcct tacccattct accctaaacc actactgtga ataggataga   11220
acggtggagt tagatgaatt ggtgcaagcc ctgacccatg ctcacaactc tcattccagc   11280
agtcccagag tgccagagcc agtattttttg ttgggcccta gaaatttagg gtattccagt   11340
ccagctcttt aaataacatg ggctgacttt acttttttcag gttttttgttg ccaaaaggaa   11400
ggagcagaga ttagctcttg agtttagctg aaaaaggaag attagtctgc tggcagattg   11460
agtgtttttt aacttctttg gcttttaggg ttttttcttac ttttggatca tgttttaaaa   11520
gtcattttta ccttctttca acagttaaac atttaagttt tatttgattt tatttgaccc   11580
tttttctgct ttacattcct ctgccttttc cccattataa tacttttagt agaggttaga   11640
ccattgttat ctgtcattaa tgtcttagct tgaggcccc aaggacttct ctgttaaact   11700
taaatatatc atatagattg aaagattatc tacagacatg tgatcctata aaaacccata   11760
ttatttattg tcctccctgc ctttacagat gtaaacccct ctcctctttt catcagagct   11820
cccccctcttt tactgctcta tcatcaggtt gcagaaaata agttttcctg caaacataga   11880
ttcccatggc aacataacaa aaaggtaata gaacaaatgt ttattttgtc tagacctgct   11940
gtctgagtac cattagaccc tgaacatgtt ggctcctgtt atttgaatat gtggttacaa   12000
attccttatt ttcctcaaaa cttacttctc ttaggccttg gtgatattgt cactgtgcct   12060
gtgatatgaa ggaaggtgtg tgtgtgtgtg agtatgtgtg tcttactgtc attctactca   12120
aaagtgtgta ttgattgcat tttcaaactt atggcttaaa atgtagacac cacacaatct   12180
gagcatgtga agaaaaaaag cataccagtt ttgttctttg ttttcgtaag ttcattaatt   12240
taatatttcc agtgcactat actagatatt ttgtttacag agattttaaa aaaagaagg   12300
gtccctcctt tcgaaagtat cagtccaggc tgggtgcagt ggctcacgcc tgtaatccca   12360
gcactttggg aggccaaggt gggcggatca cttgaggtca ggagtttgag atcagcctgg   12420
ccaacatggt gaaaccccat ctctacaaaa attagttggg catggtggtg tgtgcctgta   12480
atcccagcta ttcaggaggc tgaggcacaa gaatcacttg aacccgggag gcggaggttg   12540
cagtgagccg agatcactcc cctgcactcc tgtctgggcg atagagcaag actcagtctc   12600
aaaaaaaaaa aaaaaagaa agtatcagtc cagaggagac atatttatgt ttcctcatag   12660
```

```
atggctttgg aagtcctctg tagttttgga tcttgaagca ttttaggttt tggattttca    12720
gattagggat actcaacctg tataacccag ggtaattcaa cctattgaca ctttaggtgg    12780
gataatgttt tgttgtgggg gactgacctg tgcagtgtag tatgtttagc agcatccctg    12840
tctccaactc actgtatact aatagcaatt cccagttgtg acaaccaaaa atgtctagac    12900
attgccacat atctcttgac gggtagggag ggcaaaatca cctttagttg agaaccactt    12960
atataaccct atatatttgg attgataacc ctgtatattt gattgagtaa aaactagatg    13020
ggataacatg aaccttccac ctgcaaaaag gcagaaatgc tatactttct gcattataaa    13080
ttgggcctct ctaaacatga ttttgttat ttctaggaga gtaacagcat ttctaatggt    13140
caaggtccta gctataaccc aataagctta atggatggga gaacttgcac aagcatgttt    13200
gcaagaggcc aggtgtatca ctggcacatt tgagaaacaa ctaattagtg agggagaccc    13260
aattttcatg aataattgtg ttttgtcatt gtcatggccc caacttaggg tgttttgaat    13320
tttttctgga aaggaaatta gcatgaagtc caagttggta ggtaggtagc attttcccta    13380
gtgtctcttc tggtattctg tgtccttttct ctcctgtctt ctttcagtat ttagcgtttt    13440
caaactccta gaaataaaat gctgtttaga agaccacaaa gagagctgca cataaactaa    13500
ggagcaagaa gtagtacatt gtgaattaat tttctgtatg ttttttgaagg ttcttgcatc    13560 tgggaaggct tgcttagttt taaaaatatt aggtaataac agactgaaat tttgaagatc    13620
ttgtggatct caggtagcag taactcagga agatcagcct tctttgattt agaatgtcat    13680
ttaggcacat tatgtattct ggtaccttag aagatacaat gcattttcct gaattatcat    13740
tgctactgct ttaattactt taagggtgtg aggcagtaac taacttagt gtcacaatgt    13800 atacatctta acatttattg tgctcttttt tttttttta aacaccacct taaagtactc    13860
tgctattcag atttttcctt gtgtttctct aattctccta tttcatccat tggtcagttt    13920
tttcttcctc ttttctttct gctccatgat ccattcttaa attttctttt ctctttctgt    13980
gcatattctt tttgaattca ttatctgata gtctcaacaa tggtcttgtt catatactat    14040
ccttccaaat ttgtactttc aaacctaatc tcaagaatga ctgatccttt ggattctaaa    14100
tctattgaga tgtaatgttt catgcttttc cttgattact ttcctacaca cttcttgaag    14160
ataccagaga tgtagcacta acttccgttg gaatgggatt catgttacaa gcttgaatgg    14220
ttcagtttag atatgtgaag cggatgtcat cattagcact gatgactgac agtagttata    14280
aaaattacaa tcaggaatga accaatttac ctgaagtttt caataactct aggtattaat    14340
gcaacataat tttgaaagtt tgaaatatat aggtataaat attgatgctt atattttaga    14400
tttactgtag tgaaggaaat ttgccagtcg tccatcagtg ttaaatgccc accaatgtgt    14460
aaaagaaata gacctaaaat attaataaat tgtgtatata tgtatgaagg tattgatgtg    14520
tacagagaag tggagacatt gtgagttata gtggtcagta tggttttatg gagcagaaag    14580
gatttgaaga ttatttagaa agatgggtat ttggagagaa gaaaaggaaa cattttcaga    14640
caagagaaaa cataaaccaa gagaatagat atgaaaagga ctgttctgac aggaggaaca    14700
tctcaggtag ggtgaaccca gttgtggttc tcattcttgt tgtgcttcag actcacttgt    14760 ggaacttta aacatacctc tggaaattaa gaatgagatc tggagtggga cttaggcagt    14820
tgcatttcta aaaagtctac aaatggttct ttaggtagta gagagctgtt ggagtttctt    14880
gagttgtgaa ctgtggagga aaattgtttt aaaattggtc ttggtggagt gtaaagaatg    14940
gattagagga aacaaatgta ttgctttgtc aaagtctggt aaatttatgt gtgcctctgt    15000
tcattttgac tcctcggcta gatttcttag ttccttgagg tcataaacaa tcagctttta    15060
```

```
aagcttcagt gaaggaatat ctttttttt ttttttttt ttggctgggt tgggggacag    15120
ggttttgctc tgtcacctgg gtggaagtgt agttacgcag tcaatggctc actgcagcct   15180
tgaactcctg agttcaagtg atcttcctac ctcagccacc caaagtagct gagactacag   15240
gtgtgtgccg ccatgcccac ctaatttttt ttttttttcg tagacacgag gtctcactat   15300
gtcatgaagt tgcccaggct ggtcttgaac tcctgagctc aagcttcctc ctgcctcaga   15360
cttccgaagt gctaggatta caggtgtgag ccaccgcacc tagcaggaaa catcttataa   15420
aatcattcta ctttcatttg gaacttgcag gctcgtgcct gcaatcccag cactttggca   15480
ggctgaggca ggtgaattac ttgagctcag gagctcagga tttctaaacc agcctgggca   15540
acatggtgaa actttgtctc taccaaaaat ataaaaaat tagccaggcg tcgtggtgtg    15600
cctcagtagt agcagctact cgggaagctg aggtgggagg tttgttgggg cctgggaagt   15660
caaagctgca ttgagccgtg atcatgccac cacactctag cctgggcaac agagcaagac   15720
cccgtctcaa aaaaaaaat taaaaatgaa agtaagtttc attaaaaaat actatatatg    15780
taattacagt ggtgaaattg ttttgtgatt aaataaatac tgttgtgttg acattaaaac   15840
aagatatttg agagttagcg aagatattaa agctaatgtt ttaaattttg agttttaaa    15900 gtcaatctta aatctcctgc tactctgaag aagataaatg tatataattt taattttct    15960 atttcactag gtttgaagaa tattttttga ggttcctaaa tcaaaactta agttccaatt   16020
tttgcataaa gttgccttta ttttcaagac gttatttcca aaatggcagg acagagcatc   16080
cgcttcagag caacagtgat atttgcacat ttacttgaat atggaaggaa gaaaagctag   16140
gcttctgtaa tagaatgtaa catgtgcaga aaaatatttc cagtatgtca tttattgaaa   16200
tttgttccag gtgctacagg taaagagaaa gttccaagtt agtggtctta attatttagt   16260
tatttagaag gcaagttttg aagactatta ttaattatcc tgattcagtt ggaaaaaaag   16320
cctgaaattg tatgatccgg agaagaggtg tcatgttttt gcaaattatt tcttctcact   16380
ttatagatat tctttttct ttttctttct tttttttt tttttttt ttgagatgga       16440 gtttcgctct tgttgcccag gctggagtgc aatggcacaa tctcagctca ccacaacctc   16500
tacctcccgg gttcaagcga ttctcctgtg tcagcctccc aagtagctga gattataggc   16560
atgcaccacc acacctggct aattttgtat ttttagtaga gacgggattt ctccatgttg   16620
gtcaggctgt tcgcgaatac ccaacctcag gtgatctgcc cacctcggcc tcccaaagtt   16680
ctgggattac agtcgtgagc caccgcaccc ggccctcact ttatagatat tctaatgaat   16740
ttaatgtatt aatgagactt tgctaattca gtgtaactac agatttcaat atatttaaat   16800
atttccatta acttccaaaa gtaaaccaaa ttgtgtttat cttcttagaa gtcatctatg   16860
accattgaaa gaaattgtaa aatcacttac gatccccaca aattactcaa agacttgctg   16920
agtgattact cattcttcat attctgttga tgaaaacaca gattgttttt tgaggaaaat   16980
catggtgcag tcgtttgtac tttaatactc tgtggacatg gcacttgtc cagcaccta    17040 cctttcttaa gaggttgtct cccttctct actcagctga tgttaaattt attgatctgc    17100
cattacctta taacagaaaa tctacaagtc aggtgcccat catggaatat aaacacaagt   17160
tccctatatc tctataccta tcaaaagctc agttgacagc cgaacatggt ggctcatgcc   17220
tgtaacccaa acactttgag aggctgaggt gggaggatcg cctgaggcca ggagttcgag   17280
accagcctgg gcaacaagca aggccccatc tctacaaaag aaaattttaa aaataataaa   17340
caaaaagctc attgatagct ccagtcatct ttggaggatt gtctgaagaa tatggagctt   17400
atctgttttt ctaaatgtat ttaagatttc ctcttggatt aagtctgtca gagaggccag   17460
```

```
gtatggtggc tcatgcctgt aacccctgta cttattggga gtccaaggca ggaggatcac   17520
ttagcctagg agttcaagac cagcctaggg aacatagtgg gaccctgtgt ctacaaaaat   17580
caaaataatt agcgaagctt ggtggcacat gcctgtagtc ctggctaccc aggaggctaa   17640
ggttggagga ttgcttgagg ccaggaggtt gaggctgcag tgagccatga ttacatgact   17700
ccactccagc ctggatgaca gagtgagacc ttaaagaaaa aaaaaaaaag caacaccgta   17760
atattttgta ctcctaccct ctttgctaat aatgaactgt attttggcct tacgacagca   17820
atctgtactg atggatgctc taaaaagaaa accatctgaa acccactatt atattctttt   17880
aaagatgttg attaggacat ttttaccaca ttatatgtct ccttcttgaa cagacacaga   17940
atgaactttt ccctggttta ttacaggaat aattatgcct ctcttcagct ctcctgagta   18000
cctggttggt ttttattgta tggcttctgt gattcatgtc ctaactgatt ctgttctctt   18060
tgttaatggc tttagtgagc tttgagccaa atttgaggcc tacctctaat gggtatttaa   18120
aaaggacctc tggccgggtg tggtggctca cgcctgtaat cccagccctt gggaggctg   18180 aggtgggcgg atcacgagat caggagatcg agaccatcct ggctaacacg gtgaaacccc   18240
atctctacta aaaatacaaa aaaactagct gggtgtggtg gcatgcacct gtagtcccag   18300
ctgctgggga ggctgaggca ggagaatggc gtgaacccgg gaggcggtgc ttgcagtgag   18360
ccgagatcgc gccactgcac tccagcctgg gtgacacagc aagactctgt ctcaaaaaaa   18420
aaaaaaaaaa aaaaaaaga aagaaaggac ctcatgatat atgctaacct cagctgtaca   18480
gactttctta ttttcccctta atcacttacc attttgtcag gttttatata taaattcca   18540 gtctgcttta aatccattgt gaataaagga aggtatacat caataaattt agaagttaaa   18600
cagaattata ttaggatata tgaagaatct agtaacccac attttctatg tgtgtgtgac   18660
acaaggggag gcaagtatga atgtgtaaca aaacattgaa gtttatttaa tgattatcct   18720
tgtgtgttat gtactggatt cacggtcagc agtagatgag tgagaatgac atcctaatat   18780
tgtaataact gcttctaatt tttatatttc tttcagttat tttttactat accaatgatt   18840
ttataaaatg tgaattaatt tgataatttt ggaaaagttc atgtaaattc acaattgggg   18900
gaaaaacttg ttaaacagta tgtcctgaat tttagtttgg agaacctgtt tatcataaag   18960
ataatttcat tttatgatgt tgttcatgaa aacaaggttt tacttgtagc tctacttta   19020 cagatgtgat tgagaggcgt atttgagctt tgccatggac caagctcctt gccaaaccta   19080
ctataaaagt tattacattt aatcctaaca tatccaacag atgaaatata aacataattc   19140
tcatttcatg aaagaattta attaacatcc tcaagattat atagctatta agtggcagaa   19200
ctggaattaa aatccagata gtctaattcc aaagtcccag ctcttattta atcactctgt   19260
tggagtatta taaacatgta ataataaatt gtgattgttg gggtctatag gtactgatt   19320 aattctagcc tgccttttgc tgaatagatt caggagtcaa atagagataa aaatatttac   19380
ttttattagt aaagctggca tgcagagtgc cttgggcggg caactcaagt gggcttctta   19440
tttcttcccc agttaattga acttgcacac ttaatcagtc agatcagcta gaaaactgct   19500
gctgttcctt gctccccagc aggcttacca atggaggaga gaagaaagtg ttcagcttgc   19560
aggtggaagg caaactctga ggtgggaagt tgaagaagct gggtcccaca ggggcaatgg   19620
ccatttttcc agtctcacca gagctagttt agagaactgg gtttagagat gagtatacat   19680
ttacttgcta cttttgagag ggaagaagtt actaatttat gggtttgtag gagcaatggg   19740
agtggaaaag aagagaacca ccaccctctt ttatgtgaga taaggaagga gtcagtgagg   19800
gtgttgtgac agagtaatgg cttcttagag gtccctaaca ggttcctgag caggtgacta   19860
```

```
tttaaaccaa tacttgaagg ataaggattt agctatgggg tgggatgggg gcggaggaga     19920
agaaaatcct aggaaccagg agcagcctgt ctgaatagtt aaaagaactg aaaggagcta     19980
gcagaacata gcagctgaga gagagggaaa gagtagcaca ggaacaggtg gaataatcag     20040
tggtgaccag atcacctggg ccttgtaggc catcatgaga aatttgcatt ttactctgta     20100
tgccaaggag attccttgaa tggtttgaag gaggggagtg ttgtgatcta atttgtactt     20160
ttattgctat ttttttatttt tcattttga gacagtctca ctgtatcttc caggctagag      20220
tgcagtggtg ccatcatggc gcaccacaac aaggttgagc agcttcagcc ttcctgggct     20280
caagcaatct tcctgcctca gcctcccaag tagctgggca tggtgggcca tgcctgacta     20340
attttttttt tttttttgag atgaagtttt gctcttgttg cccaggctgg agtgcaatgg     20400
catgatctca gctcactgca acctccacct ccctggttca agcaattctc ctgcctcagc     20460
ctcccgagta gctgggatta caggtgcctg ccaccacacc cagctaattt ttttaaatat     20520
atatttttag tagagatggg gtttcaccat gttggccagg ctggtctcaa actcctaacc     20580
ttagcctccc aaagtgctgg gattataggc gtgagccact gcgcctggct gcctaatttt     20640
taatttattt attattattt ttttgagaca gagtctcact ctgttgctaa ggcttgagtg     20700
cagtgatgca atctcggctc agtgcaacct ccacctcctg gattcaagtg atcctcccac     20760
ctcagactct caagtagctg gggttacaag tgtgtgccac cacacccac taatttttat      20820 atttttttag tagagacggg tttcaccatg ttggccagac tggtattgaa ctcctgacct     20880
caagtgatcc acccgccttg gcctcacaaa gtgctgggat tacaggcgtg agccactgca     20940
cccaacccgt ttttattttt ttgcagagac agggtcttgc tatgttgctc aggctgatct     21000
caaacttctg ggctcaagca atcctcctgc cctggcctcc caaagtgcta ggattacagg     21060
cttgagccat tgtgcctggc ataatttata ttttaaaag actgtattgg atgcatttgg      21120
aaagcatatt agaaggaggt aggccagtga catggactaa tatgatattg gtgaaatgaa     21180
gagcagttga ctttgagacg tcttttggag gtgaaaacca tgagacttgc caatagattt     21240
gaatgaggac tgaggaaagg gagaaatcaa ggatgacaat caaatgtcta gctcgagcaa     21300
ctggatgaac agtccattta ttgagataac agagccatgg agaagaatag ttctgggtgt     21360
tttgaacttg gtacgcttca ggtgcttatg tgtctttctt atggagacat cagggctcag     21420
agaagagatt tcagtgagag acataaattt gggagttttc aatatataga tggcatttaa     21480
tttaaagtca tgggcataga tgagattatc tagaaagaga atgtgggaga gagaagaggg     21540
cccagtacca agtcctgaag aactccaaca tacagagttt gagtagaagc agcacatgca     21600
gtggagacag agatggagct gccagagggg tcatagaaaa ccaatggaag tgttgatata     21660
gactccagga tggacagtat ttagagaaag tggtgactat gtcaattact aatcttagaa     21720
aagtggattt ggtagcagag gtcattaatg accttgagaa gagcagtttc agtggaattg     21780
gattgaggaa agaatgggat tgaaatgagt cagttgtgta gatgtgtgct tctcacacct     21840
taagaggtat attaatcacc tggaaatctt gtcaaaaagt aaattctatt ttagggccca     21900
agatctcctt tcctttcctt ttcctttctt ttctttttc ctttcctgtt gtctgcagag       21960
atcctgcatt ttctaatgag ctcccagata atgtcaatgc tgccggtcca tggagcacac     22020
tttgaatagc aaaggtataa attagtggtt ctcaaactgt aatatgtatt agaataacat     22080
ggagagcttg ataaaataca gattattaga cccacttcaa agtttcttat tccattaact     22140
ctggggtggt acctgagaat tttcatttct tataaattcc caggtgaaac tgatgctgct     22200
gatctgggaa cctctggtgt aggtgacttt tttggagaat tttaactgtg atggagaact     22260
```

```
gttaagggaa gtcttttgtt tgttggctga aggcggtaaa caagtagagc aaatttatgc    22320
tgatgagaat ggtccagtag atagggagac actgatgatg caagagagaa gaggaatgaa    22380
gaagtgaaat ccttgagaag atgagggagg tggctccaaa gcatgtattg tggtcttgaa    22440
ttttgataag cagggcata ttcttagtta tagcaagagg gaaggtggag acgatgggtt     22500
tatagatttg gggctaagca aatggagctc ccctcctgat ggtttctgtt ttctcagtga    22560
aggcaagggc aactcttgag ggaagagggt gaattggaga tttgagagag aacatgtcaa    22620
acgatcattt tcgagtagga aaatgaactt actagaagaa aatggcttta ttgagagcct    22680
ctttgagatt aaggtcagaa actaagaatg aaaatctgat tctacagtct ttcttgttca    22740
acctcagttc cttggattca gtcatggaga attaagtggt tgagattacc caaggttaga    22800
ctttatccag gtgagtacat cagagagaca gacagacaga gagagagaag tgcaagggag    22860
tgattataat catggaacag gaagggagat gaagacagaa gagggctgaa ggatagaaac    22920
aagcaatgac aatgaggtta acaaattgtt gtagtcaggg tacaagtaaa ctagaggtaa    22980
ctaggttttt gatgaaaagc aaatgctgct ggcattcaaa attttgtagg tggggcagtt    23040
tttggtagga ataaaggtct agaatgtgac catgaagatg gctgggtgtg gtggagtttc    23100
ctagagaggt caggaaacag gatgttgggt gtgccgttca cctggatgtt gaagttgcca    23160
agaatgatga cagaagttga gagtgtagag agatcttctg gatagaaact aacttttcaa    23220
tgaatgatgg aaaatttcag gtcagtggat acctgcagca gagagggata gtttatcagg    23280
gttgtgagca ggaggtattt tatagaacaa acggaaagta atggtcctga agtggtaacg    23340
gctgccaagg aagactccta cgcacctgct agccaggagg tatctgggct attagagaat    23400
gctttctaat ggcagggcta taagagaagc agtgtcttct agaaatggcc tagtttcaga    23460
gatggagggg aggttcagaa aagaggttga agatttatag gagtttatca caaattggga    23520
tttgaagatt gagggtatgc cataaaagtt tgggagtgaa aggaagggca ctggagtagg    23580
tacagagttg taaaagcaag tttggcaggc agagagtttg gtgataacag atgaccagaa    23640
agtcttggat acatgttaga gactgagaca aactggagga tgaggcataa tggaactggc    23700
ccagacaatt tctgttatta ctatttttt tttttttga gaccgagttt cactcttatt      23760
gccaggctgg agtgcgatgg tgcaatctca gctcactgca acctccgcct cctgggatca    23820
agtgattctc ctgcctcagc ctcctgagta gctgggatta caggcacctg ccactgcgcc    23880
taattttgta ttttagtag atgggggtt tcaccatctt ggtcagactg gtctcgagct      23940
cctgacctcg tgatcctccc gcctcggcct cccaaggtgc tggattacag gcatgagcca    24000
ctgtgcctgg cgacgatttc taaaaataat taaaatacac atcgcatttt tgctatagat    24060
gtcctccatg atctagctgc tgcctgcatc tcttacgtca tcccttccca ctctcccctt    24120
gctccctgtg ctctacccac acagcctttc tgtctttctg tcactcactc cagcatgcca    24180
tacgtttcct acctctgttt cttttttcgt ttgtttgcac ttgctcttct gagagatagc    24240
agagtcaagt ggtcagtagc ataagctctg gatccagact ccctgctctg ccgcttttaa    24300
gctttgtgac cgtggtcaag ttacctaact tctctctgct tcagtttctt acttgtaagt    24360
gggagaatga taatagtact tatttcatag gggattcggg gaaatacaaa agctgaattg    24420
agacaaataa atgtaaaggg cttagaacaa tttcttgtat gtgtgggtaa agactctata    24480
aacattaata ttattattat ttcttctgct tgaagctctt tttcttatat atttatatag    24540
ggaatttaat cattatattg tttccttctc agctcagatg tcattcctca gccatcctag    24600
ctaaagtggt ataactccac tggctttctg tcactctta tcccattacc ctttttattta     24660
```

```
gtcatagtat tttcatcact acttgaaatt attttattat tctgttctgc tcttccccca   24720
ttccctgaag gtgccaagta ctttgtaggt gctcaagaaa tatttgtggc aatttattgt   24780
cctgaaaaca tggtttcctg ggcctcgact ctgagcaggc agcagatgtg gcaaggtgac   24840
gacagtgagg cctaggcagg gaagacagaa ttcaactctg tttattaatc tgttggctca   24900
tctagatcag gcagctgcca gttttttgtaa attttattag aacacagcca cacccatttt   24960
aaaacttatt ttctggctgc tttcctcata caaccacaga gttgagtagt tgtgacagag   25020
gtcttactta caaagttgaa aatattacta tctggcccctt cattgaaaaa aatttgctga   25080
cttctgattt agatacatag aaaagacaag gagaaaacac caaaaataat aacagaagct   25140
ttatttggat aatgggataa taggtcatttt tgcttttttat ctttatgctt tttttttggta   25200 ttttgttata gacccttttaa tttggaaata gccttataaa taccccaaaa taatatttag   25260
aacagctttt taatggtggg ttttttccct tttttctcct tagtgctgct tttgacacaa   25320
aaacggggtt acgtgtggca gtgaagaagc tctccagacc atttcagtcc atcattcatg   25380 cgaaagaac ctacagagaa ctgcggttac ttaaacatat gaaacatgaa aatgtaagtt   25440
attcattcaa ggaagaatac attttgatct tgaatagact ggggaaaaat gttttaatta   25500
ctgcagatgg aaatacgctg gagtgcatca aacgttggtc cctgctcctt gtcctggggt   25560
gttagtggcc acttggttat gtcaggtcaa agacttggaa tgaaagtgat gcatcttcct   25620
ggagttttag ttttactcaa agattttttag aggagaaaga actctttaaa attttaaaat   25680
taaaggatat gttatgaaat acaacacaaa attcacaata attttttaaga gaaaatatta   25740 aaaagaagtt atgtattctt tgcctggttt tcctaaggct atattatgag aatatgggag   25800
tctgtggcta ttaaaagaca aaatagccac agactcccat attctcataa tatagcctta   25860 atattttttaa gtggaaaaat ctgagaaaga gtgccttagg ctcactgaaa gtcctatcag   25920
agatggctat tatttttatat attttgttaat aattttttctt tttttccaga ttcacgtatt   25980
ttaataaata tgtcagaggc attgtttaag ttaaatataa ctttttcttt tttaccaatt   26040
tgttgattca gttgccattc tgcaaagatg cttacaaatt ctaatacgat aaataagtgg   26100
atataattgg aatactaact gaaagtaaaa agacagttga ctgaagacac ttatttttact   26160 gaatttcaaa atcaagttat gaatttctgt gactgctata tgaagggtac tgtgaagttt   26220
gtagcattgt ggaaacaatg gccatagaga tttcaaagtc ctctggctgt actgcttgtt   26280
accttgtgga agaaaattca aaatctgtga atttattatt tgactattta gactgttttta   26340 gtaatttaac ttcttcatag cgagaaaaaa gtcacagata agtgactctt cattagcgta   26400
catttgtttc attagtgcaa atttcttcta aattgagaac attaagactt aaatttgtaa   26460
ttggattatg gatgccatta taatcacagc tgctgctttt tattttcaca ttttattttg   26520
attgtatgct attgaggaaa tcctatttct acagacaact tctattcctg agtataattt   26580
tacttaagta gctatgtgca aaccagagtt ttaagaatgt tcagtgtgaa gctgcagcct   26640
tcctaatcag tgacatgttt acaagaagtt gagatatgcg gaaaaagctg gcagcagaaa   26700
ctttattcct aggtctgcat aaaatcaaag tggcctggca gctttaaggg atgtgtttgc   26760
gtttgatttt taacacattt aagtgtgtat gctgttttttc attacacatt attatatgtg   26820
acagagacag tgtcacagct ttgcaagtat aaaggatatt ttgaaagtga aatgcaagcc   26880
aaacatttat ggaaccccag agcaccttttg ggagccacta ggatcctatt gatgtggcta   26940
tgctaattta agaacatctg gtttaggaga ttatcagtgc tacactgatt gttttgcttt   27000
tcttcataaa tatgttaagc caatgtttag ggatcatggt attagaaaaa taggatttta   27060
```

```
atttctatac attgttttat aagtggcttg cttactagca gtcttttttt tatataaaga   27120
tgtttaagtt ctaacagttg gtggtcacct agatatcagt gatttgttat ttaaacaaaa   27180
taaggcacat ggctgaatgt ctcatagttc tctattccat tggcaaatgt ttgaagccaa   27240
aagacttgac tcaatgtaga aaaattcctg cattttagcc tattttgaaa acatttgtta   27300
ggtgcttata atgtcaaagt agttttaccc aataaagaac caaaacttcc ggtaagttta   27360
attgagggtt ttcagagaaa ttcatctcgt ttaccctcct cttcttttt aaaaaattac    27420
tgttttgggt caccatccaa ttttatagc ggccaaacct cccacaggca gcagcaacag    27480
gcgcttaaaa cttgtgaaca ttttaggtgt tggtaacaaa tacaattttc aggtgccaga   27540
gggcacatgt gatctttac acaaaaatgc ctctgaccca caatcggtag ttcatcttga    27600
attgtctctt ctgttagtga tcatgaataa tagataaaca tttattaggt gagtgactga   27660
agctagggga tgtcctctgt gactgtgaga gtttctctct gaacaaagtt agttggacca   27720
ttcctgattg aacttctgac cttgatctcg ttaacacctg ctctaaggaa agattaaagg   27780
gaggcagcct gccagctgca tcctttgctg tctgggcaga cactacagag atggcccata   27840
tatgggccta gagatctgta cattttagaa tttaaaaatg atcaaggaaa ttgttttgta   27900
aattttattt gggagcctta gatttaacct taccattgta gaccaagaga ttgttttggt   27960
gtgcttttgt taaatatgct aaatattgtc tctggatact gagttaaagt attttttttt   28020
ggatgtgtgc taatttaata aaaatacgac ttaatatttg ccaggctttg gaccatgatg   28080
ggataatcat tagagatatt tgctgcttat ttgtattatg aatgtctttt ctaaaaattt   28140
gattcctggg ttactttgag gtgactgaag tcatgtaaca gcagaaggag ttaaggaaat   28200
agactaaaat atgacttgat ttagaaggga atttccattt aagaaatgag aaatggctgg   28260
gcgcagtggc tcatgcctgt aatcctagca ctttgggagg ccaaggtggg tggattgctt   28320
gaacccagaa gtttgagacc agcctgggca acatggcaaa accagtctc tattattata   28380
ttaaaaaaaa aaaaagaaa tgagaaatga atagattcct aaaatatttt ccagatctat    28440
tttaatgctg ataagctttt gttttacagt attttcctta tgattaatat tcataagtat   28500
gattaatgga gtgagggata ttttgtaaaa acccatcaaa aatttaagta ctttgattta   28560
gcatgggtag ttttaatctc aaaattgtta ttttcggtgt gcttatgtta aacacattaa   28620
atattgtaaa tattgcccct tttaggaaat taaaatttgg tagggtattt actagttggc   28680
ttttctctat tttttttcag gttactttat ttttcttctt gcagtcatgg tttttaatca   28740
tttgaatagt tgagctttat gtctcatatt ctgttaatgg aagtagctgc ttcagatagt   28800
ttgcttaggt atattgtatt ttgtaattgt ctattcaact gtgtgggctg tggtcaccac   28860
ttattttgat gatccacagt gggtcagcct tttgtactag gcaccttcag atacattgtc   28920
tgctcagtct tgctgtcagt actgtgaaaa taagcaatga tgtcctcatg ttttcatat    28980
gaggaaaatg ggactcagag aagataccaa atgtatttgc caattattat ttacataaca   29040
gccattcatt gaactcctgc tgaatgccag gctccattcc aagtgccagc gttattggaa   29100
tgaagaaatt ataagctctt ggacccaaga aatcacaaac tgatactggg gttcaaactt   29160
acagctgctt ggttccaaaa tgtctgttgt gttttcagtt tgaaattgga gtttttattt   29220
gaaaatagtt ttgacttttg tcttttgagg taactcttgc atgtgtaaat cagatctcta   29280
atgatttagt tttatttcca taggaggatt ttcacaatca caatggaaac actgtaaaac   29340
aatgtaaata gttttaaact tttctattgt tttgaggaga tgggcatctc agataacaag   29400
aatcattgat tagaaaatat tggaacggtg aataaagtta gcttctagac ctcagttacc   29460
```

```
ttaagtagaa gtgggtataa gggagagtga ttaaaagacc agaggtctta agccaggagt   29520
ataccaaact caagggaaac gattatggtt tagatgagaa aggtaaaagg aaatggattt   29580
gacttaaatt taaagcacta ttgtgaatga ggtcacaggt actctattgg gaggcatgta   29640
agttggcctt acctctatgg aggaccattt gacaatatta agatccttaa atatattggt   29700
gtcctttgat tctgtaattc tgtttcttga aatttatttc ctggaagaaa atatgagatg   29760
tgcaaaatac atatattttt cttgcagtat tccttaaatg tctagagata ggaaattggt   29820
taagttatgg tatacacaaa tgatagatat gctgtataca aatatttaaa tattaagtaa   29880
aaaggcagga tataaaacta tgcatggtgt aaccccaatt taatttatgt acatcagaaa   29940
atcaaaggaa atatatctca aaatgttaat gatagttata atgggtggta taattatggg   30000
taattttggt tttcttatgt actgttgtct gggtaagatc tgaaagtgat tctatttcct   30060
ttggaacaat tttcaaggac ttgaaaccta ttcttgaatt ccaagtatgt gtcccaccac   30120
ctccttttca ggttcagact gtaaaattaa agttgctttt aaaaagtgac atttggagtc   30180
gggcgtggtg gtgcatgcct gttatcccag ctactcggga ggctgaggca ggagaatcac   30240
ttatacccag gaggcagagg ttgcagtgag ctgagattgt gccatgcact ccagcctggg   30300
caacaggagc gaaactctgt ctcaaagaaa aaaaaaaaag tctgatattt ggatgagtgg   30360
agtaacatcc taattagaag atcttttca tgataatgtt ttgagtgtta acatatctta   30420
cttctagagc tttgtgttta agttggcagt ttagaacagt gtgctagtga ggccacagtc   30480
ttgcttcata accagatact ctcaaatatg gctgggcgta ttacaaatga attatatatt   30540
tcttatttgc cttgtcaatg cctaactttg tagaaatgaa tggcctgggt tttaaggaaa   30600
atagatggga ggtaggggtt ggagggtgct gtatgtggat aaatcagtat aaattcctga   30660
tcagaaaaac tgctcaaaga ccatgggtta ttgagtatta agtagctctt tgctttatcc   30720
ctgtgtaaaa atagcttttt tttttcattt ttaaattgtc tgatttaaat accctataca   30780
ttaagacttt gtgagaataa taccaagaat atactgagaa tattttgaga ctttaaaaat   30840
gtcagttttg aagcatatac agttaatatg gaaattttttc gtggaataca ttttttaaaaa   30900 acacaatatt acggtaacaa ccatggatgt gtgacctttt tcacctgttg gattaattca   30960
ttagaccatt agtacatacg taaggcaagg accctaaatc tttttgcctt ctgataaact   31020
actgactaca tatgaataaa ttctaaagag atgaagattt taatggtaa agtgggtaa   31080 tatgagaatt gatgttaaca agtagaaaac aaaagcataa tttgggtaga aaattagttg   31140
gagttattaa gtatatgatg tgatgttatg gaactgaggt agctggtttt gaattagttc   31200
ctattaaaat gattgagacg tggctggccg tggtggctca ctgctgtaat gccagcactt   31260
tgggatgctg aagtgggagg atcgcttgag gccagaaggt caagaccagc ctgggcaatc   31320
tagtgagaca catctgtaca aaaaaagaaa aattagctag gcatggtggt ggcacgtgct   31380
tatagtccca gctactgggg aggctgagac aggattgctt gagctgcagt gaactgtgat   31440
ggtgtcactg tactctagct tgtgtgtcaa gagtgagatc ctgactcttt tttttttttt   31500
tttgagacag agtctcactc tgcacctgca ctctcccagg ctggagtgca gtggcgcaat   31560
ctcgggtcac tgcaacctcc gcttcccagg ttcaatcagt tctcctgcct cagcctcccg   31620
agtagctggg attacaggcg cccgccacca cacctggcta atgtttgtat ttttagtaga   31680
gacagggttt taccatgttg gccaggctgg tctcgaactc ctgacttcag gtgatccgcc   31740
cgcctcggcc tcccaaagtg ttgggattac aggcgtgagc cactgctccc ggcctagacc   31800
ctgactcttt aaaaaaaaag aagattaaga cctgatgggt actatactga gtttaatatt   31860
```

```
tatttacttt ttaattttta tattttctta caggtgattg gtctgttgga cgttttaca     31920 cctgcaaggt ctctggagga attcaatgat gtgtgagtaa attttttgca tttgccttcc     31980
tggtctacag aatgaagact aatagcccat ttctattcct gaaccattta gcaacatata     32040
gacttcaaaa aattctttat tcctatcatg cacctctttt tgggtgtagg gatggatacc     32100
agaagatgta tgttatgggt ggtgcgtgtt agtatttaca tcatttcagg cacattgtac     32160
cccattgaag agtcagtctt gaattcttac aaaagttcca tggagaaagg agtggagaga     32220
gttttgacta tggatttttct tttcaaagtg tttatcccag gtttggtttt gttgttgttg     32280
ttgttgttgt tgttttttgtt ttaaaagaca cggggtcttg tgatattgcc caggctggac     32340
tcaagctcct gggctgtagt gatcctccca cctcagcctc ctgaggagct ggaactacag     32400
gcacatgcta ccatgcctgg ccgatcccaa ctttttaaagg tgctcttcaa gaaatgtaac     32460
ggatccccag ccatatagac tccctcctct tttatcgccc atgcatgtgg gagatgatac     32520
tagaactaca tgctgatcct tgaagtatta gatttctata ctgggataag gggcagactc     32580
tacctgttga gaaaggcttc ttctctcagc tttgtaacca cctctgttgt tttagcctgg     32640
gataccccta gaaagcagag cctgggattc tcaggaacca gtagtggggg gctagggaaa     32700
atgaaacagg aaaggagaga aagcttctat gagtatatgt tgagttggtc accactatgg     32760
acaattgggc tgaaaactgc caagatctaa gaagctgtac gtaatgcacc tcagatgggg     32820
atcattaata cactggctcc tgaccccatt ggcaagggtt gccacgtatg tcattagtgc     32880
cttcacatgc ccaggttgca cattggtggg ccataagaca gattccagca agtgttccca     32940
tgtatgtgtg aactctctac tatagtagct tttctagtat ctgagttgac acagctctcc     33000
ctgcccccag ttcacatata cactatacca tgaaagagaa aaaaacctta aacacagtta     33060
tacttttggt cacattgaaa ttttggcatt cctaaatgga gagtgttact attatgaaag     33120
ccaaaacaga actgaagatc gtgacttctc ttccttaacc tccattcccc cattgaccccc     33180 agggctgaac ctaaccagtt tctcctcacc cttatcctgg tttcagtttc tcccattctt     33240
atcctgggct gattgcaaac accgtttact ccttccccac agaacacaaa ggggatatgt     33300
ttgaacttct atgttctgtc taaggaaagg gagaaagaaa taagaagat gaaatggaaa     33360 gggaaggagg aaaggtggca aaaacatttc tccaccatttt gaatttagtt ggaacagtgt     33420
atggctgaga gtagaagagt agaagttaag agaggagaat ttggtccacc tacaagatct     33480
ccttggctac attaaccttg atcctgctaa tgaaagttta agaaacaaag gaaaaaaata     33540
gccaataact aagaaaaatt gttcttctcg cagcccctgct tgatacaaca atatggaggc     33600
ttccagagat tactggatgt tactcagggg catgtatatt acagtttgtt gagccctact     33660
gtatgctata gttggaaaag ggaatgttac agaatgatgg ttttaaaaa tagttttcct     33720 aaatgtagaa gaaatgctga agtaatgtgt ttgtgaatta ctttggaaaa catttgagtt     33780
agatctgagc tgtatcccaa aattttaggt atactaagga tggatttata taacaaagga     33840
aatgatttgc tgacttgtgc aaagtgcaaa atgctgtatt ttggcctaat tgggcattct     33900
ggaaccggat taagaaccta ttttttcctat gtgaaaagac cttaattaag gccagtgtct     33960
atttagaagg ttaagtgtta ctgatagtgg tgccttttgtt tggctccttc atccatgtaa     34020
ggacccagca actacaaatc tacctttgaa ctaaggtttc attcattcat tcaaccattc     34080
attcattcat ttattcaata aatactatgg ctgttgagca ggaatccgtt ctttctatttt     34140 aactctagct ggatactgtt ttttataaac aataactgag tttacctctt ggaagcaaat     34200
ctcattacta cttgttgact acttactgaa tgcagaacac tgagcagagt gttagcacag     34260
```

```
gctcagaata atcagaaaca gtcgcccttc cttttgatga aagtgtctgg ttgggggaaa    34320
cgaattcaaa gcacttttgt atccaagcta ccaattggcc atatgacctt ggacaagtca    34380 cttaccact gtaggcccag tcatttcact gtaaaatgat gagaattgag gtcgttgact    34440
tctgaagtgt tttaaattac agaaagtctc tgaaaataga atgaacttgt ttgccctaag    34500
aaaaatattc cattgtttac tttttattgt gatgttcata tcactgaaaa aatcactgta    34560
gttcgactat agttatttca gtgttttctt ttttttttgag acagcgtctt gccctgttgt    34620
cacccaggtt ggagtgcagt ggcaagatct tggctcactg ccacctctgc ctcccagctc    34680
atgcaatcct cccacctcag tcccccaagt agctgggact gcaggaatgg gccaccatgt    34740
ccagctaatt tttgtatttt tggtagagac agggttttgc catgttgcct aggctggtct    34800
cgaactcctg agctcaggtg gtcgcccctcc taggccactc aaagtgctgg gattacagac    34860
atgagccgcc acacccagcc atttcagtat tttctaaagt tattttggga tatgcataag    34920
aaactaaaca tcttcaccta cacttgcagg gtttgcaaat ttaaataccct tcagggtcac    34980 acaaagaaca taaatgaggt tcagtgttac acaattggga gtggtgggt ctgtggcaaa    35040 atacatctgc acctcctaaa agtattcaaa ttcacattga aacaaaacaa gtaaacaaac    35100
gaaaacctac acttctggcc aaaccagaca taatttaggc tagagtggtt ctacaagctg    35160
cctgtttaga gcaggctata atttgaacac aaatttttaa atgctaatta gcaaaatctc    35220
tataattact ttcagattta tagttttttt ttttctttt tcttttcttt ttttttttt    35280 gaggtggagt ctcgctctgt cacccaggct ggagtgcagt ggcacgatct tagctcactg    35340
caacctccgc ctcccaggtt caagcgattc tcctacctca gcctcacaag tagctgggat    35400
tacaggcgca catcaccatg cctggttaat ttttgtattt ttagtagagg tgggatttca    35460
ctgttttggc cagactggtc atgaacgctt gacctcaagt gatccaccca cctcagcctc    35520
ccaaagtgct aggattgtag gtgtgagcca ccgcgcctgg cctacagttg gcttttaatc    35580
atgtgatacg tgtatttgtc cctttatgtt tcggttagca cttttaattt atatacagtc    35640
atgcatcagt taatgactgg gatgtgttct gagaaatatg tcattaggtg attttgtcat    35700
tgtgcagaca tcatagagta tacttccaca aacctagatg gtataatcta cacacctaat    35760
ctatatggtg tatcttgttg ctcccatact acaaacctgc atggcatgtt actgtactgg    35820
atgctgtagg taactgtaac gtgatgctat gtgtttgtgt atctaaacat aactaaacat    35880
agaaaacaac agtaaaaata tggtactgta ggccaggctt agtggcttac tcctataatc    35940
ccagcacttt gggaggccga ggtgggcaga tcacttgagc ccaagagctg gagaccagcc    36000
tgagcaacat agggaaaccc cttctctaca aaaaaattta aaaaattagc cgagcatagt    36060
ggtgcatgcc tgtagtccca gctactgggg agtctaaggt gagaggatca tttgagccca    36120
ggggcagcgg ttatattgaa ccatgattgc gccactgcat tccagcccag gtgacagagt    36180
gatatatgtg gtccactgtt gactgaaaca ttgttatgtg gtacatgact acttcagatt    36240
tttgctatgt tttaaatttt aattcttaca aatgaagact ataccttga gaaaggaaca    36300 ataggtagtg cattttgaac attaggaaca atatacagtt actgaatctg gatggagatg    36360 attttggaa aatgtagtgt taaagatgg atatactaag ttgctcttga ccaccatagg    36420
atgtggttgt acagatggca aaattttgta aagatacagt acatctagat ctcttaaatg    36480
actggaaatc ctttgggcct ttctgttggc ttcttgatag taatgtttgg caagatactg    36540
catgcatata tattcctgtg tattcagcag atattaccag tagaaatgca aaaatcttaa    36600
atagccaata tttgaaccta acaccagagc aagctgtaat tcagtattac tataatattg    36660
```

```
ccttttctttt gtgtgtgtgt gtgtgtgtgt gtgtgtgttt gttttctttt tgtagttggg    36720
gctacaggct  cacaccacta  gactcagctg  tttttatttt  tttgtaaaga  caaggccttg    36780
ctatgttgcc  ttggttggtc  ttgaactcct  ggactcaagc  aatcccccaa  ccttggcctc    36840
ccaaaatgct  gggattacag  atatgagcca  ccatgccccc  ccccacccct  ttttcttaac    36900
tgtagtggtt  ctttgcgcaa  gcatagtaga  caagaatttt  ttgattcctc  ctgggaacta    36960
tttcctcaaa  tttcatggaa  actgaattgt  catgagttaa  gtggaaatta  gtcttctgat    37020
acttttcct   ttattttaca  agttcccatc  ccaggtttct  tatactgaat  tccttatctc    37080
tgcctcattc  ttgaagaggg  aaatggaagt  ggggttttgg  attctaccat  gatagaaggg    37140
aagacctaca  acaaggctat  tcagcagcct  ttgttttagt  gaaagccaat  gagaagagat    37200
cacttcttcc  acttactaac  aatgattgct  caactaataa  gtttagcttt  tttatttcaa    37260
tgtaaaagtt  gctgaaaaca  ctgaattggt  aaaggaaatt  tctggattta  cattttaacc    37320
tgatgttgtt  caataaatat  ttgaatatct  accttatgct  aggcacagta  atagtctctg    37380
aggaatataa  cagtaaataa  gagctgaggc  tgttaatggg  agagaagaac  aatgtaaatg    37440
atcaaacaaa  ataccatgtg  gtaagacctg  aaaggtccta  catgagttgg  tctccggtgt    37500
actctctaat  ctaacctcac  ctagtcctct  ttccactctg  tctccacccc  agtcactctg    37560
gcctcttgtt  ctttgagtac  agacaaccac  atttgcaata  agacctttgc  accagtttct    37620
gttattgccc  tggaactttt  tccccacata  cctacatgac  tgtctccttt  ccttcaggac    37680
tctacccaag  ggtcttctca  tcagaagctc  ttcttttgtt  accattctaa  ctgaaatagt    37740
accccctactg tcactgttta  ctccttaccc  tgctttgttc  ttagcaaatt  ttgttattgt    37800
ctgtcttctc  cctttctttg  taagctgtgt  tcaagcacgg  agtttgtttt  cttcgttgct    37860
gaatcattat  tggagtatat  gcactccatt  gtttgttaaa  caggtgaaca  caagaattgc    37920
cattataggg  caggtataga  gtgctaaagg  actgcatagt  atggccacct  aacccagaca    37980
tggggtgtct  tcaggaaagc  ctctgcaaaa  aaaatgtata  cacagagggc  ttaacggatg    38040
aaggagagtt  ggaaaggtgg  ggaaagtaca  agttcatcca  ggggccgaga  gagggagctg    38100
agggcagaaa  aggtgtgtgt  gtgtgtgtgt  gtgtgtgtgt  gtgtgtgtgt  gtttggtggg    38160
aatagaggtg  tatatggcaa  aagatgaagc  tggaatgggg  agggactaga  tctttggggc    38220
tttataagct  aagcctcatt  aaggtggttg  ctttagagaa  gagatcaaag  ggtactggga    38280
actggaaatg  ggattggaaa  aaggatgaaa  ggttttactt  ttatgtggga  tgacatagtt    38340
acaactctct  ccccccttcct ccccacacaa  acacattcca  tagtgtgtga  taaaaagata    38400
tcattttacc  agaggcagtt  ttctcctgga  tccttaacac  attaggaaat  attttggatg    38460
agcatactag  ttgaaaatct  gaatggata   taagactttt  ctgggaactt  aaatttatgt    38520
aatgatgctt  ctcattgtta  atatctgact  ttaatttctt  ttggtttgac  ttcttgccaa    38580
cattacaact  atgtcctttc  ttcaaaaaac  agggtcttat  gcttatgagt  gaaactgaca    38640
aaacatgtgg  gtgagcagtt  ctataaaaac  tctttttttt  tcagtaacat  cttggagggt    38700
acaaagggct  ttcacataat  cttatttgac  acaacaatcc  tgtgaaacag  atggtattat    38760
ctctaatttt  cagatgaggg  aactgaggtt  gagagagatg  aacctaattg  tataatatca    38820
catacaaaat  tgcatctctc  cctggtcttt  tggctctaaa  cctatttctc  atcacatttt    38880
tctgatctaa  ggctatgatt  attatttgaa  agtctgctac  cccttcttat  tgagtaaata    38940
ttgtgttaag  ttcatgtgtaa gatgccaaaa ctagggcct   gtctcgtttt  ccaattgcta    39000
tggtcttatt  aaagaaatga  ggcatttctt  attaagaaat  gcttacctaa  aataactgaa    39060
```

```
gggctgagtc aaatctgtaa tgtctagaca acttacaggg tgctgcatga aactcagaat    39120
attagagaag cttagtggag aaaagcctct aaagaaggta ataactgtgt ccgaagaaac    39180
aaatagggat aggatgtgga agttgaaatt tattccagac agagaatgaa ggaaatatgt    39240
aaagtgtaca gaaaagagat ttgtatggaa tggagagtgt taaatgagaa taactattga    39300
tacttctttt gtacttggat aaaaattgtg cattgatgaa ttctgggtgt gtgtgtgtgt    39360
gtgtatgtgt gtatgtgtgt atgtgtaggg ttattcctga tttagctaat aaatgtgatc    39420
tttttggaaa taatggtgaa agaaatacct agccgagttg cttggactta caggttattt    39480
cctaatttag ctaataaaca tggtagtttt ggaaataatg ctgaaagaaa tactagccta    39540
gttgcttgaa actaggctaa gtgctcaaga tagtgaacac aggaagagaa gtggtctagg    39600
aaaaagatta atgagttaac tattaacatt tatgtttaca attttttttt tatcagagag    39660
gtctgctgaa atggagatgg tgggtggcga aactccttgt agatgttttt acaaactcac    39720
atttgaaatc taaataagtt acatatctct taagaaaata tcattcagtt tttgcctgac    39780
atgatcaata agatgccacc ttttctcag attagctagt tttaaaaggt aaagaagctt    39840
caaggcctag cttagagttt gagtccttca gcaatctctc tctaattcac ttcttcctaa    39900
gtctgtgctg ggaccctctc ctgtgtgttc tccatcaccg tatgtcccct tattatgatt    39960
atatattcat atatgccttc cttcatcta aaggctgtat ctgtctttcc cactgctgca    40020
tccccagggc ccagaaatac gtatttgttg atggagtgat agaatgagtg aataactttg    40080
tgctgtcact gtttataact ggttgatgat ttggttgtct gaaagcatgc tcagtgctct    40140
ctcctttgac tagctttttt gttttcatcc tgtaatgtag actgtgtggt aaaatattga    40200
gtctagtttc actgatgcag gtaatgtaga gggcatcttt tagtaatctt tgcttcaagt    40260
gagaataatt tgttgtgaaa taagcctact aagctgccta cttggctgct gaatgattct    40320 tttacccta aattagaaca gtctggtctg cttaccagta agatctttgg cacatgtatt    40380
tcaataaaat gagcccttgt cttatcttac tagtagtgct gtgtgagttg tcctgagtca    40440
ttcagtggta attgagtgcc tactatctat cagacactgt tctcggtact ttagatacta    40500
cagggaacaa aaaataaccc tgtcctccac gaacattgta caagcagata acaataaaca    40560
acagtgagca tataaaaaag gaattacat agtctgttag cagacaataa tgctataact    40620
aaaaagaaaa ggtagaaagg tagaacagga aaggggaatt aggagtacaa gggtgggggg    40680
aagatgaaat tttaaatgga taggccttat tgagatgaat tttgagcaaa agtgtgaaga    40740
agtagaggaa ttagacctgg ggatatctag aggaagagca ttccaggcag aagaggaagt    40800
cagtgcaaag gtcctgaggc agactgcatg atatattgga actggagcaa ggaggccagt    40860
gtggagctga gtaagagcaa gggacagaga catagactat gaaatcagag acataattag    40920
gggcagtgta ctggattagg tagggcttta tctgccattg aaaggaattt tgtgttttac    40980
tcttagtaaa ataggagcc ttttgaggaa aggagtgccc tgatctgagt tttatttcta    41040
aagaaacact cttcccctgt gttgagaata gactgtagta agtcccaagg atcaataggt    41100
gagttgcaga agcttgtgct tacaaattgt caatccctgt gattgtttta agcaccctgt    41160
ttaaatatgg aataaatggg ttttttttgtt ttgttttgtt ttttgccttt tgataattgc    41220
tttgaatagg actgatagta gtaagagacg ccagtctata gatatcgaag agttttttct    41280
acataggttc tttctgattg ttctgtgctt taaaaagtgg gaggtgggga ggaagagggc    41340
gggggcagtg gtgctggtct taacaattgg gtattatcca agaagtataa atgaagctgt    41400
aaaatggggt gctgtctaga gtactgaaaa gcatttatga cagagttctt ccttcttgct    41460
```

```
gtcacagtac attttactca caggagtcac attgagaaat gtgatttgtg ctctctatac   41520
tttgattaaa tttaaagaag accaacttca caagaaaagt gaaaaacaag atttgtatca   41580
gtccatgaaa ttgttttcag cttttagcct aataaagtcc aacttaactt aattcctttg   41640
taaagatgtg agaactagat agcttttcaa ccatactcaa gtctaacctt ccttaattta   41700
ctttaattta ctttacttaa tttactttag gtgttatata cattgacaat attaggcatg   41760
tctttactaa aatgtaattg actatgcttt ccagaaacaa atactataga aattatgtga   41820
ctctccatta atgcctcttt tggaatgtgc ttcttaaaat gtgctcattt atattccttg   41880
ccccccatcc tgttcattat ttttagaagt tggtgcatct tccataaaca atcagcaact   41940
ttgcatgatg cttgcttttg tcccctgttg taagacttat tttgaaaatc tttctatatg   42000
ggagttagaa tgtaacaatt ggtggtcatg gattggtctt tgggcctcct ggaaacaagt   42060
atagtgatta agttagttcc tgcaagatgc ttctgccata aataatgcct ttcagtttat   42120
ttcattgtag cttagtagta atgcttgata gttattacta tatagactga ttaatcttat   42180
aaacttacat aatgttttgg cagtctcacc ctcgttctaa attttggtga taaaatggat   42240
gtggtctctg aggggaaag gatttgagag aaattacata gtggtaaact gttctaatta   42300
aaagctcttt ccctctctct ctctctctct ctgttgccat gcagtcagtg gtcctctggc   42360
tgcctaagat ttcttaactc actggtaacc atttacacat aatagctgta cttgaagttg   42420
ctatggtttc attagtagtt ttgcctaacc tttgtgaact ggctcaggcc tattagttag   42480
gactagtatt attttttattt aaaataagt tatgtttgtc tcttctccat aaaattattt   42540
agaaaagttc aaagaataac cctcttatta tccaatgtca aaaatataa ttatgtgcaa   42600 agtagtctta tatgaccgaa attagattct gtcttcctca gcttatgcat caattaggg   42660 ttaaaaaata cagtaactgt gattaggaca gaatactgct atgttcttgc cagcctgaga   42720
actttgttaa gattaacttt gatagtaaat acagtattga gaattactaa ggaaattatt   42780
cagacatatt gcttccctag ttattgtgac gtttaaagag ttttaaaaag gtcattccct   42840
tgatgtaaat tttgtatcag ctgaaagaat tgttggaaga atatgtgctg tgattaagat   42900
catggtctgt ggggtcagtt agttttagat ccaactcctg acattactac tcttttgac   42960 cttgagtaga tggcttatcc ttattctgtc tctatttcct tgtcaatgaa atgggaacgc   43020
taatggacat tatctcacag agttattggg aagagtacat gagacataat gagtacatgg   43080
acataataaa ctgcttgctg cagtgctgga cacagaataa gtgctagtta gtgcctttgg   43140
ttatgttgtg ttgagattgg aacatttctt aaaacgtttc agtctcattt acttattaat   43200
tacatttaga gtctactctt tcctcaaggc cgtataaaca tgcaagtttt aaaaatatga   43260
aatgctaaca tcttaaggtt gcaactaggt taagtcctgt tgatcttcat gaaattgaga   43320
actgaccatg gcagccctac caggaaatta tgacagagaa aaaaattcca ttcctcttgg   43380
aggacagaaa gtaataaata tagtgtatta gttgtgtgtg taggtatata aagagaggtc   43440
acacacacac acgtttattc ttataatata ttaataatag atctaaatta ctgacctgct   43500
ttcttccctc caaaattcat aaaaaaatga aaatagaaat gaaatcagca ttctttatag   43560
ctcagctgat atatattatt acccaatctc aggaatagga atgattctta gacagtaaat   43620
aaaacttaca cttatttta aaaattcagc ctcttagcca ggcacggtag ctcactcctg   43680
taatcccagc acttgggag gccatggtgg gtggatcact tgagatcagg agttcgagac   43740
cagcctggcc aacatgatga aaccccgcct ctactaaaaa tacaaaaatt agccaggcat   43800
ggtggcgagt acctgtaatc ccagctactc gggaggctga ggcacgagaa tcgcttaatc   43860
```

```
ccaggaggtg gaggttgcag tgagccgagc ttgtgccact gcactccagc ctgggcgaca    43920
gagcaaggct ctgtctcaag aaaaaaaaaa aaatcagcc tttttagaac cgatctactt    43980
tctatgtttc catagctgtg taatacagta atgagtgggt taaggcattg tgtctagaat    44040
atgtgtggtg aacctgttgg acttgaatgt aatcattccc taatcttacc acataaagat    44100
gggattaata accagcacca cacctgtgag gagaaattct ggaatgcctc atcttgcctc    44160
cagataaaac atgttcctcc ttcctttaag gtaaatgcag gaatattgtc aatgaacaaa    44220
atcctttcac tagtcattcc tgaaaagaa ttacagttgg aaaataaaaa aaatactcct    44280
attttagaac ctgtaatgtg gaagacttat aatgaggtga aaatgtagcg gtggatttaa    44340
aactacaaga tacttaatta tagccatgca gtaagttata ctatatattt gtcatgcaag    44400
aataacattt gtaagaaaac tgatactgac acatgtatct ttctaatccc tacctttgct    44460 gttttttgttt tcttttctct tttatttttt gtagagatgg ggtttccctg tgttacccag    44520
gctgatctca cactcctgcc tcagcctccc aaagtgctaa gattataggt gtgagccaca    44580
aagcttggcc tggtttcttt tttcttgaga taacctggaa aaagatatgt caagtaggaa    44640
taagtatgta aatgtttaga acagatggca ggtagtaaa gttagaatag taatgttggg    44700
aggctaaatt gggaggatca cctgagacca agagttagag cccagcctga gcaacatagt    44760 gagacccat ctctacagga aaatttaaaa aaattagctg tgcgtggtgg tgcacacctt    44820
tagtcctagc tactcggaag gctgaggtag gaggatcact tgagcccagg agtttgaggt    44880
tgcagtgaat tactatgatt gctccactgc atgacagagc atgaccctgt ctctaaaaaa    44940
aagaaaagta aagaatagc gatgttgaaa atgaggtaat gaggtgccct tcccccaaa    45000 aaatgagtag ttgttagctt ttagctgtca tcgtggtaca gctaccattt taagggaagg    45060
gtagccttcc cttaaaaact tagaagtcgg gccaggtgcg gtggctcacg cttgtaatcc    45120
cagcactttg ggaggctgag gcgggggat catgaggtca ggagatcaag accatcttgg    45180
ccaacacggt gaaacctcgt ctccactaaa aatacaaaga ttagccgggc atggtggtgg    45240
gcacctggag tcccagcaac tcgggaggct gaggcaggag aatggcgtga acctgggagg    45300
cagaggttgt agtgagctga gattgcgcca ctgcactcca gcctggcagt agagcgagac    45360
tccatttcaa aaacaaaaac aaaaaccaaa aaaaccaaaa aacttataaa agtcttctga    45420
agataagaac tttcttaggg gttctagatt gttatgtaac ttttcactaa tttctaggta    45480
tctggtgacc catctcatgg gggcagatct gaacaacatt gtgaaatgtc agaagcttac    45540
agatgaccat gttcagttcc ttatctacca aattctccga ggtctaaagg tacagataat    45600
acaagtaata atttttaaa atgaattctc cctttctccc ctccttttag ggcttaaaca    45660
aacaagtaaa caactttctct aatggaaaat tcaaacacat aaaatcacag gtaaggtca    45720 tatagtacag taaactgcca tgttcactca gtgacaacag ttaccgacat atggccaatc    45780
atgtttcttt tgtatttccc aagccctgga ttattttaaa gcaagtctag acattatata    45840
ataccatcca tagatacttc agtttgcata tctgaaagat aaggactctt cattcttaca    45900
tctaaacaat aatttattga tgtaatctaa tatctggtca gcgtaatgtt gagattttca    45960
aaaaatcctc aagaaagact aatttatttg ttggagggc agataaacag tgttttaaaa    46020
ttaaacccat ctttgatatt tagctgcttt gagtccttat tgagctccag agtgccaacc    46080
agaaaataga ttaaaagctc aactgagtgg agtcaatggc tgtggaaatt atagtaatgg    46140
taaatgtaca caatactgat agttactta gctgatttct aatcttacta ttaacactag    46200
cagttcttac tgattcatga aaatgtgcag caaatatgtt atataatatg acaatagaag    46260
```

```
gttggaggta actttgactt ttttctcttt tgcagtatat acattcagct gacataattc    46320
acagggtatg tattgtgact ttgattacat tattttgggg aagtggggtg agagtggaag    46380
aatggcattt agccaagatc ctaatctaaa ctttagccat tgaaatgttg attgattgca    46440
actttactgt aggtttaagc tgattaaaga aagaagatgt gtagttttt tctatgtaag     46500 gctaacttgg actggatatt gactgtagga tggagattgt cttttgatag ctggatgaag    46560
tcttttatgt ctggatcctc attattacct gtaggggag aattgatcat gcatcataaa     46620
gttgatcctg tcttccctgt atttgcttcc taggacctaa aacctagtaa tctagctgtg    46680
aatgaagact gtgagctgaa ggtaaaatga agagacagta ttcattgttt gctttacttt    46740
gagattatat gtttgactaa gcaggcagac tttcttaggg agtagctttg tgagccatga    46800
ctatctgaaa ttcgtattat ttttattatc agactttgaa atttaaacca tttctgagta    46860
agctaagtga cattgaaagt ggcatcactt gttttattt taacataaag ttaaattata     46920
aatttgatat attagtcata ataaaggagg ataatagtca aatatcaagt aagtaggccc    46980
aaagaggtga taactagatt aaatacattt ctaagaggag aaatggcaga aacccactca    47040
ctcaaaataa ttcaaataaa aaataagtga attaattgtt tctaaatagc aagcagctct    47100 agaactttg ttccatttca tttttttaac ttgaaaaaat gtctgtacat tagaatgcac      47160
catttcattt ggcaaaatta tatatccact taactcacat ttatgataaa gaccatttct    47220
ttttttttcc ttttttttgg gatgcagtct cactctgttg cccagtctag agtgcagtgg    47280
tgtgatcttg gctcactgca acctctgcct cccgggttca gcgattctc ctgcctcagc     47340 ctcccgagta gctgggacta caggtgcacg ccatcacacc cggctaattt ttgtattttt    47400
agtagagatg gatttcacc atgttggcta ggatggtgtc gatctcctga cctcgtgatc     47460
cacctgcctc ggcctctcaa agtgctggga ttgcaggtgt gagccattgc tcccagccaa    47520
gaacatttgg attactttaa aaagtttatg ccaggcgtg gtggctcatg cctgtaatcc      47580
cagcactttg ggaggccaag gcgggtggat tatgaggtca ggagatagag accatcttgg    47640
ccaacacggt gaaaccctcat ctccactaaa aatacaaaaa tttagttggg catggtggcg   47700
ggcacctgga gtcccagcta cttgagaggc tgaggcagga aatggcgtg aacctgggag     47760 gcagagcttg cagtgcgccg agatagtgcc actgcacccc agcctgggca acagagcaag    47820
actccgtctc aaaaaaaaaa aaaaaaaaaa aaaagtttat tgtgtccctt cctagtcaat    47880
ccctacccct ccacccctaa ctctggctcc aggcaactat ggatctgctt ctaacactat    47940
agattaggtt tatcttttct ggagtttcat gtaaatggaa tcatatagtg tgtattttg     48000 tgtgtctggc ctttgcttgg tgtaatgatt cggtattgtt gtgtgtgtca gtggtttctt    48060 ccttttatt ggtaatagta ttttgtttta tgaacataac agaattttta aatctatcca     48120
cctgctgatg gacatttgct tgagtttgag gctgtgtaaa gcaactgtga atgtttatgt    48180
gcaaaccttt gtatggacgt aagttctcat tgcacttgat taaatacctg ggagtgacat    48240
ttttgttttg cttttgtaa tttcattta agttcttgct gtatatttac catacattct      48300
aagtatggac caggaaatct ctttatgaaa gtgctatttt gttctccttt ttaataaggc    48360
aacagaggtt tgtttgttgt tgttgttttg ttttttttc cctgcctgtt tctaagtctt     48420
agcagtttgt ctgttcctct tctgcccttt agattctgga ttttggactg gctcggcaca    48480
cagatgatga aatgacaggc tacgtggcca ctaggtggta cagggctcct gagatcatgc    48540
tgaactggat gcattacaac cagacaggta ttactcgcct tggttattta gggccttatt    48600
taattccatg ttggatgcat ttgggattct cagaaataga gatggtggga gtgggaagaa    48660
```

```
atgtcttttc ttccctcagt gatccttta aagcctgcaa gtaaaaatat ttcacttcct    48720
cagatgggga agtggggttt tatacacagc ttttaaacct tgtgatttag caattgggtt    48780
tttatttatt tagattttga atatattctc tgagtactta tacctaaaga caattagtcc    48840
ataattttaa cccctcaatg ttacttggaa gaatctacca ttctactaat aagaaacttg    48900
cccctttta aacagcttat ttctcttaag tgtgttttga cttaccccac ctttgaacag    48960
cccttagtc aggtgaagat cttagtaagc tatttatttc tgtaaaaatg agtatgattg    49020
ttgagcctca gatgtcttaa atagtaattt gaatatttca ccctagtta cggtttcatt    49080
tgttgccaag aattgtaaca gtgacattgc atatactttt acttcttttt aattttgcca    49140
gttgatattt ggtcagtggg atgcataatg gccgagctgt tgactggaag aacattgttt    49200
cctggtacag accgtatcct ttaaaaagtt ttggattctt gtttcttatc tgtattccag    49260
tgtccatggg tgtatactcc ttttacttat ctctagggaa gactctcagt attttgcttt    49320
tatagtctag ataatgcatt atgaggtctt tcttcaaact gagtagcttg ccttgccaag    49380
aaagaggctt cagtttactt ttgtgagttg gaaaaattcc tcataagttg aaaaacccat    49440
caagtctgtc ttcttttttgc aacagtccct tattaatcat cccacagcag ttctgagacc    49500
tgagcatact catgagaaac tccagatccc agtgacagtt ttagtcttct tgtataaaca    49560
cttaatgagc acaagatgcc catttataaa tgaagggcat cttgctgtta tgtttatgta    49620
ttaaaagggc tatgtttggt acctgcagtg atatactgct tacttgttat gtttgttgtt    49680
tgacaacaaa tagtaaaagc aagaagtgaa aagcttacca tgtaatgtac ttttgttttt    49740
ccagcacaac ttttttcccag attgcagcca aaccctaatt tactccaaga cttactgtct    49800
agtttatggt ttattatagc cccttttattt tagctccttt cctatctgcg gtatgcttgt    49860
ttcatggttt agtattaatg tcatgaaaaa tgtggtctgt tggaactctc atcagttcta    49920
cttatgaaag atgtttaggt gagaaagatt gttaaaatat atgtctagaa ttagttttgg    49980
ggatttttc ttttttaat agaattgagt taactagcct tcaggtggtt ttggttaggc    50040
aatattagac atgctacctc tgatctatta tgcctagaga tctaaaagcc atttagtcc    50100
cttacctaaa taaactaatt gagtttataa accagaatgt caattcactt gcttacagtt    50160
tgggatatac ttctgtaatg gctatgatgt tcatgatatc tacccacgtg ttctaactat    50220
cttctgctag agagaatgta ctttcattat gaactgaaaa aacctctatt tctcaggtaa    50280
agctgtttct ttctctctga atattaggat tgataacaga gttcagtctc cctgtattta    50340
gcttacctta ttactcccta cctctggatt ttaaattagt ttaatacctg gtgttttctcc    50400
tttgtccttt gtttcattca ccttatatct gtttctcaga aatttggtat atatatatta    50460
cagtccaagg taagagaatt agggaaaatt catacttccc cctttcctca ggtacatatc    50520
tcagagtccc atccttgctt tgtcctctag agtagctgct gtcctgatgc tattctctgt    50580
tccctgctcc ccttcctctt cttgtgtctg tatctccagc taccatttag tcagtcacag    50640
acctccatgc cggtgtagac acacaaggtg gcagagaggg aaaggcagta taacatacag    50700
gttaagcaca tgctctggag ccagatttcc tggatttaga tcttagctct tttatttcca    50760
gctatgtaac tttgagtaag tttcctaacc tctatttctc tcagtttcct taaccgtaaa    50820
atgataataa tcatacatac tcacaaggtt gtcgtaagaa ttcagccaga aaataactgg    50880
aaagtactga gacgagcctg ccagtaaatg ttagccatca tgttcagtaa tggccttgca    50940
aaacagatta ccccttcacc ttctcactta attgtctacc tatgaatcat taatgttttg    51000
ttttgttttt aattctgtga taggtaggaa aggatggaac tccttggcag actagtgtta    51060
```

```
gaaagttttc gaagcagtgt gagtcttgta cctttgtggt cctgtctcac agacacctgt    51120
ctattccctg accctttaa  atgctaactt tctgcctgta ggaaatcttc cctttgtgct    51180
taggtctttt tcttctgtga gctttagata aacaacctag tgtttaaact ttttaataag    51240
ggattcattt tttaatacat gagaattcat ttcaaaattt tggttttagt tatttatttt    51300
attctacttg gctcttttc  agacagatgt tctctcctgg attgtaaaag tcgaattcaa    51360 aggatttta  tttgtaatat acttaacctt tctcttgtaa gttgccatct gtgtagatac    51420
agctttgatt gcctgacaag aggaaaatgt ttcccattat cttttcctgc ctgaactata    51480
cggtcacttg tgttccagca tagtggttct taaccctcat agtgtgtcag aatcactttg    51540
cagagctttt aaaaactcta gatgcctggg gaccaccca  aagactccat tttgttgtca    51600
tgggtcaaag cacagtcttc tagtttgcag ctagtgttga gtacaactag agtttaaccc    51660
agttgaattt tagtttaatc ttggctggtc ttgaagatgt tagtaatctc tattcatttt    51720
ttttgaaaag taccaatgag atcagaaagt taattagaaa acatctagtt gaatcccctg    51780
tttttaatag atggggaaac caagacccag agaatataat ccaaagctac ctgtcacata    51840
ggccacaatt tcttttccaa tattctgttc ttcgctgttc ttctaatttg cagaactcct    51900
ctttaaaaaa cctttggaga atgtattggc ctcataccct cttccttcag cctgaaagac    51960
atgcacctgt cacttattta tgatatttaa atgcaacctc tagaacaggg gtgtccaatc    52020
ttctggcttc cctgggccac attggaagaa gaaatgtcct gggccacaca taaaatacac    52080
taatgatagc cgatgaactt aaaaaaaatt gcaaaaaaaa aatctcgtaa tgttttcaga    52140
aagtttacaa atttgtgatg ggctgcatcc aaagccctgg gccacgtgca gcccgcaggc    52200
cctgggttgg aaaagcttgc tctagaaggt actcattgtt tgagtgtcca gttttctccc    52260
tgttttcctt atttattgat cattttgcat ttggaattgg tggtttgggc ttgtaagtaa    52320
gaactgtgta ctagaactt  tgtggtattg caaatgtttt atatctgtgc tatccaatgt    52380
ggtggttata ggcaccagct gcctgtggct aattattaag caactgaaat gcagctagtg    52440
gtgagcagta acgttgtgga gaagaaaaaa aagaaatgta gctagtttaa cttggaaatt    52500
gaattgaaaa tattttgtg  gttaaatgta tttaacataa aatttaccat tttaaccttt    52560 tttttttga  acagtcttg  ctttgttgcc cacgctggag tgcagtggca tgatcttggc    52620
tcactacaac ctccgcctcc cgggctcaag cgattctcct gcctcagcct cccaagtagc    52680
tgggattata ggtgtgtacc accatgtaat ttttgtattt ttagtagaga cagggtttca    52740
ccatgttagc caggctggtc tcaaactcct ggcctcaagt gatccgccca ccttagcctc    52800
ccaaattgct agattacagg cgcgagccac tgcacccggc ccatttaa   ccattttaag    52860 tttacaattc agcggcatta attacattca tgatgtacaa tcactactac tacctatttc    52920
cagaattttt tcatcaccgc agatggaaac actcagcccg tgaaacagta acttcccatt    52980
ctcccctctg gtaacctctg ttcttctgt  ctctgtggat ttgcttattc tagaaatttc    53040
atagaagtag aatcatatta tactgtattt gtccttttgt ttctggatta tttcacttag    53100
tataatgttt tcatggttct tccatgatgt agcatgtatc agaatactat tccattgtaa    53160
gtatttaata tatcccacat tttgttgacc tgttcatctg ttagtagaca gttgagttgt    53220
ttttaccttt ggctattgtg aataatgctg cagtgaacat tgtcatacaa gcatctgttt    53280
gagtccctgc ttttgattct tttggttatg tacctaggag tggaattgtt gcatcatatg    53340
gtaactctat gtttaacttt ctgaagagcc accaaactct tttccatagt gtctgcacca    53400
ttttacatgc ccaccagcaa tgcatgagga ttcctgtatc tccaaacttg ttcttttttt    53460
```

```
tttttttaata gtcacccaag tagttacaaa gtggtatctc actgtggttt tgatttgcat    53520
ttctctcatg actaatgatt ttgagcatct tttcatctgc ttattggcca tttgtatgtc    53580
ttctttggag aaatgtctat tcaagtcttg cctattctta attaggttgt ttgtgttttt    53640
gttgttcagt ggtggttctt tatatatctt agacccttat cagatacatg atttgcaagt    53700
attttcacct attttgtggg ttgtcttttc actttcttga taatgtcctt tgatacataa    53760 aacatttta attttgatta agttccaatt tatttttttt ctgtccttgc tcatgctttt    53820
ttgatgtcat attttagact gtattgccaa attcaaggtc atgaataatt taccccctatg   53880 ttttctacta agagttttgt aactactagg aatataatag ggtttagctc ttatacttag    53940
gtctttgatc cattttgaat taattttat agatgatgtg aggtaggggc ccaacttcat    54000
tcttttgcat ctggaagtcc agttattcta gcaccataaa gagactatta cttcccccat    54060
cgaatcaaca tgataccctta ggatttctcc tttgttttt gtttctttca ccttttacct    54120
gtttcttaga aatttggtat atataattag caatacacgt gtgggtttaa ttctggactc    54180
tcagttctat tctattggtt tatatatcta tccttatggc aataccacac tgttttgatc    54240
actgtagctt tatagtaagc tttgaaatca ggaagtgtga gtcttccagc tttgttcttc    54300
tttttcaaga ttgctttgac tattctgggt cccttgtaat ttcatatgaa tttaacaatt    54360
ggcatttcta tttctgcaaa aaaaaggctt tagaattttg atagggattg tgtcagattt    54420
ttagatcact ttaagtgata ttgacatctt aaccactatt aagtcatcct gttcatgaac    54480
aaaggatctc tttccattta tttaagtctt tattttttt tcagcagtgt tttatagttt    54540
tcagttgtaa agtattttac cttggttaaa tttttttccta tgtattttat tattttttgct   54600 gcgattatag atggaaattc tttggtgtgt tcattgttga tatatagaaa ccaaattaat    54660
ttttgattgt tgatcttaca ccctgcaaat ttgctcaatt tatttattag ctctagcagc    54720
tttcttctag attctttgtg attttctatg tataggggtta tgtcatctgc aaacagagat    54780
agttttattt cttcctttcc aatttagatg cttttaattc tttctcttgt ctaatgtaat    54840
ggctctgtct agaacttctg ctacaatgct gaatagcaac agtgaaagta ggcatccttg    54900
tcttgttcct gtcttagggg gaaagcttc agtctcttcc cattgagtat gatgttagct    54960
gttggttttt cataaatgcc ctttatcatg ttggggaagt tctcttcttt ggtagtccat    55020
ttcacattgc tatgaaggaa tacctgaaac taggtaattt atcaagaaaa gaggtttatt    55080
tggctcacag ttgcatagct gtaaagaag cattgtgcca gcatctgttt ctggtcagga    55140
cctcaggaag ctttcactta tggtggtagg ggaacaggc atgtcacatg tcaaaggagg    55200
gagcaagaga gatgccagac tctttttaaac aaccagcatt tgcatgaact gatagagcga    55260
gaactcactc attaatgtgg ggagggaacc aagccattca tgagggatcc aagaccctaa    55320
caccttcaat caggccccac ctccaacatt ggggatcaca tttcaacata cttggagggg    55380
acaaaacatc caaaccctat caccttctgt tcacagtttt ctgagtatt taatctgaat    55440 tttaaatgcc attaaaattt tatttagatt acattgaaac ttaattacac atggctagtg    55500
gtattggttt atgcattttt agatcccttc aagttatctt cctgttctac ctttttcttg    55560
ggttttgtaa ttagtctcct tcttgaaaga ttattttggt actggttgtt agtaattcct    55620
ggatttcctt taaagatata agaaatactg ggagggggac aagatggaca actagaaata    55680
gctgcaatca gaggcttcca acaagaagaa cgaaaacggt gagtgaatcc tgcaccggca    55740
actgaggtat tcaccttctc tcaatgggac tgactaggtg gttggcatga cccatggaga    55800
gtgaggaaaa gcagggtgga gcgacagccc acctgggagc tgcaaagggc aagggagct    55860
```

```
cccacccccaa gccaagggag gtggtgagtg attgttctac cctgtccagg aaatcatgct    55920
ttttccaagg atctgtgcaa cctgtgattc aggagatccc cctcatgagc acatgccacc    55980
agggccttgg gtcccaagca cagagctgtg taggttcttg gtagccctt ggctggagac    56040 tacataagac tactgagttc cttggggag gggttgctgt catcactgca gctccagtct    56100
gctgttttcc cctgctggtg ctggagagac tgggcggttg ggacccagaa ggaattccct    56160
acagtgcaga ccctacagtg gtggtggcac atcatggcca gactgactct ttaggctgaa    56220
ctctgactca tcccctaca cggggcaggg cctctctgcg ggaatttcag caactccagc    56280
caggggttta cagacagaat tccaatctcc ctgggatgga gccctggtg ggaggggtgg    56340 ccacagtctc cacagatcag cagagttagt ctttccccctt gctggctctg aggaatccag    56400
gcagtctgga tgagtgagat ttcccccagt gcagcacacc ccctccacca aggggcagcc    56460
agagtgcttc gttaggtggg cctgtgcctc ttgactggat gagacccctc caacaggggt    56520
cgccagacac cttatgcaag agcattccca ctggcatcag gttggtgccc ctctgggacg    56580
gagctcccag aggaaggaac aggcagccat cttttgctgtt ctgcagtctc cactggtgac    56640
acctccaggt acaggaggga cccaggcaaa gagtctggag tggacccca gcaaactgca    56700 gcagccctat ggaagagggg cctgactgtt aaaagcaaaa caaatggaaa gcaacaacaa    56760
catcaacaaa aaggtcccca ccaaaacccc tccaaaggtt agcagcctca aagttcaaag    56820
ctaggtaaag tcatgaagat gagaaagaat caatgaaaaa acgctgaaaa ctcaaaaagc    56880
cagagtgctt cttttcctcc aaatgatcac agcacctctc tggcaagggc atagatgtgg    56940
gctgaggctg agatggatga attgacagaa gtagacttcc gaaggtggat aataatgaat    57000
ttcactgagc taaaggagca tgttctaacc caatgcaaag aatctaagaa ccatgataaa    57060
acattacagg agctgttaac cagaataacc agtttagaaa ggaacataaa tgatggagct    57120
gaaaaacaca acatgagaac ttcataatgc aaccacaagt atcaatagcc aaatagacca    57180
agtggaggaa agaatttcag agcttgaaga ctatcttgct gacaagataa gagaagaatg    57240
aaaggaaatg aacaaaactt ttgagaacta tgggattatt taaaaagact gaacctgcga    57300
atgatagggg tacctaaaag aattggggag aatggaaaca agttggaaaa cacacttcag    57360
gatatcagcc aggagaactt ccccaaccta gcaagacagg ccagcattca aatcaggaaa    57420
tccctagaga accccagtaa gctacccat gagaagatca accccaagat acataatcat    57480
cagattctcc aaggttgaaa tgaaggaaaa aatactaagg gcagccagag agaaaggcta    57540
ggtcacctac aaagggaagc ccatcaggct aagagtggac ctcagcaaaa accctacaag    57600
ccagaagaga ttcggggcca atattcaaca ttcttaaaga atttccaacc caaagtttca    57660
tatctggcca aactaagctt catagtcaaa gaagaaataa aatcctttt agacaagcaa    57720 atgctgaggg aattcgtcac caccaggcct gtcttgcaag agctcctgaa ggaagcacta    57780
aatatggaaa ggaaaaactt actggccact acagaaacac actgttttct tttaccagta    57840
acactatgaa gcagttacct caacaagtct gcaaataac cagctagcat catgatgata    57900
ggatcaaatt cacacataaa aaatattaac cttaaatgta agtgggctaa atgccccaat    57960
taaaaaacac agaacggcaa gctggataaa gaatcacgac ccatcagtat gctgttgtat    58020
tcaagagacc catctaacat gcaaagacat acaaaggctc agaataaagg gatgagggaa    58080
aatttaccaa gcaaatggaa agcagaaaaa agcaggggtt gcaatcctat tttctgacaa    58140
aacagacttt gaaccagcaa atatcaaaaa agacaagggc attacatagt ggtaaagggc    58200
tcaattcaac aagaaaagct aactatccta aatatatatg cacctaatac aggagcaccc    58260
```

```
agatttataa accaagttct tagagaccta cacagagact tagactccca tacaataata  58320
gtgtgagact ttaataccccc actgtcaata ttagacagat catcaagcag aaaattaaca  58380
aggatattca ggacttgaac tcagctctgg acctgataga tagctacaga actctctata  58440
cagaaacaac agaatataca ttcttcttag cagcacatcg cacttaggct aaaattgatc  58500
acataattgg aagtaaaaca ctcctcagta actgcaaaag aactgaaaat ataacacaca  58560
gcctctcaca ccacagcaca atcaaattag aactaagatt aagaaactca ctcaaaacca  58620
cacaattacg tggaaattgg acaacctgct cctgaatgac tcctggataa ataatgaaat  58680
taaggcggaa atcagaagtt ctttgaaacc aatgagaaca agagaacat accagaatct  58740 ctgggacaca gctaaagcag tgttaagagg aagtttata gcactaaatg cccacatcaa  58800
aaagctagaa agatctcaaa ttgacaccct aacatcacaa ctaaaagaac tagggaacca  58860
agaccaaaca aaccctaaag ctagcagagg acaagaaata accaagatca gagtggaact  58920
gaaggagata gagacaggaa aaaccccttcc aaaaatatca gtgactccca agatctggta  58980
ttttgaaaaa cataaaataa aataaaatag actcctagct agagtaatga agaaagaaga  59040
atcaaataga cacaataaaa atgataaagg gggtatcacc actgaccctg cagaaatatg  59100
aacaactatc agagaatact ataaacacct ctatgcaaat aaactagaaa atctagaaga  59160
aatggatgaa ttcctggaca catatgacct cccaagactg aaccaggaaa acgttgaatc  59220
taccaataac aagttctcaa attgaggcag taataaatag cctaccaagc aagaaaagcc  59280
caggaccaga cagattacag ccaaattcta ccagaggtac aaagaagagc tggtaccatt  59340
tcttctgaaa ctattccaaa catacaaaag gagggactcc cctataactc attttatgag  59400
gccagtatta tcccaatacc aaagcctgcc agaaatacaa cagaaaaga aaacttaagg  59460 ccaatatccc tgatgaacat cgatgcaaaa atcctcagta aaatactggc aaaccaaatc  59520
cagcagcatg tcaaaagctt atccatccac cacggtcaag tcagcttcat ccctgggatg  59580
caaggctgtt ttaacatatg caaatcaata acataattg atcacataaa cagaactaaa  59640
ggcaaaaacc acatgattat ctcaatggat gcagaaaagg cctttaataa aattcaacat  59700
cccttcatgt taaaaactct cagtaaacta ggtgttgatg gaacatacct caaaataagc  59760
catgtaagac aaacccacag ccagtatctt actgaatagg caaagctgg aagtattccc  59820 cttcaaaact ggcacaagga tgccctcttt ccctactcct attcaacata gtattggaaa  59880
ttctggccag ggcaatcagg caaaagaaag aagaaaggg tattcaaata ggaagagagg  59940
aagtaaaact ctgtttgcag gtgacatgat cctatatcta gaaaaccttg ttgtctcagc  60000
ccaaaagctt cttaagctga taagcaactt cagcaaagtc tcgggataca aaatcaaagt  60060
gcaaaaatca caactattcc tatacaccaa cagtaggcaa gcagagagcc aaatcatgaa  60120
tgaactctta ttcacaactg ctaaaagaga ataaaatacc cagaactata gctattaata  60180
acaagggaag tgaaggacct cttcaaggag aactacaaac cactgctgaa ggaaatcaga  60240
gaggacacaa acaaatggaa aaacattctg tgctcatgga taggaagaat caatatcatg  60300
aaaatggcca tattgcccaa agtaatttat aaatttaatg ctattcccat aaactactg  60360 ttgacattct tcacagaatt agaaaaaaac tttaaaattc atatggaacc aaaaaagagt  60420
ccatatagcc caaacaattc taagcaaaaa gaacaaacct ggaggcatca cactacctga  60480
cttcaaacta tactacgagg ctacagtaat caaaacagca tggtactagt acaaaaacag  60540
accaatggaa cagaatagag atctcagaaa taaaactgca catctacaac catctgatct  60600
tcaacaaacc tgacaaaacg agcaatgggg aaaggattcc ctatttaata aatggtgctg  60660
```

```
ggagaactgg ctagccatgt gcagaaaatt gaaactggac cccttcctta caccttatac    60720
aaaaattaac tcaagatgga ttaaagactt aaatgtagaa cccaaaacga taaaaaccct    60780
agaagaaaat ctaggcaata tcattaagga catagacatg ggcaaaaatt tcatgatgaa    60840
aacatcaaaa gcaatggcaa caaaagcaga aactgacaaa tgggcttctg cacagcaaaa    60900
gaaactatcg tcagagtgaa cagacaacct acagaatggg agacagtttt tgcaatctat    60960
ccatctgaca aaagtctaat atccagaatc tacaaggaat ttaaacaaat ttacaaggaa    61020 aaaaccatt aaaaagttgg caaagggcca ggcacagtga ctcatgcctg taatcccagc    61080
actttgggag gctgaggcag gtggatcacg aggtcaggag atcgagatca tcctgactaa    61140
tttggcgaaa ccccatctct actaaaaatg caaaaaatta gccaggcatg gtggtgtgcg    61200
cctgtagtcc cagctactca ggaggctggg gcaggagaat gacgtgaacc caggaggcgg    61260
agctggcagt gagccgagat cacaccactg cactccagcc tgggcgacag agcgagactc    61320
cgtctcaaaa aaaaaaaaaa aatattggca aaggacatga acaaacactt ctcaaaagaa    61380
gacatttata cagccaacaa acatgaaaaa aagctcagtg tcactgacca ttagagaaat    61440
gcaaatgaaa accacaatga gatactgtct catgctagtc agaatggtga ttattaaaaa    61500
gtcaagaaac aacagatgct ggtgaggcta tggagaaata tgaacacttt tacaccgttg    61560
gtaggaatgt aaattagttc aaccattgtg gaagactggt gaaatcctca agacctaga    61620 accagaaata acatttgacc cagcaatccc attactgggt atatacccaa aggaatataa    61680
atcattctgt tacaaagata catgcatgtg tatgttgatt gcagcagtat tcagaatagc    61740
aaagacatgg aatcaaccca aatgcccatc agtgatggac tggataaaaa aacatggtac    61800
atatacacca tggaatacta tacacccata aaaatgaatg agattgtgcc ctttgcgggg    61860
acactgatgg agcttgaagc catttttcctc agaaagccaa acaccacatg ttctcacaag    61920
tgggagctga acaatgagaa cacatggaca catggaggag aacaacacac gctgggcct    61980 gttggtgggg tggggtcag gcggagggaa cgcatcagga taaatagcta aggcatgcgg    62040
ggcttaacac ctaggtgatg gattgatagg tggagcaaac cacgatggca catatttacc    62100
tatgtaacaa acctgcacat cctgcacttg tatctcagaa cttttaattta atttttaaaaa    62160 aatataagaa atactcattt ttgtcttaaa gccaataatg tgttatcaga ttagaaatta    62220
ttcttgtttg tgactttgca gaacccttcc atctggccta atgatagcat tattattttt    62280
taaagaatga agccctttct taaaagccta gttgactagg gatatcaagt ggacacagct    62340
gacagaactt tgtactagaa aggagggagg atacagaatg tctcttcagg tacagtacta    62400
acttatttca aataccatag atcttgaaat gaataagcca ctttgaaaat tctgttacca    62460
acgcttaaca ctctgcagct taaggaagag agaaagtttt atagccctgt tatgcatcaa    62520
ataccgtttt tctaccagag atcacagcct tggcttgctg ttgttttcct tttctccata    62580
atcaagtgaa tttccttatg tgtaaaacct tctttaattt taacagaaat ggtgctctta    62640
agacataatg ggttaatgga gctgagttaa aatccacttg ccatcagtta ctgccctggt    62700
ctatgggagt tttcctagtg tattaaattt gcttcttata tatttttttt tatttcttct    62760
tttgcaaaca tgttttgaaa tatttcagac atactgctag acaaagaata taaacacct    62820 ctgttcatac tgtcctgctt gtgagttaaa acactggcaa tagagctaaa gcttctggag    62880
acccttctct cacatctgcc catcactttc agtcattggt ttcaaatact cttttctttt    62940 tttttttgaga tggagtctca ctctgttgcc taggctggaa tgcagtggcg caatctcggc    63000
tcactgcaac ctccacctcc tgaggctggt ctagaactcc agacctcaag tgatctgccc    63060
```

```
gccttggcct accaaaatgt tgggattaca ggtgtggcca ctgcaccctg ccaaatattc   63120
tccctctctc tctttttttt tttttttgga gacagagtct cgctctgtcg cccaggctgg   63180
agtgcaatgg cgcaatctct gctcactgca acctccacct cccgtgttca agcgattctc   63240
cctgcctcag cctcccgagt agctgggatt acaggtgcac gtcatcacgc ccggctaatt   63300
tttgtatttt tagtagagac aggattttgc catgttggcc agcctggatg ttctctcatt   63360
tttaaaaagc agtttcactt tagacaccaa agcaagtgt ccaataaatg ctgaagaaga   63420
aaaatatttt attaggttat ttgccctttc ctctctaact tgaaaataca ttttctcagg   63480
aaaaggtaga atcctcagat ttgtccataa accaagggtc ccttaagaaa ttttctttgt   63540
gttacagtga aaatgactat tttgacaact tggaagataa ggagctaggc taagtcttat   63600
tctagtctat cctgtctgtc accaggaaga tttcctacct tcccaaaggt tagtgctcca   63660
cttcacccct atgtggattt atgtctttga aaattactgc tcatggcagg taggtcctgc   63720
aattggtcct tttatttatc ttcaactttc tggcctgtgg aggtttttta ggagtgcctg   63780
gagcacttag aactgactag aatatccctc ttttactttc cctagaaata tcctgttatg   63840
cttagttttt ttgttttttt ttttctttac ctgttcattc tgactgactt gcttctgtta   63900
aagatgactt cgtctaaaga gtaatcttag gcttaagttg ttcttttctt catttgtttt   63960
agaaagattc aggagattta tgatttaaat tttgacgttg tgatcattac aattaaaaca   64020
cattttaaac taatagtaaa aatattttct acctaagaga aacagggcta aacctattac   64080
aaaggatggc tcactgtgga ataactgat tgtcatgatg tggtgagttt tgctttactc   64140
cgctaatgtg gctacgtgac gctccttctg gtcttaactg cctggacaaa tcatagtggc   64200
cttatagtag ctggtactgt tggaagactg gcctgtattt cagtggattt gccagctttt   64260
gaagaaccca tggtgatttc ttctgaggtt tgcatgtttt aacttccttc atgcaaatgc   64320
ttttagttac taagattttt attttatgtt gtgtgttttt ccatggagta tggtcattct   64380
gtgttttgag ggcaaggcag tggggtaaag ctgagttgaa aagcataata tggctcatct   64440
tttcttttct tttttttttt tttttcattt tttgctgctt ttattttacg aaaaagctaa   64500
ttcaaatcta cattaaacta agttgaatac aaagcctttg tgaagaaggc ctggtagtct   64560
catttacaaa aatggccagt gtcgtctttg gccttaaaat ttcaggacgg gcacttcaga   64620
tggcttcaca tttgcatgtt tcagtgctag agcatgggaa tagactttgg catccactgt   64680
aagatgtttt tcagctacga gagcatcgag tccctgcagc aggtcattct tgggtaacga   64740
aatgacttcc acaaattctc catccctgg ctttggcttg ggccttacat tttctgcgtc   64800
atctccgtta atgattactg tcacgatgtg tgtggtacag tttgacaaac ctgggtccat   64860
atagaccact ggagaacatt cagcagcgtc ccctttgtag ccagtttctt cctcaagctc   64920
ccaaagagca gctgctcctg gggtttcacc atcttctatg agttccctgc agggaactct   64980
atgcagtagc cacccattgg tggtcaggac tgtttcacca gaacgataca ctcgtagtga   65040
agcgttctct gcagcacagg gatgaccgct acatcatcac cagtctgttc tttcctggtt   65100
gtatgtttca ctgagtccca gttccagtt ttaccaatag gagccatgta tgttgttttt   65160
tcaagtttga cccattttcc ttctgaaatt aactcctctg aaataatata gtgtttccat   65220
tctgagacaa ttcagttggt tcttggctct cccttttcaa actagtcttt acagccctca   65280
ggagagaagt tcacctccaa agtgtagggg tgacaaaggg aagaggacaa aagaactact   65340
ggaggcagca gtgtcagcat acgccggtgt cacgactcaa gacatcggca cctcccgagg   65400
tgatgaaagg atgtgccatg gctcatcttt tcaagtcaac tagtatttat caagctgctc   65460
```

```
tgtggaaggt gctggggaca ggatggtacc tgtccttaaa accagaatga tcagactcag   65520
tggaaagaga gttacaagag ttacttgaac aactgtctct gattataaaa taagatggag   65580
tgataaatac actagaatag agttatagat aagctattga aaaaaatcca agaagacttc   65640
atggcagagt tcttgtttga ataggacttc aaagtgtaaa taggaataga aaaggcttgg   65700
aaggacggga gaaggggag gtattctggt ttatgagtac ataaataagt acttggaagc   65760
ttagaagtgc ctggaatatc tgatgtgagt tgaagcattg agtgcattaa agaataataa   65820
tttgagccag agtcaaacta ggcttgattc ttcaggcctg atattgtttc atgccagcag   65880
aggtgggaga gagagggttt ctcagctcat tgatgtaatg agccactgtg actaatggaa   65940
attgcgtatt cttcaggtag gttggggtga agttcaggta gttgagaaat tcacagctca   66000
gagagcctgt cttccttaga gagtataaa aaattgactc tcagccaggc acggtggctc   66060
acgcctgtaa tcccagccct tgggaggcc gaggcaggcg gatcatgagg acaggagatt   66120
gagaccattc tggctaacat ggtgaaaccc cgtctctact aaaaatacaa aaaattagcc   66180
gggtgtggtg gcaggcgcct gtagtcccag ctactctgga ggctgaggca ggagaatggc   66240
gtgaacctgg gaggtggaac ttgcagtgag ccgagatcgc gccactgcac cccagcctgg   66300
gcgacagagc gagagactcc gtctcaaaaa aaaaaaaaa aaaaaaaca actgactctc   66360 attgttaagt agtcagaaag aagtctctta aacaagagta ccaatatcaa aagcttcatt   66420
ttagagatta cttttgatgc atatattgta aagccacttg tttgagattt gaagtagtca   66480 agattttttcc catatatgat ttactttatc tgtggtggc tacccagtta aatatattcc   66540
tgaagagtgt taatgtgagg aaactaaatt ttttgaattg agtcatttta gatgagcaag   66600
aatttttttt actgatttct attgtaatat aattaatctg attattttag agcaagacag   66660
tatccatccc accccattc ctactctgtc ccatgaacat atgctataag attttttact   66720
tgtcaacatc ttgaactgag aagccagtat taaaatctta accttataaa cacaatgatt   66780
tttgccattt gcagatgaca aaattccctg ttattcttaa tttagaaata atgtgagtgg   66840
acttgtttct agtttgtttt tgcttgctaa agaacacaag ttgtttgggt ttagggtggg   66900
gtttggcgca ccttttctga aagggccagg tagttaatat tttaggcttg ggaaccatat   66960
ggtaactgtg cttgttgtaa ttggaaacac ctatagactg tacataaatg aatgggcatg   67020
gctgtgttct aataaaactt tatatataaa acaggcagag cctggggttt ggtgactcca   67080
gcctagaatt ttcttccatt taagctgatt tcatgtctga agaaagtaa aagacaggat   67140 gtcaaattac tgcattaagt tattcctata acgtaggcac ctgtggctta tagagactgt   67200 tgttttaag tgctgctatg ttgcctttat atgtataacc ataagcaaaa atttctttca   67260
tcctgctcta ccttttcctc aaatattttg actacctgtc atgtaccaga tgttaggctg   67320
gggataaatg gtgaagaggc agagtggccc ctgtcctcgt agagctgtag accagtacag   67380
ggggcagaca gtaagcaaat aaagtaaattc taggctgtga taagcactat gatgttatca   67440
agcatggtgc tgagagagaa ttgggggtg gggtgttatg tatatagagt gttgagggga   67500
ggcctccctt aggaggtgaa gttgaagctg agacctgaag ccaagaggat ttagtcatgt   67560
gaaaaacctg atgggtcaga agacagtcat cctcccttc tccctccctg gaatgtcagt   67620
cagtataaac gtggataaac tgttcacatt ttcagaggaa atattaaag ctatttata    67680 atatttttcc ccctcttttt aacttccttt ttaggtaaga ttaaaagcaa tgagaacaaa   67740 caaattttttg tcttctggtt aacacatgca catacattct gagtatacat tgaagtgtta   67800
gctaccagga taaaagttat ggcattgtgg cctattattt agagcctttg ggatgtgtga   67860
```

```
agtttgttaa gcattgttca tttgcatttt ataaggttga aaccgcctgt atttgcgttc   67920
tcatggcgct cctaaaggaa catgcgatgg gagagcgccc tctgctggcg actctccctc   67980
atagtgcctg ctatagccag tgtgagaggc gaggcttccc tttccagagg gtgtgctcca   68040
gtggtcaggc tttggggtct cacaggcctt ccactgtcat atcacaagct ctttaggtca   68100
cgcttgggag aatattcata aatagacttg tacatcccta gctcctgtct tctgctgctt   68160
ttttccttat ctgtggccct ctaattatca gtgcactttg ctgaactggt tactgacact   68220
gtgatggcag atgaagaggg cagtgtaaac tgagtgaagc tcttgtgttt tcacctgctg   68280
tctttggcag ctaagaacca gctaaagttg cctcacttta ctgatacatg ctgttgacag   68340
atgcataaaa tgaatataaa gtggatatgt gtttggtagc attttgaatc tttgtacagg   68400
aggagcatgc cctacgtgaa gtgatcatcc tgcaggagcc ttgacctaga gggattcacc   68460
gtgttggcta ggtttggggt gtttcatttt tgttctcggt gtgttctgtt tgtttgtttt   68520
tgttttgttt gtcattgttt gtttttcatt tttattttgt cccaacatttt tcctttatgg   68580
tccaccatta gatattgatc agttgaagct cattttaaga ctcgttggaa ccccaggggc   68640
tgagcttttg aagaaaatct cctcagagtc tgtgagttga tgctttgtaa ttatctgccc   68700
tgttgggagc ctctgccact tgccttctac caatctgtac tttgacctgg gtgtgtttgt   68760
aagcacacat gcccttttgtg tgctgacttc ccggatgagt gaggtataag acagtgtgag   68820
tgtgtgtgtg cgtgcacgca tgtgtgcctg cttgcatgca caagtgtgtt ttattctcta   68880
tctgggtaca cactaagatc acgggagcct ccattagaca atagtatccc agtaaagcaa   68940
tgagatttga gattctaatt cattccaaga gattaatgta aactttgtgt ctctgtcctc   69000
aagacctgac tttcttcttt ctcagaagtt tcacgtatgc tctagagctc ttttcactgt   69060
ttctagtgtt tgttctcaga gcatgagctt caccatgtat ttagtttaac ttaatcacta   69120
aaagaataaa atgtacattg tctgcacact gttgcccctt cccagaagtt attttttatt   69180
gttttagaat agatactcac atatcctatg taaaatgttt gttcccaaca gagggacctt   69240
tctacccagt ccctagaccc cactcagaag aaacagcttc actcctgata cctcagatac   69300
acaggaatgt ggttataaat tttcctccta ttgccttgta attataagtt agataacctg   69360
agacagagtt tggaactagt gctttcttgc ttctaagcag ggacttagac agaagccatg   69420
ggaatgtgag tctggcttac ttttgctatg atttcctgct cttggtcatt tcttgggcc    69480
agaggcatga gagaagccat gaaagcccag cttttctttt tccctcgatc tgctgccagg   69540
cagttgaaca aaagaaaaaa agagctatgg agccaagctc cagttatgcc ttcctggatt   69600
ctcctcccaa catttatgac tgaaggggcc ctttgcctag ttgggaagat ggctgggtag   69660
cttgaggcaa gcataagcag gtgagttgga accgttcatc atcttcctga caaaataaag   69720
aataccgtca tctggtatgt atccggtaca tttcttgaaa ggatcccaaa gcccagtgta   69780
tttctgaacc tccactctga atttgtttca tttacttatt taagataaag aagcaaaagc   69840
ccagaagggc agtgactttt ccatgtcatg cactgaatca cgtggcagag ctgagtatag   69900
atcccagatg ttctgataac atgatccaaa ctataatccc atgtgattac acactatttt   69960
gaaagtcatt gtcagtgtta ccacaatgtc aacctaaaga ggtatttttt tctcctttat   70020
gatatgtaga agctgaatta gagtgaatca aagatatcag atgatgctta gaaagagcag   70080
tactttttttt ttaatgtttt tgcttagaaa cactgtctta cagtaagagg acctaagggc   70140
agagggagga gctcaattaa taaatagtgc taatgagacc aagcaaattc atttccttcc   70200
tgagagtgtc tcctagcagc cctttcttag tcttctcttc catcccaacc atctgcccta   70260
```

```
tagatacgtg ctattagtca tttggaattg gattaggaat tcaaaccaaa gtctaggtaa    70320
aatagtcaat agtatttatc tgtcattaat ccatcactta tttttaagaa agaaacaatg    70380
agtgcacagc ctaataatgg aggtctctct gtgaaatgag gcacattata catttcaaca    70440
gctctactga aattgagtac cagaatacag aacttaactc aaataatatt atattgagta    70500
taagaataag aaaggttttt tttttttggtt tgtttcctac ataattgggg tgagtggata    70560
aaagtagttt aaacatccta aggggtagac aagattaatt tgatgttcgt gacacggccc    70620
aagtacctgt ttatcttaaa agcgcatgat gtatgggaac agaatggaaa ataaggcca    70680 ggtgagtaaa attgttcaga gattttaaaa attaaaaaaa gaaaaaagac attagtgaag    70740
gagtgcagta aatagccaac agctgttttc attctcctga aaagtagtga agtagtgatg    70800
gcaataatta tgaagaaatt gaatgccgag taagagaatg cagtaatgga tttagaacct    70860
attagaatga gccataggaa aaggtataaa tgggttgtga tggaggccaa ggacagagaa    70920
ttcatttggt taatgtccca gtatctataa taatcagtga aagaacaaga aaatcatatt    70980
aagaaagcaa aagcagactg ggcacagtgg ctcacatttg tcatcacagc actttgggag    71040
gctgaggcag gaggatcact cgaggccagg agtttgaggc tgcagggagt ggtgatcatg    71100
cactgcactc cagcctgggc aacagagcaa gaccttgtct ttaaaaataa ataaactaat    71160
taattaaatt agataaaaaa gcgaagacct gactcattca cattttcctc cagaaataga    71220
atctttctaa cttcttgaca gaaaggggat ataataacct ctttgactaa aggagacaaa    71280
gacagaaaat gtgcaggcca ggtatcattc acagaaagaa aggggaagtg gaggattttt    71340
acattttaag acccaactgg tattctgcta ttgctggttt actttgtggc cccttttttgt    71400 tatttccctt ggcatgaaaa gtatcatttg ttatgtgatt tgttaaaggt aactctaaat    71460
tctgttatct gtactcctaa caaaataaag aattccatca tctggtatgg atctgttaac    71520
gtttcttaaa aggaccgcaa atcaaagtgt atttcctatc ccttttgga atttactggc    71580 ctctgtcttt gggcttaggg agcgtaaaag gcagcgtgga gcacatggct ctagctccct    71640
ccctgtggcc agccttaaac agattactgc taagtcatct gaccactagg gagttcagtt    71700
cagaggacga gctaaagtag aaaaattatt tgggaaagcc atgaagtaaa attgcttggc    71760
catggtgctt attaaagatg acacttcacc tgaatgaggg aattagtagt taacaagaac    71820
aggactagaa aagggggttta ttgaattaca ttgaatattt ttaaaatctc atcacttctg    71880
ctcttagtag gaacatgata aacagttctg acattttaga agagggtgag ttgtattaac    71940
attgatggaa cagttaaaag agagaagttg tagtacagct tacatatgtg cctatacata    72000
tagaaaatct catagttctg cccttatcag atgcttgcag agtattctgc agacttccct    72060
ccagctgttt gttaaatgag gttagtctgt tcgctagttg aagagacttg tggaggaaat    72120
catgtggcat gctttaacac tctcagcagc ctgtgacttc tgttttgcct ttgccattag    72180
cctctaacct tctcctcttc tcctctttct tcatttacca ttttgtgttt gtggcaagta    72240
ttttaaatgt accactaact aatgtctttg aaatgtggca ttgcttatta acccagatgc    72300
ccacgtgtgt cttaattcgg agggatggtg ccttggagaa cctgtgccgc aaaagtttag    72360
tctcttcctt gaatggatat gttggatatt ttatttttgtt caaagttgag tcaaaatttt    72420
tggaatcatc tatatttctc ccacaaacag gttttggcca tcagtacttg aaaacagttc    72480
tatggctggc atcctggatc aagggggcagt ctgtttccag ggaacctaaa atatttaaca    72540
gtaaagatga tgctaaaacc aaagaaaagt aatttttctt atctgcatgg ccagtcactg    72600
gctacgtgcc tagttactca tgtcattcac agaagtgtac tgtagcatgc agctgtgggc    72660
```

```
tctcgggtag ggggaatgga gggtaggttt ttttgtctgt ttgggggtgg cttttttgacc   72720 tttttaaaaa cttgagttga aaattatttt ttgcactgta tgtttaacaa tgcccttgac   72780
taggcatcta agatattaac cagcttcagc agattatgcg tctgacagga acacccccg    72840 cttatctcat taacaggatg ccaagccatg aggtgagaac aaagagactg tacagggatg   72900
tcgcactgag aagccacatt ctcattttat tgccaccgta taaccaacag ttcttaacat   72960
cactggatgc ttgcatgtgc cttgaggcct gcctatgtgc tattgcaaga tgttgacttt   73020
tgggataaaa tgtcatccag tcctgtgaga ttgggaatat aattagtaag cttgtaaatg   73080
gaaaattgtt atttttatat ttggttgtgt gaatttagtg cttgtgaggc ggtttctttc   73140
taggtgctct gcctgtagct agggtgtgct actatcgtga cctttatcag aagggtagtt   73200
aactgaagtc cattagcatg cttttccaatt catccatttt tttaatgacc aaaagaggat   73260
tctttattta aaacaaaac tgaaatatcc aatactaata tgtactatat ttaaaagaaa    73320
atacacaaat aatatagaat aaatacaaac actttggtac agttaggtac cttctttatt   73380
aattattaac tacttagtct aactcttgtt ttattatcag agatgattgg ggcacttctt   73440
tctttgtaag atacccttaa tattttgggg aaccaggttg gcatcacaga gggcccttcc   73500
cagcagcttt gtttctactt cagctatatt caggtcgtct tttgatttat ctttattaaa   73560
gggatgactg ttctctgaat gagatagttc tctcttacct gttttcccctt cctctttta   73620 tttacatgtt caagtagaaa gggattacag ccatttatgt attcaattcc taaaactttc   73680
ttttcaaatc agaagagattc tcaattgctt ttcaaagcag acctttcctc ctgactccac   73740
atgcaataat taagaagcgg aaggctgggt gtggtggcgt gcacctgcaa cctcagcact   73800
ttggaaggct gagatgggag gatcagttga gcccaggagt ttgagaccat cctgggcaac   73860
acagcaatac tgcagctcta caaaaaaatt taaaaattag ggcatgatag cacatgcctg   73920
tagtcccagc tacttgggaa gctgaggcag gaggggttgct tgagtcagga gttagaggcc   73980
atagtgagct gtgattgtgc cagtgacctc cagcctaggc aacagagcag agactgtgtc   74040
tctaaaaaaa ttttttttaat aaataaagaa ggtgaacttg cccaagcaac cagatttttt   74100 ttttttttaag acaggatctt aactctgtca ccccagctgg agtgcagtgg cacgatctta   74160
gctcactgga acctccacct cctgggctca agcttcctgg gctccatctc cctgctcaag   74220
cgatcctgtt acctcagtct cccaagtagc tgggaccaca ggcatgcgtc accacacctg   74280
gctaattttt tgtattttg gagacaagtt ttcaccatgt tacccaggct ggtctcaaag   74340
tcctgggctc aagcgatctg cccaccttgg cctcccaaag tgctgggatt acaggcgtga   74400
gtcaccgtgc ctgggcaacc agaacttttt ataaacttgt gtgtgtatgt gtaaacataa   74460
atatacatac atacttttac tgttggactg tattaaaaca ggagttttaa agaggtggtt   74520
aagatagaca gcagactttg cttctgaagg tgatagtggg atagcagata atgtttcttg   74580
aactgtcact tggaaccaag tactgtgtta agaaagtact aggtttgtta tctctaatct   74640
tcactccaac cctgtgaggt aggactgtta tattaagttt atattaactt ttttgttacc   74700
accgttactt tgttagcaag gtttaatatt gatatccttt gatgtactaa gagcacctac   74760
tgaagtcagc actgtcaaaa gactgctggt ccaagacttg ctttgggaat accaacccct   74820
ctaccaattt agctgtttga gaaggctgtc tcagggctac ttcttacata tcttggcctc   74880
agttttaaaa cttctcatcc tgtgatcaga aagctaatga aagagaattt gattgatgag   74940
cattctcgtt cacttgaaat gcaactgtga gagatagcag gaataaagaa ggtgatgatc   75000
ataactaggg aagttaggat ggcagtaagg gagaagttct atcaaagaca gttagaaaca   75060
```

```
ctgaagttag tggactttgt cagttaacac tcgttcctta gcaggaccaa gattctttct  75120
ttgagagcag taacattatt gaacaaagtc attctgaaaa cccttgtttt ttcaggcaag  75180
aaactatatt cagtctttga ctcagatgcc gaagatgaac tttgcgaatg tatttattgg  75240
tgccaatccc ctgggtaagt tgaccatata tcctcacctc atggatattg aattggttat  75300
gatataaatt ggggatttga agaagagttt ctccttttga ccaaataaag taccattagt  75360
tgaatcttgg aaggtgataa atacggcttt tattatctat ttgtgttgtc agatttttt  75420 ttaatcacat gagatgattg tatgtttaaa tgatcacaga acttgggatt ggggaatgg  75480 gcaggtacag tggagaaagg agagaaagta atgggaatgt tgagagaaaa gattggtgag  75540
gcaggaagaa gcagatacag aagaaagctg taacttgctc acaactgctg tggatttatg  75600
gtgtctctga gtgaggaca gaaaccactg aagtgcaggt gggtgtttag aggagccacc  75660
caggagctcc ctgcagggtg ctctgctcta acggtagctg ccgttgctac agatcctgtc  75720
gtcttccaca ctcatgaact tttcccctct cctcttcttt ctctgccctc agaggcataa  75780
ccgtcctctc ctgtttgtgg agcttatttg ctacctaaac ttaaaggaat ggcttcctat  75840
gccttcaaga tccttggcag agggaagtga tggtggcagc tgaagatatg tgttgccttg  75900
gctaaaaaag gagttgcttt attattatta tttatttatt tatttattta tttatttgg  75960 tagtgtcagg gtctcgctct tttacccagg ctagagtaca gtggcacaat catagctcac  76020
tgcaagcttg aactcctggg ctccagtgat cctcctgcct cagccttcca aatagctagg  76080
actacaggca tgcatcccca agcctggcta attttttaaa gaattctttg tagagacagg  76140
gtctcaccat cttactaatc gtggactcct ggactcatgc agtctgccca cttcaacttc  76200
caaaagtgct gggattcaga cgtgagacac tgtgcctggc ggactatatt ctttgaaggg  76260
gaggagtgat gtgtgcttca gatggcccct gaaagctgct ttgcctgagg ctcattccct  76320
gactcttgaa gaggacagtg gacagtgctg tttaatggtg gacacagaag gatcagacca  76380
ggacctccct acaataggga agggagctat gctatggtaa cgagtataat ctgccttctc  76440
acttttctta agattgtatt gtgtggtgtg ttttaaaatc tcactgcatt tctttgcatc  76500
tgtttgggtc atctgtcttc ttaagggtct tggcagctat gcttcaggtt tagttttatc  76560
tttttgaggg ctgacagcca tgctgacctc tttagaagct ggggtgaagg ctaggtgatt  76620 ttacctttt aagtacttca tccatagtga ttatggagag gaattttagt gtcgctgtga  76680
taattcttat aatagcagag atactcacgc tctttgaagt tttgggcagt tgtggatgag  76740
ttcgtgtcag ccttggagac agagagtatg tcatatctca gctgggtcgc tctcctgccc  76800
taggatgaat ccacagtctc atcaggggtg ggtacgattc tactgagact ggcttaggtt  76860
tgcatctgcc ctggcatgct ctcattggct ttgtgtgatt tatttgagct gtattatcta  76920
gttcaagggt ctgtgagaag ctctctttga gccttaagta ctacaggatg ttgggaaaag  76980
atgttgtgtt ctttctttcc ttttttttt gagacagagt ctcgctctgt cgtccaggtt  77040
ggagtgcagt ggtgcgatct cggctcattg caagctccac ctcccggctt taagtgattc  77100
ttctgcctca gcctcctgag tagctgggaa tacaagtgtg tgccaccaca cctggctaat  77160 ttttttgtatc tttagtaaag acggggtttc accgtgttag ccaggatggt ctcgatctcc  77220
tgacctcgtg acctgcccgc ctcggcctcc caaagtgctg ggattacagg catgagccac  77280
tgcacccagc ccgtcgtgtt ctttcttgtc gtcattctgt tctgaagttg tttcatttta  77340
taagccttaa gttttgaaca gggcagtact cactgacacc ctcttaacag actcagaaag  77400
atgtgttaat tcatttttta gggggagagg ggagatattt gtgttccagc agcttattta  77460
```

```
ggtcacatac ctcctgatag gtcttcccat tctttgaaat catgacattg aaacctccaa    77520
aagaactaga taccactttg ctaatgagtt gaaaggaggc tttggtccat ctggtgctca    77580
gcactgtact tctcagcatt taaacgtgcc ttacagccca ttgccaaaca gtgatgtcat    77640
ataatgaggc tccccttgct gggcagatgg agcacagtgt tactatcaca agctcgtgcc    77700
cagcatatta actgagcagg aacatgccag aaatataaat attaacagct ctgttttgtc    77760
agccactgac tttgtttcac tgctattccc aaaacatgaa ttaaaactta aattacccct    77820
tgatgttagt gtatgtattt atctgtcaag atttttttt tttaagagat ggcatctcac     77880
tctgtcaccc aggttagagt acagtggcac agtcacggtt catgataacc tcgaactctt    77940
gtgtttaagt gatccttcct cttccctatc ccaagtagct gagacaacag gcacataatg    78000
ccatgcccag ctaataagat ctttgaggaa tttgttcttg ccctgacct tattggttat     78060 aagaacatgg tccttttac cctaagggta acagagactt gtcgtataat ctgtgttcaa     78120
ttataaaatc aacagctgat aaggtttctt tttctaagaa gagaagacca tcagaagaat    78180
atatatatat ataatccagg cattcaccta gtactgtaaa gtgtaaactt atgaacttga    78240
attgacacat gaatatttac tttgtttctg tatccccttg aagcccatat ttctccagtg    78300
gattactctg gaattcaagc tgtaggacgg gtgttttaca gcctccaata tacacagcag    78360
tagatctcta taggaagctg tcctcttcac tactcacccc cacaccctcc acatttaagg    78420
agtaatttgc aaagtctcaa aagccttttt caccacagtg ataactggtt atatggcagt    78480
atttattctc ccaagtgcca ccatgctgaa acacaaaaat actcatttga aatatagagt    78540
tagacaaatt accattttgt aaccccttat gaaataattg cttttgggaa ggaaacccag    78600
tgaatgcaga aagccataag tgaaaagaat ggatatttac ttggtaccaa aatatcccgc    78660
agattacttg cttggtcaa aggggaaaca tcttaaccca gtgatcaatt ttagctcatt     78720
agtagtggga cagatggcct taatgcactg tcacgtgcac agcatcacct gtattttgc     78780 tgaaaatgtt taacctgatt cttaccaaaa tttttgacct aacttccggt ttttgggaag    78840
tacaggggat agtggaaagc agggtataga cacatgacag caaagaagc aaaatcagac     78900 acatcccgag aaacggtcat tctcaggaca atcagaggg ctctttagat caaaatcagg     78960
aaagaacagg gcttagaagt aagaagatta ttctagacta agagagacta aagaaaacca    79020
gtcagttgca gtgcatggcc cctaattgaa tcctggtttc aacaaactag ttctaaaga    79080 caacgttgga ataattggag aaatcttaac atgaactgga ttttagatga tatttagaaa    79140
ttatttgtca gagataataa cagtattatg attatatagg aagatgtctt cgtgttgaaa    79200
tatttgggga gggtaaagtg tcatgtctat aatttatt taaaacagtt cagaaaaaaa      79260
tacatataaa tacagaaata taaaatgtt aattgttgaa tatgctaggc atatgagtgt     79320
tcactttatc atagttttta ctttttctgtt tctgtatatt tgaaattttt catagtgaaa    79380
tttttaaaaa taaattccc tttgatttta ataccatgtc tcaccctcat caccatgtaa     79440 aaccccccagt ttattcactg tttgaagatc tgttgatgaa tatttgatgt tagtaaataa    79500
acagcttagg gggacaaaaa aaaaacagcc ctgcctacct attgtaggtt acttcagctg    79560
taggctttgt tttatacagt ttgactacac tggtagcagt ttgacattga cggtccacaa    79620
aagcctgttc aaacagaatc ccagtcattt aaaaaaattc ttctttagta acatattctt    79680
taaaaataca aaatacagga ggagggtgag ggttgagaga taacctatcg ggtacaatgt    79740
tcactatttg gttaatgggc acgctagaag cccagtcccc atcagtccgt ggtgagaccc    79800
atgtaacaaa tgtgcacatg tacccccaaa tcaaaaataa aataaaaaaa ttttaaaaca    79860
```

```
tagaaaatac agatacacac acacacacac acacataaag gagaagaggg    79920
ctaatatatc ctagagtagg tattttggag gagagttctt tgtttggata tgaagggtca    79980
aaactatgtt tgctcaataa ggcatacttt tttgtaacat gttaaaaact cttttccttc    80040
ctgtctatgg tactgatagc tgtcgacttg ctggagaaga tgcttgtatt ggactcagat    80100
aagagaatta cagcggccca agcccttgca catgcctact ttgctcagta ccacgatcct    80160
gatgatgaac cagtggccga tccttatgat cagtcctttg aaagcaggga cctccttata    80220
gatgagtgga aaagtaagtc ctaagggtag gattaacatc ttgaaccact aaccaaaagc    80280
ggtgggaaaa ataaaaactg aatggtcata accaacttgc taaagcttgt agatgaggtc    80340
tctaatgcag aatgaatatg ttctctggtg gaaactgttg tagacagtga tactctctgg    80400
acctttgaga tacttatgtc tggtctgatt ttatgcacag cccctcacat aggagttttg    80460
catggagagt tgaggttttc agagtcattg catttacaac atctctctga gcttttacag    80520
ttttacaatt agtagaactg gggcaaagag aattatgtc ttatcagtta acttagaact    80580
agttagggac atagccagga atggaaccca tgtatcctgt gtccagtccc atattctttc    80640
cacaaaacac aagttcagaa ctctagttaa atcccaagag ccaagaccat ctgttgctgt    80700
agcttgtgag agtgctcttt cattcttgag cacctccgta gagagcttaa aagaagaggc    80760
actcagcgat gaaaaacatg agaaaaaaaa tggttctttt ctatgtccct tgaacttctg    80820
tgtgataacg tgttccagta ggctattaca tacaagctgt gaggtagccc atcaaaccac    80880
tacctggaca gagaggaagg atcttgagct tagaagtcag agtgcttgcc agcaaagaga    80940
atagcctaaa ctctcacatc ttactttttcc ttcccaattt ctaggcctga cctatgatga    81000
agtcatcagc tttgtgccac cacccccttga ccaagaagag atggagtcct gagcacctgg    81060
tttctgttct gttgatccca cttcactgtg aggggaaggc cttttcacgg gaactctcca    81120
aatattattc aagtgcctct tgttgcagag atttcctcca tggtggaagg gggtgtgcgt    81180
gcgtgtgcgt gcgtgttagt gtgtgtgcat gtgtgtgtct gtctttgtgg gagggtaaga    81240
caatatgaac aaactatgat cacagtgact ttacaggagg ttgtggatgc tccagggcag    81300
cctccacctt gctcttcttt ctgagagttg gctcaggcag acaagagctg ctgtcctttt    81360
aggaatatgt tcaatgcaaa gtaaaaaaat atgaattgtc cccaatcccg gtcatgcttt    81420
tgccactttg gcttctcctg tgaccccacc ttgacggtgg ggcgtagact tgacaacatc    81480
ccacagtggc acggagagaa ggcccatacc ttctggttgc ttcagacctg acaccgtccc    81540
tcagtgatac gtacagccaa aaaggaccaa ctggcttctg tgcactagcc tgtgattaac    81600
ttgcttagta tggttctcag atcttgacag tatatttgaa actgtaaata tgtttgtgcc    81660
ttaaaaggag agaagaaagt gtagatagtt aaaagactgc agctgctgaa gttctgagcc    81720
gggcaagtcg agagggctgt tggacagctg cttgtgggcc cggagtaatc aggcagcctt    81780
cataggcggt catgtgtgca tgtgagcaca tgcgtatatg tgcgtctctc tttctcccctc    81840
accccccaggt gttgccattt ctctgcttac ccttcacctt tggtgcagag gtttcttgaa    81900
tatctgcccc agtagtcaga agcaggttct tgatgtcatg tacttcctgt gtactcttta    81960
tttctagcag agtgaggatg tgttttgcac gtcttgctat ttgagcatgc acagctgctt    82020
gtcctgctct cttcaggagg ccctggtgtc aggcaggttt gccagtgaag acttcttggg    82080
tagtttagat cccatgtcac ctcagctgat attatggcaa gtgatatcac ctctcttcag    82140
cccctagtgc tattctgtgt tgaacacaat tgatacttca ggtgcttttg atgtgaaaat    82200
catgaaaaga ggaacaggtg gatgtatagc attttttattc atgccatctg ttttcaacca    82260
```

```
actattttg aggaattatc atgggaaaag accagggctt tcccaggaa tatcccaaac    82320 ttcggaaaca agttattctc ttcactccca ataactaatg ctaagaaatg ctgaaaatca   82380
aagtaaaaaa ttaaagccca taaggccaga aactccttt gctgtctttc tctaaatatg    82440
attactttaa aataaaaaag taacaagtg tcttttccac tcctatggaa aagggtcttc    82500
ttggcagctt aacattgact tcttggtttg gggagaaata aattttgttt cagaattttg   82560
tatattgtag gaatcctttg agaatgtgat tcctttgat ggggagaaag gcaaattat     82620 tttaatattt tgtattttca actttataaa gataaaatat cctcaggggt ggagaagtgt    82680
cgttttcata acttgctgaa tttcaggcat tttgttctac atgaggactc atatatttaa    82740 gcctttgtg taataagaaa gtataaagtc acttccagtg ttggctgtgt gacagaatct    82800
tgtatttggg ccaaggtgtt tccattctc aatcagtgca gtgatacatg tactccagag     82860
ggacagggtg dacccctga gtcaactgga gcaagaagga aggaggcaga ctgatggcga     82920
ttccctctca cccgggactc tccccctttc aaggaaagtg aacctttaaa gtaaaggcct    82980
catctccttt attgcagttc aaatcctcac catccacagc aagatgaatt ttatcagcca    83040
tgtttggttg taaatgctcg tgtgatttcc tacagaaata ctgctctgaa tattttgtaa   83100
taaggtcctt tgcacatgtg accacatacg tgttaggagg ctgcatgctc tggaagcctg   83160
gactctaagc tggagctctt ggaagagctc ttcggttct gagcataatg ctcccatctc    83220
ctgatttctc tgaacagaaa acaaaagaga gaatgaggga aattgctatt ttatttgtat    83280
tcatgaactt ggctgtaatc agttatgccg tataggatgt cagacaatac cactggttaa    83340
aataaagcct atttttcaaa tttagtgagt ttctcaagtt tattatatt ttctcttgtt    83400 tttatttaat gcacaatatg gcattatatc aatatccttt aaactgtgac ctggcatact    83460
tgtctgacag atcttaatac tactcctaac atttagaaaa tgttgataaa gcttcttagt    83520
tgtacatttt ttggtgaaga gtatccaggt ctttgctgtg gatgggtaaa gcaaagagca    83580
aatgaacgaa gtattaagca ttggggcctg tcttatctac actcgagtgt aagagtggcc     83640
gaaatgacag ggctcagcag actgtggcct gagggccaaa tctggcccac cacctgtttg    83700
gtgtagcctg ctaagaatgg cttttacatt tttaaatggt tgggaaagaa aaaaaagaa     83760 gta                                                                   83763
```

<210> SEQ ID NO 275
<211> LENGTH: 397
<212> TYPE: DNA
<213> ORGANISM: Homo sapiens
<220> FEATURE:

<400> SEQUENCE: 275

```
ccaagctcta atacgactca ctatagggaa agctggtacg cctgcaggta ccggtccgga    60
attcccgggt cgacccacgc gtccgaatct cggctctcgg agagtcccgg gagctgttct   120
cgcgagagta ctgcgggagg ctcccgtttg ctggctcttg gaaccgcgac cactggagcc   180
ttagcgggcg cagcagctgg aacgggagta ctgcgacgca gcccggagtc ggccttgtag   240
gggcgaaggt gcagggagat cgcggcgggc gcagtcttga gcgccggagc gcgtccctgc   300
ccttagcggg gcttgcccca gtcgcagggg cacatccagc cgctgcggct gacagcagcc   360
gcgcgcgcgg gagtctgcgg ggtcgcggca gccgcac                            397
```

<210> SEQ ID NO 276
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 276
ctgctgggct tcagctcgga                                          20

<210> SEQ ID NO 277
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 277
taaggctcca gtggtcgcgg                                          20

<210> SEQ ID NO 278
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 278
ggctgcgtcg cagtactccc                                          20

<210> SEQ ID NO 279
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 279
gccgcagcgg ctggatgtgc                                          20

<210> SEQ ID NO 280
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 280
agccgccggg caagaaggtg                                          20

<210> SEQ ID NO 281
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 281
ccacaacctc ctgtaaagtc                                          20

<210> SEQ ID NO 282
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 282
gcctgagcca actctcagaa                                          20
```

```
<210> SEQ ID NO 283
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 283
aggacagcag ctcttgtctg                                              20

<210> SEQ ID NO 284
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 284
caaaagcatg accgggattg                                              20

<210> SEQ ID NO 285
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 285
aggagaagcc aaagtggcaa                                              20

<210> SEQ ID NO 286
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 286
tgaagcaacc agaaggtatg                                              20

<210> SEQ ID NO 287
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 287
caggtctgaa gcaaccagaa                                              20

<210> SEQ ID NO 288
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 288
ggctgtacgt atcactgagg                                              20

<210> SEQ ID NO 289
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 289
```
agaagccagt tggtccttt                                                    20

<210> SEQ ID NO 290
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 290
atactaagca agttaatcac                                                   20

<210> SEQ ID NO 291
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 291 tctccttta aggcacaaac                                                    20

<210> SEQ ID NO 292
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 292
ctgcagtctt ttaactatct                                                   20

<210> SEQ ID NO 293
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 293
tctcgacttg cccggctcag                                                   20

<210> SEQ ID NO 294
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 294
agccctctcg acttgcccgg                                                   20

<210> SEQ ID NO 295
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 295
ctatgaaggc tgcctgatta                                                   20

<210> SEQ ID NO 296
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 296
aggtgaaggg taagcagaga                                                   20

<210> SEQ ID NO 297
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 297
ttcaagaaac ctctgcacca                                                   20

<210> SEQ ID NO 298
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 298
aacctgcttc tgactactgg                                                   20

<210> SEQ ID NO 299
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 299
tacatgacat caagaacctg                                                   20

<210> SEQ ID NO 300
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 300
ggacaagcag ctgtgcatgc                                                   20

<210> SEQ ID NO 301
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 301
agagcaggac aagcagctgt                                                   20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302
gcctcctgaa gagagcagga                                                   20
```

```
<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303
aagtcttcac tggcaaacct                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 304
atgggatcta aactacccaa                                               20

<210> SEQ ID NO 305
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 305
gccataatat cagctgaggt                                               20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306
gggctgaaga gaggtgatat                                               20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307
ttcaacacag aatagcacta                                               20

<210> SEQ ID NO 308
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 308
catcaaaagc acctgaagta                                               20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309
```

| | |
|---|---|
| taaaaatgct atacatccac | 20 |

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310

| | |
|---|---|
| ttggttgaaa acagatggca | 20 |

<210> SEQ ID NO 311
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 311

| | |
|---|---|
| tcagcatttc ttagcattag | 20 |

<210> SEQ ID NO 312
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 312

| | |
|---|---|
| gcaaaaggag tttctggcct | 20 |

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313

| | |
|---|---|
| ttaaagtaat catatttaga | 20 |

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314

| | |
|---|---|
| ggaaaagaca ccttgttact | 20 |

<210> SEQ ID NO 315
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 315

| | |
|---|---|
| ttccatagga gtggaaaaga | 20 |

<210> SEQ ID NO 316
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 316
aagggattcc tacaatatac                                               20

<210> SEQ ID NO 317
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 317
aataatttgc cctttctccc                                               20

<210> SEQ ID NO 318
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 318
tctttataaa gttgaaaata                                               20

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319
tctccacccc tgaggatatt                                               20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320
agttatgaaa acgacacttc                                               20

<210> SEQ ID NO 321
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 321
tctgtcacac agccaacact                                               20

<210> SEQ ID NO 322
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 322
attgagaaat ggaaacacct                                               20
```

```
<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323
cctctggagt acatgtatca                                               20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 324
cttgctccag ttgactcagg                                               20

<210> SEQ ID NO 325
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325
tttctgtagg aaatcacacg                                               20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326
tacaaaatat tcagagcagt                                               20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327
gtatgtggtc acatgtgcaa                                               20

<210> SEQ ID NO 328
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 328
cattatgctc agaaaccgaa                                               20

<210> SEQ ID NO 329
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 329
```
tacggcataa ctgattacag                                              20

<210> SEQ ID NO 330
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 330
ctttatttta accagtggta                                              20

<210> SEQ ID NO 331
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 331
ataggcttta ttttaaccag                                              20

<210> SEQ ID NO 332
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 332
tgatcaatat ggtctgtacc                                              20

<210> SEQ ID NO 333
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 333
aacgagtctt aaaatgagct                                              20

<210> SEQ ID NO 334
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 334
agtttcttgc agactctgag                                              20

<210> SEQ ID NO 335
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 335
tatccatgag gtgaggatat                                              20

<210> SEQ ID NO 336
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 336
aagtcgacag agactctgag                                               20

<210> SEQ ID NO 337
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 337
cgacactcac cacacagagc                                               20

<210> SEQ ID NO 338
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 338
gcaacaaggc tgtgttgctt                                               20

<210> SEQ ID NO 339
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 339
aactacagag gacttccaaa                                               20

<210> SEQ ID NO 340
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 340
aataacttac attttcatgt                                               20

<210> SEQ ID NO 341
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 341
gagaccaact catgtaggac                                               20

<210> SEQ ID NO 342
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 342
ttcattttac cttcagctca                                               20

```
<210> SEQ ID NO 343
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 343
tgatcaatat ctaatggtgg                                               20

<210> SEQ ID NO 344
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 344
atgaaacaaa ttcagagtgg                                               20

<210> SEQ ID NO 345
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 345
tggttaatat cttagatgcc                                               20

<210> SEQ ID NO 346
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 346
aacagctccc gggactctcc                                               20

<210> SEQ ID NO 347
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 347
gacattttcc agcggcagcc                                               20

<210> SEQ ID NO 348
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 348
tagaacgtgg gcctctcctg                                               20

<210> SEQ ID NO 349
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 349
```

```
gccggtagaa cgtgggcctc                                              20
```

<210> SEQ ID NO 350
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 350

```
cgctcgggca cctcccagat                                              20
```

<210> SEQ ID NO 351
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 351

```
cactggagac aggttctggt                                              20
```

<210> SEQ ID NO 352
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 352

```
cgccagagcc cactggagac                                              20
```

<210> SEQ ID NO 353
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 353

```
agcagcacac acagagccat                                              20
```

<210> SEQ ID NO 354
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 354

```
tttgtgtcaa aagcagcaca                                              20
```

<210> SEQ ID NO 355
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 355

```
taaccccgtt tttgtgtcaa                                              20
```

<210> SEQ ID NO 356
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 356
ctgccacacg taaccccgtt                                               20

<210> SEQ ID NO 357
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 357
tggactgaaa tggtctggag                                               20

<210> SEQ ID NO 358
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 358
gcatgaatga tggactgaaa                                               20

<210> SEQ ID NO 359
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 359
taaccgcagt tctctgtagg                                               20

<210> SEQ ID NO 360
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 360
tatgtttaag taaccgcagt                                               20

<210> SEQ ID NO 361
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 361
aatcacattt tcatgtttca                                               20

<210> SEQ ID NO 362
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 362
aacagaccaa tcacattttc                                               20
```

```
<210> SEQ ID NO 363
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 363
agagaccttg caggtgtaaa                                               20

<210> SEQ ID NO 364
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 364
gaattcctcc agagaccttg                                               20

<210> SEQ ID NO 365
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 365
acacatcatt gaattcctcc                                               20

<210> SEQ ID NO 366
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 366
gtcaccagat acacatcatt                                               20

<210> SEQ ID NO 367
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 367
cccatgagat gggtcaccag                                               20

<210> SEQ ID NO 368
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 368
gttcagatct gcccccatga                                               20

<210> SEQ ID NO 369
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 369
```

-continued tttcacaatg ttgttcagat                                          20

<210> SEQ ID NO 370
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 370
gcttctgaca tttcacaatg                                          20

<210> SEQ ID NO 371
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 371
tcatctgtaa gcttctgaca                                          20

<210> SEQ ID NO 372
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 372
agataaggaa ctgaacatgg                                          20

<210> SEQ ID NO 373
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 373
ctttagacct cggagaattt                                          20

<210> SEQ ID NO 374
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 374
aatgtatata ctttagacct                                          20

<210> SEQ ID NO 375
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 375
tccctgtgaa ttatgtcagc                                          20

<210> SEQ ID NO 376
<211> LENGTH: 20
<212> TYPE: DNA
<213> ORGANISM: Artificial Sequence

```
<220> FEATURE:
<223> OTHER INFORMATION: Antisense Oligonucleotide

<400> SEQUENCE: 376
ttaggtccct gtgaattatg                                               20

<210> SEQ ID NO 377
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 377
attcacagct agattactag                                               20

<210> SEQ ID NO 378
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 378
tctgtgtgcc gagccagtcc                                               20

<210> SEQ ID NO 379
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 379
catttcatca tctgtgtgcc                                               20

<210> SEQ ID NO 380
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 380
cgtagcctgt catttcatca                                               20

<210> SEQ ID NO 381
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 381
ccacctagtg gccacgtagc                                               20

<210> SEQ ID NO 382
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 382
acagctcggc cattatgcat                                               20
```

```
<210> SEQ ID NO 383
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 383
cttccagtca acagctcggc                                              20

<210> SEQ ID NO 384
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 384
aaacaatgtt cttccagtca                                              20

<210> SEQ ID NO 385
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 385
tggtctgtac caggaaacaa                                              20

<210> SEQ ID NO 386
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 386
cagacgcata atctgctgaa                                              20

<210> SEQ ID NO 387
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 387
gtgttcctgt cagacgcata                                              20

<210> SEQ ID NO 388
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 388
gtttcttgcc tcatggcttg                                              20

<210> SEQ ID NO 389
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 389
```

```
actgaatata gtttcttgcc                                              20

<210> SEQ ID NO 390
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 390
tgagtcaaag actgaatata                                              20

<210> SEQ ID NO 391
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 391
acattcgcaa agttcatctt                                              20

<210> SEQ ID NO 392
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 392
ttggcaccaa taaatacatt                                              20

<210> SEQ ID NO 393
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 393
agtccaatac aagcatcttc                                              20

<210> SEQ ID NO 394
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 394
aggcatgtgc aagggcttgg                                              20

<210> SEQ ID NO 395
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 395
cgtggtactg agcaaagtag                                              20

<210> SEQ ID NO 396
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 396
ttcatcatca ggatcgtggt                                              20

<210> SEQ ID NO 397
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 397
cggccactgg ttcatcatca                                              20

<210> SEQ ID NO 398
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 398
gatcataagg atcggccact                                              20

<210> SEQ ID NO 399
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 399
tccctgcttt caaaggactg                                              20

<210> SEQ ID NO 400
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 400
ctataaggag gtccctgctt                                              20

<210> SEQ ID NO 401
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 401
ttccactcat ctataaggag                                              20

<210> SEQ ID NO 402
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 402
ggtcaggctt ttccactcat                                              20
```

```
<210> SEQ ID NO 403
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 403
tcataggtca ggcttttcca                                              20

<210> SEQ ID NO 404
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 404
acttcatcat aggtcaggct                                              20

<210> SEQ ID NO 405
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 405
tgatgacttc atcataggtc                                              20

<210> SEQ ID NO 406
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 406
aaagctgatg acttcatcat                                              20

<210> SEQ ID NO 407
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 407
gtggtggcac aaagctgatg                                              20

<210> SEQ ID NO 408
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 408
gactccatct cttcttggtc                                              20

<210> SEQ ID NO 409
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 409
```

```
ccaggtgctc aggactccat                                              20

<210> SEQ ID NO 410
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 410
agaaaccagg tgctcaggac                                              20

<210> SEQ ID NO 411
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 411
agaacagaaa ccaggtgctc                                              20

<210> SEQ ID NO 412
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 412
gtgaagtggg atcaacagaa                                              20
```

ANTISENSE MODULATION OF P38 MITOGEN ACTIVATED PROTEIN KINASE EXPRESSION

RELATED APPLICATIONS

This application is a US National Phase Application of PCT/US2004/026344 filed on Aug. 12, 2004 which claims priority to U.S. patent application Ser. No. 10/641,455, filed Aug. 15, 2003, which is incorporated herein by reference in their entirety.

SEQUENCE LISTING

A sequence listing is filed herewith in accordance with CFR 1.821 and is hereby incorporated by reference.

FIELD OF THE INVENTION

This invention relates to compositions and methods for modulating expression of p38 mitogen activated protein kinase genes, a family of naturally present cellular genes involved in signal transduction, and inflammatory and apoptotic responses. This invention is also directed to methods for inhibiting inflammation or apoptosis; these methods can be used diagnostically or therapeutically. Furthermore, this invention is directed to treatment of diseases or conditions associated with expression of p38 mitogen activated protein kinase genes.

BACKGROUND OF THE INVENTION

Cellular responses to external factors, such as growth factors, cytokines, and stress conditions, result in altered gene expression. These signals are transmitted from the cell surface to the nucleus by signal transduction pathways. Beginning with an external factor binding to an appropriate receptor, a cascade of signal transduction events is initiated. These responses are mediated through activation of various enzymes and the subsequent activation of specific transcription factors. These activated transcription factors then modulate the expression of specific genes.

The phosphorylation of enzymes plays a key role in the transduction of extracellular signals into the cell. Mitogen activated protein kinases (MAPKs), enzymes which effect such phosphorylations are targets for the action of growth factors, hormones, and other agents involved in cellular metabolism, proliferation and differentiation (Cobb et al., *J. Biol. Chem.*, 1995, 270, 14843). Mitogen activated protein kinases were initially discovered due to their ability to be tyrosine phosphorylated in response to exposure to bacterial lipopolysaccharides or hyperosmotic conditions (Han et al, *Science*, 1994, 265, 808). These conditions activate inflammatory and apoptotic responses mediated by MAPK. In general, MAP kinases are involved in a variety of signal transduction pathways (sometimes overlapping and sometimes parallel) that function to convey extracellular stimuli to protooncogene products to modulate cellular proliferation and/or differentiation (Seger et al., *FASEB J.*, 1995, 9, 726; Cano et al., *Trends Biochem. Sci.*, 1995, 20, 117).

One of the MAPK signal transduction pathways involves the MAP kinases p38α and p38β (also known as CSaids Binding Proteins, CSBP). These MAP kinases are responsible for the phosphorylation of ATF-2, MEFC2 and a variety of other cellular effectors that may serve as substrates for p38 MAPK proteins (Kummer et al, *J. Biol. Chem.*, 1997, 272, 20490). Phosphorylation of p38 MAPKs potentiates the ability of these factors to activate transcription (Raingeaud et al, *Mol. Cell Bio.*, 1996, 16, 1247; Han et al, *Nature*, 1997, 386, 296). Among the genes activated by the p38 MAPK signaling pathway is IL-6 (De Cesaris, P., et al., *J. Biol. Chem.*, 1998, 273, 7566-7571).

Besides p38α and p38β, other p38 MAPK family members have been described, including p38γ (Li et al, *Biochem. Biophys. Res. Commun.*, 1996, 228, 334), and p38δ (Jiang et al, *J. Biol. Chem.*, 1997, 272, 30122). The term "p38" as used herein shall mean a member of the p38 MAPK family, including but not limited to p38α, p38β, p38γ and p38δ, their isoforms (Kumar et al, *Biochem. Biophys. Res. Commun.*, 1997, 235, 533) and other members of the p38 MAPK family of proteins whether they function as p38 MAP kinases per se or not.

Modulation of the expression of one or more p38 MAPKs is desirable in order to interfere with inflammatory or apoptotic responses associated with disease states and to modulate the transcription of genes stimulated by ATF-2, MEFC2 and other p38 MAPK phosphorylation substrates.

Inhibitors of p38 MAPKs have been shown to have efficacy in animal models of arthritis (Badger, A. M., et al., *J. Pharmacol. Exp. Ther.*, 1996, 279, 1453-1461) and angiogenesis (Jackson, J. R., et al., *J. Pharmacol. Exp. Ther.*, 1998, 284, 687-692). MacKay, K. and Mochy-Rosen, D. (*J. Biol. Chem.*, 1999, 274, 6272-6279) demonstrate that an inhibitor of p38 MAPKs prevents apoptosis during ischemia in cardiac myocytes, suggesting that p38 MAPK inhibitors can be used for treating ischemic heart disease. p38 MAPK also is required for T-cell HIV-1 replication (Cohen et al, *Mol. Med.*, 1997, 3, 339) and may be a useful target for AIDS therapy. Other diseases believed to be amenable to treatment by inhibitors of p38 MAPKs are disclosed in U.S. Pat. No. 5,559,137, herein incorporated by reference.

Therapeutic agents designed to target p38 MAPKs include small molecule inhibitors and antisense oligonucleotides. Small molecule inhibitors based on pyridinyl imidazole are described in U.S. Pat. Nos. 5,670,527; 5,658,903; 5,656,644; 5,559,137; 5,593,992; and 5,593,991. WO 98/27098 and WO 99/00357 describe additional small molecule inhibitors, one of which has entered clinical trials. Other small molecule inhibitors are also known.

Antisense therapy represents a potentially more specific therapy for targeting p38 MAPKs and, in particular, specific p38 MAPK isoforms. Nagata, Y., et al. (*Blood*, 1998, 6, 1859-1869) disclose an antisense phosphothioester oligonucleotide targeted to the translational start site of mouse p38b (p38β). Aoshiba, K., et al. (*J. Immunol.*, 1999, 162, 1692-1700) and Cohen, P. S., et al. (*Mol. Med.*, 1997, 3, 339-346) disclose a phosphorothioate antisense oligonucleotide targeted to the coding regions of human p38α, human p38β and rat p38.

There remains a long-felt need for improved compositions and methods for modulating the expression of p38 MAP kinases.

SUMMARY OF THE INVENTION

The present invention provides antisense compounds which are targeted to nucleic acids encoding a p38 MAPK and are capable of modulating p38 MAPK expression. The present invention also provides oligonucleotides targeted to nucleic acids encoding a p38 MAPK. The present invention also comprises methods of modulating the expression of a p38 MAPK, in cells and tissues, using the oligonucleotides of the invention. Methods of inhibiting p38 MAPK expression are provided; these methods are believed to be useful both therapeutically and diagnostically. These methods are also useful as tools, for example, for detecting and determining the role of p38 MAPKs in various cell functions and physiological processes and conditions and for diagnosing conditions associated with expression of p38 MAPKs.

The present invention also comprises methods for diagnosing and treating inflammatory diseases, particularly rheumatoid arthritis and asthma. These methods are believed to be useful, for example, in diagnosing p38 MAPK-associated disease progression. These methods employ the oligonucleotides of the invention. These methods are believed to be useful both therapeutically, including prophylactically, and as clinical research and diagnostic tools.

Figure 1A:
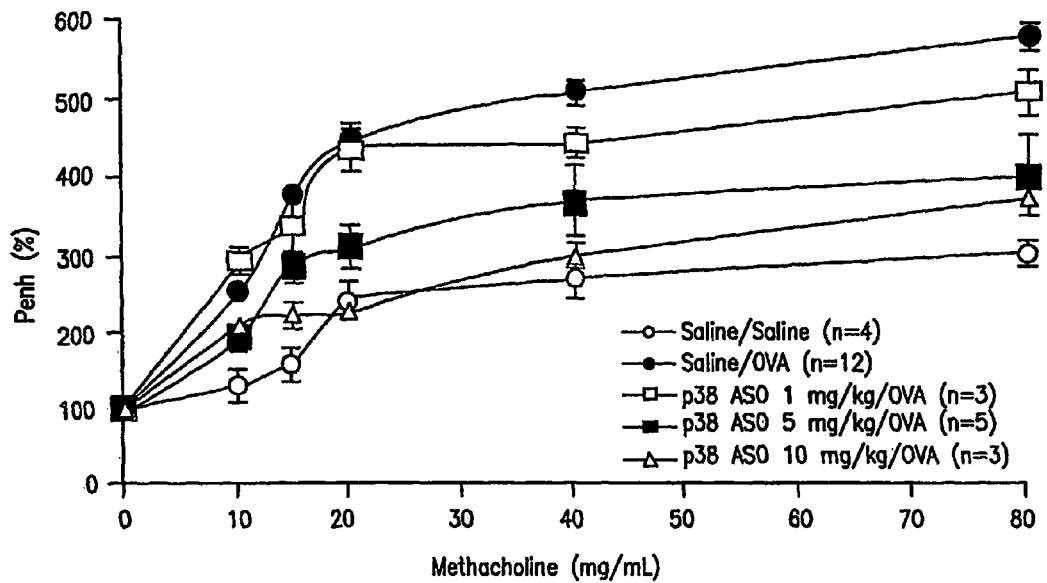
FIGS. 1A-1B are graphs showing the effect of inhaled p38α MAP kinase antisense oligonucleotide ISIS 101757 (ASO, FIG. 1A) and mismatched control oligonucleotide ISIS 101758 (MM ASO, FIG. 1B) on ovalbumin (OVA)-induced airway hyperresponsiveness in a murine asthma model.

DETAILED DESCRIPTION OF THE INVENTION p38 MAPKs play an important role in signal transduction in response to cytokines, growth factors and other cellular stimuli. Specific responses elicited by p38 include inflammatory and apoptotic responses. Modulation of p38 may be useful in the treatment of inflammatory diseases, such as rheumatoid arthritis.

The present invention employs antisense compounds, particularly oligonucleotides, for use in modulating the function of nucleic acid molecules encoding a p38 MAPK, ultimately modulating the amount of a p38 MAPK produced. This is accomplished by providing oligonucleotides which specifically hybridize with nucleic acids, preferably mRNA, encoding a p38 MAPK.

The antisense compounds may be used to modulate the function of a particular p38 MAPK isoform, e.g. for research purposes to determine the role of a particular isoform in a normal or disease process, or to treat a disease or condition that may be associated with a particular isoform. It may also be desirable to target multiple p38 MAPK isoforms. In each case, antisense compounds can be designed by taking advantage of sequence homology between the various isoforms. If an antisense compound to a particular isoform is desired, then the antisense compound is designed to a unique region in the desired isoform's gene sequence. With such a compound, it is desirable that this compound does not inhibit the expression of other isoforms. Less desirable, but acceptable, are compounds that do not "substantially" inhibit other isoforms. By "substantially", it is intended that these compounds do not inhibit the expression of other isoforms by more than 10%, preferably not by more than 25%. If an antisense compound is desired to target multiple p38 isoforms, then regions of significant homology between the isoforms can be used.

This relationship between an antisense compound such as an oligonucleotide and its complementary nucleic acid target, to which it hybridizes, is commonly referred to as "antisense". "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding a p38 MAPK; in other words, a p38 MAPK gene or RNA expressed from a p38 MAPK gene. p38 MAPK mRNA is presently the preferred target. The targeting process also includes determination of a site or sites within the nucleic acid sequence for the antisense interaction to occur such that modulation of gene expression will result.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. Since, as is known in the art, the translation initiation codon is typically 5'-AUG (in transcribed MRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding p38, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene) and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene). mRNA splice sites may also be preferred target regions, and are particularly useful in situations where aberrant splicing is implicated in disease, or where an overproduction of a particular mRNA splice product is implicated in disease. Aberrant fusion junctions due to rearrangements or deletions may also be preferred targets.

Once the target site or sites have been identified, oligonucleotides are chosen which are sufficiently complementary to the target, i.e., hybridize sufficiently well and with sufficient specificity, to give the desired modulation.

"Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

"Specifically hybridizable" and "complementary" are terms which are used to indicate a sufficient degree of complementarity such that stable and specific binding occurs between the DNA or RNA target and the oligonucleotide.

It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment and, in the case of in vitro assays, under conditions in which the assays are conducted.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA.

The overall effect of interference with mRNA function is modulation of p38 MAPK expression. In the context of this invention "modulation" means either inhibition or stimulation; i.e., either a decrease or increase in expression. In one embodiment, p38 MAPK expression is inhibited by at least 10%, by at least 20%, by at least 30%, by at least 40% and preferably by at least 50%.

Modulation of target (i.e., p38 MAPK) expression can be measured in ways which are routine in the art, for example by Northern blot assay of mRNA expression as taught in the examples of the instant application or by Western blot or ELISA assay of protein expression, or by an immunoprecipitation assay of protein expression, as taught in the examples of the instant application. Effects on cell proliferation or tumor cell growth can also be measured, as taught in the examples of the instant application.

The oligonucleotides of this invention can be used in diagnostics, therapeutics, prophylaxis, and as research reagents and in kits. Since the oligonucleotides of this invention hybridize to nucleic acids encoding a p38 MAPK, sandwich, colorimetric and other assays can easily be constructed to exploit this fact. Furthermore, since the oligonucleotides of this invention hybridize specifically to nucleic acids encoding particular isoforms of p38 MAPK, such assays can be devised for screening of cells and tissues for particular p38 MAPK isoforms. Such assays can be utilized for diagnosis of diseases associated with various p38 MAPK isoforms. Provision of means for detecting hybridization of oligonucleotide with a p38 MAPK gene or mRNA can routinely be accomplished. Such provision may include enzyme conjugation, radiolabelling or any other suitable detection systems. Kits for detecting the presence or absence of p38 MAPK may also be prepared.

The present invention is also suitable for diagnosing abnormal inflammatory states in tissue or other samples from patients suspected of having an inflammatory disease such as rheumatoid arthritis. The ability of the oligonucleotides of the present invention to inhibit inflammation may be employed to diagnose such states. A number of assays may be formulated employing the present invention, which assays will commonly comprise contacting a tissue sample with an oligonucleotide of the invention under conditions selected to permit detection and, usually, quantitation of such inhibition. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal. Similarly, the present invention can be used to distinguish p38 MAPK-associated diseases, from diseases having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

The antisense compounds in accordance with this invention preferably comprise from about 5 to about 50 nucleobases. Particularly preferred are antisense oligonucleotides comprising from about 8 to about 30 nucleobases (i.e. from about 8 to about 30 linked nucleosides), from about 20 to about 50 nucleobases, from about 20 to about 30 nucleobases, from about 13 to about 30 nucleobases, or from about 19 to about 23 nucleobases. Preferred embodiments comprise at least an 8-nucleobase portion of a sequence of an antisense compound which inhibits the expression of a p38 mitogen activated kinase. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell*, 1995, 81, 611-620). Montgomery et al. have shown that the primary interference effects of dsRNA are posttranscriptional (Montgomery et al., *Proc. Natl. Acad. Sci. USA*, 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697). Single stranded and double stranded RNA (RNAi) inhibition of human p38 MAP kinase is also within the scope of the present invention.

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —$CH_2$—NH—O—$CH_2$—, —$CH_2$—N($CH_3$)—O—$CH_2$— [known as a methylene (methylimino) or MMI backbone], —$CH_2$—O—N ($CH_3$)—$CH_2$—, —$CH_2$—N($CH_3$)—N($CH_3$)—$CH_2$— and —O—N($CH_3$)—$CH_2$—$CH_2$— [wherein the native phosphodiester internucleotide linkage is represented as —O—P(=O)(OH)—O—$CH_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., *Science*, 1991, 254, 1497-1500.

One oligonucleotide mimetic that has been reported to have excellent hybridization properties is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497-1500.

PNA has been modified to incorporate numerous modifications since the basic PNA structure was first prepared. The basic structure is shown below:

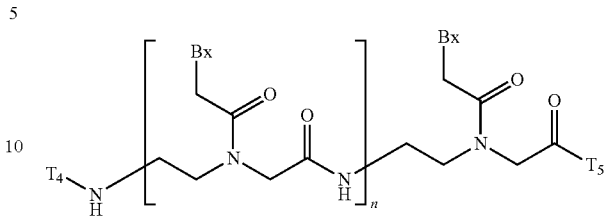

wherein

Bx is a heterocyclic base moiety;

$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups is have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

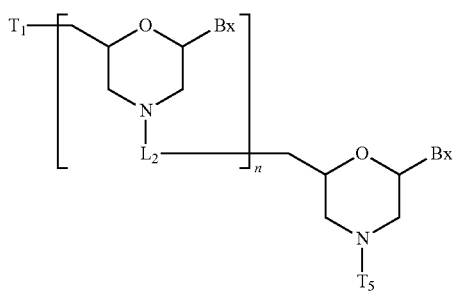

wherein

T$_1$ is hydroxyl or a protected hydroxyl;

T$_5$ is hydrogen or a phosphate or phosphate derivative;

L$_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

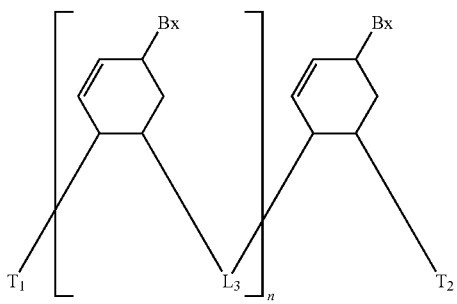

wherein each Bx is a heterocyclic base moiety;

T$_1$ is hydroxyl or a protected hydroxyl; and

T2 is hydroxyl or a protected hydroxyl.

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

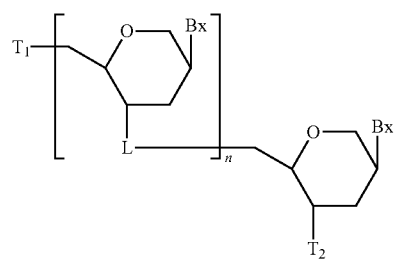

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene (—CH$_2$—)$_n$ group bridging the 2' oxygen atom and the 4' carbon atom wherein n is 1 or 2 (Singh et al., *Chem. Commun.*, 1998, 4, 455-456). When n is 1 (i.e, a methylene group) the modification is commonly referred to as LNA, and where n is 2 (i.e., an ethylene group) the modification is commonly referred to as ENA, which is a form of LNA. LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

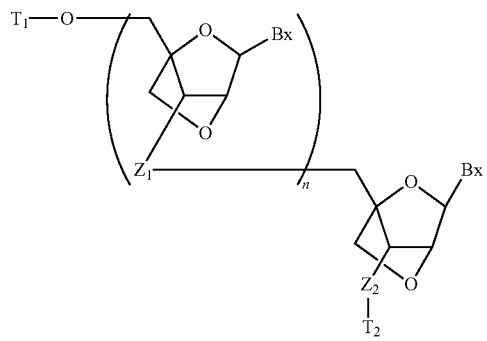

The conformations of LNAs determined by 2D NMR spectroscopy have shown that the locked orientation of the INA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs. Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

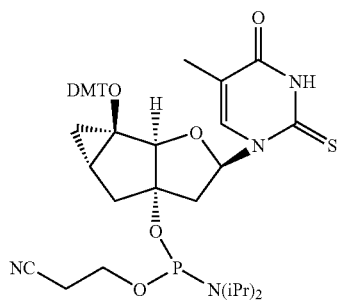

-continued

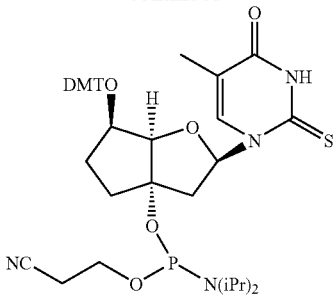

(see Steffens et al., *Helv. Chim. Acta*, 1997, 80, 2426-2439; Steffens et al., *J. Am. Chem. Soc.*, 1999, 121, 3249-3255; and Renneberg et al., *J. Am. Chem. Soc.*, 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

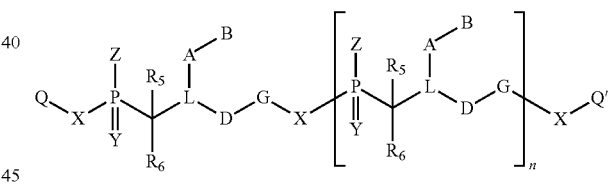

Another oligonucleotide mimetic has been reported wherein the furanosyl ring has been replaced by a cyclobutyl moiety.

Modified Sugars

Oligomeric compounds of the invention may also contain one or more substituted sugar moieties. Preferred oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA leaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethylaminoethoxy-ethyl or 2'-DMAEOE), i.e., 2'-O—CH$_2$—O—CH$_2$—N(CH$_3$)$_2$.

Other preferred sugar substituent groups include methoxy (—O—CH$_3$), aminopropoxy (—OCH$_2$CH$_2$CH$_2$NH$_2$), allyl (—CH$_2$—CH=CH$_2$), —O-allyl (—O—CH$_2$—CH=CH$_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula I$_a$ or II$_a$:

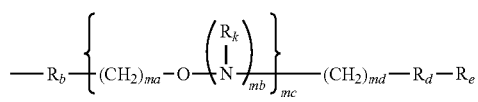

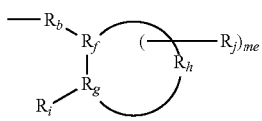

wherein:
R$_b$ is O, S or NH;
R$_d$ is a single bond, O, S or C(=O);
R$_e$ is C$_1$-C$_{10}$ alkyl, N(R$_k$) (R$_m$), N(R$_k$) (R$_n$), N=C (R$_p$) (R$_q$), N=C(R$_p$) (R$_r$) or has formula III$_a$;

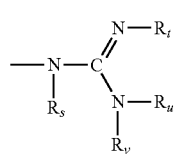

R$_p$ and R$_q$ are each independently hydrogen or C$_1$-C$_{10}$ alkyl;
R$_r$ is —R$_x$-R$_y$;
each R$_s$, R$_t$, R$_u$ and R$_v$ is, independently, hydrogen, C(O)R$_w$, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_u$ and R$_v$, together form a phthalimido moiety with the nitrogen atom to which they are attached;

each R$_w$ is, independently, substituted or unsubstituted C$_1$-C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

R$_k$ is hydrogen, a nitrogen protecting group or —R$_x$-R$_y$;
R$_p$ is hydrogen, a nitrogen protecting group or —R$_x$-R$_y$;
R$_x$ is a bond or a linking moiety;
R$_y$ is a chemical functional group, a conjugate group or a solid support medium;

each R$_m$ and R$_n$ is, independently, H, a nitrogen protecting group, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3^+$, N(R$_u$) (R$_v$), guanidino and acyl where said acyl is an acid amide or an ester;

or R$_m$ and R$_n$, together, are a nitrogen protecting group, are joined in a ring structure that optionally includes an additional heteroatom selected from N and O or are a chemical functional group;

R$_i$ is OR$_z$, SR$_z$, or N(R$_z$)$_2$;
each R$_z$ is, independently, H, C$_1$-C$_8$ alkyl, C$_1$-C$_8$ haloalkyl, C(=NH)N(H)R$_u$, C(=O)N(H)R$_u$ or OC(=O)N(H)R$_u$;

R$_f$, R$_g$ and R$_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

R$_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, N(R$_k$) (R$_m$) OR$_k$, halo, SR$_k$ or CN;

m$_a$ is 1 to about 10;
each mb is, independently, 0 or 1;
mc is 0 or an integer from 1 to 10;
md is an integer from 1 to 10;
me is from 0, 1 or 2; and
provided that when mc is 0, md is greater than 1.

Representative substituents groups of Formula I are disclosed in U.S. Pat. No. 6,172,209, hereby incorporated by reference in its entirety.

Representative cyclic substituent groups of Formula II are disclosed in U.S. Pat. No. 6,217,358, hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10.

Representative guanidino substituent groups that are shown in formula III and IV are disclosed in co-owned U.S. Pat. No. 6,593,466, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Publication WO 00/08044, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also eferred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH₃) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

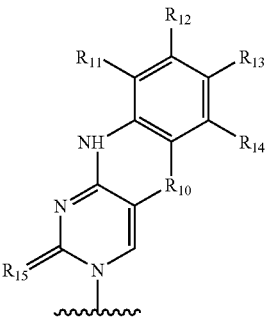

Representative cytosine analogs that make 3 hydrogen bonds with a guanosine in a second strand include 1,3-diazaphenoxazine-2-one (R10=O, R11-R14=H) [Kurchavov, et al., Nucleosides and Nucleotides, 1997, 16, 1837-1846], 1,3-diazaphenothiazine-2-one (R10=S, R11-R14=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one (R10=O, R11-R14=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see Publication No US2003-0207804; and Publication No. US2003-0185906, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold (R₁₀=O, R₁₁=—O—(CH₂)₂—NH₂, R₁₂₋₁₄=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a ΔT$_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The T$_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, and U.S. Pat. No. 6,007,992, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyclic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and Publication No US 2003-0158403, certain of which are commonly owned with the instant application, and each of which is herein incorporated by reference.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of HCV mRNA and/or HCV replication.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730 which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound. The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results, can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

3'-endo Modifications

In one aspect of the present invention oligomeric compounds include nucleosides synthetically modified to induce 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference or an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

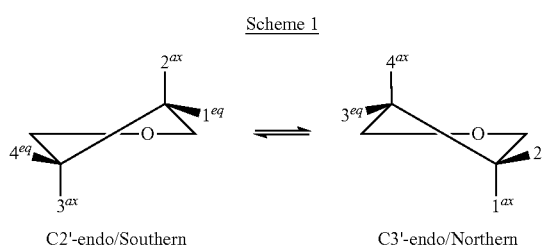

Figure 2:
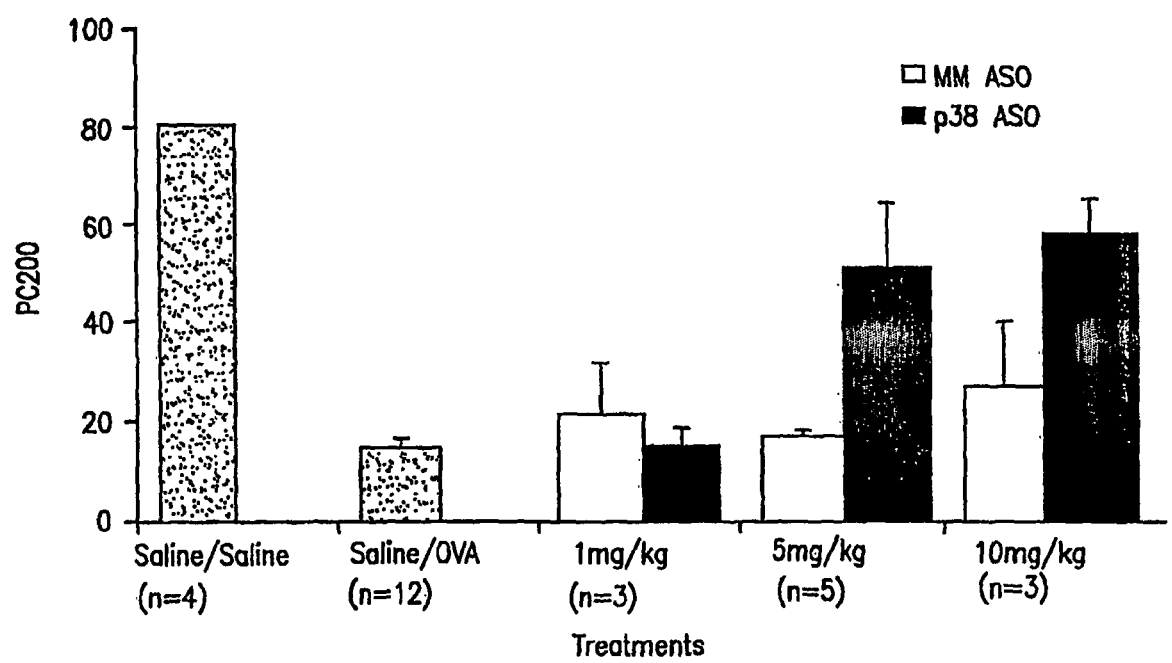
FIG. 2 is a graph showing that inhaled ISIS 101757 increases the provocation concentration of methacholine required to achieve doubling of airway reactivity (PC200) in OVA-challenged mice.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.) Examples of modified nucleosides amenable to the present invention are shown below in Table I. These examples are meant to be representative and not exhaustive.

TABLE I

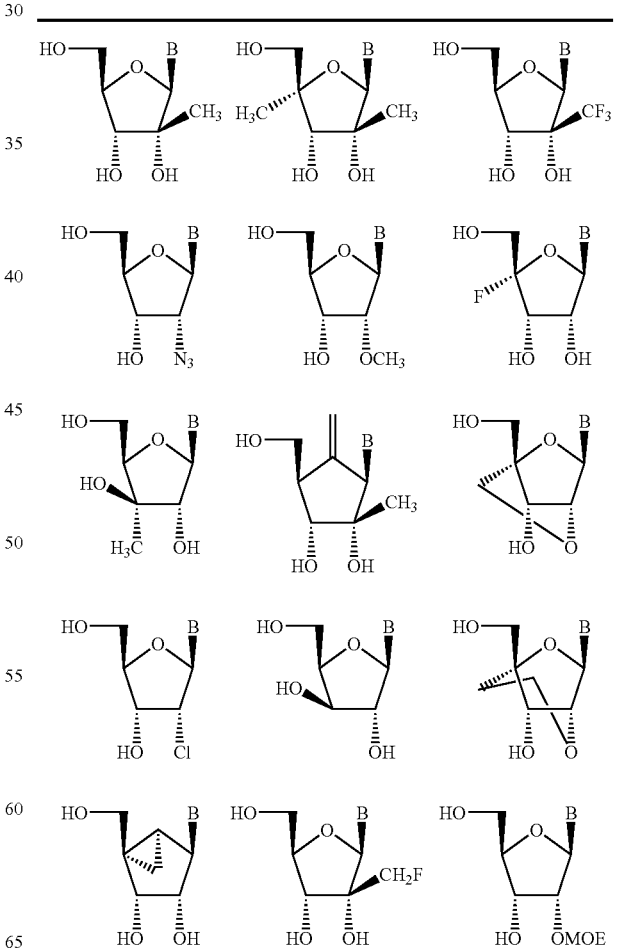

TABLE I-continued

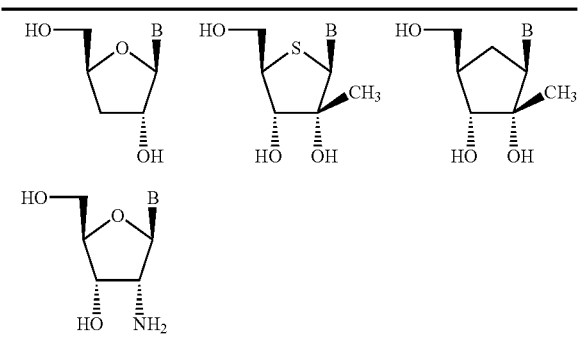

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligoncleotides of the present invention. The synthesis of numerous modified nucleosides amenable to the present invention are known in the art (see for example, Chemistry of Nucleosides and Nucleotides Vol 1-3, ed. Leroy B. Townsend, 1988, Plenum press., and the examples section below.)

In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonulceotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research*, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

Chemistries Defined

Unless otherwise defined herein, alkyl means C$_1$-C$_{12}$, preferably C$_1$-C$_8$, and more preferably C$_1$-C$_6$, straight or (where possible) branched chain aliphatic hydrocarbyl.

Unless otherwise defined herein, heteroalkyl means C$_1$-C$_{12}$, preferably C$_1$-C$_8$, and more preferably C$_1$-C$_6$, straight or (where possible) branched chain aliphatic hydrocarbyl containing at least one, and preferably about 1 to about 3, hetero atoms in the chain, including the terminal portion of the chain. Preferred heteroatoms include N, O and S. Unless otherwise defined herein, cycloalkyl means C$_3$-C$_{12}$, preferably C$_3$-C$_8$, and more preferably C$_3$-C$_6$, aliphatic hydrocarbyl ring.

Unless otherwise defined herein, alkenyl means C$_2$-C$_{12}$, preferably C$_2$-C$_8$, and more preferably C$_2$-C$_6$ alkenyl, which may be straight or (where possible) branched hydrocarbyl moiety, which contains at least one carbon-carbon double bond.

Unless otherwise defined herein, alkynyl means C$_2$-C$_{12}$, preferably C$_2$-C$_6$, and more preferably C$_2$-C$_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring embers are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl(hetaryl and alkyl), aralkyl(aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, NO$_2$, NH$_3$ (substituted and unsubstituted), acid moieties (e.g. —CO$_2$H, —OSO$_3$H$_2$, etc.), heterocycloalkyl moieties, hetaryl moieties, aryl moieties, etc. In all the preceding formulae, the squiggle (~) indicates a bond to an oxygen or sulfur of the 5'-phosphate.

Phosphate protecting groups include those described in U.S. Pat. No. 5,760,209, U.S. Pat. No. 5,614,621, U.S. Pat. No. 6,051,699, U.S. Pat. No. 6,020,475, U.S. Pat. No. 6,326,478, U.S. Pat. No. 6,169,177, U.S. Pat. No. 6,121,437, U.S. Pat. No. 6,465,628 each of which is expressly incorporated herein by reference in its entirety.

The oligonucleotides in accordance with this invention (single stranded or double stranded) preferably comprise from about 8 to about 80 nucleotides, more preferably from about 12-50 nucleotides and most preferably from about 15 to 30 nucleotides. As is known in the art, a nucleotide is a base-sugar combination suitably bound to an adjacent nucleotide through a phosphodiester, phosphorothioate or other covalent linkage.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of p38α MAP kinase mRNA.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is well known to use similar techniques to prepare oligonucleotides such as the phosphorothioates and 2'-alkoxy or 2'-alkoxyalkoxy derivatives, including 2'-o-methoxyethyl oligonucleotides [Martin, P., *Helv. Chim. Acta,* 78, 486 (1995)]. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other conjugated oligonucleotides.

The antisense compounds of the present invention include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to pharmaceutically acceptable salts of the nucleic acids of the invention and prodrugs of such nucleic acids.

Pharmaceutically acceptable "salts" are physiologically and pharmaceutically acceptable salts of the nucleic acids of the invention: i.e., salts that retain the desired biological activity of the parent compound and do not impart undesired toxicological effects thereto [see, for example, Berge et al., "Pharmaceutical Salts," *J. of Pharma Sci.,* 66:1 (1977)].

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993.

For therapeutic or prophylactic treatment, oligonucleotides are administered in accordance with this invention. Oligonucleotide compounds of the invention may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide. Such compositions and formulations are comprehended by the present invention.

Pharmaceutical compositions comprising the oligonucleotides of the present invention may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems,* 1991, 8:91-192; Muranishi, *Critical Reviews in Therapeutic Drug Carrier Systems,* 1990, 7:1). One or more penetration enhancers from one or more of these broad categories may be included.

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Regardless of the method by which the oligonucleotides of the invention are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration [see, generally, Chonn et al., *Current Op. Biotech.,* 6, 698 (1995)].

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation of powders or aerosols, including by nebulizer, metered dose inhaler or dry powder inhaler; intratracheal, intranasal, or intracranial, e.g., intrathecal or intraventricular, administration. Oligonucleotides with at least one 2'-O-methoxyethyl modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide of the invention in conjunction with other traditional therapeutic modalities in order to increase the efficacy of a treatment regimen. In the context of the invention, the term "treatment regimen" is meant to encompass therapeutic, palliative and prophylactic modalities. For example, a patient may be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, *The Merck Manual of Diagnosis and Therapy*, 15th Ed., pp. 1206-1228, Berkow et al., eds., Rahay, N.J., 1987). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

Antisense inhibitors of p38 mitogen-activated protein kinase, particularly p38α mitogen-activated protein kinase, are shown herein to decrease expression of p38 mitogen-activated protein kinase in cells collected by bronchoalveolar lavage. They are also shown to reduce pulmonary inflammatory responses, airway hyperreactivity and mucus production in an asthma model, as well as modulating cytokine release into the airway. It is therefore believed that antisense inhibitors of p38 mitogen-activated protein kinase, particularly p38α mitogen-activated protein kinase, are useful for decreasing airway hyperresponsiveness or airway inflammation in animals, including humans and thus for treating inflammatory diseases of the airway, such as asthma (including allergic asthma).

The compositions and methods of the present invention may be used to treat airway hyperreactivity and airway inflammation. The combined use of antisense compounds targeted to human p38 MAP kinase with one or more conventional asthma medications including, but not limited to, montelukast sodium (Singulair™), albuterol, beclomethasone dipropionate, triamcinolone acetonide, ipratropium bromide (Atrovent™), flunisolide, fluticasone propionate (Flovent™) and other steroids is also contemplated. The antisense compounds may be given topically into the airway, e.g., by inhalation of aerosol (such as via a metered dose inhaler) or dry powder. Topical administration into the airway includes intranasal, intratracheal or intrapulmonary administration.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

Thus, in the context of this invention, by "therapeutically effective amount" is meant the amount of the compound which is required to have a therapeutic effect on the treated mammal. This amount, which will be apparent to the skilled artisan, will depend upon the type of mammal, the age and weight of the mammal, the type of disease to be treated, perhaps even the gender of the mammal, and other factors which are routinely taken into consideration when treating a mammal with a disease. A therapeutic effect is assessed in the mammal by measuring the effect of the compound on the disease state in the animal. For example, if the disease to be treated is an inflammatory disease, symptomatic measurements (redness, swelling, or in the case of airway, penh (a measurement of pulmonary airflow). Cytokine release is another marker for inflammation which is routinely measured.

The following examples illustrate the present invention and are not intended to limit the same.

EXAMPLES

Example 1

Synthesis of Oligonucleotides

Unmodified oligodeoxynucleotides are synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2 M solution of $^3$H-1,2-benzodithiole-3-one 1,1-dioxide in acetonitrile for the stepwise thiation of the phosphite linkages. The thiation cycle wait step was increased to 68 seconds and was followed by the capping step.

2'-methoxy oligonucleotides are synthesized using 2'-methoxy β-cyanoethyldiisopropyl-phosphoramidites (Chemgenes, Needham, Mass.) and the standard cycle for unmodified oligonucleotides, except the wait step after pulse delivery of tetrazole and base was increased to 360 seconds. Other 2'-alkoxy oligonucleotides were synthesized by a modification of this method, using appropriate 2'-modified amidites such as those available from Glen Research, Inc., Sterling, Va.

2'-fluoro oligonucleotides are synthesized as described in Kawasaki et al., *J. Med. Chem.*, 36, 831 (1993). Briefly, the protected nucleoside $N^6$-benzoyl-2'-deoxy-2'-fluoroadenosine is synthesized utilizing commercially available 9-β-D-arabinofuranosyladenine as starting material and by modifying literature procedures whereby the 2'-α-fluoro atom is introduced by a $S_N2$-displacement of a 2'-β-O-trifyl group. Thus $N^6$-benzoyl-9-9-D-arabinofuranosyladenine is selectively protected in moderate yield as the 3',5'-ditetrahydropyranyl (THP) intermediate. Deprotection of the THP and $N^6$-benzoyl groups is accomplished using standard methodologies and standard methods are used to obtain the 5'-dimethoxytrityl-(DMT) and 5'-DMT-3'-phosphoramidite intermediates.

The synthesis of 2'-deoxy-2'-fluoroguanosine is accomplished using tetraisopropyldisiloxanyl (TPDS) protected 9-β-D-arabinofuranosylguanine as starting material, and is conversion to the intermediate diisobutyryl-arabinofuranosylguanosine. Deprotection of the TPDS group is followed by protection of the hydroxyl group with THP to give diisobutyryl di-THP protected arabinofuranosylguanine. Selective O-deacylation and triflation is followed by treatment of the crude product with fluoride, then deprotection of the THP groups. Standard methodologies are used to obtain the 5'-DMT- and 5'-DMT-3'-phosphoramidites.

Synthesis of 2'-deoxy-2'-fluorouridine is accomplished by the modification of a known procedure in which 2,2'-anhydro-1-β-D-arabinofuranosyluracil is treated with 70% hydrogen fluoride-pyridine. Standard procedures are used to obtain the 5'-DMT and 5'-DMT-3'phosphoramidites.

2'-deoxy-2'-fluorocytidine is synthesized via amination of 2'-deoxy-2'-fluorouridine, followed by selective protection to give $N^4$-benzoyl-2'-deoxy-2'-fluorocytidine. Standard procedures are used to obtain the 5'-DMT and 5'-DMT-3'phosphoramidites.

2'-(2-methoxyethyl)-modified amidites were synthesized according to Martin, P., *Helv. Chim. Acta*, 78,486 (1995). For ease of synthesis, the last nucleotide was a deoxynucleotide. 2'-O—$CH_2CH_2OCH_3$-cytosines may be 5-methyl cytosines. Synthesis of 5-Methyl cytosine monomers:

2,2'-Anhydro[1-(β-D-arabinofuranosyl)-5-methyluridine]

5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 hours) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane(4:1). Pure product fractions were evaporated to yield 96 g (84%).

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in CH$_3$CN (700 mL) and set aside. Triethylamine (189 mL, 1.44 M) was added to a solution of triazole (90 g, 1.3 M) in CH$_3$CN (1 L), cooled to −5° C. and stirred for 0.5 h using an overhead stirrer. POCl$_3$ was added dropwise, over a 30 minute period, to the stirred solution maintained at 0-10EC, and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5'-O-dimethoxytrityl-5-methyl-cytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. MeOH (400 ml) saturated with NH$_3$ gas was added and the vessel heated to 100° C. for 2 hours (tlc showed complete conversion). The vessel contents were evaporated to dryness and the residue was dissolved in EtOAC (500 mL) and washed once with saturated NaCl (200 ml). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 ml) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/-Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoyl-2'-O-methoxyethyl-5'-O-dimethoxytrityl-5-methylcytidine (74 g, 0.10 M) was dissolved in CH$_2$Cl$_2$ (1 L) Tetrazole diisopropylamine (7.1 g) and 2-cyanoethoxy-tetra(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

5-methyl-2'-deoxycytidine (5-me-C) containing oligonucleotides were synthesized according to published methods [Sanghvi et al., *Nucl. Acids Res.*, 21, 3197 (1993)] using commercially available phosphoramidites (Glen Research, Sterling Va. or ChemGenes, Needham Mass.).

2'-O-(dimethylaminooxyethyl) nucleoside amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) are dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) is added in one portion. The reaction is stirred for 16 h at ambient temperature. TLC (Rf 0.22, ethyl acetate) indicates a complete reaction. The solution is concentrated under reduced pressure to a thick oil. This is partitioned between dichloromethane (1 L) and saturated sodium bicarbonate (2×1 L) and brine (1 L). The organic layer is dried over sodium sulfate and concentrated under reduced pressure to a thick oil. The oil is dissolved in a 1:1 mixture of ethyl acetate and ethyl ether (600 mL) and the solution is cooled to −10° C. The resulting crystalline product is collected by filtration, washed with ethyl ether (3×200 mL) and dried (40° C., 1 mm Hg, 24 h) to 149 g (74.8%) of white solid. TLC and NMR are used to check consistency with pure product.

5'-O-tert-Butyldiphenylsilyl-2'-O-(2-hydroxyethyl)-S-methyluridine

In a 2 L stainless steel, unstirred pressure reactor is added borane in tetrahydrofuran (1.0 M, 2.0 eq, 622 mL). In the fume hood and with manual stirring, ethylene glycol (350 mL, excess) is added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) are added with manual stirring. The reactor is sealed and heated in an oil bath until an internal temperature of 160° C. is reached and then maintained for 16 h (pressure <100 psig). The reaction vessel is cooled to ambient and opened. TLC (Rf 0.67 for desired product and Rf 0.82 for ara-T side product, ethyl acetate) indicates % conversion to the product. In order to avoid additional side product formation, the reaction is stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue is purified by column chromatography (2 kg silica gel, ethyl acetate-hexanes gradient 1:1 to 4:1). The appropriate fractions are combined, stripped and dried to product as a white crisp foam (84 g, 50%), contaminated starting material (17.4 g) and pure reusable starting material 20 g. TLC and NMR are used to determine consistency with pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40° C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) is dissolved in dry $CH_2Cl_2$ (4.5 mL) and methylhydrazine (300 mL, 4.64 mmol) is added dropwise at −10° C. to 0° C. After 1 hr the mixture is filtered, the filtrate is washed with ice cold $CH_2Cl_2$ and the combined organic phase is washed with water, brine and dried over anhydrous $Na_2SO_4$. The solution is concentrated to get 2'-O-(aminooxyethyl)thymidine, which is then dissolved in MeOH (67.5 mL). To this formaldehyde (20% aqueous solution, w/w, 1.1 eg.) is added and the mixture for 1 hr. Solvent is removed under vacuum; residue chromatographed to get 5'-O-tert-butyldiphenylsilyl-2'-O-[(2-formadoximinooxy)ethyl]-5-methyluridine as white foam.

5'-O-tert-Butyldiphenylsilyl-2'-O—[N,N-dimethylaminooxyethyl]-5-methyluridine 5'-O-tert-butyldiphenylsilyl-2'-O-[(2-formadoximinooxy)ethyl]-5-methyluridine (1.77 g, 3.12 mmol) is dissolved in a solution of 1M pyridinium p-toluenesulfonate (PPTS) in dry MeOH (30.6 mL). Sodium cyanoborohydride (0.39 g, 6.13 mmol) is added to this solution at 10° C. under inert atmosphere. The reaction mixture is stirred for 10 minutes at 10° C. After that the reaction vessel is removed from the ice bath and stirred at room temperature for 2 hr, the reaction monitored by TLC (5% MeOH in $CH_2Cl_2$). Aqueous $NaHCO_3$ solution (5%, 10 mL) is added and extracted with ethyl acetate (2×20 mL). Ethyl acetate phase is dried over anhydrous $Na_2SO_4$, evaporated to dryness. Residue is dissolved in a solution of 1M PPTS in MeOH (30.6 mL). Formaldehyde (20% w/w, 30 mL, 3.37 mmol) is added and the reaction mixture is stirred at room temperature for 10 minutes. Reaction mixture cooled to 10° C. in an ice bath, sodium cyanoborohydride (0.39 g, 6.13 mmol) is added and reaction mixture stirred at 10° C. for 10 minutes. After 10 minutes, the reaction mixture is removed from the ice bath and stirred at room temperature for 2 hrs. To the reaction mixture 5% $NaHCO_3$ (25 mL) solution is added and extracted with ethyl acetate (2×25 mL). Ethyl acetate layer is dried over anhydrous $Na_2SO_4$ and evaporated to dryness. The residue obtained is purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g).

2-O-(dimethylaminooxyethyl)-5-methyluridine

Triethylamine trihydrofluoride (3.91 mL, 24.0 mmol) is dissolved in dry THF and triethylamine (1.67 mL, 12 mmol, dry, kept over KOH). This mixture of triethylamine-2HF is then added to 5'-O-tert-butyldiphenylsilyl-2'-O—[N,N-dimethylaminooxyethyl]-5-methyluridine (1.40 g, 2.4 mmol) and stirred at room temperature for 24 hrs. Reaction is monitored by TLC (5% MeOH in $CH_2Cl_2$). Solvent is removed under vacuum and the residue placed on a flash column and eluted with 10% MeOH in $CH_2Cl_2$ to get 2'-O-(dimethylaminooxyethyl)-5-methyluridine (766 mg).

5'-O-DMT-2'-O-(dimethylaminooxyethyl)-5-methyluridine

2'-O-(dimethylaminooxyethyl)-5-methyluridine (750 mg, 2.17 mmol) is dried over $P_2O_5$ under high vacuum overnight at 40° C. It is then co-evaporated with anhydrous pyridine (20 mL). The residue obtained is dissolved in pyridine (11 ml) under argon atmosphere. 4-dimethylaminopyridine (26.5 mg, 2.60 mmol), 4,4'-dimethoxytrityl chloride (880 mg, 2.60 mmol) is added to the mixture and the reaction mixture is stirred at room temperature until all of the starting material disappeared. Pyridine is removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) is co-evaporated with toluene (20 mL). To the residue N,N-diisopropylamine tetrazonide (0.29 g, 1.67 mmol) is added and dried over $P_2O_5$ under high vacuum overnight at 40° C. Then the reaction mixture is dissolved in anhydrous acetonitrile (8.4 mL) and 2-cyanoethyl-N,N,$N^1$,$N^1$-tetraisopropylphosphoramidite (2.12 mL, 6.08 mmol) is added. The reaction mixture is stirred at ambient temperature for 4 hrs under inert atmosphere. The progress of the reaction was monitored by TLC (hexane:ethyl acetate 1:1). The solvent is evaporated, then the residue is dissolved in ethyl acetate (70 mL) and washed with 5% aqueous $NaHCO_3$ (40 mL). Ethyl acetate layer is dried over anhydrous $Na_2SO_4$ and concentrated. Residue obtained is chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl) guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

Oligonucleotides having methylene (methylimino) (MMI) backbones are synthesized according to U.S. Pat. No. 5,378,825, which is coassigned to the assignee of the present invention and is incorporated herein in its entirety. For ease of synthesis, various nucleoside dimers containing MMI linkages were synthesized and incorporated into oligonucleotides. Other nitrogen-containing backbones are synthesized according to WO 92/20823 which is also coassigned to the assignee of the present invention and incorporated herein in its entirety.

Oligonucleotides having amide backbones are synthesized according to De Mesmaeker et al., *Acc. Chem. Res.*, 28, 366 (1995). The amide moiety is readily accessible by simple and well-known synthetic methods and is compatible with the conditions required for solid phase synthesis of oligonucleotides.

Oligonucleotides with morpholino backbones are synthesized according to U.S. Pat. No. 5,034,506 (Summerton and Weller).

Peptide-nucleic acid (PNA) oligomers are synthesized according to P. E. Nielsen et al., *Science*, 254, 1497 (1991).

After cleavage from the controlled pore glass column (Applied Biosystems) and deblocking in concentrated ammonium hydroxide at 55° C. for 18 hours, the oligonucleotides are purified by precipitation twice out of 0.5 M NaCl with 2.5 volumes ethanol. Synthesized oligonucleotides were analyzed by polyacrylamide gel electrophoresis on denaturing gels and judged to be at least 85% full length material. The relative amounts of phosphorothioate and phosphodiester linkages obtained in synthesis were periodically checked by $^{31}$P nuclear magnetic resonance spectroscopy, and for some studies oligonucleotides were purified by HPLC, as described by Chiang et al., *J. Biol. Chem.*, 266, 18162 (1991). Results obtained with HPLC-purified material were similar to those obtained with non-HPLC purified material.

RNA Oligonucleotides:

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand,.* 1990, 44, 639-641; Reddy, M. P., et al., *Tetrahedron Lett.*, 1994, 25, 4311-4314; Wincott, F. et al., *Nucleic Acids Res.*, 1995, 23, 2677-2684;

Griffin, B. E., et al., *Tetrahedron*, 1967, 23, 2301-2313; Griffin, B. E., et al., *Tetrahedron*, 1967, 23, 2315-2331).

Example 2

Human p38α Oligonucleotide Sequences

Antisense oligonucleotides were designed to target human p38α. Target sequence data are from the p38 MAPK cDNA sequence; Genbank accession number L35253, provided herein as SEQ ID NO: 1. Oligonucleotides was synthesized as chimeric oligonucleotides ("gapmers") 20 nucleotides in length, composed of a central "gap" region consisting of eight 2'-deoxynucleotides, which is flanked on both sides (5' and 3' directions) by six-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 1.

The human Jurkat T-cell line (American Type Culture Collection, Manassas, Va.) was maintained in RPMI 1640 growth media supplemented with 10% fetal bovine serum (FBS; Hyclone, Logan, Utah). HUVEC cells (Clonetics, San Diego, Calif.) were cultivated in endothelial basal media supplemented with 10% FBS (Hyclone, Logan, Utah).

Jurkat cells were grown to approximately 75% confluency and resuspended in culture media at a density of $1 \times 10^7$ cells/ml. A total of $3.6 \times 10^6$ cells were employed for each treatment by combining 360 μl of cell suspension with oligonucleotide at the indicated concentrations to reach a final volume of 400 μl. Cells were then transferred to an electroporation cuvette and electroporated using an Electrocell Manipulator 600 instrument (Biotechnologies and Experimental Research, Inc.) employing 150 V, 1000 μF, at 13Ω. Electroporated cells were then transferred to conical tubes containing 5 ml of culture media, mixed by inversion, and plated onto 10 cm culture dishes.

HUVEC cells were allowed to reach 75% confluency prior to use. The cells were washed twice with warm (37° C.) OPTI-MEM™ (Life Technologies). The cells were incubated in the presence of the appropriate culture medium, without the growth factors added, and the oligonucleotide formulated in LIPOFECTIN7 (Life Technologies), a 1:1 (w/w) liposome formulation of the cationic lipid N-[1-(2,3-dioleyloxy)propyl]-n,n,n-trimethylammonium chloride (DOTMA), and dioleoyl phosphotidylethanolamine (DOPE) in membrane filtered water. HUVEC cells were treated with 100 nM oligonucleotide in 10 μg/ml LIPOFECTIN7. Treatment was for four hours.

Total mRNA was isolated using the RNEASY7 Mini Kit (Qiagen, Valencia, Calif.; similar kits from other manufacturers may also be used), separated on a 1% agarose gel, transferred to HYBOND™-N+ membrane (Amersham Pharmacia Biotech, Piscataway, N.J.), a positively charged nylon membrane, and probed. p38 MAPK probes were made using the Prime-A-Gene7 kit (Promega Corporation, Madison, Wis.), a random primer labeling kit, using mouse p38α or p38β cDNA as a template. A glyceraldehyde 3-phosphate dehydrogenase (G3PDH) probe was purchased from Clontech (Palo Alto, Calif.), Catalog Number 9805-1. The fragments were purified from low-melting temperature agarose, as described in Maniatis, T., et al., *Molecular Cloning: A Laboratory Manual*, 1989. The G3PDH probe was labeled with REDI-VUE™ $^{32}$P-dCTP (Amersham Pharmacia Biotech, Piscataway, N.J.) and Strip-EZ labelling kit (Ambion, Austin, Tex.).

mRNA was quantitated by a PhosphoImager (Molecular Dynamics, Sunnyvale, Calif.).

TABLE 1

Nucleotide Sequences of Human p38α Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 16486 | AAGACCGGGCCCGGAATTCC | 3 | 0001-0020 | 5'-UTR |
| 16487 | GTGGAGGCCAGTCCCCGGGA | 4 | 0044-0063 | 5'-UTR |
| 16488 | TGGCAGCAAAGTGCTGCTGG | 5 | 0087-0106 | 5'-UTR |
| 16489 | CAGAGAGCCTCCTGGGAGGG | 6 | 0136-0155 | 5--UTR |
| 16490 | TGTGCCGAATCTCGGCCTCT | 7 | 0160-0179 | 5'-UTR |
| 16491 | GGTCTCGGGCGACCTCTCCT | 8 | 0201-0220 | 5'-UTR |
| 16492 | CAGCCGCGGGACCAGCGGCG | 9 | 0250-0269 | 5'-UTR |
| 16493 | CATTTTCCAGCGGCAGCCGC | 10 | 0278-0297 | AUG |
| 16494 | TCCTGAGACATTTTCCAGCG | 11 | 0286-0305 | AUG |
| 16495 | CTGCCGGTAGAACGTGGGCC | 12 | 0308-0327 | coding |
| 16496 | GTAAGCTTCTGACATTTCAC | 13 | 0643-0662 | coding |
| 16497 | TTTAGGTCCCTGTGAATTAT | 14 | 0798-0817 | coding |
| 16498 | ATGTTCTTCCAGTCAACAGC | 15 | 0939-0958 | coding |
| 16499 | TAAGGAGGTCCCTGCTTTCA | 16 | 1189-1208 | coding |
| 16500 | AACCAGGTGCTCAGGACTCC | 17 | 1368-1387 | stop |
| 16501 | GAAGTGGGATCAACAGAACA | 18 | 1390-1409 | 3'-UTR |
| 16502 | TGAAAAGGCCTTCCCCTCAC | 19 | 1413-1432 | 3'-UTR |
| 16503 | AGGCACTTGAATAATATTTG | 20 | 1444-1463 | 3'-UTR |
| 16504 | CTTCCACCATGGAGGAAATC | 21 | 1475-1494 | 3'-UTR |
| 16505 | ACACATGCACACACACTAAC | 22 | 1520-1539 | 3'-UTR |

[1]Emboldened residues, 2'-methoxyethoxy- residues (others are 2'-deoxy-) including "C" residues, 5-methyl-cytosines; all linkages are phosphorothioate linkages.
[2]Co-ordinates from Genbank Accession No. L35253, locus name "HUMMAPKNS", SEQ ID NO. 1.

For an initial screen of human p38α antisense oligonucleotides, Jurkat cells were electroporated with 10 μM oligonucleotide. mRNA was measured by Northern blot. Results are shown in Table 2. Oligonucleotides 16496 (SEQ ID NO. 13), 16500 (SEQ ID NO. 17) and 16503 (SEQ ID NO. 20) gave 35% or greater inhibition of p38α mRNA.

TABLE 2

Inhibition of Human p38α mRNA expression in Jurkat Cells by Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 16486 | 3 | 5'-UTR | 212% | — |
| 16487 | 4 | 5'-UTR | 171% | — |
| 16488 | 5 | 5'-UTR | 157% | — |
| 16489 | 6 | 5'-UTR | 149% | — |
| 16490 | 7 | 5'-UTR | 152% | — |

TABLE 2-continued

Inhibition of Human p38α mRNA expression in Jurkat Cells by
Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| 16491 | 8 | 5'-UTR | 148% | — |
| 16492 | 9 | 5'-UTR | 125% | — |
| 16493 | 10 | AUG | 101% | — |
| 16494 | 11 | AUG | 72% | 28% |
| 16495 | 12 | coding | 72% | 28% |
| 16496 | 13 | coding | 61% | 39% |
| 16497 | 14 | coding | 104% | — |
| 16498 | 15 | coding | 88% | 12% |
| 16499 | 16 | coding | 74% | 26% |
| 16500 | 17 | stop | 63% | 37% |
| 16501 | 18 | 3'-UTR | 77% | 23% |
| 16502 | 19 | 3'-UTR | 79% | 21% |
| 16503 | 20 | 3'-UTR | 65% | 35% |
| 16504 | 21 | 3'-UTR | 72% | 28% |
| 16505 | 22 | 3'-UTR | 93% | 7% |

The most active human p38α oligonucleotides were chosen for dose response studies. Oligonucleotide 16490 (SEQ ID NO. 7) which showed no inhibition in the initial screen was included as a negative control. Jurkat cells were grown and treated as described above except the concentration of oligonucleotide was varied as indicated in Table 3. Results are shown in Table 3. Each of the active oligonucleotides showed a dose response effect with $IC_{50}$s around 10 nM. Maximum inhibition was approximately 70% with 16500 (SEQ ID NO. 17). The most active oligonucleotides were also tested for their ability to inhibit p38β. None of these oligonucleotides significantly reduced p38β mRNA expression.

TABLE 3

Dose Response of p38α mRNA in Jurkat cells to human p38α
Chimeric (deoxy gapped) Phosphorothioate Oligonucleotides

| ISIS # | SEQ ID NO: | ASO Gene Target | Dose | % mRNA Expression | % mRNA Inhibition |
|---|---|---|---|---|---|
| control | — | — | — | 100% | 0% |
| 16496 | 13 | coding | 2.5 nM | 94% | 6% |
| " | " | " | 5 nM | 74% | 26% |
| " | " | " | 10 nM | 47% | 53% |
| " | " | " | 20 nM | 41% | 59% |
| 16500 | 17 | stop | 2.5 nM | 82% | 18% |
| " | " | " | 5 nM | 71% | 29% |
| " | " | " | 10 nM | 49% | 51% |
| " | " | " | 20 nM | 31% | 69% |
| 16503 | 20 | 3'-UTR | 2.5 nM | 74% | 26% |
| " | " | " | 5 nM | 61% | 39% |
| " | " | " | 10 nM | 53% | 47% |
| " | " | " | 20 nM | 41% | 59% |
| 16490 | 7 | 5'-UTR | 2.5 nM | 112% | — |
| " | " | " | 5 nM | 109% | — |
| " | " | " | 10 nM | 104% | — |
| " | " | " | 20 nM | 97% | 3% |

Example 3

Human p38β Oligonucleotide Sequences

Antisense oligonucleotides were designed to target human p38β. Target sequence data are from the p38β MAPK cDNA sequence; Genbank accession number U53442, provided herein as SEQ ID NO: 23. Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 4.

TABLE 4

Nucleotide Sequences of Human p38β
Phosphorothioate oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 17891 | CGACATGTCCGGAGCAGAAT | 25 | 0006-0025 | AUG |
| 17892 | TTCAGCTCCTGCCGGTAGAA | 26 | 0041-0060 | coding |
| 17893 | TGCGGCACCTCCCACACGGT | 27 | 0065-0084 | coding |
| 17894 | CCGAACAGACGGAGCCGTAT | 28 | 0121-0140 | coding |
| 17895 | GTGCTTCAGGTGCTTGAGCA | 29 | 0240-0259 | coding |
| 17896 | GCGTGAAGACGTCCAGAAGC | 30 | 0274-0293 | coding |
| 17897 | ACTTGACGATGTTGTTCAGG | 31 | 0355-0374 | coding |
| 17898 | AACGTGCTCGTCAAGTGCCA | 32 | 0405-0424 | coding |
| 17899 | ATCCTGAGCTCACAGTCCTC | 33 | 0521-0540 | coding |
| 17900 | ACTGTTTGGTTGTAATGCAT | 34 | 0635-0654 | coding |
| 17901 | ATGATGCGCTTCAGCTGGTC | 35 | 0731-0750 | coding |
| 17902 | GCCAGTGCCTCAGCTGCACT | 36 | 0935-0954 | coding |
| 17903 | AACGCTCTCATCATATGGCT | 37 | 1005-1024 | coding |
| 17904 | CAGCACCTCACTGCTCAATC | 38 | 1126-1145 | stop |
| 17905 | TCTGTGACCATAGGAGTGTG | 39 | 1228-1247 | 3'-UTR |
| 17906 | ACACATGTTTGTGCATGCAT | 40 | 1294-1313 | 3'-UTR |
| 17907 | CCTACACATGGCAAGCACAT | 41 | 1318-1337 | 3'-UTR |
| 17908 | TCCAGGCTGAGCAGCTCTAA | 42 | 1581-1600 | 3'-UTR |
| 17909 | AGTGCACGCTCATCCACACG | 43 | 1753-1772 | 3'-UTR |
| 17910 | CTTGCCAGATATGGCTGCTG | 44 | 1836-1855 | 3'-UTR |

[1]Emboldened residues, 2'-methoxyethoxy- residues (others are 2'-deoxy-) including "C" residues, 5-methyl-cytosines; all linkages are phosphorothioate linkages.
[2]Co-ordinates from Genbank Accession No. U53442, locus name "HSU53442", SEQ ID NO. 23.

For an initial screen of human p38β antisense oligonucleotides, HUVEC cells were cultured and treated as described in Example 2. mRNA was measured by Northern blot as described in Example 2. Results are shown in Table 5. Every oligonucleotide tested gave at least 50% inhibition. Oligonucleotides 17892 (SEQ ID NO. 26), 17893 (SEQ ID NO. 27), 17894 (SEQ ID NO. 28), 17899 (SEQ ID NO. 33), 17901 (SEQ ID NO. 35), 17903 (SEQ ID NO. 37), 17904 (SEQ ID NO. 38), 17905 (SEQ ID NO. 39), 17907 (SEQ ID NO. 41), 17908 (SEQ ID NO. 42), and 17909 (SEQ ID NO. 43) gave greater than approximately 85% inhibition and are preferred.

TABLE 5

Inhibition of Human p38β mRNA expression in Huvec Cells by
Chimeric (deoxy gapped) Phosphorothioate Oligonucleotides

| ISIS No: | SEQ ID NO: | GENE TARGET REGION | % mRNA EXPRESSION | % mRNA INHIBITION |
|---|---|---|---|---|
| control | — | — | 100% | 0% |
| 17891 | 25 | AUG | 22% | 78% |
| 17892 | 26 | coding | 10% | 90% |
| 17893 | 27 | coding | 4% | 96% |
| 17894 | 28 | coding | 13% | 87% |
| 17895 | 29 | coding | 25% | 75% |
| 17896 | 30 | coding | 24% | 76% |
| 17897 | 31 | coding | 25% | 75% |
| 17898 | 32 | coding | 49% | 51% |
| 17899 | 33 | coding | 5% | 95% |
| 17900 | 34 | coding | 40% | 60% |
| 17901 | 35 | coding | 15% | 85% |
| 17902 | 36 | coding | 49% | 51% |
| 17903 | 37 | coding | 11% | 89% |
| 17904 | 38 | stop | 9% | 91% |
| 17905 | 39 | 3'-UTR | 14% | 86% |
| 17906 | 40 | 3'-UTR | 22% | 78% |
| 17907 | 41 | 3'-UTR | 8% | 92% |
| 17908 | 42 | 3'-UTR | 17% | 83% |
| 17909 | 43 | 3'-UTR | 13% | 87% |
| 17910 | 44 | 3'-UTR | 26% | 74% |

Oligonucleotides 17893 (SEQ ID NO. 27), 17899 (SEQ ID NO. 33), 17904 (SEQ ID NO. 38), and 17907 (SEQ ID NO. 41) were chosen for dose response studies. HUVEC cells were cultured and treated as described in Example 2 except that the oligonucleotide concentration was varied as shown in Table 6. The Lipofectin7/Oligo ratio was maintained at 3 μg Lipofectin7/100 nM oligo, per ml. mRNA was measured by Northern blot as described in Example 2.

Results are shown in Table 6. Each oligonucleotide tested had an IC$_{50}$ of less than 10 nM. The effect of these oligonucleotides on human p38α was also determined. Only oligonucleotide 17893 (SEQ ID NO. 27) showed an effect on p38α mRNA expression. The IC$_{50}$ of this oligonucleotide was approximately 4 fold higher for p38α compared to p38β.

TABLE 6

Dose Response of p38β in Huvec cells to human p38β
Chimeric (deoxy gapped) Phosphorothioate Oligonucleotides

| ISIS # | SEQ ID NO: | ASO Gene Target | Dose | % mRNA Expression | % mRNA Inhibition |
|---|---|---|---|---|---|
| control | — | — | — | 100% | 0% |
| 17893 | 27 | coding | 10 nM | 37% | 63% |
| " | " | " | 25 nM | 18% | 82% |
| " | " | " | 50 nM | 16% | 84% |
| " | " | " | 100 nM | 19% | 81% |
| 17899 | 33 | coding | 10 nM | 37% | 63% |
| " | " | " | 25 nM | 23% | 77% |
| " | " | " | 50 nM | 18% | 82% |
| " | " | " | 100 nM | 21% | 79% |
| 17904 | 38 | stop | 10 nM | 31% | 69% |
| " | " | " | 25 nM | 21% | 79% |
| " | " | " | 50 nM | 17% | 83% |
| " | " | " | 100 nM | 19% | 81% |
| 17907 | 41 | 3'-UTR | 10 nM | 37% | 63% |
| " | " | " | 25 nM | 22% | 78% |
| " | " | " | 50 nM | 18% | 72% |
| " | " | " | 100 nM | 18% | 72% |

Example 4

Rat p38α Oligonucleotide Sequences

Antisense oligonucleotides were designed to target rat p38α. Target sequence data are from the p38 MAPK cDNA sequence; Genbank accession number U73142, provided herein as SEQ ID NO: 45. Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages in the wings are phosphodiester (P=O). Internucleoside linkages in the central gap are phosphorothioate (P=S). All 2'-MOE cytosines and 2'-OH cytosines were 5-methyl-cytosines. These oligonucleotide sequences are shown in Table 7.

bEND.3, a mouse endothelial cell line (gift of Dr. Werner Risau; see Montesano et al., Cell, 1990, 62, 435, and Stepkowski et al., J. Immunol., 1994, 153, 5336) were grown in high-glucose DMEM (Life Technologies, Gaithersburg, Md.) medium containing 10% fetal bovine serum (FBS) and 1% Penicillin/Streptomycinin. Cells were plated at approximately $2\times10^5$ cells per 100 mm dish. Within 48 hours of plating, the cells were washed with phosphate-buffered saline (Life Technologies). Then, Opti-MEM7 medium containing 3 μg/mL LIPOFECTIN[7] and an appropriate amount of oligonucleotide were added to the cells. As a control, cells were treated with LIPOFECTIN[7] without oligonucleotide under the same conditions and for the same times as the oligonucleotide-treated samples.

After 4 hours at 37° C., the medium was replaced with high glucose DMEM medium containing 10% FBS and 1% Penicillin/Streptomycinin. The cells were typically allowed to recover overnight (about 18 to 24 hours) before RNA and/or protein assays were performed as described in Example 2. The p38α, p38β and G3PDH probes used were identical to those described in Example 2.

TABLE 7

Nucleotide Sequences of Rat p38α
Phosphorothioate Oligonucleotides

| ISIS NO. | NUCLEOTIDE SEQUENCE[1] (5' -> 3') | TARGET GENE SEQ ID NO | GENE CO-ORDINATES[2] | TARGET GENE REGION |
|---|---|---|---|---|
| 21844 | CoToGoCoGsAsCsAsTsTsTsTsCsCsAsGoCoGoGoC | 47 | 0001-0020 | AUG |
| 21845 | GoGoToAoAsGsCsTsTsCsTsGsAsCsAsCoToToCoA | 48 | 0361-0380 | coding |

TABLE 7-continued

Nucleotide Sequences of Rat p38α
Phosphorothioate Oligonucleotides

| ISIS NO. | NUCLEOTIDE SEQUENCE[1] (5' -> 3') | SEQ ID NO | TARGET GENE NUCLEOTIDE CO-ORDINATES[2] | GENE TARGET REGION |
|---|---|---|---|---|
| 21846 | GoGoCoCoAsGsAsGsAsCsTsGsAsAsTsGoToAoGoT | 49 | 0781-0800 | coding |
| 21871 | CoAoToCoAsTsCsAsGsGsGsTsCsGsTsGoGoToAoC | 50 | 0941-0960 | coding |
| 21872 | GoGoCoAoCsAsAsAsGsCsTsAsAsTsGsAoCoToToC | 51 | 1041-1060 | coding |
| 21873 | AoGoGoToGsCsTsCsAsGsGsAsCsTsCsCoAoToToT | 52 | 1081-1100 | stop |
| 21874 | GoGoAoToGsGsAsCsAsGsAsAsCsAsGsAoAoGoCoA | 53 | 1101-1120 | 3'-UTR |
| 21875 | GoAoGoCoAsGsGsCsAsGsAsCsTsGsCsCoAoAoGoG | 54 | 1321-1340 | 3'-UTR |
| 21876 | AoGoGoCoTsAsGsAsGsCsCsCsAsGsGsAoGoCoCoA | 55 | 1561-1580 | 3'-UTR |
| 21877 | GoAoGoCoCsTsGsTsGsCsCsTsGsGsCsAoCoToGoG | 56 | 1861-1880 | 3'-UTR |
| 21878 | ToGoCoAoCsCsAsCsAsAsGsCsAsCsCsToGoGoAoG | 57 | 2081-2100 | 3'-UTR |
| 21879 | GoGoCoToAsCsCsAsTsGsAsGsTsGsAsGoAoAoGoA | 58 | 2221-2240 | 3'-UTR |
| 21880 | GoToCoCoCsTsGsCsAsCsTsGsAsTsAsGoAoGoAoA | 59 | 2701-2720 | 3'-UTR |
| 21881 | ToCoToToCsCsAsAsTsGsGsAsGsAsAsAoCoToGoG | 60 | 3001-3020 | 3'-UTR |

[1]Emboldened residues, 2'-methoxyethoxy- residues (others are 2'deoxy-); 2'-MOE cytosines and 2'-deoxy cytosine residues are 5-methyl-cytosines; "s" linkages are phosphorothioate linkages; "o" linkages are phosphodiester linkages.
[2]Co-ordinates from Genbank Accession No. U73142, locus name "RNU73142", SEQ ID NO. 45.

Rat p38α antisense oligonucleotides were screened in bEND.3 cells for inhibition of p38α and p38β mRNA expression. The concentration of oligonucleotide used was 100 nM. Results are shown in Table 8. Oligonucleotides 21844 (SEQ ID NO. 47), 21845 (SEQ ID NO. 48), 21872 (SEQ ID NO. 51), 21873 (SEQ ID NO. 52), 21875 (SEQ ID NO. 54), and 21876 (SEQ ID NO. 55) showed greater than approximately 70% inhibition of p38α mRNA with minimal effects on p38β mRNA levels. Oligonucleotide 21871 (SEQ ID NO. 50) inhibited both p38α and p38β levels greater than 70%.

TABLE 8

Inhibition of Mouse p38 mRNA expression in bEND.3 Cells by Chimeric (deoxy gapped) Mixed Backbone p38α Antisense Oligonucleotides

| ISIS No: | SEQ ID NO: | GENE TARGET REGION | % p38α mRNA INHIBITION | % p38β mRNA INHIBITION |
|---|---|---|---|---|
| control | — | — | 0% | 0% |
| 21844 | 47 | AUG | 81% | 20% |
| 21845 | 48 | coding | 75% | 25% |
| 21871 | 50 | coding | 90% | 71% |
| 21872 | 51 | coding | 87% | 23% |
| 21873 | 52 | stop | 90% | 3% |
| 21874 | 53 | 3'-UTR | 38% | 21% |
| 21875 | 54 | 3'-UTR | 77% | — |
| 21876 | 55 | 3'-UTR | 69% | — |
| 21877 | 56 | 3'-UTR | 55% | 13% |
| 21878 | 57 | 3'-UTR | 25% | 10% |
| 21879 | 58 | 3'-UTR | — | — |
| 21881 | 60 | 3'-UTR | — | — |

Several of the most active oligonucleotides were selected for dose response studies. bEND.3 cells were cultured and treated as described above, except that the concentration of oligonucleotide was varied as noted in Table 9. Results are shown in Table 9.

TABLE 9

Dose Response of bEND.3 cells to rat p38β Chimeric (deoxy gapped) Phosphorothioate Oligonucleotides

| ISIS # | SEQ ID NO: | ASO Gene Target | Dose | % p38α mRNA Inhibition | % p38β mRNA Inhibition |
|---|---|---|---|---|---|
| control | — | — | — | 100% | 0% |
| 21844 | 47 | AUG | 1 nM | — | — |
| " | " | " | 5 nM | — | — |
| " | " | " | 25 nM | 36% | 8% |
| " | " | " | 100 nM | 80% | 5% |
| 21871 | 50 | coding | 1 nM | 1% | — |
| " | " | " | 5 nM | 23% | 4% |
| " | " | " | 25 nM | 34% | 24% |
| " | " | " | 100 nM | 89% | 56% |
| 21872 | 51 | stop | 1 nM | — | — |
| " | " | " | 5 nM | — | — |
| " | " | " | 25 nM | 35% | — |
| " | " | " | 100 nM | 76% | 1% |
| 21873 | 52 | stop | 1 nM | — | 53% |
| " | " | " | 5 nM | — | 31% |
| " | " | " | 25 nM | 54% | 28% |
| " | " | " | 100 nM | 92% | 25% |
| 21875 | 54 | 3'-UTR | 1 nM | — | 11% |
| " | " | " | 5 nM | — | 16% |
| " | " | " | 25 nM | 33% | 2% |
| " | " | " | 100 nM | 72% | 4% |

Example 5

Mouse p38β Oligonucleotide Sequences

Antisense oligonucleotides were designed to target mouse p38β. Target sequence data are from a mouse EST sequence; Genbank accession number AI119044, provided herein as SEQ ID NO: 61. Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages in the wings are phosphodiester (P=O). Internucleoside linkages in the central gap are phosphorothioate (P=S). All 2'-MOE cytosines and 2'-OH cytosines were 5-methyl-cytosines. These oligonucleotide sequences are shown in Table 10.

TABLE 10

Nucleotide Sequences of Mouse p38β Chimeric (deoxy gapped) Phosphorothioate Oligonucleotides

| ISIS NO. | NUCLEOTIDE SEQUENCE[1] (5' ->3') | SEQ ID NO: | TARGET GENE NUCLEOTIDE CO-ORDINATES[2] |
|---|---|---|---|
| 100800 | CoAoCoAoGsAsAsGsCsAsGsCsTsGsGsAoGoCoGoA | 63 | 0051-0070 |
| 100801 | ToGoCoGoGsCsAsCsCsTsCsCsCsAsTsAoCoToGoT | 64 | 0119-0138 |
| 100802 | CoCoCoTsGsCsAsGsCsCsGsCsTsGsCsGoGoCoAoC | 65 | 0131-0150 |
| 100803 | GoCoAoGoAsCsTsGsAsGsCsCsGsTsAsGoGoCoGoC | 66 | 0171-0190 |
| 100804 | ToToAoCoAsGsCsCsAsCsCsTsTsCsTsGoGoCoGoC | 67 | 0211-0230 |
| 100805 | GoToAoToGsTsCsCsTsCsCsTsCsGsCsGoToGoGoA | 68 | 0261-0280 |
| 100806 | AoToGoGoAsTsGsTsGsGsCsCsGsGsCsGoToGoAoA | 69 | 0341-0360 |
| 100807 | GoAoAoTsGsAsAsCsAsTsGsCsTsCsAoToCoGoC | 70 | 0441-0460 |
| 100808 | AoCoAoTsGsCsTsGsGsGsGsCsTsTsCsAoGoGoToC | 71 | 0521-0540 |
| 100809 | AoToCoCoTsCgAsGsCsTsCsGsCsAsGsToCoCoToC | 72 | 0551-0570 |
| 100810 | ToAoCoCoAsCsCsGsTsGsTsGsGsCsCsAoCoAoToA | 73 | 0617-0636 |
| 100811 | CoAoGoToTsTsAsGsCsAsTsGsAsTsCsToCoToGoG | 74 | 0644-0663 |
| 100812 | CoAoGoGoCsCsAsCsAsGsAsCsCsAsGsAoToGoToC | 75 | 0686-0705 |
| 100813 | CoCoToTsCsCsAsGsCsAsGsTsTsCsAsAoGoCoCoA | 76 | 0711-0730 |
| 101123 | CoAoGoCoAsCsCsAsTsGsGsAsCsGsCsGoGoAoAoC | 77 | 21871 mismatch |

[1]Emboldened residues, 2'-methoxyethoxy- residues (others are 2'-deoxy-), including 2'-MOE and 2'-deoxy residues, 5-methyl-cytosines; "s" linkages are phosphorothioate linkages, "o" linkages are phosphodiester.
[2]Co-ordinates from Genbank Accession No. AI119044, locus name "AI119044", SEQ ID NO. 61.

Mouse p38β antisense sequences were screened in bEND.3 cells as described in Example 4. Results are shown in Table 11.

Oligonucleotides 100800 (SEQ ID NO. 63), 100801 (SEQ ID NO. 64), 100803 (SEQ ID NO. 66), 100804 (SEQ ID NO. 67), 100805 (SEQ ID NO. 68), 100807 (SEQ ID NO. 70), 100808 (SEQ ID NO. 71), 100809 (SEQ ID NO. 72), 100810 (SEQ ID NO. 73), 100811 (SEQ ID NO. 74), and 100813 (SEQ ID NO. 76) resulted in at least 50% inhibition of p38β mRNA expression. Oligonucleotides 100801 (SEQ ID NO. 64), 100803 (SEQ ID NO. 66), 100804 (SEQ ID NO. 67), 100805 (SEQ ID NO. 68), 100809 (SEQ ID NO. 72), and 100810 (SEQ ID NO. 73) resulted in at least 70% inhibition and are preferred. Oligonucleotides 100801 (SEQ ID NO. 64), 100805 (SEQ ID NO. 68), and 100811 (SEQ ID NO. 74) resulted in significant inhibition of p38α mRNA expression in addition to their effects on p38β.

TABLE 11

Inhibition of Mouse p38 mRNA expression in bEND.3 Cells by Chimeric (deoxy gapped) Mixed Backbone p38β Antisense Oligonucleotides

| ISIS No: | SEQ ID NO: | % p38β mRNA INHIBITION | % p38α mRNA INHIBITION |
|---|---|---|---|
| control | — | 0% | 0% |
| 100800 | 63 | 51% | — |

TABLE 11-continued

Inhibition of Mouse p38 mRNA expression in bEND.3 Cells by Chimeric (deoxy gapped) Mixed Backbone p38β Antisense Oligonucleotides

| ISIS No: | SEQ ID NO: | % p38β mRNA INHIBITION | % p38α mRNA INHIBITION |
|---|---|---|---|
| 100801 | 64 | 74% | 31% |
| 100802 | 65 | 35% | — |

TABLE 11-continued

Inhibition of Mouse p38 mRNA expression in bEND.3 Cells by Chimeric (deoxy gapped) Mixed Backbone p38β Antisense Oligonucleotides

| ISIS No: | SEQ ID NO: | % p38β mRNA INHIBITION | % p38α mRNA INHIBITION |
|---|---|---|---|
| 100803 | 66 | 74% | 18% |
| 100804 | 67 | 85% | 18% |
| 100805 | 68 | 78% | 58% |
| 100806 | 69 | 22% | 3% |
| 100807 | 70 | 64% | — |
| 100808 | 71 | 53% | 13% |
| 100809 | 72 | 84% | 14% |
| 100810 | 73 | 72% | 1% |
| 100811 | 74 | 60% | 43% |
| 100812 | 75 | 36% | 17% |
| 100813 | 76 | 54% | — |

Example 6

Effect of p38 MAPK Antisense Oligonucleotides on IL-6 Secretion p38 MAPK antisense oligonucleotides were tested for their ability to reduce IL-6 secretion. bEND.3 cells were cultured and treated as described in Example 4 except that 48 hours after oligonucleotide treatment, cells were stimulated for 6 hours with 1 ng/mL recombinant mouse IL-1 (R&D Systems, Minneapolis, Minn.). IL-6 was measured in the medium using an IL-6 ELISA kit (Endogen Inc., Woburn, Mass.).

Results are shown in Table 12. Oligonucleotides targeting a specific p38 MAPK isoform were effective in reducing IL-6 secretion greater than approximately 50%.

TABLE 12

Effect of p38 Antisense Oligonucleotides on IL-6 secretion

| ISIS No: | SEQ ID NO: | GENE TARGET | DOSE (μM) | % IL-6 INHIBITION |
|---|---|---|---|---|
| control | — | — | | 0% |
| 21873 | 52 | p38α | 100 | 49% |
| 100804 | 67 | p38β | 100 | 57% |
| 21871 | 50 | p38α and p38β | 200 | 23% |

Example 7

Activity of p38α Antisense Oligonucleotides in Rat Cardiomyocytes

Rat p38α antisense oligonucleotides were screened in Rat A-10 cells. A-10 cells (American Type Culture Collection, Manassas, Va.) were grown in high-glucose DMEM (Life Technologies, Gaithersburg, Md.) medium containing 10% fetal calf serum (FCS). Cells were treated with oligonucleotide as described in Example 2. Oligonucleotide concentration was 200 nM. mRNA was isolated 24 hours after time zero and quantitated by Northern blot as described in Example 2.

Results are shown in Table 13. Oligonucleotides 21845 (SEQ ID NO. 48), 21846 (SEQ ID NO. 49), 21871 (SEQ ID NO. 50), 21872 (SEQ ID NO. 51), 21873 (SEQ ID NO. 52), 21874 (SEQ ID NO. 53), 21875 (SEQ ID NO. 54), 21877 (SEQ ID NO. 56), 21878 (SEQ ID NO. 57), 21879 (SEQ ID NO. 58), and 21881 (SEQ ID NO. 60) inhibited p38α mRNA expression by 65% or greater in this assay. Oligonucleotides 21846 (SEQ ID NO. 49), 21871 (SEQ ID NO. 50), 21872 (SEQ ID NO. 51), 21877 (SEQ ID NO. 56), and 21879 (SEQ ID NO. 58) inhibited p38α mRNA expression by greater than 85% and are preferred.

TABLE 13

Inhibition of Rat p38α mRNA expression in A-10 Cells by Chimeric (deoxy gapped) Mixed Backbone p38α Antisense Oligonucleotides

| ISIS No: | SEQ ID NO: | GENE TARGET REGION | % p38α mRNA EXPRESSION | % p38α mRNA INHIBITION |
|---|---|---|---|---|
| control | — | — | 100% | 0% |
| 21844 | 47 | AUG | 75% | 25% |
| 21845 | 48 | coding | 25% | 75% |
| 21846 | 49 | coding | 8% | 92% |
| 21871 | 50 | coding | 12% | 88% |
| 21872 | 51 | coding | 13% | 87% |
| 21873 | 52 | stop | 19% | 81% |
| 21874 | 53 | 3'-UTR | 22% | 78% |
| 21875 | 54 | 3'-UTR | 26% | 74% |
| 21876 | 55 | 3'-UTR | 61% | 39% |
| 21877 | 56 | 3'-UTR | 12% | 88% |
| 21878 | 57 | 3'-UTR | 35% | 65% |
| 21879 | 58 | 3'-UTR | 11% | 89% |
| 21881 | 60 | 3'-UTR | 31% | 69% |

The most active oligonucleotide in this screen (SEQ ID NO. 49) was used in rat cardiac myocytes prepared from neonatal rats (Zechner, D., et. al., J. Cell Biol., 1997, 139, 115-127). Cells were grown as described in Zechner et al. and transfected with oligonucleotide as described in Example 2. Oligonucleotide concentration was 1 μM. mRNA was isolated 24 hrs after time zero and quantitated using Northern blotting as described in Example 2. An antisense oligonucleotide targeted to JNK-2 was used as a non-specific target control.

Results are shown in Table 14. Oligonucleotide 21846 (SEQ ID NO. 49) was able to reduce p38α expression in rat cardiac myocytes by nearly 60%. The JNK-2 antisense oligonucleotide had little effect on p38α expression.

TABLE 14

Inhibition of Rat p38α mRNA expression in Rat Cardiac Myocytes by A Chimeric (deoxy gapped) Mixed Backbone p38α Antisense Oligonucleotide

| ISIS No: | SEQ ID NO: | GENE TARGET REGION | % p38α mRNA EXPRESSION | % p38α mRNA INHIBITION |
|---|---|---|---|---|
| control | — | — | 100% | 0% |
| 21846 | 49 | coding | 41% | 59% |

Example 8

Additional Human p38α Oligonucleotide Sequences

Additional antisense oligonucleotides were designed to target human p38α based on active rat sequences. Target sequence data are from the p38 MAPK cDNA sequence; Genbank accession number L35253, provided herein as SEQ ID NO: 1. Oligonucleotides were synthesized as chimeric oligonucleotides ("gapmers") 20 nucleotides in length, composed of a central "gap" region consisting of ten 2'-deoxy-nucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines and 2'-OH cytosines were 5-methyl-cytosines. These oligonucleotide sequences are shown in Table 15.

TABLE 15

Additional Nucleotide Sequences of Human p38α Chimeric (deoxy gapped) Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 100860 | CTGAGACATTTTCCAGCGGC | 78 | 0284-0303 | Start |
| 100861 | ACGCTCGGGCACCTCCCAGA | 79 | 0344-0363 | coding |
| 100862 | AGCTTCTTCACTGCCACACG | 80 | 0439-0458 | coding |
| 100863 | AATGATGGACTGAAATGGTC | 81 | 0464-0483 | coding |
| 100864 | TCCAACAGACCAATCACATT | 82 | 0538-0557 | coding |
| 100865 | TGTAAGCTTCTGACATTTCA | 83 | 0644-0663 | coding |
| 100866 | TGAATGTATATACTTTAGAC | 84 | 0704-0723 | coding |
| 100867 | CTCACAGTCTTCATTCACAG | 85 | 0764-0783 | coding |
| 100868 | CACGTAGCCTGTCATTTCAT | 86 | 0824-0843 | coding |
| 100869 | CATCCCACTGACCAAATATC | 87 | 0907-0926 | coding |
| 100870 | TATGGTCTGTACCAGGAAAC | 88 | 0960-0979 | coding |
| 100871 | AGTCAAAGACTGAATATAGT | 89 | 1064-1083 | coding |
| 100872 | TTCTCTTATCTGAGTCCAAT | 90 | 1164-1183 | coding |
| 100873 | CATCATCAGGATCGTGGTAC | 91 | 1224-1243 | coding |
| 100874 | TCAAAGGACTGATCATAAGG | 92 | 1258-1277 | coding |
| 100875 | GGCACAAAGCTGATGACTTC | 93 | 1324-1343 | coding |
| 100876 | AGGTGCTCAGGACTCCATCT | 94 | 1364-1383 | stop |
| 100877 | GCAACAAGAGGCACTTGAAT | 95 | 1452-1471 | 3'-UTR |

[1]Emboldened residues, 2'-methoxyethoxy- residues (others are 2'-deoxy-) including "C" and "C" residues, 5-methyl-cytosines; all linkages are phosphorothioate linkages.
[2]Co-ordinates from Genbank Accession No. L35253, locus name "HUMMAPKNS", SEQ ID NO. 1.

For an initial screen of human p38α antisense oligonucleotides, T-24 cells, a human transitional cell bladder carcinoma cell line, were obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis. A control oligonucleotide ISIS 118965 (TTATCCTAGCTTAGAC-CTAT, herein incorporated as SEQ ID NO: 96) was synthesized as chimeric oligonucleotide ("gapmer") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines and 2'-OH cytosines were 5-methyl-cytosines.

For Northern blotting or other analysis, cells may be seeded onto 100 mm or other standard tissue culture plates and treated similarly, using appropriate volumes of medium and oligonucleotide. mRNA was measured by Northern blot. Results are shown in Table 16. Oligonucleotides 100861 (SEQ ID NO. 79), 100862 (SEQ ID NO. 80), 100863 (SEQ ID NO. 81), 100866 (SEQ ID NO. 84), 100867 (SEQ ID NO. 85), 100868 (SEQ ID NO. 86), 100870 (SEQ ID NO. 88), 100871 (SEQ ID NO. 89), 100872 (SEQ ID NO. 90), 100873 (SEQ ID NO. 91), and 100874 (SEQ ID NO. 92) 100875 (SEQ ID NO. 93) and 100877 (SEQ ID NO. 95) gave greater than approximately 40% inhibition and are preferred.

TABLE 16

Inhibition of Human p38α mRNA expression in T-24 Cells by Chimeric (deoxy gapped) Phosphorothioate Oligonucleotides

| ISIS No: | SEQ ID NO: | GENE TARGET REGION | % P38α mRNA EXPRESSION | % P38β mRNA EXPRESSION |
|---|---|---|---|---|
| 100860 | 78 | 0284-0303 | 73% | 71% |
| 100861 | 79 | 0344-0363 | 60% | 47% |
| 100862 | 80 | 0439-0458 | 56% | 45% |
| 100863 | 81 | 0464-0483 | 49% | 67% |
| 100864 | 82 | 0538-0557 | 66% | 70% |
| 100865 | 83 | 0644-0663 | 64% | 63% |
| 100866 | 84 | 0704-0723 | 55% | 65% |
| 100867 | 85 | 0764-0783 | 58% | 33% |
| 100868 | 86 | 0824-0843 | 47% | 60% |
| 100869 | 87 | 0907-0926 | 61% | 100% |
| 100870 | 88 | 0960-0979 | 51% | No data |
| 100871 | 89 | 1064-1083 | 57% | 96% |
| 100872 | 90 | 1164-1183 | 37% | 77% |
| 100873 | 91 | 1224-1243 | 34% | 70% |
| 100874 | 92 | 1258-1277 | 42% | 76% |
| 100875 | 93 | 1324-1343 | 39% | 90% |
| 100876 | 94 | 1364-1383 | 77% | 93% |
| 100877 | 95 | 1452-1471 | 47% | 95% |

Oligonucleotides 100872 (SEQ ID NO. 90), 100873 (SEQ ID NO. 91), 100874 (SEQ ID NO. 92), and 100875 (SEQ ID NO. 93) were chosen for dose response studies.

Results are shown in Table 17. The effect of these oligonucleotides on human p38β was also determined.

TABLE 17

Dose Response of p38α in T-24 cells to human p38α Chimeric (deoxy gapped) Phosphorothioate Oligonucleotides

| ISIS # | SEQ ID NO: | ASO Gene Target | Dose | % p38α mRNA Expression | % p38β mRNA Inhibition |
|---|---|---|---|---|---|
| Control 118965 | 96 | — | — | 94% | 80% |
| 100872 | 90 | coding | 50 nM | 45% | 108% |
| " | " | " | 100 nM | 18% | 91% |
| " | " | " | 200 nM | 17% | 92% |
| 100873 | 91 | coding | 50 nM | 19% | 90% |
| " | " | " | 100 nM | 12% | 78% |
| " | " | " | 200 nM | 8% | 44% |
| 100874 | 92 | coding | 50 nM | 47% | 107% |
| " | " | " | 100 nM | 27% | 101% |
| " | " | " | 200 nM | 13% | 51% |
| 100875 | 93 | coding | 50 nM | 30% | 105% |
| " | " | " | 100 nM | 13% | 92% |
| " | " | " | 200 nM | 8% | 69% |

Example 9

Additional Human p38β Oligonucleotide Sequences

Additional antisense oligonucleotides were designed to target human p38β based on active rat sequences. Target sequence data are from the p38 MAPK cDNA sequence; Genbank accession number U53442, provided herein as SEQ ID NO: 23.

Oligonucleotides was synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages in the wings are phosphodiester (P=O). Internucleoside linkages in the central gap are phosphorothioate (P=S). All 2'-MOE cytosines and 2'-OH cytosines were 5-methyl-cytosines. These oligonucleotide sequences are shown in Table 18. A control oligonucleotide ISIS 118966 (GTTCGATCGGCTCGTGTCGA), herein incorporated as SEQ ID NO: 107) was synthesized as chimeric oligonucleotide ("gapmer") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) in the gap and phosphodiester in the wings. All 2'-MOE cytosines and 2'-OH cytosines were 5-methyl-cytosines.

TABLE 18

Additional Nucleotide Sequences of Human p38β Chimeric (deoxy gapped) Mixed-Backbone Phosphorothioate Oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 107869 | ACAGACGGAGCCGTAGGCGC | 97 | 117-136 | coding |
| 107870 | CACCGCCACCTTCTGGCGCA | 98 | 156-175 | coding |
| 107871 | GTACGTTCTGCGCGCGTGGA | 99 | 207-226 | coding |
| 107872 | ATGGACGTGGCCGGCGTGAA | 100 | 287-306 | coding |
| 107873 | CAGGAATTGAACGTGCTCGT | 101 | 414-433 | coding |
| 107874 | ACGTTGCTGGGCTTCAGGTC | 102 | 491-510 | coding |
| 107875 | TACCAGCGCGTGGCCACATA | 103 | 587-606 | coding |
| 107876 | CAGTTGAGCATGATCTCAGG | 104 | 614-633 | coding |
| 107877 | CGGACCAGATATCCACTGTT | 105 | 649-668 | coding |
| 107878 | TGCCCTGGAGCAGCTCAGCC | 106 | 682-701 | coding |

[1]Emboldened residues, 2'-methoxyethoxy- residues (others are 2'-deoxy-) including "C" and "C" residues, 5-methyl-cytosines.?
[2]Co-ordinates from Genbank Accession No. U53442, SEQ ID NO. 23.

For an initial screen of human p38β antisense oligonucleotides, T-24 cells, a human transitional cell bladder carcinoma cell line, were obtained from the American Type Culture Collection (ATCC) (Manassas, Va.). T-24 cells were routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 micrograms per mL (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis. A control oligonucleotide ISIS 118966 (TTATCCTAGCTTAGACCTAT, herein incorporated as SEQ ID NO: 106) was synthesized as chimeric oligonucleotide ("gapmer") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. The internucleoside (backbone) linkages are phosphorothioate (P=S) in the gap and phosphodiester in the wings. All 2'-MOE cytosines and 2'-OH cytosines were 5-methyl-cytosines.

For Northern blotting or other analysis, cells may be seeded onto 100 mm or other standard tissue culture plates and treated similarly, using appropriate volumes of medium and oligonucleotide. mRNA was measured by Northern blot. Results are shown in Table 19. For comparison, ISIS 17893 and ISIS 17899, both targeting human p38β (SEQ ID NO: 27) and ISIS 100802 targeting mouse p38β (SEQ ID NO: 65) described in Examples 3 and 5 above, respectively, were included in the screen.

Oligonucleotides 107869 (SEQ ID NO. 97), 107871 (SEQ ID NO. 99), 107872 (SEQ ID NO. 100), 107873 (SEQ ID NO. 101), 107878 (SEQ ID NO. 106), 17893 (SEQ ID NO. 27), 17899 (SEQ ID NO. 33) and 100802 (SEQ ID NO. 65, targeted to mouse p38β) gave greater than approximately 40% inhibition and are preferred.

TABLE 19

Inhibition of Human p38β mRNA expression in T-24 Cells by Chimeric (deoxy gapped) Mixed-Backbone Phosphorothioate Oligonucleotides

| ISIS No: | SEQ ID NO: | GENE TARGET REGION | % p38β mRNA EXPRESSION | % p38α mRNA EXPRESSION |
|---|---|---|---|---|
| 107869 | 97 | Coding | 60% | 93% |
| 107870 | 98 | Coding | 74% | 97% |
| 107871 | 99 | Coding | 60% | 111% |
| 107872 | 100 | Coding | 57% | 123% |
| 107873 | 101 | Coding | 58% | 120% |
| 107874 | 102 | Coding | 61% | 100% |
| 107875 | 103 | Coding | 92% | 112% |
| 107876 | 104 | Coding | 127% | 137% |
| 107877 | 105 | Coding | No data | No data |
| 107878 | 106 | Coding | 54% | 112% |
| 17893 | 27 | Coding | 31% | 61% |
| 17899 | 33 | Coding | 56% | 117% |
| 100802 | 65 | Coding | 47% | 78% |

Oligonucleotides 107871, 107872, 107873, 107874, 107875, 107877, 107878, 17893 and 17899 were chosen for dose response studies.

Results are shown in Table 20. The effect of these oligonucleotides on human p38α was also determined.

TABLE 20

Dose Response of p38β in T-24 cells to human p38β Chimeric (deoxy gapped) Mixed-backbone Phosphorothioate Oligonucleotides

| ISIS # | SEQ ID NO: | ASO Gene Target | Dose | % p38β mRNA Expression | % p38α mRNA Inhibition |
|---|---|---|---|---|---|
| Control 118966 | 107 | — | — | 100% | 100% |
| 107871 | 99 | coding | 50 nM | 41% | 105% |
| " | " | " | 100 nM | 42% | 132% |
| " | " | " | 200 nM | 10% | 123% |
| 107872 | 100 | coding | 50 nM | 71% | 124% |
| " | " | " | 100 nM | 13% | 84% |
| " | " | " | 200 nM | 22% | 102% |
| 107873 | 101 | coding | 50 nM | 69% | 132% |
| " | " | " | 100 nM | 41% | 119% |
| " | " | " | 200 nM | 23% | 131% |
| 107874 | 102 | coding | 50 nM | 75% | 109% |
| " | " | " | 100 nM | 34% | 99% |
| " | " | " | 200 nM | 23% | 87% |
| 107875 | 103 | coding | 50 nM | 82% | 93% |
| " | " | " | 100 nM | 38% | 101% |
| " | " | " | 200 nM | 40% | 91% |
| 107877 | 105 | coding | 50 nM | 50% | 127% |
| " | " | " | 100 nM | 34% | 125% |
| " | " | " | 200 nM | 22% | 106% |
| 107878 | 106 | coding | 50 nM | 70% | 110% |
| " | " | " | 100 nM | 43% | 109% |
| " | " | " | 200 nM | 27% | 116% |
| 17893 | 27 | coding | 50 nM | 28% | 8% |
| " | " | " | 100 nM | 27% | 115% |
| " | " | " | 200 nM | 16% | 108% |
| 17899 | 33 | coding | 50 nM | 89% | 87% |
| " | " | " | 100 nM | 36% | 104% |
| " | " | " | 200 nM | 15% | 80% |

These data show that the oligonucleotides designed to target human p38β, do so in a target-specific and dose-dependent manner.

Example 10

Real-Time Quantitative PCR Analysis of p38α mRNA Levels

Quantitation of p38α mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus MgCl$_2$, 6.6 mM MgCl$_2$, 375 μM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human p38α were designed to hybridize to a human p38α sequence, using published sequence information (GenBank accession number L35253, incorporated herein as SEQ ID NO:1). For human p38α the PCR primers were: forward primer: GATGAGTG- GAAAAGCCTGAC (SEQ ID NO: 108) reverse primer: CTGCAACAAGAGGCACTTGA (SEQ ID NO: 109) and the PCR probe was: FAM-GATGAAGTCATCAGCTTTGT-GCCACCACCCCTTGACCAAGAAGAGATGGA-TAMRA (SEQ ID NO: 110) where FAM is the fluorescent dye and TAMRA is the quencher dye. For human GAPDH the PCR primers were: forward primer: GAAGGTGAAG-GTCGGAGTC (SEQ ID NO: 111) reverse primer: GAA-GATGGTGATGGGATTTC (SEQ ID NO: 112) and the PCR probe was: 5' JOE-CAAGCTTCCCGTTCTCAGCC-TAMRA 3' (SEQ ID NO: 113) where JOE is the fluorescent reporter dye and TAMRA is the quencher dye.

Probes and primers to mouse p38α were designed to hybridize to a mouse p38α sequence, using published sequence information (GenBank accession number U10871.1, incorporated herein as SEQ ID NO: 114). For mouse p38α the PCR primers were:
forward primer: AAGGGAACGAGAAAACTGCTGTT (SEQ ID NO: 115)
reverse primer: TATTTTAACCAGTGGTATTATCTGA-CATCCT (SEQ ID NO: 116) and the PCR probe was: FAM-TTGTATTTGTGAACTTGGCTGTAATCTG-GTATGCC-TAMRA (SEQ ID NO: 117) where FAM is the fluorescent reporter dye and TAMRA is the quencher dye. For mouse GAPDH the PCR primers were:
forward primer: GGCAAATTCAACGGCACAGT(SEQ ID NO: 118)
reverse primer: GGGTCTCGCTCCTGGAAGAT(SEQ ID NO: 119) and the PCR probe was: 5' JOE-AAGGC-CGAGAATGGGAAGCTTGTCATC-TAMRA 3' (SEQ ID NO: 120) where JOE is the fluorescent reporter dye and TAMRA is the quencher dye.

Probes and primers to rat p38α were designed to hybridize to a rat p38α sequence, using published sequence information (GenBank accession number U73142, incorporated herein as SEQ ID NO: 45). For rat p38α the PCR primers were: forward primer: ATCATTTGGAGCCCAGAAGGA (SEQ ID NO: 121) reverse primer: TGGAGCTGGACTGCATACTGA (SEQ ID NO: 122) and the PCR probe was: FAM-CTGGC-CAGGCCTCACCGC-TAMRA (SEQ ID NO: 123) where FAM is the fluorescent reporter dye and TAMRA is the quencher dye. For rat GAPDH the PCR primers were:
forward primer: TGTTCTAGAGACAGCCGCATCTT(SEQ ID NO: 124)
reverse primer: CACCGACCTTCACCATCTTGT(SEQ ID NO: 125) and the PCR probe was: 5' JOE-TTGTGCAGT-GCCAGCCTCGTCTCA-TAMRA 3' (SEQ ID NO: 126) where JOE is the fluorescent reporter dye and TAMRA is the quencher dye.

Example 11

Additional Human p38α Oligonucleotide Sequences

Additional antisense oligonucleotides were designed to target human p38α using published sequence (Genbank accession number NM_001315.1, provided herein as SEQ ID NO: 127). Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. Internucleoside linkages are phosphorothioate (P=S). These oligonucleotide sequences are shown in Table 21. "Target site" indicates the first (5'-most) nucleotide number on the particular target sequence to which the compound binds. The compounds can be analyzed for their effect on human p38α mRNA levels by quantitative real-time PCR as described in other examples herein.

TABLE 21

Additional chimeric phosphorothioate antisense oligonucleotides targeted to human p38α

| ISIS # | Region | Target Sequence Accession # | Target Site | SEQUENCE | SEQ ID NO: |
|---|---|---|---|---|---|
| 186877 | coding | NM_001315.1 | 1271 | GAGCAAAGTAGGCATGTGCA | 128 |
| 186878 | 3' UTR | NM_001315.1 | 2703 | GTTTCCGAAGTTTGGGATAT | 129 |
| 186879 | 3' UTR | NM_001315.1 | 2735 | GCATTAGTTATTGGGAGTGA | 130 |
| 186880 | 3' UTR | NM_001315.1 | 1671 | CCCTGGAGCATCCACAACCT | 131 |
| 186881 | coding | NM_001315.1 | 1021 | TGTACCAGGAAACAATGTTC | 132 |
| 186882 | 5' UTR | NM_001315.1 | 326 | CGGGCAAGAAGGTGGCCCTG | 133 |
| 186883 | 3' UTR | NM_001315.1 | 3296 | ATCGCCATCAGTCTGCCTCC | 134 |
| 186884 | 3' UTR | NM_001315.1 | 2312 | TGACATCAAGAACCTGCTTC | 135 |
| 186885 | 3' UTR | NM_001315.1 | 2134 | GGCCCACAAGCAGCTGTCCA | 136 |
| 186886 | 3' UTR | NM_001315.1 | 3063 | TGAAAACGACACTTCTCCAC | 137 |
| 186887 | 3' UTR | NM_001315.1 | 3307 | GGTGAGAGGGAATCGCCATC | 138 |
| 186888 | 3' UTR | NM_001315.1 | 2007 | ATACTGTCAAGATCTGAGAA | 139 |
| 186889 | 3' UTR | NM_001315.1 | 2702 | TTTCCGAAGTTTGGGATATT | 140 |
| 186890 | 3' UTR | NM_001315.1 | 2205 | AGAGAGACGCACATATACGC | 141 |

TABLE 21-continued

Additional chimeric phosphorothioate antisense oligonucleotides targeted to human p3Bα

| ISIS # | Region | Target Sequence Accession # | Target Site | SEQUENCE | SEQ ID NO: |
|---|---|---|---|---|---|
| 186891 | 3' UTR | NM_001315.1 | 1516 | CAAGAGGCACTTCAATAATA | 142 |
| 186892 | coding | NM_001315.1 | 638 | ATTCCTCCAGAGACCTTGCA | 143 |
| 186893 | 3' UTR | NM_001315.1 | 2848 | AAGACACCTTGTTACTTTTT | 144 |
| 186894 | 3' UTR | NM_001315.1 | 2989 | TGCCCTTTCTCCCCATCAAA | 145 |
| 186895 | coding | NM_001315.1 | 1096 | TGGCATCCTGTTAATGAGAT | 146 |
| 186896 | 3' UTR | NM_001315.1 | 1477 | AAGGCCTTCCCCTCACAGTG | 147 |
| 186897 | 3' UTR | NM_001315.1 | 3728 | AATAGGCTTTATTTTAACCA | 148 |
| 186898 | 3' UTR | NM_001315.1 | 2455 | ACCCAAGAAGTCTTCACTGG | 149 |
| 186899 | 3' UTR | NM_001315.1 | 3135 | TTTCTTATTACACAAAAGGC | 150 |
| 186900 | 3' UTR | NM_001315.1 | 3445 | GGAAATCACACGAGCATTTA | 151 |
| 186901 | coding | NM_001315.1 | 794 | GGTCCCTGTGAATTATGTCA | 152 |
| 186902 | 3' UTR | NM_001315.1 | 3112 | AATATATGAGTCCTCATGTA | 153 |
| 186903 | 3' UTR | NM_001315.1 | 3511 | CTAACACGTATGTGGTCACA | 154 |
| 186904 | 3' UTR | NM_001315.1 | 2984 | TTTCTCCCCATCAAAAGGAA | 155 |
| 186905 | coding | NM_001315.1 | 727 | CTGAACATGGTCATCTGTAA | 156 |
| 186906 | 3' UTR | NM_001315.1 | 3681 | ATAACTGATTACAGCCAAGT | 157 |
| 186907 | 3' UTR | NM_001315.1 | 2959 | TTCTCAAAGGGATTCCTACA | 158 |
| 186908 | coding | NM_001315.1 | 678 | TCTGCCCCATGAGATGGGT | 159 |
| 186909 | coding | NM_001315.1 | 540 | TTCGCATGAATGATGGACTG | 160 |
| 186910 | coding | NM_001315.1 | 1275 | TACTGAGCAAAGTAGGCATG | 161 |
| 186911 | coding | NM_001315.1 | 1336 | GTCCCTGCTTTCAAAGGACT | 162 |
| 186912 | coding | NM_001315.1 | 577 | CATATGTTTAAGTAACCGCA | 163 |
| 186913 | 3' UTR | NM_001315.1 | 2963 | CACATTCTCAAAGGGATTCC | 164 |

Additional antisense oligonucleotides were designed to target human p38α using published sequence (Genbank accession number NM_001315.1, provided herein as SEQ ID NO: 127. Oligonucleotides were synthesized as oligonucleotides comprised of 2'-deoxynucleotides and phosphodiester internucleoside linkages (P=O). These oligonucleotide sequences are shown in Table 22. "Target site" indicates the first (5'-most) nucleotide number on the particular target sequence to which the compound binds.

TABLE 22

Additional phosphodiester oligonucleotides targeted to p3Bα

| ISIS # | Region | Target Sequence Accession # | Target Site | SEQUENCE | SEQ ID NO |
|---|---|---|---|---|---|
| 169107 | coding | NM_001315.1 | 1420 | GGACTCCATCTCTTCTTGGTCAA | 165 |
| 336747 | 3' UTR | NM_001315.1 | 1454 | GAAGTGGGATCAACAGAACAGAAA | 166 |
| 336750 | coding | NM_001315.1 | 436 | AGCCCACTGGAGACAGGTTCT | 167 |

Example 12

Mouse and Rat p38α Antisense Oligonucleotides

Antisense oligonucleotides were designed to target mouse p38α using published sequences (Genbank accession number U10871.1, provided herein as SEQ ID NO: 114, GenBank accession number D83073.1, provided herein as SEQ ID NO: 168, GenBank accession number AA002328.1, provided herein as SEQ ID NO: 169, GenBank accession number AF128892.1, provided herein as SEQ ID NO: 170, GenBank accession number BY159314.1, provided herein as SEQ ID NO: 171 and Genbank accession number BY257628.1, provided herein as SEQ ID NO: 172). These compounds are shown in the tables included in this example.

Antisense oligonucleotides were also designed to target rat p38α using published sequences (GenBank accession number U73142, provided herein as SEQ ID NO: 45, and Genbank accession number U91847.1, provided herein as SEQ ID NO: 173). These compounds are shown in the tables in this example.

Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. Internucleoside linkages are phosphorothioate (P=S). In Table 23, "Target site" indicates the first (5'-most) nucleotide number on the particular target sequence to which the compound binds.

The compounds in Table 23 were analyzed for their effect on mouse p38α mRNA levels by quantitative real-time PCR as described in other examples herein. Data are averages from two experiments in which bEND.3 cells were treated with the antisense oligonucleotides of the present invention and are presented in the column labeled "% inhib, mouse p38α". If present, "N.D." indicates "no data". ISIS 18078 is (GTGCGCGCGAGCCCGAAATC, SEQ ID NO: 174) was used as a scrambled control oligonucleotide.

The compounds in Table 23 were also analyzed for their effect on rat p38α mRNA levels in NR-8383 cells by quantitative real-time PCR as described in other examples herein. The rat normal lung alveolar macrophage cell line NR-8383 was obtained from the American Type Culture Collection (Manassas, Va.). NR-8383 cells were routinely cultured in Ham's F12 medium (Gibco/Life Technologies, Gaithersburg, Md.) supplemented with 10% fetal bovine serum (Gibco/Life Technologies, Gaithersburg, Md.), and 1% Penicillin/Streptomycin (Gibco/Life Technologies, Gaithersburg, Md.). Cells were routinely passaged by trypsinization and dilution when they reached 90% confluence. For transfection with oligonucleotides, NR-8383 cells were plated on 24 well plates at a density of $4 \times 10^4$ cells/cm2 ($8.0 \times 10^4$ cells/well) in serum-free F12 Nutrient Medium (Gibco/Life Technologies, Gaithersburg, Md.). After 2 hours, media was removed and replaced with 400 ul of Ham's F12 Nutrient Medium supplemented with 15% fetal bovine serum and 1% Penicillin/Streptomycin. Cells were then transfected with 300 nM of antisense oligonucleotides mixed with FuGENE 6 Transfection Reagent (Roche Applied Science, Indianapolis, Ind.) for 24 hours, after which mRNA was quantitated as described in other examples herein. Data are averages from two experiments in which NR-8383 cells were treated with the antisense oligonucleotides of the present invention and are presented in the column labeled "% inhib, rat p38α". If present, "N.D." indicates "no data". ISIS 18078 (GTGCGCGCGAGCCCGAAATC, SEQ ID NO: 174) was used as a scrambled control oligonucleotide.

One additional compound, ISIS 186911 (SEQ ID NO: 143), targeted to human p38α, was also tested for its effect on mouse and rat p38α mRNA expression in bEND.3 cells and NR-8383 cells, respectively.

An asterisk (*) adjacent to the ISIS oligonucleotide number in Table 23 indicates that the oligonucleotide targets human, mouse and rat p38α sequences. Compounds in Table 23, with the exception of ISIS 101753, ISIS 320119, ISIS 320120 and 320121 target both mouse and rat p38α.

TABLE 23

Inhibition of mouse and rat p38α by chimeric phosphorothioate oligonucleotides having 2'-HOE wings and a deoxy gap

| ISIS # | Region | Target Sequence Accession # | Target Site | Sequence | % Inhib, mouse p38α | % Inhib, rat p38α | Seq ID NO |
|---|---|---|---|---|---|---|---|
| 100864* | coding | L35253 | 538 | TCCAACAGACCAATCACATT | 83 | 57 | 82 |
| 101753 | start codon | U73142 | 1 | CTGCGACATTTTCCAGCGGC | 64 | 43 | 175 |
| 101755* | coding | U10871.1 | 1226 | CATCATCAGGGTCGTGGTAC | 84 | 74 | 176 |
| 101757* | coding | U10871.1 | 1336 | AGGTGCTCAGGACTCCATTT | 88 | 53 | 177 |
| 186911* | coding | NM_001315.1 | 1336 | GTCCCTGCTTTCAAAGGACT | 81 | 40 | 178 |
| 306022* | coding | U73142 | 781 | GGCCAGAGACTGAATGTAGT | 78 | 53 | 179 |
| 320103* | coding | U10871.1 | 315 | AGCTCCTGCCGGTAGAACGT | 81 | 55 | 180 |
| 320104* | coding | U10871.1 | 405 | TCAAAAGCAGCACACACCGA | 82 | 42 | 181 |
| 320105* | coding | U10871.1 | 417 | CCCGTCTTTGTATCAAAAGC | 89 | 59 | 182 |
| 320106* | coding | U10871.1 | 453 | AACGGTCTCGACAGCTTCTT | 91 | 67 | 183 |
| 320107* | coding | U10871.1 | 483 | TAGGTCCTTTTGGCGTGAAT | 84 | 60 | 184 |
| 320108* | coding | U10871.1 | 600 | AGATGGGTCACCAGGTACAC | 61 | 57 | 185 |

TABLE 23-continued

Inhibition of mouse and rat p38α by chimeric phosphorothioate oligonucleotides having 2'-HOE wings and a deoxy gap

| ISIS # | Region | Target Sequence Accession # | Target Site | Sequence | % Inhib, mouse p38α | % Inhib, rat p38α | Seq ID NO |
|---|---|---|---|---|---|---|---|
| 320109* | coding | U10871.1 | 609 | GCCCCCATGAGATGGGTCAC | 69 | 34 | 186 |
| 320110* | coding | U10871.1 | 807 | TCATCAGTGTGCCGAGCCAG | 87 | 54 | 187 |
| 320111* | coding | U10871.1 | 930 | GTCAACAGCTCAGCCATGAT | 86 | 55 | 188 |
| 320112* | coding | U10B71.1 | 940 | CGTTCTTCCGGTCAACAGCT | 93 | 58 | 189 |
| 320113* | coding | U10871.1 | 967 | ATCAATATGGTCTGTACCAG | 35 | 9 | 190 |
| 320114* | coding | U10871.1 | 987 | CTTAAAATGAGCTTCAACTG | 71 | 60 | 191 |
| 320115* | coding | U10871.1 | 1001 | GGGTTCCAACGAGTCTTAAA | 67 | 53 | 192 |
| 320116* | coding | U10871.1 | 1019 | TCAGAAGCTCAGCCCCTGGG | 95 | 73 | 193 |
| 320117* | coding | U10871.1 | 1030 | GGAGATTTTCTTCAGAAGCT | 72 | 55 | 194 |
| 320118* | coding | U10871.1 | 1040 | CAGACTCTGAGGAGATTTTC | 47 | 69 | 195 |
| 320119 | coding | U10871.1 | 1050 | TAGTTTCTTGCAGACTCTGA | 53 | 32 | 196 |
| 320120 | coding | U10871.1 | 1060 | AGACTGAATGTAGTTTCTTG | 74 | 39 | 197 |
| 320121 | coding | U10871.1 | 1083 | TTCATCTTCGGCATCTGGGC | 83 | 57 | 198 |
| 320122 | coding | U10871.1 | 1093 | ATTTGCGAAGTTCATCTTCG | 73 | 48 | 199 |
| 320123 | coding | U10871.1 | 1103 | CAATAAATACATTTGCGAAG | 79 | 32 | 200 |
| 320124 | coding | U10871.1 | 1113 | GGATTGGCACCAATAAATAC | 29 | 31 | 201 |
| 320125 | coding | U10871.1 | 1176 | GCTGCTGTGATCCTCTTATC | 67 | 63 | 202 |
| 320126 | coding | U10871.1 | 1196 | AGGCATGCGCAAGAGCTTGG | 90 | 69 | 203 |
| 320127 | coding | U10871.1 | 1206 | TGAGCAAAGTAGGCATGCGC | 73 | 56 | 204 |
| 320128 | coding | U10871.1 | 1260 | TCAAAGGACTGGTCATAAGG | 79 | 37 | 205 |
| 320129 | coding | U10871.1 | 1351 | CATTTCTTCTTGGTCAAGGG | 69 | 65 | 206 |
| 320130 | stop codon | U10871.1 | 1358 | AGGACTCCATTTCTTCTTGG | 81 | 61 | 207 |
| 320131 | 3' UTR | U10871.1 | 1406 | CTTCCCCTCACAGTGAAGTG | 92 | 39 | 208 |
| 320132 | 3' UTR | U10871.1 | 1432 | TATTTGGAGAGTTCCCATGA | 85 | 56 | 209 |
| 320133 | 3' UTR | U10871.1 | 1442 | ACTTGAATGGTATTTGGAGA | 52 | 61 | 210 |
| 320134 | 3' UTR | U10871.1 | 1452 | AACAAGAGGCACTTGAATGG | 85 | 74 | 211 |
| 320135 | 3' UTR | U10871.1 | 1480 | ACCCCCTTCCACCATGAAGG | 95 | 47 | 212 |
| 320136 | 3' UTR | U10871.1 | 1608 | AGCAGGCAGACTGCCAAGGA | 83 | 34 | 213 |
| 320137 | 3' UTR | U10871.1 | 1663 | CACACACATCCCTAAGGAGA | 80 | 44 | 214 |
| 320138 | 3' UTR | U10871.1 | 1745 | TAAAGGCAGGGCCACAGGAG | 87 | 46 | 215 |
| 320139 | 3' UTR | U10871.1 | 1771 | GCAGCCTCTCTCTGTCACTG | 87 | 61 | 216 |
| 320140 | 3' UTR | U10871.1 | 1791 | GGGATAGCCTCAGACCTGAA | 61 | 37 | 217 |
| 320141 | 3' UTR | U10871.1 | 1801 | GCATGGCTGAGGGATAGCCT | 83 | 73 | 218 |
| 320142 | 3' UTR | U10871.1 | 1828 | GAGCCAGTTGGTTCTCTTGG | 85 | 53 | 219 |
| 320143 | 3' UTR | U10871.1 | 1910 | AGGCACAAACAGACTGACAG | 88 | 54 | 220 |
| 320144 | 3' UTR | U10871.1 | 1917 | CCTTTTAAGGCACAAACAGA | 83 | 39 | 221 |

TABLE 23-continued

Inhibition of mouse and rat p38α by chimeric phosphorothioate oligonucleotides having 2'-HOE wings and a deoxy gap

| ISIS # | Region | Target Sequence Accession # | Target Site | Sequence | % Inhib, mouse p38α | % Inhib, rat p38α | Seq ID NO |
|---|---|---|---|---|---|---|---|
| 320145 | 3' UTR | U10871.1 | 2138 | GACCTCTGCACTGAGGTGAA | 52 | 44 | 222 |
| 320146 | 3' UTR | U10871.1 | 2147 | GGCACTGGAGACCTCTGCAC | 74 | 57 | 223 |
| 320147 | 3' UTR | U10871.1 | 2228 | AGAGCACAGCATGCAAACAC | 66 | 43 | 224 |
| 320148 | 3' UTR | U10871.1 | 2259 | CCAGGGCTTCCAGAAGACAG | 78 | 33 | 225 |
| 320149 | 3' UTR | U10871.1 | 2576 | AAGGAGCTCCTGGCTTCAGG | 74 | 25 | 226 |
| 320150 | 3' UTR | U10871.1 | 2738 | GGATTCCTACAACATACAAA | 82 | 62 | 227 |
| 320151 | 3' UTR | U10871.1 | 2758 | GAAGGAACCACACTCTCTAA | 90 | 47 | 228 |
| 320152 | 3' UTR | U10871.1 | 2778 | TTTGCCCTTTCTCCCCATCA | 93 | 66 | 229 |
| 320153 | 3' UTR | U10871.1 | 2791 | AATATTAAATAATTTGCCC | 0 | 22 | 230 |
| 320154 | 3' UTR | U10871.1 | 2817 | TCATGTTTATAAAGGTGAAA | 52 | 50 | 231 |
| 320155 | 3' UTR | U10871.1 | 2827 | CCCTGAGGATTCATGTTTAT | 93 | 73 | 232 |
| 320156 | 3' UTR | U10871.1 | 2930 | GGAATTGGCTTTACACTTTC | 91 | 64 | 233 |
| 320157 | 3' UTR | U10871.1 | 2941 | CGTCCAACACTGGAATTGGC | 96 | 71 | 234 |
| 320158 | 3' UTR | U10871.1 | 3042 | CCTTCTGGGCTCCAAATGAT | 91 | 71 | 235 |
| 320159 | 3' UTR | U10871.1 | 3386 | TCTGACATCCTATGQCATAC | 94 | 69 | 236 |
| 320160 | coding | D83073.1 | 900 | GTTAATATGGTCTGTACCAG | 53 | 43 | 237 |
| 320161 | coding | D83073.1 | 910 | GCTGAAGCTGGTTAATATGG | 80 | 66 | 238 |
| 320162 | coding | D83073.1 | 920 | CGCATTATCTGCTGAAGCTG | 92 | 62 | 239 |
| 320163 | coding | D83073.1 | 955 | TGTTAATGAGATAAGCAGGG | 0 | 40 | 240 |
| 320164 | coding | D83073.1 | 965 | CTTGGCATCCTGTTAATGAG | 80 | 73 | 241 |
| 320165 | coding | D83073.1 | 975 | TGCCTCATGGCTTGGCATCC | 81 | 53 | 242 |
| 320166 | coding | D83073.1 | 991 | ACTGAATGTAGTTTCTTGCC | 53 | 35 | 243 |
| 320167 | 5' UTR | AA002328.1 | 155 | CTTGCCTGTAAAAACACAGA | 7 | 11 | 244 |
| 320168 | stop codon | AF128892.1 | 1059 | TCACCTCATGGCTTGGCATC | 83 | 56 | 245 |
| 320169 | stop codon | AF128892.1 | 1066 | TTTGTTCTCACCTCATGGCT | 92 | 64 | 246 |
| 320170 | 3' UTR | AF128892.1 | 1132 | TGCTGGCTATACACAGACAC | 83 | 55 | 247 |
| 320171 | intron | BY159314.1 | 58 | TGGAAAACTGTTTTGTCAAA | 35 | 2 | 248 |
| 320172 | intron | BY257628.1 | 39 | ACTCTCGCGAGAACAGCTCC | 39 | 0 | 249 |
| 320173 | intron | BY257628.1 | 72 | TCCCACAGGCAGCGGCCGGG | 16 | 0 | 250 |
| 320174 | intron | BY257628.2 | 97 | CCCGCTTGGGCTCCAGTGGC | 62 | 29 | 251 |

All compounds in Table 23 inhibited either mouse or rat p38α RNA expression by at least 10%. Compounds with SEQ ID NO: 82, 175, 176, 177, 178, 179, 180, 181, 182, 183, 184, 185, 186, 187, 188, 189, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 231, 232, 233, 234, 235, 236, 237, 238, 239, 241, 242, 243, 245, 246, 247 and 251 inhibited expression of both mouse and rat p38α by at least 10%.

Additional antisense oligonucleotides were designed to target mouse p38α using published sequences (Genbank accession number U10871.1, provided herein as SEQ ID NO: 114). Oligonucleotides are composed of 2'-deoxynucleotides. Internucleoside linkages are phosphorodiester (P=O). These oligonucleotide sequences are shown in Table 24. "Target site" indicates the first (5'-most) nucleotide number on the particular target sequence to which the compound binds.

TABLE 24

Antisense oligonucleotides targeted to mouse p38α having 2'-deoxynucleotides and phosphodiester linkages

| ISIS # | Region | Target Sequence Accession # | Start Site | SEQUENCE | SEQ ID NO |
|---|---|---|---|---|---|
| 137934 | 3' UTR | U10871.1 | 3331 | GCAGTTTTCTCGTTCCCTTG | 252 |
| 264006 | coding | U10871.1 | 1207 | CTGAGCAAAGTAGGCATGCG | 253 |
| 320184 | 3' UTR | U10871.1 | 2306 | GGAGGCAATGTGGACAGGAA | 254 |
| 279221 | coding | U10871.1 | 521 | CATTTTCGTGTTTCATGTGCTTC | 255 |
| 326403 | 3' UTR | U10871.1 | 3395 | TATTTTAACCAGTGGTATTATCTACATCCT | 256 |

Additional antisense oligonucleotides were designed to target mouse p38α using published sequences (Genbank accession number U10871.1, provided herein as SEQ ID NO: 114). Oligonucleotides were synthesized as chimeric oligonucleotides ("gapmers") 20 nucleotides in length, composed of a central "gap" region consisting of ten 2'-deoxynucleotides, which is flanked on both sides (5' and 3' directions) by five-nucleotide "wings." The wings are composed of 2'-methoxyethyl (2'-MOE) nucleotides. Internucleoside linkages in the central gap region are phosphorothioate (P=S), and internucleoside linkages in the wings are phosphodiester (P=O). These oligonucleotide sequences are shown in Table 25. "Target site" indicates the first (5'-most) nucleotide number on the particular target sequence to which the compound binds.

TABLE 25

Chimeric oligonucleotides targeted to mouse p38α having 2'-MOE wings and a deoxy gap and mixed phophorothioate and phosphodiester internucleoside linkages

| ISIS # | Region | Target Sequence Accession # | Start Site | SEQUENCE | SEQ ID NO |
|---|---|---|---|---|---|
| 101369 | start codon | U10871.1 | 286 | CTGCGACATCTTCCAGCGGC | 257 |
| 101370 | coding | U10871.1 | 646 | GGTCAGCTTCTGGCACTTCA | 258 |
| 101372 | 3' UTR | U10871.1 | 1609 | AAGCAGGCAGACTGCCAAGG | 259 |

Additional antisense oligonucleotides were designed to target rat p38α using published sequences (GenBank accession number U73142, provided herein as SEQ ID NO: 45, and GenBank accession number U91847.1, provided herein as SEQ ID NO: 173). Oligonucleotides are composed of 2'-deoxynucleotides. Internucleoside linkages are phosphorodiester (P=O). These oligonucleotide sequences are shown in Table 26. "Target site" indicates the first (5'-most) nucleotide number on the particular target sequence to which the compound binds.

TABLE 26

Antisense oligonueleotides targeted to rat p38α having 2'-deoxynucleotides and phosphodiester linkages

| ISIS # | Region | Target Sequence Accession # | Start Site | SEQIENCE | SEQ ID NO |
|---|---|---|---|---|---|
| 336744 | coding | U91847.1 | 902 | AGGCATGCGCAAGAGCTT | 260 |
| 336741 | coding | U91847.1 | 66 | GGGACAGGTTCTGGTATCGC | 261 |

TABLE 26-continued

Antisense oligonucleotides targeted to rat p38α having
2'-deoxynucleotides and phosphodiester linkages

| ISIS # | Region | Target Sequence Accession # | Start Site | SEQIENCE | SEQ ID NO |
|---|---|---|---|---|---|
| 257014 | coding | U91847.1 | 224 | TCTCGTGCTTCATGTGCTTCA | 262 |
| 320187 | 3' UTR | U73142 | 2800 | TGGAGCTGGACTGCATACTGA | 263 |

Additional antisense oligonucleotides were designed to target rat p38α using published sequences (GenBank accession number U73142, provided herein as SEQ ID NO: 45). Oligonucleotides were synthesized as chimeric oligonucleotides, composed 2'-deoxynucleotides and 2'-methoxyethyl (2'-MOE) nucleotides (indicated in bold type in Table 27). Internucleoside linkages in the central gap region are phosphorothioate (P=S), and internucleoside linkages in the wings are phosphodiester (P=O). These oligonucleotide sequences are shown in Table 27. "Target site" indicates the first (5'-most) nucleotide number on the particular target sequence to which the compound binds.

TABLE 27

Chimeric oligonucleotides targeted to rat
p38α having 2'-MOE wings and a deoxy gap and
mixed phophorothicate and phospliodiester
internucleoside linkages

| ISIS # | Region | Target Sequence Accession # | Start Site | SEQUENCE | SEQ ID NO |
|---|---|---|---|---|---|
| 111831 | coding | U73142 | 941 | CATCAGGGTCGTGGTAC | 264 |
| 111830 | coding | U73142 | 942 | CATCATCAGGGTCGT | 265 |

Example 13

Mouse Model of Allergic Inflammation

In the mouse model of allergic inflammation, mice were sensitized and challenged with aerosolized chicken ovalbumin (OVA). Airway responsiveness was assessed by inducing airflow obstruction with a methacholine aerosol using a non-invasive method. This methodology utilized unrestrained conscious mice that are placed into the main chamber of a plethysmograph (Buxco Electronics, Inc., Troy, N.Y.). Pressure differences between this chamber and a reference chamber were used to extrapolate minute volume, breathing frequency and enhanced pause (Penh). Penh is a dimensionless parameter that is a function of total pulmonary airflow in mice (i.e., the sum of the airflow in the upper and lower respiratory tracts) during the respiratory cycle of the animal. The lower the Penh, the greater the airflow. This parameter closely correlates with lung resistance as measured by traditional invasive techniques using ventilated animals (Hamelmann et al., 1997). Dose-response data were plotted as raw Penh values to increasing concentrations of methacholine. This system was used to test the efficacy of an antisense oligonucleotide targeted to mouse p38α (ISIS 101757; SEQ ID NO: 177). Six-base-mismatched p38α oligonucleotide (ISIS 101758; SEQ ID NO: 266) was used as a negative control.

There are several important features common to human asthma and the mouse model of allergic inflammation. One of these is pulmonary inflammation, in which cytokine expression and Th2 profile is dominant. Another is goblet cell hyperplasia with increased mucus production. Lastly, airway hyperresponsiveness (AHR) occurs resulting in increased sensitivity to cholinergic receptor agonists such as acetylcholine or methacholine. The compositions and methods of the present invention may be used to treat AHR and pulmonary inflammation. The combined use of antisense oligonucleotides targeted to human p38 MAP kinase with one or more conventional asthma medications including, but not limited to, montelukast sodium (Singulair™), albuterol, beclomethasone dipropionate, triamcinolone acetonide, ipratropium bromide (Atrovent™), flunisolide, fluticasone propionate (Flovent™) and other steroids is also contemplated.

Ovalbumin-Induced Allergic Inflammation

For intratracheal administration of ISIS 101757, female Balb/c mice (Charles Rivers Laboratory, Taconic Farms, N.Y.) were maintained in micro-isolator cages housed in a specific pathogen-free (SPF) facility. The sentinel cages within the animal colony surveyed negative for viral antibodies and the presence of known mouse pathogens. Mice were sensitized and challenged with aerosolized chicken OVA. Briefly, 20 µg alum-precipitated OVA was injected intraperitoneally on days 0 and 14. On day 24, 25 and 26, the animals were exposed for 20 minutes to 1.0% OVA (in saline) by nebulization. The challenge was conducted using an ultrasonic nebulizer (PulmoSonic, The DeVilbiss Co., Somerset, Pa.). Animals were analyzed about 24 hours following the last nebulization using the Buxco electronics Biosystem. Lung function (Penh), lung histology (cell infiltration and mucus production), target mRNA reduction in the lung, inflammation (BAL cell type & number, cytokine levels), spleen weight and serum AST/ALT were determined.

For the aerosol studies, the protocol described above was slightly modified. Male Balb/c mice were injected IP with OVA (20 µg) in aluminum hydroxide on days 0 and 14. Aerosol dosing was performed with nebulized sterile saline, antisense oligonucleotide or mismatched control oligonucleotide using 25, 125 and 250 µg/ml solutions (5 mg/kg) for 30 min. on days 14-20 in a closed chamber. Aerosol lung challenge was carried out with nebulized saline or 1% OVA for 20 min. on days 18, 19 and 20. BAL fluid was collected at 24 hr post-last lung challenge (cell differentials) or at 2-12 h post-challenge (cytokine analysis). AHR was measured 24 hours after OVA challenge. Mice were exposed to aerosolized methacholine 24 hr post-last lung challenge from 2-80 mg/ml for 3 min. until a 200% increase in Penh was achieved.

Intratracheal Oligonucleotide Administration

Antisense oligonucleotides (ASOs) were dissolved in saline and used to intratracheally dose mice every day, four times per day, from days 15-26 of the OVA sensitization and challenge protocol, or used as an aerosol. Specifically, the is mice were anesthetized with isofluorane and placed on a board with the front teeth hung from a line. The nose was covered and the animal's tongue was extended with forceps and 25 µl of various doses of ASO, or an equivalent volume of saline (control) was placed at the back of the tongue until inhaled into the lung.

Mouse antisense oligonucleotides to p38α are phosphorothioates with 2'-MOE modifications on nucleotides 1-5 and 16-20, and 2'-deoxy at positions 6-15. These ASOs were identified by mouse-targeted ASO screening of 10 p38α antisense oligonucleotides by target p38α mRNA reduction in mouse bEND.3 cells, as described in Example 12. Dose-response confirmation led to selection of ISIS 21873 (>70% reduction at 50 nM). ISIS 101757 contains all phosphorothioate linkages, whereas ISIS 21873 is a mixed phosphodiester/phosphorothioate compound. ISIS 101757 had an IC50<50 nM for reducing p38α mRNA in endothelial cells, and an IC50 of about 250 nM in fibroblasts.

Results of Aerosol Administration

Figure 1B:
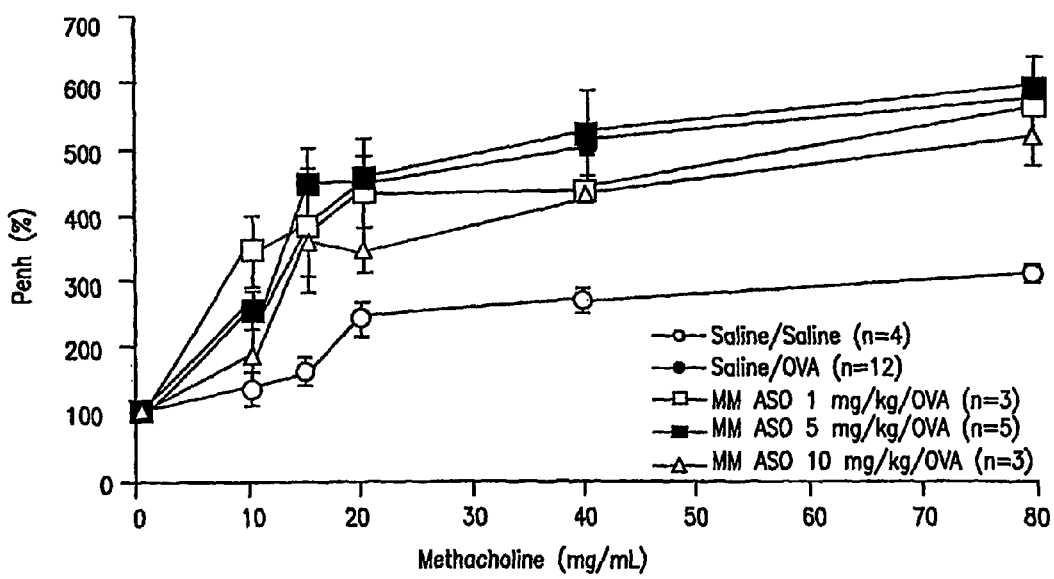
Figure 3A:
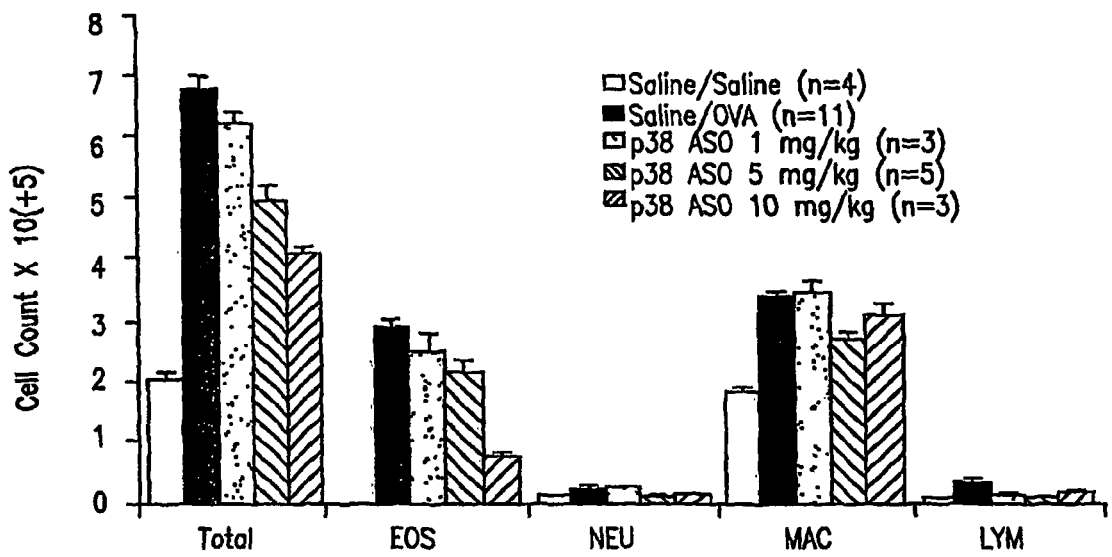
FIGS. 3A-3B are graphs showing the effect of inhaled ISIS 101757 (FIG. 3A) and 101758 (FIG. 3B) on immune cells in broncheolar lavage (BAL) fluid of OVA-challenged mice. EOS=eosinpophils, NEU=neutrophils, MAC-macrophages, LYM=lymphocyes.
Figure 3B:
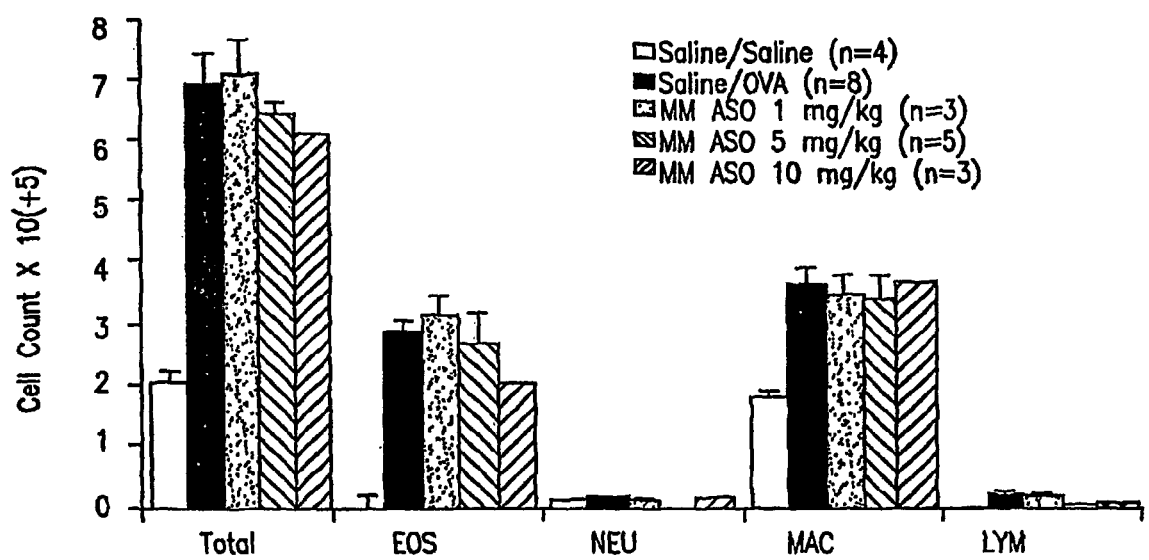
Figure 4:
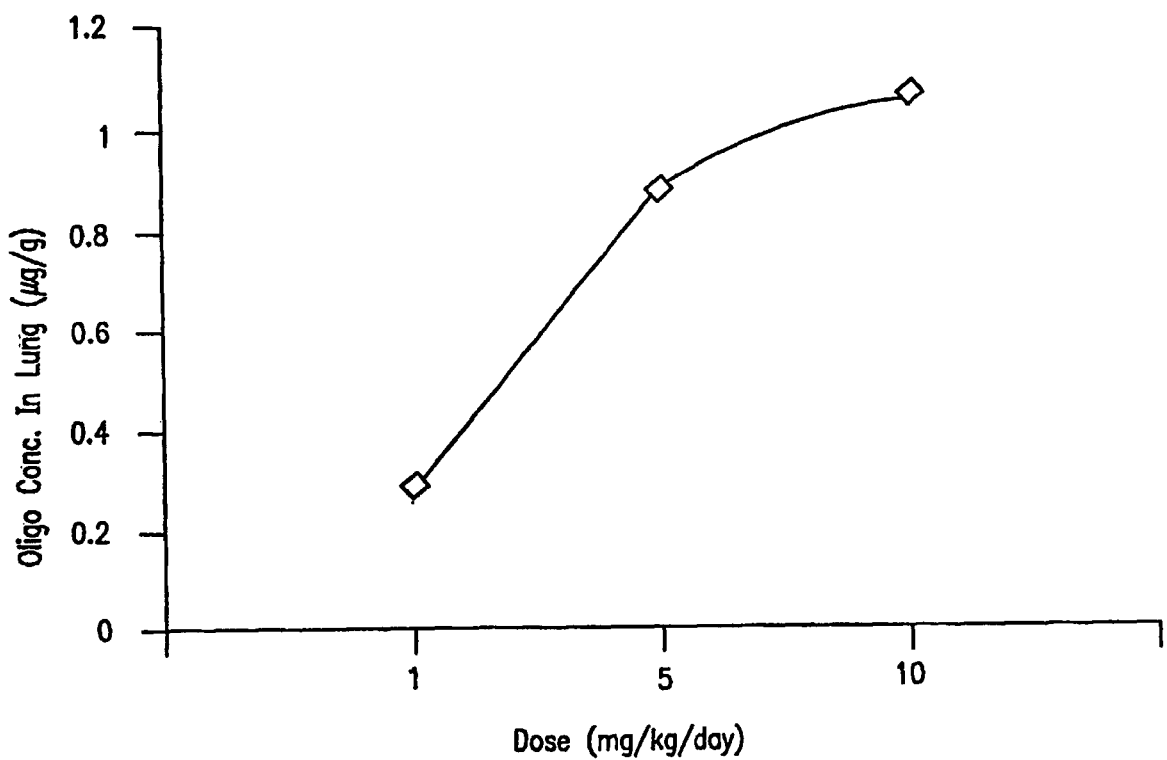
FIG. 4 is a graph showing aerosolized ISIS 101757 concentration in mouse lung vs. dose.

The p38α knock-down effect of ISIS 101757 was confirmed in a mouse T cell line (EL4) and a mouse macrophage cell line (RAW264.7) using Western blotting. ISIS 101757, but not the mismatched control, dose-dependently suppressed methacholine-induced AHR in sensitized mice measured by whole body plethysmography (FIG. 1A-1B). The PC200 values for methacholine (FIG. 2) significantly (P<0.05) reduced OVA-induced increases in total cell counts and eosinophils recovered in BAL fluid (FIG. 3). In addition, histological studies revealed that ISIS 101757 markedly inhibited OVA-induced inflammatory cell infiltration into the lungs (H&E stain) and mucus hypersecretion in the airway epithelium (PAS stain). ISIS 101757 also significantly (P<0.05); lowered blood levels of total IgE, OVA-specific IgE and OVA-specific IgG$_1$ in sensitized mice as compared to the mismatched control. Oligonucleotide levels of up to 1 µg/g of lung tissue were sufficient to achieve the pharmacological effects described above. The aerosolized ISIS 101757 concentration in mouse lung vs. dose is shown in FIG. 4. There was no significant effect of aerosol oligonucleotide administration on spleen weight. These data indicate that p38α antisense oligonucleotides are useful for the treatment of asthma.

Intratracheal Administration Results

Figure 5:
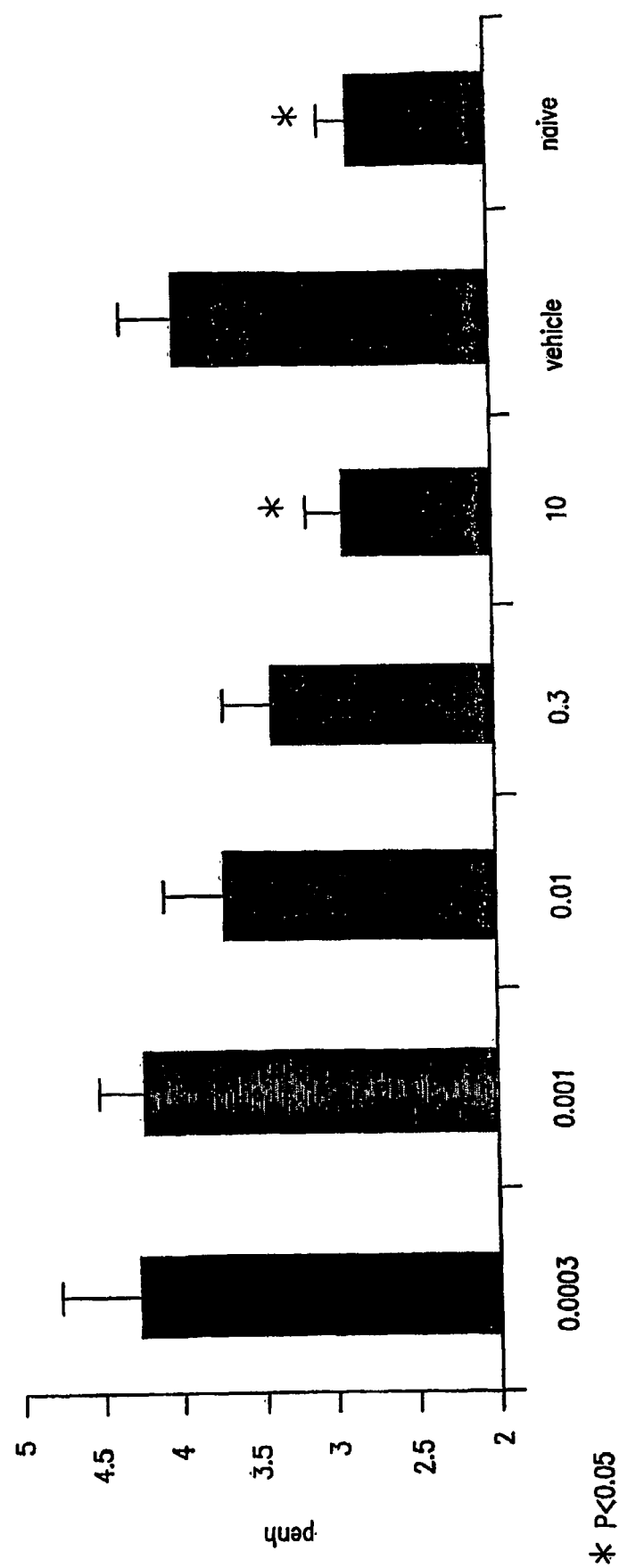
FIG. 5 is a graph showing dose-dependent inhibition of the penh response to methacholine (50 mg/ml) challenge by ISIS 101757. ISIS 101757 doses are in mg/kg (x-axis).
Figure 6:
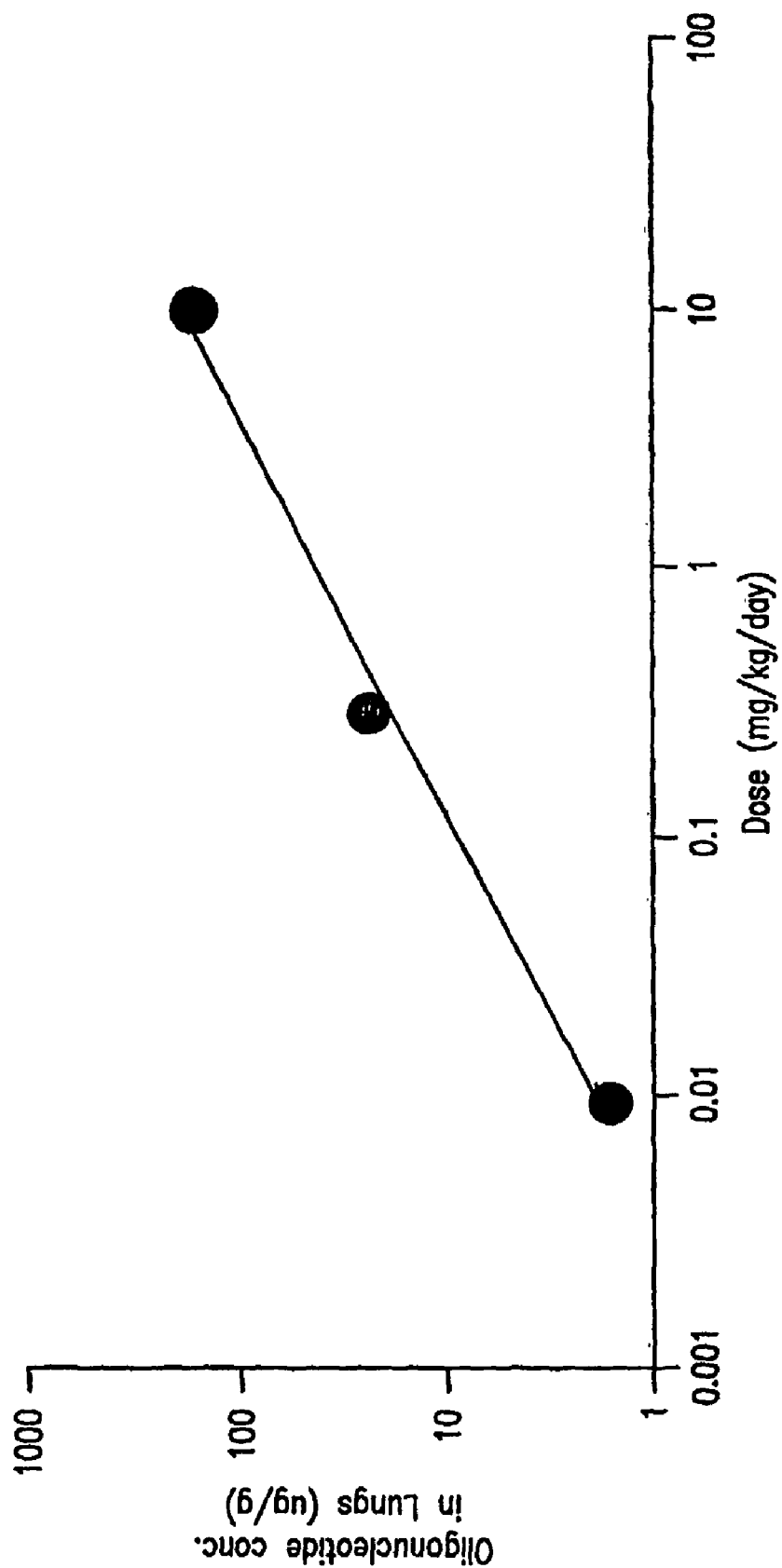
FIG. 6 is a graph showing ISIS 101757 concentration (μg/g) in the lungs vs. dose (intratracheal administration).

After intratracheal administration of ISIS 101757 as described above, dose-dependent inhibition of the Penh response to methacholine (50 mg/ml) challenge was observed (FIG. 5). The oligonucleotide concentration (µg/g) in lungs vs. dose is shown in FIG. 6.

RT-PCR Analysis

RNA was harvested from experimental lungs removed on day 28 of the OVA protocol. P38α levels were measured by quantitative RT-PCR as described in other examples herein.

Collection of Bronchial Alveolar Lavage (BAL) Fluid and Blood Serum for the Determination of Cytokine and Chemokine Levels Animals were injected with a lethal dose of ketamine, the trachea was exposed and a cannula was inserted and secured by sutures. The lungs were lavaged twice with 0.5 ml aliquots of ice cold PBS with 0.2% FCS. The recovered BAL fluid was centrifuged at 1,000 rpm for 10 min at 4° C., frozen on dry ice and stored at −80° C. until used. Luminex was used to measure cytokine levels in BAL fluid and serum.

BAL Cell Counts and Differentials

Cytospins of cells recovered from BAL fluid were prepared using a Shandon Cytospin 3 (Shandon Scientific LTD, Cheshire, England). Cell differentials were performed from slides stained with Leukostat (Fisher Scientific, Pittsburgh, Pa.). Total cell counts were quantified by hemocytometer and, together with the percent type by differential, were used to calculate specific cell number.

Tissue Histology

Before resection, lungs were inflated with 0.5 ml of 10% phosphate-buffered formalin and fixed overnight at 4° C. The lung samples were washed free of formalin with 1×PBS and subsequently dehydrated through an ethanol series prior to equilibration in xylene and embedded in paraffin. Sections (6µ) were mounted on slides and stained with hematoxylin/eosin, massons trichome and periodic acid-schiff (PAS) reagent. Parasagittal sections were analyzed by bright-field microscopy. Mucus cell content was assessed as the airway epithelium staining with PAS. Relative comparisons of mucus content were made between cohorts of animals by counting the number of PAS-positive airways.

Example 14

Design and Screening of Duplexed Antisense Compounds Targeting p38α MW Kinase

In accordance with the present invention, a series of nucleic acid duplexes comprising the antisense compounds of the present invention and their complements can be designed to target p38α MAP kinase. The nucleobase sequence of the antisense strand of the duplex comprises at least a portion of an oligonucleotide to p38α MAP kinase as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. For example, a duplex comprising an antisense strand having the sequence CGAGAGGCGGACGGGACCG and having a two-nucleobase overhang of deoxythymidine(dT) would have the following structure:

```
cgagaggcggacgggaccgTT  Antisense Strand
||||||||||||||||||||     (SEQ ID NO: 267)
TTgctctccgcctgccctggc  Complement (SEQ ID NO: 268)
```

In another embodiment, a duplex comprising an antisense strand having the same sequence CGAGAGGCGGACGG-GACCG may be prepared with blunt ends (no single stranded overhang) as shown:

```
cgagaggcggacgggaccg  Antisense Strand
|||||||||||||||||||   (SEQ ID NO: 269)
gctctccgcctgccctggc  Complement (SEQ ID NO: 270)
```

The duplex may be unimolecular or bimolecular, i.e., the sense and antisense strands may be part of the same molecule (which forms a hairpin or other self structure) or two (or even more) separate molecules.

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 15 µL of a 5× solution of annealing buffer. The final concentration of said buffer is 100 mM potassium acetate, 30 mM HEPES-KOH pH 7.4, and 2 mM magnesium acetate. The final volume is 75 µL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate p38α MAP kinase expression according to the protocols described herein.

Example 15

Design of Phenotypic Assays and in Vivo Studies for the Use of p38α MAP Kinase Inhibitors Once p38α MAP kinase inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of p38α MAP kinase in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with p38α MAP kinase inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the p38α MAP kinase inhibitors. Hallmark genes, or those genes suspected to be associated with a specific disease state, condition, or phenotype, are measured in both treated and untreated cells.

Example 16

Mouse Model of Allergic Inflammation; Second Aerosol Chamber Experiment

A second aerosol chamber experiment was conducted with additional animals using methods described in Example 13. Aerosolized p38α antisense oligonucleotide (ISIS 101757, SEQ ID NO: 177), a 6-mismatch negative control (ISIS 101758; SEQ ID NO: 266) or saline (vehicle control) were given to mice daily for 30 minutes in an aerosol chamber from days 14-20. Aerosol was delivered via a DeVilbiss ultrasonic nebulizer (Model 099HD, Sunrise Medical, Carlsbad Calif.) with a usable nebulizer output at 6 ml/min and particle sizes <4 microns. Estimated inhalable doses were 0.3, 1.5 and 3.0 mg/kg from nebulization of 12.5, 62.5 and 125 µg/ml solutions of antisense oligonucleotide, respectively. Using capillary gel electrophoresis (Leeds et al., 1996, Anal. Biochem. 235, 36-43; Geary et al., 1997, Drug Metab. Dispos., 25, 1272-1281), p38α antisense oligonucleotide levels present in lung tissue 24 hours later were determined to be 0.3, 0.8 and 1.1 µg per gram of lung tissue, respectively, indicating dose-dependent accumulation of aerosolized oligonucleotide in lung tissue.

As in the previous aerosol chamber experiment, the p38α antisense oligonucleotide inhibited OVA-induced eosinophil recruitment to the lung, as measured by cell counts in BAL fluid. This effect was mainly due to a significant reduction in eosinophil count in the antisense-treated mice, which was dose-dependent. The numbers of neutrophils, macrophages and lymphocytes was not affected by the p38α antisense compound.

Lung tissue was collected 24 hours after the last OVA challenge. OVA aerosol challenge induced marked infiltration of inflammatory cells into the peribronchiolar and perivascular connective tissues as compared to saline challenge, with eosinophils constituting the majority of infiltrating inflammatory cells. Inhalation of p38α antisense oligonucleotide (1.5 mg/kg) significantly attenuated the eosinophil-rich leukocyte infiltration as compared to a 6-base mismatch control oligonucleotide. In addition, the OVA-induced mucus secretion within the bronchi of the lung that was a marked observation (along with goblet cell hyperplasia) in the OVA-challenged mice was substantially reduced by the p38α antisense compound (1.5 mg/kg oligonucleotide), but not by the 6-base mismatch control.

To determine the levels of cytokines in vivo, BAL fluid samples were collected 2 hours after the last OVA challenge. IL-4, IL-5, IL-13 and IFNγ levels were measured by ELISA. Mouse IL-4 and IL-5 ELISA were obtained from BD PharMingen (San Diego Calif.). Mouse IL-13 and IFNγ ELISA were purchased from R&D Systems (Minneapolis Minn.). Lower limits of detection for IL-4 and IL-4 was 4 pg/ml and for IL-13 and IFNγ were 15.6 pg/ml. OVA inhalation in sensitized mice induced substantial cytokine release into BAL fluid as compared to untreated mice. Treatment of mice with aerosolized p38α antisense (ISIS 101757) significantly reduced levels of Th2 cytokines IL-4, IL-5 and IL-13 in BAL fluid as compared to the 6-mismatch control. In contrast, p38α antisense treatment did not show a significant effect on levels of IFNγ, a Th1 cytokine, in BAL fluid.

The effect of aerosolized p38α antisense compound on the development of AHR (airway hyperresponsiveness) in mice was examined. Sensitized animals challenged with 1% OVA aerosol for 20 minutes daily developed AHR to inhaled methacholine. Airway responsiveness was determined by Penh and was substantially increased in the OVA-challenged group in response to methacholine provocation, as compared to the saline-challenged group. Inhalation of p38α antisense oligonucleotide (ISIS 101757) significantly reduced AHR to inhaled methacholine in a dose-dependent manner as in a previous experiment. This suggests that the decreased immune-mediated pathology observed in mice treated with p38α antisense compound resulted in decreased airway smooth muscle constriction as well.

To verify that the effects of the inhaled p38α antisense compound on lung inflammatory and airway responses in the mouse asthma model were mediated by p38α knockdown, the effects of the antisense compound on p38α gene expression in BAL fluid cells and peri-bronchial lymph node cells were examined. The level of p38α mRNA was significantly reduced in both BAL fluid cells (over 50% reduction in p38α mRNA) and peri-bronchial lymph node cells (over 60% reduction in p38α mRNA) of p38α antisense-treated mice (3.0 mg/kg) as compared to mice treated with mismatch control.

Example 17

Nose-Only Aerosol Exposure of Mice to p38α Antisense Oligonucleotide is Effective To determine whether nose-only exposure of mice would result in similar pharmacology to that observed with the aerosol chamber, key endpoints were reproduced using a nose-only delivery system known in the art. Silbaugh et al., 1987, J. Pharm. Methods, 18, 295-303. Male Balb/c mice (25 grams, Charles River Laboratories) were sensitized with an i.p. injection (100 µl) of 20 µg OVA emulsified in 2 mg of Imject Alum (Pierce) on days 0 and 14. The mice were subsequently challenged with aerosolized OVA (1%) for 20 minutes on days 24 to 26. Different concentrations of antisense oligonucleotides (estimated inhalable doses of 3.3, 33, and 333 µg/kg) were administered by aerosol delivery for 5 days (days 17, 19, 21, 24 and 26). Aerosol administration of the oligonucleotides was achieved by means of a nose-only inhalation system. Silbaugh et al., 1987, J. Pharm. Methods, 18, 295-303. Particle size range was 0.9-1.2 µm. Oligonucleotide deposition in the lungs was measured using a quantitative hybridization-dependent nuclease ELISA method (Yu et al., 2002, Anal. Biochem., 304, 19-25. Exposure of mice to aerosolized p38α antisense oligonucleotide resulted in 11.5, 80.3 and 324 ng/g antisense oligonucleotide (ISIS 101757; SEQ ID NO: 177) per gram of lung tissue at estimated inhalable doses of 3.3, 33 and 333 µg/kg. p38α antisense oligonucleotide delivered at these doses via this apparatus produced pronounced inhibition of BAL eosinophilia and AHR in a dose-related manner and also suppressed mucus overproduction (determined by PAS staining). Lung histopathology also showed reduction of tissue eosinophilia and mucus.

Example 18

Further Characterization of p38α Antisense Effects

The active antisense oligonucleotide against mouse p38α was further characterized for potency and specificity for the α isoform. Following lipofectin-mediated transfection of b.END cells, the p38α antisense compound reduced basal mRNA level of p38α in a dose-dependent manner, as determined by RT-PCR as in above examples. p38α mRNA was inhibited by approximately 30% at 1 nM oligonucleotide concentration, by approximately 62% at 5 nM oligonucleotide, by approximately 75% at 10 nM oligonucleotide and by approximately 83% at 25 nM oligonucleotide concentration. The IC50 was thus determined to be in the low nM range. p38α protein levels were also shown to be inhibited in a dose-dependent manner. To confirm an antisense mechanism of p38α reduction, the ISIS 101757 sequence was tested at the same concentration range in parallel with oligonucleotides containing 1, 2, 4, or 6 mismatches to the ISIS 101757 target site. Activity was compromised in accordance with increasing number of mismatched bases in the sequence, indicating the importance of RNA hybridization for the inhibitory effect. The 1-mismatch sequence had an IC50 in the 5-10 nM range, the 2-mismatch sequence had an IC50 near 25 nM and the 4- and 6-mismatch sequences did not inhibit by 50% at any of these concentrations. An antisense oligonucleotide with the same sequence as ISIS 101757 but with 2'-O-methoxyethyl modifications at every position was also without effect, suggesting that the ISIS 101757-mediated target reduction is dependent upon RNase H1. Evaluation of p38β mRNA levels in b.END cells treated with ISIS 101757 showed no change in expression, suggesting specificity of the p38α antisense oligonucleotide for the α-isoform.

Example 19

Additional Antisense Compounds Targeted to Human p38α

An additional set of antisense oligonucleotides were designed to target human p38α. Human p38α target sequences are: Genbank accession number L35253, provided herein as SEQ ID NO: 1; Genbank accession number NM_001315.1, provided herein as SEQ ID NO: 127; accession number NM_139012.1. which uses exons 1-8, exon 8a (a unique exon) and exons 10-12 (skips exon 9), provided herein as SEQ ID NO: 271; accession number NM_139013.1, which uses exons 1-8, exon 8a and exon 10a (extends exon 10 in the 3' direction), provided herein as SEQ ID NO: 272; accession number NM_139014.1, which uses exons 1-8, exon 8a and exons 11-12 (skips exons 9 and 10), provided herein as SEQ ID NO: 273; nucleotides 26792300-26876062 of the genomic sequence with accession number NT_007592.13, provided herein as SEQ ID NO: 274; and BG898314.1, which extends 5' from SEQ ID NO: 1, provided herein as SEQ ID NO: 275. Oligonucleotides were synthesized as chimeric oligonucleotides ("gapmers") 20 nucleotides in length, composed of a central "gap" region consisting of eight 2'-deoxynucleotides, which is flanked on both sides (5' and 3' directions) by six-nucleotide "wings." The wings are composed of 2'-methoxyethyl (2'-MOE) nucleotides. The internucleoside (backbone) linkages are phosphorothioate (P=S) throughout the oligonucleotide. All 2'-MOE cytosines were 5-methyl-cytosines. These oligonucleotide sequences are shown in Table 28. These were tested in T-24 cells for ability to reduce human p38α mRNA levels, as measured by RT-PCR as in other examples herein. "Target site" indicates the first (5'-most) nucleotide number on the particular target nucleic acid to which the oligonucleotide binds. Also shown in Table 28 is the species to which each of the oligonucleotides is targeted. Oligo concentration was 75 nM.

TABLE 28

Activity of human p38α antisense compounds in T-24 cells

| Isis No | Sequence | Target site | Target sequence SEQ ID NO: | % inhib | Species | SEQ ID NO |
|---|---|---|---|---|---|---|
| 100872 | ttctcttatctgagtccaat | 1164 | 1 | 61 | Human, Chimp | 90 |
| 186888 | atactgtcaagatctgagaa | 2007 | 127 | 91 | Human | 139 |

TABLE 28-continued

Activity of human p38α antisense compounds in T-24 cells

| Isis No | Sequence | Target site | Target sequence SEQ ID NO: | % inhib | Species | SEQ ID NO |
|---|---|---|---|---|---|---|
| 186891 | caagaggcacttgaataata | 1516 | 127 | 68 | Human | 142 |
| 186902 | aatatatgagtcctcatgta | 3112 | 127 | 85 | Human | 153 |
| 320131 | cttcccctcacagtgaagtg | 1472 | 127 | 92 | Human, Mouse, Rat | 208 |
| 320152 | tttgccctttctccccatca | 2991 | 127 | 69 | Human, Mouse, Rat, Rattus sp. | 229 |
| 320153 | aatattaaaataatttgccc | 3004 | 127 | 51 | Human, Mouse, Rat, Rattus sp. | 230 |
| 342597 | ctgctgggcttcagctcgga | 74 | 1 | 0 | Human | 276 |
| 342598 | taaggctccagtggtcgcgg | 5 | 127 | 51 | Human | 277 |
| 342599 | ggctgcgtcgcagtactccc | 45 | 127 | 82 | Human | 278 |
| 342600 | gccgcagcggctggatgtgc | 171 | 127 | 60 | Human | 279 |
| 342601 | agccgccgggcaagaaggtg | 332 | 127 | 52 | Human | 280 |
| 342602 | ccacaacctcctgtaaagtc | 1660 | 127 | 81 | Human | 281 |
| 342603 | gcctgagccaactctcagaa | 1712 | 127 | 93 | Human | 282 |
| 342604 | aggacagcagctcttgtctg | 1731 | 127 | 77 | Human | 283 |
| 342605 | caaaagcatgaccgggattg | 1796 | 127 | 97 | Human | 284 |
| 342606 | aggagaagccaaagtggcaa | 1813 | 127 | 76 | Human, Mouse | 285 |
| 342607 | tgaagcaaccagaaggtatg | 1898 | 127 | 71 | Human | 286 |
| 342608 | caggtctgaagcaaccagaa | 1904 | 127 | 93 | Human | 287 |
| 342609 | ggctgtacgtatcactgagg | 1932 | 127 | 87 | Human | 288 |
| 342610 | agaagccagttggtccttt | 1953 | 127 | 94 | Human | 289 |
| 342611 | atactaagcaagttaatcac | 1985 | 127 | 28 | Human | 290 |
| 342612 | tctccttttaaggcacaaac | 2045 | 127 | 96 | Human, Rat | 291 |
| 342613 | ctgcagtcttttaactatct | 2076 | 127 | 94 | Human | 292 |
| 342614 | tctcgacttgcccggctcag | 2107 | 127 | 95 | Human | 293 |
| 342615 | agccctctcgacttgcccgg | 2112 | 127 | 93 | Human | 294 |
| 342616 | ctatgaaggcigcctgatta | 2159 | 127 | 80 | Human | 295 |
| 342617 | aggtgaagggtaagcagaga | 2253 | 127 | 59 | Human | 296 |
| 342618 | ttcaagaaacctctgcacca | 2274 | 127 | 48 | Human | 297 |
| 342619 | aacctgcttctgactactgg | 2302 | 127 | 87 | Human | 298 |
| 342620 | tacatgacatcaagaacctg | 2316 | 127 | 41 | Human | 299 |
| 342621 | ggacaagcagctgtgcatgc | 2398 | 127 | 82 | Human | 300 |

TABLE 28-continued

Activity of human p38α antisense compounds in T-24 cells

| Isis No | Sequence | Target site | Target sequence SEQ ID NO: | % inhib | Species | SEQ ID NO |
|---|---|---|---|---|---|---|
| 342622 | agagcaggacaagcagctgt | 2404 | 127 | 90 | Human | 301 |
| 342623 | gcctcctgaagagagcagga | 2415 | 127 | 88 | Human | 302 |
| 342624 | aagtcttcactggcaaacct | 2448 | 127 | 90 | Human | 303 |
| 342625 | atgggatctaaactacccaa | 2469 | 127 | 83 | Human | 304 |
| 342626 | gccataatatcagctgaggt | 2492 | 127 | 93 | Human | 305 |
| 342627 | gggctgaagagaggtgatat | 2517 | 127 | 87 | Human | 306 |
| 342628 | ttcaacacagaatagcacta | 2538 | 127 | 75 | Human | 307 |
| 342629 | catcaaaagcacctgaagta | 2567 | 127 | 72 | Human | 308 |
| 342630 | taaaaatgctatacatccac | 2611 | 127 | 29 | Human | 309 |
| 342631 | ttggttgaaaacagatggca | 2635 | 127 | 85 | Human | 310 |
| 342632 | tcagcatttcttagcattag | 2748 | 127 | 94 | Human | 311 |
| 342633 | gcaaaaggagtttctggcct | 2796 | 127 | 94 | Human | 312 |
| 342634 | ttaaagtaatcatatttaga | 2824 | 127 | 10 | Human | 313 |
| 342635 | ggaaaagacaccttgttact | 2852 | 127 | 89 | Human | 314 |
| 342636 | ttccataggagtggaaaaga | 2864 | 127 | 0 | Human | 315 |
| 342637 | aagggattcctacaatatac | 2953 | 127 | 62 | Human | 316 |
| 342638 | aataatttgccctttctccc | 2996 | 127 | 57 | Human, Mouse, Rat, Rattus sp. | 317 |
| 342639 | tctttataaagttgaaaata | 3027 | 127 | 48 | Human | 318 |
| 342640 | tctccacccctgaggatatt | 3050 | 127 | 70 | Human | 319 |
| 342641 | agttatgaaaacgacacttc | 3068 | 127 | 81 | Human | 320 |
| 342642 | tctgtcacacagccaacact | 3171 | 127 | 70 | Human | 321 |
| 342643 | attgagaaatggaaacacct | 3208 | 127 | 78 | Human | 322 |
| 342644 | cctctggagtacatgtatca | 3236 | 127 | 85 | Human | 323 |
| 342645 | cttgctccagttgactcagg | 3270 | 127 | 92 | Human | 324 |
| 342646 | tttctgtaggaaatcacacg | 3453 | 127 | 81 | Human | 325 |
| 342647 | tacaaatattcagagcagt | 3474 | 127 | 92 | Human | 326 |
| 342648 | gtatgtggtcacatgtgcaa | 3504 | 127 | 74 | Human | 327 |
| 342649 | cattatgctcagaaaccgaa | 3585 | 127 | 41 | Human | 328 |
| 342650 | tacggcataactgattaCag | 3687 | 127 | 90 | Human | 329 |
| 342651 | ctttattttaaccagtggta | 3722 | 127 | 94 | Human, Mouse | 330 |
| 342652 | ataggctttattttaaccag | 3727 | 127 | 95 | Human | 331 |
| 342653 | tgatcaatatggtctgtacc | 1035 | 271 | 66 | Human, Mouse, Rat, Dog | 332 |

TABLE 28-continued

Activity of human p38α antisense compounds in T-24 cells

| Isis No | Sequence | Target site | Target sequence SEQ ID NO: | % inhib | Species | SEQ ID NO |
|---|---|---|---|---|---|---|
| 342654 | aacgagtcttaaaatgagct | 1060 | 271 | 81 | Human, Mouse, Rat, Dog | 333 |
| 342655 | agtttcttgcagactctgag | 1115 | 271 | 63 | Human, Mouse, Rat, Dog | 334 |
| 342656 | tatccatgaggtgaggatat | 1217 | 272 | 66 | Human | 335 |
| 342657 | aagtcgacagagactctgag | 1115 | 273 | 24 | Human | 336 |
| 342658 | cgacactcaccacacagagc | 869 | 274 | 61 | Human | 337 |
| 342659 | gcaacaaggctgtgttgctt | 8307 | 274 | 86 | Human | 338 |
| 342660 | aactacagaggacttccaaa | 12666 | 274 | 21 | Human | 339 |
| 342661 | aataacttacattttcatgt | 25424 | 274 | 0 | Human | 340 |
| 342662 | gagaccaactcatgtaggac | 37475 | 274 | 70 | Human | 341 |
| 342663 | ttcattttaccttcagctca | 46692 | 274 | 0 | Human | 342 |
| 342664 | tgatcaatatctaatggtgg | 68582 | 274 | 51 | Human, Rat | 343 |
| 342665 | atgaaacaaattcagagtgg | 69792 | 274 | 85 | Human | 344 |
| 342666 | tggttaatatcttagatgcc | 72783 | 274 | 80 | Human | 345 |
| 342667 | aacagctcccgggactctcc | 99 | 275 | 41 | Human | 346 |

Antisense compounds with SEQ ID NOs 90, 139, 142, 153, 208, 229, 230, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 316, 317, 318, 319, 320, 321, 322, 323, 324, 325, 326, 327, 328, 329, 330, 331, 332, 333, 334, 335, 336, 337, 338, 339, 341, 343, 344, 345 and 346 inhibited p38α RNA expression by at least 10% in this assay.

Compounds of SEQ ID NOs 90, 139, 142, 153, 208, 229, 230, 277, 278, 279, 280, 281, 282, 283, 284, 285, 286, 287, 288, 289, 291, 292, 293, 294, 295, 296, 298, 300, 301, 302, 303, 304, 305, 306, 307, 308, 310, 311, 312, 314, 316, 319, 320, 321, 322, 323, 324, 325, 326, 327, 329, 330, 331, 332, 333, 334, 335, 337, 338, 341, 343, 344 and 345 gave greater than 50% inhibition of human p38α mRNA expression in this assay.

The compounds shown in the previous table were also screened in A549 cells. The human lung carcinoma cell line A549 is obtained from the American Type Culture Collection (ATCC) (Manassas, Va.). A549 cells are routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells were treated with antisense compounds at a concentration of 50 nM. Results are shown in Table 29.

TABLE 29

Activity of human p38α antisense compounds in A549 cells

| Isis No | Sequence | % inhib | SEQ ID NO |
|---|---|---|---|
| 100872 | ttctcttatctgagtccaat | 42 | 90 |
| 186888 | atactgtcaagatctgagaa | 74 | 139 |
| 186891 | caagaggcacttgaataata | 59 | 142 |
| 186902 | aatatatgagtcctcatgta | 57 | 153 |
| 320131 | cttccectcacagtgaagtg | 68 | 208 |
| 320152 | tttgcccttctccccatca | 47 | 229 |
| 320153 | aatattaaaataatttgccc | 13 | 230 |
| 342597 | ctgctgggcttcagctcgga | 0 | 276 |
| 342598 | taaggctccagtggtcgcgg | 13 | 277 |
| 342599 | ggctgcgtcgcagtactccc | 62 | 278 |
| 342600 | gccgcagcggctggatgtgc | 40 | 279 |
| 342601 | agccgccgggcaagaaggtg | 32 | 280 |
| 342602 | ccacaacctcctgtaaagtc | 72 | 281 |

TABLE 29-continued

Activity of human p38α antisense compounds in A549 cells

| Isis No | Sequence | % inhib | SEQ ID NO |
|---|---|---|---|
| 342603 | gcctgagccaactctcagaa | 65 | 282 |
| 342604 | aggacagcagctcttgtctg | 40 | 283 |
| 342605 | caaaagcatgaccgggattg | 78 | 284 |
| 342606 | aggagaagccaaagtggcaa | 65 | 285 |
| 342607 | tgaagcaaccagaaggtatg | 49 | 286 |
| 342608 | caggtctgaagcaaccagaa | 73 | 287 |
| 342609 | ggctgtacgtatcactgagg | 67 | 288 |
| 342610 | agaagccagttggtcctttt | 74 | 289 |
| 342611 | atactaagcaagttaatcac | 39 | 290 |
| 342612 | tctccttttaaggcacaaac | 75 | 291 |
| 342613 | ctgcagtcttttaactatct | 54 | 292 |
| 342614 | tctcgacttgcccggctcag | 66 | 293 |
| 342615 | agccctctcgacttgcccgg | 62 | 294 |
| 342616 | ctatgaaggctgcctgatta | 22 | 295 |
| 342617 | aggtgaagggtaagcagaga | 51 | 296 |
| 342618 | ttcaagaaacctctgcacca | 44 | 297 |
| 342619 | aacctgcttctgactactgg | 61 | 298 |
| 342620 | tacatgacatcaagaacctg | 38 | 299 |
| 342621 | ggacaagcagctgtgcatgc | 46 | 300 |
| 342622 | agagcaggacaagcagctgt | 60 | 301 |
| 342623 | gcctcctgaagagagcagga | 69 | 302 |
| 342624 | aagtcttcactggcaaacct | 60 | 303 |
| 342625 | atgggatctaaaactacccaa | 63 | 304 |
| 342626 | gccataatatcagctgaggt | 60 | 305 |
| 342627 | gggctgaagagaggtgatat | 33 | 306 |
| 342628 | ttcaacacagaatagcacta | 51 | 307 |
| 342629 | catcaaaagcacctgaagta | 61 | 308 |
| 342630 | taaaaatgctatacatccac | 14 | 309 |
| 342631 | ttggttgaaaacagatggca | 67 | 310 |
| 342632 | tcagcatttcttagcattag | 84 | 311 |
| 342633 | gcaaaaggagtttctggcct | 60 | 312 |
| 342634 | ttaaagtaatcatatttaga | 21 | 313 |
| 342635 | ggaaaagacaccttgttact | 50 | 314 |
| 342636 | ttccataggagtggaaaaga | 7 | 315 |
| 342637 | aagggattcctacaatatac | 20 | 316 |
| 342638 | aataatttgcccttttctccc | 37 | 317 |
| 342639 | tctttataaagttgaaaata | 4 | 318 |
| 342640 | tctccaccccctgaggatatt | 56 | 319 |
| 342641 | agttatgaaaacgacacttc | 60 | 320 |
| 342642 | tctgtcacacagccaacact | 55 | 321 |
| 342643 | attgagaaatggaaacacct | 48 | 322 |
| 342644 | cctctggagtacatgtatca | 48 | 323 |
| 342645 | cttgctccagttgactcagg | 70 | 324 |
| 342646 | tttctgtaggaaatcacacg | 69 | 325 |
| 342647 | tacaaaatattcagagcagt | 70 | 326 |
| 342648 | gtatgtggtcacatgtgcaa | 20 | 327 |
| 342649 | cattatgctcagaaaccgaa | 30 | 328 |
| 342650 | tacggcataactgattacag | 69 | 329 |
| 342651 | ctttattttaaccagtggta | 77 | 330 |
| 342652 | ataggctttattttaaccag | 75 | 331 |
| 342653 | tgatcaatatggtctgtacc | 20 | 332 |
| 342654 | aacgagtcttaaaatgagct | 44 | 333 |
| 342655 | agtttcttgcagactctgag | 34 | 334 |
| 342656 | tatccatgaggtgaggatat | 25 | 335 |
| 342657 | aagtcgacagagactctgag | 2 | 336 |
| 342658 | cgacactcaccacacagagc | 20 | 337 |
| 342659 | gcaacaaggctgtgttgctt | 30 | 338 |
| 342660 | aactacagaggacttccaaa | 31 | 339 |
| 342661 | aataacttacattttcatgt | 0 | 340 |
| 342662 | gagaccaactcatgtaggac | 50 | 341 |
| 342663 | ttcattttaccttcagctca | 9 | 342 |
| 342664 | tgatcaatatctaatggtgg | 42 | 343 |
| 342665 | atgaaacaaattcagagtgg | 72 | 344 |
| 342666 | tggttaatatcttagatgcc | 52 | 345 |
| 342667 | aacagctcccgggactctcc | 1 | 346 |

Antisense compounds with SEQ ID NOs: 90, 139, 142, 153, 208, 229, 230, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 316, 317, 319, 320, 321, 322, 323, 324, 325, 326, 327, 328, 329, 330, 331, 332, 333, 334, 335, 337, 338, 339, 341, 343, 344, 345 inhibited p38α RNA expression by at least 10% in this assay.

Compounds with SEQ ID NOs 139, 142, 153, 208, 278, 281, 282, 284, 285, 287, 288, 289, 291, 292, 293, 294, 296, 298, 301, 302, 303, 304, 305, 307, 308, 310, 311, 312, 314, 319, 320, 321, 324, 325, 326, 329, 330, 331, 341, 344 and 345 demonstrated at least 50% inhibition of p38α expression and are preferred.

Example 20

Additional Compounds Targeted to Human p38α

An additional set of antisense oligonucleotides were designed to target human p38α (Genbank accession no. NM_001315.1; SEQ ID NO: 127). Human p38α target sequences are indicated in the table. Oligonucleotides were synthesized as chimeric oligonucleotides ("gapmers") 20 nucleotides in length, composed of a central "gap" region consisting of eight 2'-deoxynucleotides, which is flanked on both sides (5' and 3' directions) by six-nucleotide "wings." The wings are composed of 2'-methoxyethyl (2'-MOE) nucleotides. The internucleoside (backbone) linkages are phosphorothioate (P=S) throughout the oligonucleotide. All 2'-MOR cytosines were 5-methyl-cytosines. These oligonucleotide sequences are shown in Table 30. These were tested in A549 cells for ability to reduce human p38α mRNA levels, as measured by RT-PCR as in other examples herein. "Target site" indicates the first (5'-most) nucleotide number on the particular target nucleic acid to which the oligonucleotide binds. Also shown in Table 30 is the species to which each of the oligonucleotides is targeted. Oligo concentration was 50 nM.

TABLE 30

Activity of antisense oligonucleotides targeted to p38α

| Isis No | Sequence | % inhib | Species | Target Site | SEQ ID NO: |
|---------|----------|---------|---------|-------------|------------|
| 342531 | GACATTTTCCAGCGGCAGCC | 54 | Human, Chimp | 348 | 347 |
| 342532 | TAGAACGTGGGCCTCTCCTG | 65 | Human, Mouse, Rat, Chimp | 369 | 348 |
| 342533 | GCCGGTAGAACGTGGGCCTC | 40 | Human, Mouse, Rat, Chimp | 374 | 349 |
| 342534 | CGCTCGGGCACCTCCCAGAT | 65 | Human, Chimp, Dog | 411 | 350 |
| 342535 | CACTGGAGACAGGTTCTGGT | 63 | Human, Chimp | 433 | 351 |
| 342536 | CGCCAGAGCCCACTGGAGAC | 46 | Human, Chimp | 443 | 352 |
| 342537 | AGCAGCACACACAGAGCCAT | 64 | Human, Chimp | 466 | 353 |
| 342538 | TTTGTGTCAAAAGCAGCACA | 62 | Human, Chimp, Dog | 477 | 354 |
| 342539 | TAACCCCGTTTTGTGTCAA | 55 | Human, Chimp | 487 | 355 |
| 342540 | CTGCCACACGTAACCCCGTT | 76 | Human, Chimp | 497 | 356 |
| 342541 | TGGACTGAAATGGTCTGGAG | 75 | Human, Chimp, Dog | 527 | 357 |
| 342542 | GCATGAATGATGGACTGAAA | 69 | Human, Chimp, Dog | 537 | 358 |
| 342543 | TAACCGCAGTTCTCTGTAGG | 60 | Human, Chimp, Dog | 565 | 359 |
| 342544 | TATGTTTAAGTAACCGCAGT | 31 | Human, Chimp | 575 | 360 |
| 342545 | AATCACATTTTCATGTTTCA | 33 | Human, Chimp, Dog | 595 | 361 |
| 342546 | AACAGACCAATCACATTTTC | 27 | Human, Mouse, Chimp | 603 | 362 |
| 342547 | AGAGACCTTGCAGGTGTAAA | 33 | Human, Chimp, Dog | 630 | 363 |
| 342548 | GAATTCCTCCAGAGACCTTG | 38 | Human, Chimp, Dog | 640 | 364 |
| 342549 | ACACATCATTGAATTCCTCC | 49 | Human, Chimp, Dog | 650 | 365 |

TABLE 30-continued

Activity of antisense oligonucleotides targeted to p38α

| Isis No | Sequence | % inhib | Species | Target Site | SEQ ID NO: |
|---|---|---|---|---|---|
| 342550 | GTCACCAGATACACATCATT | 21 | Human, Chimp, Dog | 660 | 366 |
| 342551 | CCCATGAGATGGGTCACCAG | 76 | Human, Mouse, Rat, Chimp | 672 | 367 |
| 342552 | GTTCAGATCTGCCCCCATGA | 73 | Human, Chimp | 685 | 368 |
| 342553 | TTTCACAATGTTGTTCAGAT | 45 | Human, Chimp, Dog | 697 | 369 |
| 342554 | GCTTCTGACATTTCACAATG | 67 | Human, Chimp, Dog | 707 | 370 |
| 342555 | TCATCTGTAAGCTTCTGACA | 68 | Human, Chimp | 717 | 371 |
| 342556 | AGATAAGGAACTGAACATGG | 65 | Human, Chimp, Dog | 737 | 372 |
| 342557 | CTTTAGACCTCGGAGAATTT | 40 | Human, Chimp | 760 | 373 |
| 342558 | AATGTATATACTTTAGACCT | 34 | Human, Chimp | 770 | 374 |
| 342559 | TCCCTGTGAATTATGTCAGC | 71 | Human, Mouse, Chimp, Dog | 792 | 375 |
| 342560 | TTAGGTCCCTGTGAATTATG | 68 | Human, Mouse, Chimp, Dog | 797 | 376 |
| 342561 | ATTCACAGCTAGATTACTAG | 49 | Human, Chimp | 820 | 377 |
| 342562 | TCTGTGTGCCGAGCCAGTCC | 66 | Human, Chimp | 870 | 378 |
| 342563 | CATTTCATCATCTGTGTGCC | 56 | Human, Chimp | 880 | 379 |
| 342564 | CGTAGCCTGTCATTTCATCA | 67 | Human, Chimp | 890 | 380 |
| 342565 | CCACCTAGTGGCCACGTAGC | 52 | Human, Chimp | 904 | 381 |
| 342566 | ACAGCTCGGCCATTATGCAT | 46 | Human, Chimp | 992 | 382 |
| 342567 | CTTCCAGTCAACAGCTCGGC | 72 | Human, Chimp | 1002 | 383 |
| 342568 | AAACAATGTTCTTCCAGTCA | 30 | Human, Chimp | 1012 | 384 |
| 342569 | TGGTCTGTACCAGGAAACAA | 50 | Human, Mouse, Rat, Chimp, Dog | 1026 | 385 |
| 342570 | CAGACGCATAATCTGCTGAA | 68 | Human, Chimp | 1057 | 386 |
| 342571 | GTGTTCCTGTCAGACGCATA | 81 | Human, Chimp | 1067 | 387 |
| 342572 | GTTTCTTGCCTCATGGCTTG | 16 | Human, Mouse, Rat, Chimp | 1114 | 388 |

TABLE 30-continued

Activity of antisense oligonucleotides targeted to p38α

| Isis No | Sequence | % inhib | Species | Target Site | SEQ ID NO: |
|---|---|---|---|---|---|
| 342573 | ACTGAATATAGTTTCTTGCC | 34 | Human, Chimp | 1124 | 389 |
| 342574 | TGAGTCAAAGACTGAATATA | 26 | Human, Chimp | 1134 | 390 |
| 342575 | ACATTCGCAAAGTTCATCTT | 2 | Human, Chimp | 1161 | 391 |
| 342576 | TTGGCACCAATAAATACATT | 50 | Human, Mouse, Rat, Chimp, Dog | 1176 | 392 |
| 342577 | AGTCCAATACAAGCATCTTC | 39 | Human, Chimp, Dog | 1220 | 393 |
| 342578 | AGGCATGTGCAAGGGCTTGG | 75 | Human, Chimp | 1262 | 394 |
| 342579 | CGTGGTACTGAGCAAAGTAG | 60 | Human, Mouse, Rat, Chimp | 1280 | 395 |
| 342580 | TTCATCATCAGGATCGTGGT | 73 | Human, Chimp | 1294 | 396 |
| 342581 | CGGCCACTGGTTCATCATCA | 66 | Human, Chimp | 1304 | 397 |
| 342582 | GATCATAAGGATCGGCCACT | 27 | Human, Chimp | 1316 | 398 |
| 342583 | TCCCTGCTTTCAAAGGACTG | 60 | Human, Mouse, Rat, Chimp, Dog | 1335 | 399 |
| 342584 | CTATAAGGAGGTCCCTGCTT | 23 | Human, Rat, Chimp, Dog | 1346 | 400 |
| 342585 | TTCCACTCATCTATAAGGAG | 58 | Human, Chimp | 1356 | 401 |
| 342586 | GGTCAGGCTTTTCCACTCAT | 70 | Human, Chimp | 1366 | 402 |
| 342587 | TCATAGGTCAGGCTTTTCCA | 50 | Human, Chimp | 1371 | 403 |
| 342588 | ACTTCATCATAGGTCAGGCT | 63 | Human, Mouse, Chimp | 1377 | 404 |
| 342589 | TGATGACTTCATCATAGGTC | 53 | Human, Mouse, Chimp | 1382 | 405 |
| 342590 | AAAGCTGATGACTTCATCAT | 38 | Human, Mouse, Chimp | 1387 | 406 |
| 342591 | GTGGTGGCACAAAGCTGATG | 68 | Human, Mouse, Chimp | 1397 | 407 |
| 342592 | GACTCCATCTCTTCTTGGTC | 57 | Human, Mouse, Chimp, Dog | 1422 | 408 |
| 342593 | CCAGGTGCTCAGGACTCCAT | 75 | Human, Mouse, Chimp | 1434 | 409 |
| 342594 | AGAAACCAGGTGCTCAGGAC | 77 | Human, Mouse, Chimp | 1439 | 410 |

TABLE 30-continued

Activity of antisense oligonucleotides targeted to p38α

| Isis No | Sequence | % inhib | Species | Target Site | SEQ ID NO: |
|---------|----------|---------|---------|-------------|------------|
| 342595 | AGAACAGAAACCAGGTGCTC | 66 | Human, Mouse, Chimp | 1444 | 411 |
| 342596 | GTGAAGTGGGATCAACAGAA | 65 | Human, Chimp | 1460 | 412 |

Antisense compounds having SEQ ID NO: 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 392, 393, 394, 395, 396, 397, 398, 399, 400, 401, 402, 403, 404, 405, 406, 407, 408, 409, 410, 411, and 412 inhibited p38α RNA expression by at least 10% in this assay.

Compounds having SEQ ID NOs: 347, 348, 350, 351, 353, 354, 355, 356, 357, 358, 359, 367, 368, 370, 371, 372, 375, 376, 378, 379, 380, 381, 383, 385, 386, 387, 392, 394, 395, 396, 397, 399, 401, 402, 403, 404, 405, 407, 408, 409, 410, 411 and 412 inhibited p38α expression by at least 50% in this assay.

Example 21

Dose Response Experiments—Human p38α Oligonucleotides

Four of the most active human p38α oligonucleotides (ISIS 186910, 342578, 342651 and 342652) were chosen for dose response studies in human A549 cells at concentrations of 5, 10, 25, 50 and 100 nM. A dose-dependent decrease in p38α mRNA expression was observed with ISIS 342578, 342651 and 342652. For 186910, a dose dependent response was observed from 25 to 100 nM oligonucleotide. A dose dependent decrease in expression of p38α using an antisense oligonucleotide to an unrelated gene (PP2A) was not observed.

A dose response experiment was also performed in human HepG2 cells with ISIS 100872, 342578, 342651 and 342652 at the same concentrations as in the A549 cells. Dose-dependent inhibition of mRNA expression was observed for ISIS 342758, 342651 and 342652. For 100872, a dose dependent response was observed from 25 to 100 nM oligonucleotide. A dose dependent decrease in expression of p38α using an antisense oligonucleotide to an unrelated gene (PTP1B) was not observed. In addition, little or no inhibition of p38P mRNA expression was observed in A549 cells with 5, 10, 25, 50 or 100 nM concentrations of these oligonucleotides.

Lastly, p38α protein reduction was also observed 60 hours after transfection of HepG2 and A549 cells In HepG2 cells, the reduction in protein level was about 50% for ISIS 100872, 60% for ISIS 342578, 90% for ISIS 342561 and 87% for ISIS 342652. In A549 cells, ISIS 100872 did not reduce protein levels; however, the reduction in protein level was about 95% for ISIS 342578, 85% for ISIS 342561 and 80% for ISIS 342652. Specific inhibition of p38α expression was observed in HepG2 cells.

What is claimed is:

1. An antisense compound comprising a modified oligonucleotide consisting of about 13 to not more than 23 linked nucleosides targeted to a nucleic acid molecule encoding a p38α mitogen-activated protein kinase, wherein said modified oligonucleotide comprises at least one modified sugar moiety or at least one modified nucleobase, wherein said modified oligonucleotide is complementary to at least an 8 contiguous nucleobase portion of nucleotides 1194 to 1277 of SEQ ID NO. 1, wherein said modified oligonucleotide specifically hybridizes to SEQ ID NO:1, and wherein the modified oligonucleotide does not comprise SEQ ID NO: 91, or 92.

2. The antisense compound of claim 1 comprising a chimeric oligonucleotide.

3. The antisense compound of claim 1 which is a single-stranded or a double-stranded compound.

4. The antisense compound of claim 1 comprising at least one modified internucleoside linkage.

5. The antisense compound of claim 4 wherein the modified internucleoside linkage is a phosphorothioate linkage.

6. The antisense compound of claim 1 comprising at least one modified sugar moiety.

7. The antisense compound of claim 6 wherein the modified sugar moiety is a 2'-O-methoxyethyl moiety or a 4'-(CH$_2$)$_n$—O—2' bridge, wherein n is 1 or 2.

8. The antisense compound of claim 1 comprising at least one modified nucleobase.

9. The antisense compound of claim 8 wherein the modified nucleobase is a 5-methyl cytosine.

10. A pharmaceutical composition comprising the antisense compound of claim 1, or a pharmaceutically acceptable salt thereof, and a pharmaceutically acceptable carrier or diluent.

11. The antisense compound of claim 1, wherein the modified oligonucleotide comprises:
   a gap segment consisting of linked deoxynucleosides;
   a 5' wing segment consisting of linked nucleosides;
   a 3' wing segment consisting of linked nucleosides;
   wherein the gap segment is positioned between the 5' wing segment and the 3' wing segment and wherein each nucleoside of each wing segment comprises a modified sugar.

12. The antisense compound of claim 11, wherein the modified oligonucleotide comprises:
   a gap segment consisting of eight to ten linked deoxynucleosides;
   a 5' wing segment consisting of five to six linked nucleosides;
   a 3' wing segment consisting of five to six linked nucleosides;
   wherein the gap segment is positioned between the 5' wing segment and the 3' wing segment, wherein each nucleoside of each wing segment comprises a 2'-O-methoxyethyl sugar, wherein each cytosine in said modified oligonucleotide is a 5-methylcytosine, and wherein each internucleoside linkage of said modified oligonucleotide is a phosphorothioate linkage.

13. The antisense compound of claim 12, wherein the modified oligonucleotide consists of 20 linked nucleosides.

* * * * *